(12) United States Patent
Wang et al.

(10) Patent No.: US 11,439,707 B2
(45) Date of Patent: Sep. 13, 2022

(54) HYPOCRELLIN DERIVATIVE SUBSTITUTED BOTH IN A PERI-POSITION AND IN 2-POSITION BY AMINO, PREPARATION METHOD, AND APPLICATION THEREOF

(71) Applicant: TECHNICAL INSTITUTE OF PHYSICS AND CHEMISTRY OF THE CHINESE ACADEMY OF SCIENCES, Beijing (CN)

(72) Inventors: Pengfei Wang, Beijing (CN); Jiasheng Wu, Beijing (CN); Weimin Liu, Beijing (CN); Xiuli Zheng, Beijing (CN); Ying Gu, Beijing (CN)

(73) Assignee: TECHNICAL INSTITUTE OF PHYSICS AND CHEMISTRY OF THE CHINESE ACADEMY OF SCIENCES, Beijing (CN)

( * ) Notice: Subject to any disclaimer, the term of this patent is extended or adjusted under 35 U.S.C. 154(b) by 75 days.

(21) Appl. No.: 16/645,301

(22) PCT Filed: Sep. 5, 2018

(86) PCT No.: PCT/CN2018/104124
§ 371 (c)(1),
(2) Date: Mar. 6, 2020

(87) PCT Pub. No.: WO2019/047846
PCT Pub. Date: Mar. 14, 2019

(65) Prior Publication Data
US 2021/0145968 A1     May 20, 2021

(30) Foreign Application Priority Data

Sep. 6, 2017  (CN) .................... 201710794566.X
Sep. 3, 2018  (CN) .................... 201811020381.4

(51) Int. Cl.
   *A61K 47/10*      (2017.01)
   *A61K 41/00*      (2020.01)
             (Continued)

(52) U.S. Cl.
   CPC .......... *A61K 41/0057* (2013.01); *A61K 47/10* (2013.01); *C07C 221/00* (2013.01);
             (Continued)

(58) Field of Classification Search
   CPC .................................................. A61K 41/0057
             (Continued)

(56) References Cited

U.S. PATENT DOCUMENTS 8,747,811 B2 *  6/2014  Sharma ................... A61P 17/00
                                    424/9.1
11,154,548 B2 * 10/2021  Wang ..................... C07D 221/02

\* cited by examiner

*Primary Examiner* — Nizal S Chandrakumar
(74) *Attorney, Agent, or Firm* — Paratus Law Group, PLLC

(57) ABSTRACT

The present invention discloses a hypocrellin derivative substituted both in a pen-position and in a 2-position by an amino, and a preparation method and use thereof. A general structural formula of the derivative is as represented by formulas I-a to I-d:

I-a

I-b

I-c (Continued)

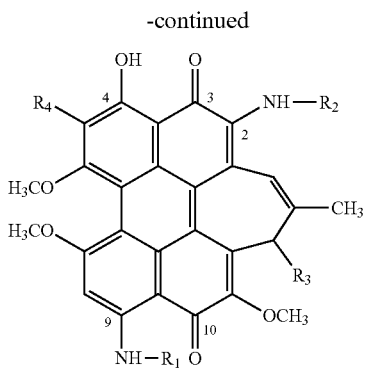

I-d

The hypocrellin derivative substituted both in a peri-position and in a 2-position by an amino prepared in the present invention has a maximum absorption wavelength of 600-650 nm and a molar extinction coefficient reaching about 20000-40000 $M^{-1}cm^{-1}$. Compared with unmodified hypocrellin or hypocrellin having only a 2-position modified, an absorption spectrum of the derivative is significantly red-shifted and the molar extinction coefficient is greatly improved, and the derivative can efficiently produce reactive oxygen species such as singlet oxygen in a photosensitive condition. In the same condition, the hypocrellin derivative substituted both in a pen-position and in a 2-position by an amino involved in the present invention, when used as a photosensitizer, has a stronger ability to photo-dynamically inactivate tumor cells than the first and second generation commercial photosensitizers.

6 Claims, 11 Drawing Sheets

(51) Int. Cl.

| | | |
|---|---|---|
| *C07C 221/00* | (2006.01) | |
| *C07C 225/32* | (2006.01) | |
| *C07C 227/28* | (2006.01) | |
| *C07C 229/16* | (2006.01) | |
| *C07C 229/28* | (2006.01) | |
| *C07C 241/02* | (2006.01) | |
| *C07C 243/20* | (2006.01) | |
| *C07C 323/30* | (2006.01) | |
| *C07C 323/38* | (2006.01) | |
| *C07D 295/13* | (2006.01) | |
| *C07D 295/205* | (2006.01) | |
| *C07D 401/12* | (2006.01) | |
| *C07D 403/12* | (2006.01) | |
| *C07D 519/00* | (2006.01) | |

(52) U.S. Cl.
CPC .......... *C07C 225/32* (2013.01); *C07C 227/28* (2013.01); *C07C 229/16* (2013.01); *C07C 229/28* (2013.01); *C07C 241/02* (2013.01); *C07C 243/20* (2013.01); *C07C 323/30* (2013.01); *C07C 323/38* (2013.01); *C07D 295/13* (2013.01); *C07D 295/205* (2013.01); *C07D 401/12* (2013.01); *C07D 403/12* (2013.01); *C07D 519/00* (2013.01)

(58) Field of Classification Search
USPC .......................................................... 544/79
See application file for complete search history.

HYPOCRELLIN DERIVATIVE SUBSTITUTED BOTH IN A PERI-POSITION AND IN 2-POSITION BY AMINO, PREPARATION METHOD, AND APPLICATION THEREOF

CROSS REFERENCE TO PRIOR APPLICATION

This application is a National Stage Patent Application of PCT International Patent Application No. PCT/CN2018/104124 (filed on Sep. 5, 2018) under 35 U.S.C. § 371, which claims priority to Chinese Patent Application Nos. 201710794566.X (filed on Sep. 6, 2017) and 201811020381.4 (filed on Sep. 3, 2018), which are all hereby incorporated by reference in their entirety.

TECHNICAL FIELD OF THE INVENTION

The present invention relates to the technical filed of photosensitizer drugs, in particular to a hypocrellin derivative substituted both in a peri-position and in a 2-position by an amino, a preparation method, and an application thereof.

BACKGROUND OF THE INVENTION

In photodynamic therapy (PDT for short), photosensitizer molecules are irradiated by light with a specific wavelength, so as to convert light energy into intramolecular energy through photochemical reactions and energy transfer processes, in which case, multiple reactive oxygen species (ROS) are produced in an aerobic condition, including singlet oxygen, hydroxyl radicals, superoxide radicals, hydrogen peroxide, etc., thereby destroying biomacromolecules such as proteins and nucleic acids in the organism, damaging the structure and function of cells, resulting in apoptosis of the diseased cells, which plays a therapeutic role. The PDT is a rapidly developing new technology for selective treatment to various malignant tumors and precancerous lesions in recent years, that is, tumor-targeted photodynamic therapy (T-PDT). The T-PDT is a very promising tumor-targeted therapy due to its advantages such as the ability to selectively kill tumor cells in the relatively specific manner, less damage to healthy tissues, low incidence rate of complications, and less toxic and side effects. The PDT is also used for non-tumor diseases, for example, vascular targeted photodynamic therapy (V-PDT) can selectively treat multiple vascular diseases (such as nevus flammeus, fundus macular degeneration, psoriasis, rheumatoid arthritis), and antimicrobial targeted photodynamic therapy (A-PDT) can selectively treat infectious diseases (such as acne, condyloma acuminatum, esophagitis, and onychomycosis) caused by bacteria, viruses, and fungi, etc., both cases having very significant therapeutic effects. The effect of photodynamic therapy is related to the type of the photosensitizer used, the irradiation condition, the status of tissue oxygen metabolism, and the type of cells, wherein the photosensitizer is the key factor that affects the effect of photodynamic therapy. At present, the clinical first-generation photosensitizers-porphyrin photosensitive drugs and second-generation photosensitizers-phthalocyanine photosensitive drugs have the most prominent problem of difficulty in separation of geometric isomers, making it difficult to obtain single-component photosensitive drugs. The relatively complex components of these composite photosensitive drugs are not conducive to the evaluation of later drug metabolism and toxicological analyses. Currently, the photosensitive drugs required by clinical practice in China are still very scarce, and new high-efficiency photosensitive drugs are urgently required to fill the shortage. In order to make better use of PDT in treatment to vascular diseases and tumors, it is necessary to develop high-efficiency, low-toxicity, and stable photosensitizers with a high absorptivity in the phototherapy window.

Hypocrellin is a natural photosensitizer extracted from *Hypocrella bambusae*, which is a parasitic fungus on Fargesia growing 4000 meters above sea level in Yunnan Plateau of China. Natural hypocrellin primarily includes hypocrellin A (HA for short) and hypocrellin B (HB for short). The hypocrellin has a strong absorption ability in the visible light region, with a large molar extinction coefficient, and can efficiently produce reactive oxygen species in a photosensitive condition; and it also has advantages such as a low phototoxicity, a low dark toxicity, a clear structure, and fast in-vivo metabolism, thus having a wide application prospect (Research and Progress on Novel Photodynamic Drugs-Hypocrellin Derivatives, Chinese Science Bulletin, 2003, 48, 1005-1015). However, the hypocrellin has a main absorption wavelength range of 450-530 nm, where light of this wavelength range can only penetrate tissues less than 1 mm, thus having a relatively weak absorptivity in the photodynamic treatment window (600-900 nm). In the past ten years, there have been many chemical modifications to the hypocrellin, where a hypocrellin derivative having a 2-position modified by an amino group has a maximum absorption wavelength significantly red-shifted to about 580 nm, and a molar extinction coefficient significantly increased to about 10000-20000 $M^{-1}$ $cm^{-1}$ (Photochem. Photobiol. 2003, 78, 411-415). Recently, it has been found from the research that, the peri-position (the 3-, 4-, 9-, or 10-position marked in formulas I-a to I-d) on a fused ring parent of the hypocrellin is also an active site for amino substitution, that is, in addition to the 2-position on the hypocrellin, an amino substitution reaction can also occur at its peri-position. The product of the peri-position amino substitution has a maximum absorption wavelength significantly red-shifted to above 600 nm and a molar extinction coefficient significantly increased to about 20000-40000 $M^{-1}cm^{-1}$, and can also effectively produce reactive oxygen species in a photosensitive condition, to inactivate tumor cells. However, there is some difficulty in finding, separation, and representation of the product obtained from the peri-position amino substitution of the hypocrellin, and related compounds have not been formally reported yet. Therefore, there is an urgent need to provide a method for preparing a hypocrellin derivative having a peri-position substituted by an amino group and an application thereof.

SUMMARY OF THE INVENTION

An objective of the present invention is to provide a hypocrellin derivative substituted both in a peri-position and in a 2-position by an amino.

Another objective of the present invention is to provide a method for preparing a hypocrellin derivative substituted both in a peri-position and in a 2-position by an amino.

A third objective of the present invention is to provide a use of a hypocrellin derivative substituted both in a peri-position and in a 2-position by an amino.

In order to achieve the above first objective, the present invention employs the following technical solution.

A hypocrellin derivative substituted both in a peri-position and in a 2-position by an amino has a general structural formula as represented by formulas I-a to I-d:

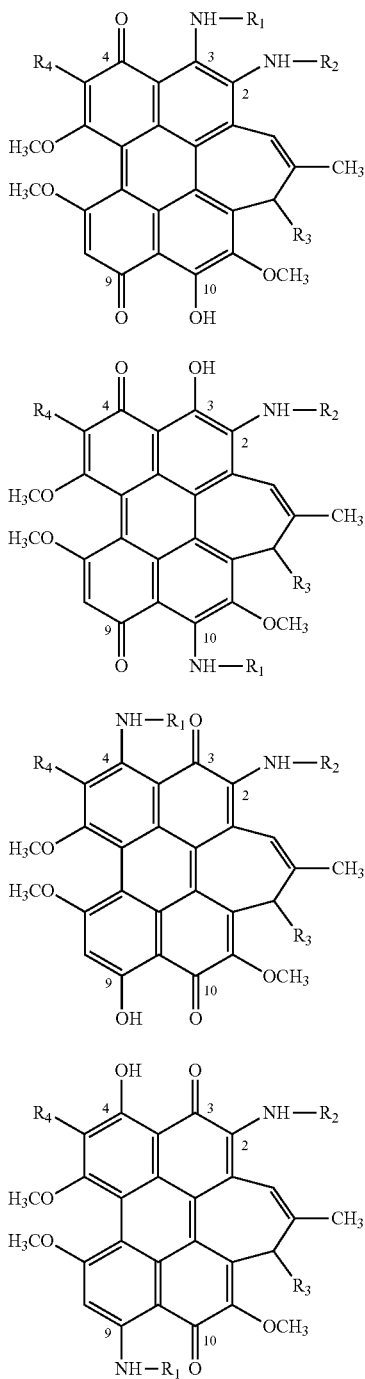

wherein the peri-position of hypocrellin is a 3-, 4-, 9-, or 10-position marked in formulas I-a to I-d; derivatives of the above four general structural formulas can be generated at the same time, with different ratios in final products obtained in different preparation conditions;

a substituent $R_3$ is —COCH$_3$ or —H; a substituent $R_4$ is —H, —F, —Cl, —Br, —I, or —S—$R_5$, wherein $R_5$ is a C2-12 alkyl group, a C2-12 alkyl group having a hydroxyl group as a terminal group, or a C2-12 alkyl group having a carboxyl group as a terminal group;

substituents $R_1$ and $R_2$ are respectively connected to the amino group; $R_1$ and $R_2$ can be identical or different; general structural formulas of $R_1$ and $R_2$ are respectively as represented by formula II:

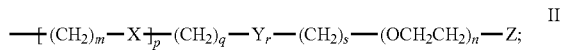

in formula II, $0 \leq m \leq 8$, $0 \leq n \leq 50$, $0 \leq p \leq 8$, $0 \leq q \leq 8$, $0 \leq r \leq 1$, and $0 \leq s \leq 8$; m, n, p, q, r, and s are respectively zero or a positive integer; X and Y are respectively linking groups; Z is a terminal group; $(OCH_2CH_2)_n$ is a polyethylene glycol unit;

the linking groups X and Y in formula II are respectively —NH—, —O—, —S—, a carboxylate group, an amide group, a sulfonate group, a sulfonamide group, a carbonyl group, a phosphate group, a C3-12 unsaturated hydrocarbyl group, a C3-12 cyclic hydrocarbyl group, a C6-12 aryl group, or a C3-12 heterocyclic group;

the C3-12 unsaturated hydrocarbyl group is substituted or unsubstituted or heteroatom-containing alkene or alkyne; the C3-12 cyclic hydrocarbyl group is substituted or unsubstituted or heteroatom-containing cycloalkane, cycloalkene, or cycloalkyne, and the heteroatom is an oxygen, nitrogen, or sulfur atom; the C6-12 aryl group is a substituted or unsubstituted aryl group, wherein the substituted aryl group is a mono- or poly-substituted aryl group, and a substituted position is an ortho-position, a meta-position, or a para-position in the aryl group; the C3-12 heterocyclic group is a substituted or unsubstituted heterocyclic group, the substituted heterocyclic group is mono- or poly-substituted, and a substituted position is an ortho-position, a meta-position, or a para-position in a heterocycle; the heterocyclic group is furan, pyrrole, thiophene, pyrazole, imidazole, oxazole, thiazole, pyridine, piperidine, pyrimidine, pyrazine, piperazine, indole, quinoline, isoquinoline, purine, pyrimidine, or acridine;

a substituent in the above cycloalkyl, cycloalkenyl, aryl, or heterocyclic group is respectively a C1-8 alkyl group, a C2-8 alkenyl group, a C2-8 alkynyl group, a C3-8 cycloalkyl group, an aryl group, a C6-12 aralkyl group, or an alkyl group having a terminal group containing a hydroxyl group, a carboxylic acid group, a sulfonic acid group, or a carboxylate;

a terminal group Z in formula II is selected from hydrogen, a C1-8 alkyl group, a C1-8 alkoxy group, a C3-8 cycloalkyl group, a phenyl group, a pyridyl group, a hydroxyl group, an amino group, a mercapto group, a carboxylic acid group, a carboxylate, a sulfonic acid group, a sulfonate, a phosphoric acid group, a phosphate, an amino acid, triphenylphosphine, a quaternary ammonium salt, a pyridinium, and one of a carboxylic acid salt, a sulfonic acid salt, and an amino acid salt formed by cations acceptable by a pharmaceutical preparation;

when the terminal group Z in formula II is a quaternary ammonium salt, three substituents of the quaternary ammonium salt are respectively: a C1-8 alkyl group, a C2-8 alkenyl group, a C2-8 alkynyl group, a C3-8 cycloalkyl group, a C3-8 cycloalkenyl group, an aryl group, a C6-12 aralkyl group, or an alkyl group having a terminal group containing a hydroxyl group, a carboxylic acid group, a sulfonic acid group, or a carboxylate, and anions in the quaternary ammonium salt are anions acceptable by a pharmaceutical preparation; and when the terminal group Z in formula II is a pyridinium, a substituent on a pyridine ring of the pyridinium is in an ortho-position, a meta-position, or a para-position, the pyridinium is obtained by quaternizing pyridine and halogenated hydrocarbons having 1 to 8 carbon atoms of different chain lengths, and anions in the pyridinium are anions acceptable by a pharmaceutical preparation.

Specifically, the hypocrellin derivatives represented by formulas I-a to I-d respectively have an enol tautomer, mula; formula I-b and formula I-b' represent enol tautomers regarding positions 3 and 4 in the structural formula; formula I-c and formula I-c' represent enol tautomers regarding positions 9 and 10 in the structural formula; and formula I-d and formula I-d' represent enol tautomers regarding positions 3 and 4 in the structural formula:

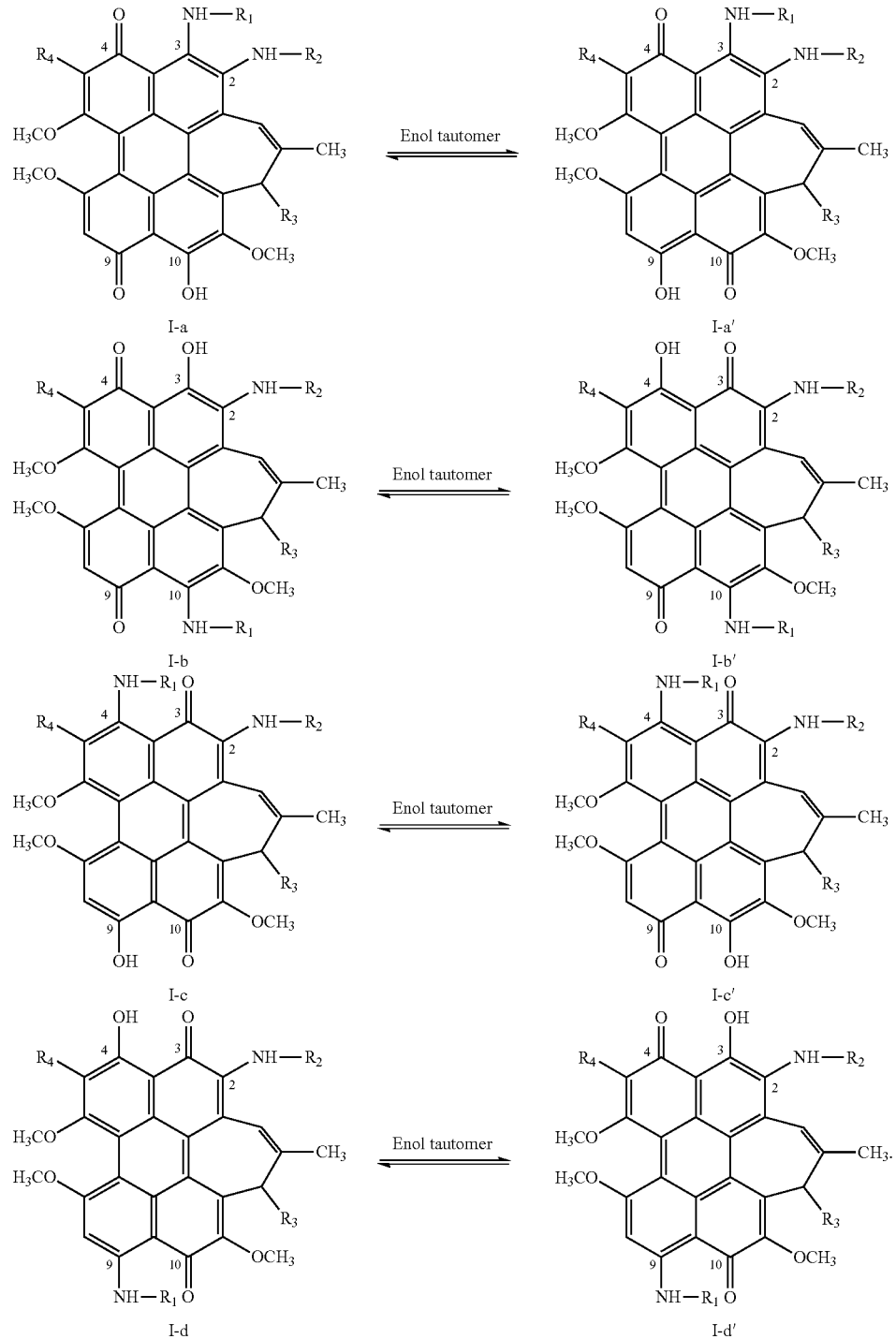

wherein formula I-a and formula I-a' represent enol tautomers regarding positions 9 and 10 in the structural for- Preferably, the linking groups X and Y in formula II are respectively: —NH—, —O—, —S—, —COO—, —OC (=O)—, —CONH—, —NHC(=O)—, —SO₃—, —SO₂NH—, —C(=O)—, —PO₃—, —CH=CH—, —C(CH₃)=CH—, —C(CH₃)=C(CH₃)—, —C(COOH)=CH—, —C(CH₂COOH)=CH—, —C≡C—, —C₃H₄— (a cyclopropyl group), —C₃H₃(CH₃)— (a methylcyclopropyl group), —C₃H₃(OH)— (a hydroxylcyclopropyl group), —C₃H₃(COOH)— (a carboxylcyclopropyl group), —C₄H₆— (a cyclobutyl group), —C₄H₅(CH₃)— (a methylcyclobutyl group), —C₄H₅(OH)— (a hydroxylcyclobutyl group), —C₄H₅(COOH)— (a carboxylcyclobutyl group), —C₅H₈— (a cyclopentyl group), —C₅H₇(CH₃)— (a methylcyclopentyl group), —C₅H₇(OH)— (a hydroxylcyclopentyl group), —C₅H₇(NH₂)— (an aminocyclopentyl group), —C₅H₇(COOH)— (a carboxylcyclopentyl group), —C₆H₁₀— (a cyclohexyl group), —C₆H₉(CH₃)— (a methylcyclohexyl group), —C₆H₉(C₂H₅)— (an ethylcyclohexyl group), —C₆H₉(C₃H₇)— (a propylcyclohexyl group), —C₆H₉(OH)— (a hydroxylcyclohexyl group), —C₆H₉(NH₂)— (an aminocyclohexyl group), —C₆H₉(COOH)— (a carboxylcyclohexyl group), —C₆H₉(CH₂COOH)— (a carboxylmethylcyclohexyl group), —C₆H₈(COOH)₂— (a dicarboxylcyclohexyl group), —C₇H₁₂— (a cycloheptyl group), —C₇H₁₁(COOH)— (a carboxylcycloheptyl group), —C₇H₁₁(OH)— (a hydroxylcycloheptyl group), —C₇H₁₁(CH₃)— (a methylcycloheptyl group), —C₆H₄—, —C₆H₃(CH₃)—, —C₆H₃(C₂H₅)—, —C₆H₂(CH₃)₂—, —C₆H₃(OH)—, —C₆H₃(OCH₃)—, —C₆H₃(OC₂H₅)—, —C₆H₃(CH₂OH)—, —C₆H₃(NH₂)—, —C₆H₃(CH₂NH₂)—, —C₆H₃(F)—, —C₆H₃(Cl)—, —C₆H₃(Br)—, —C₆H₃(I)—, —C₆H₃(COOH)—, —C₆H₂(COOH)₂—, —C₆H₃(SO₃H)—, —C₆H₃(CH₂COOH)—, —C₆H₃(CH₂CH₂COOH)—, —C₅H₃N—, —C₅H₂N(CH₃)—, —C₅H₂N(OH)—, —C₅H₂N(NH₂)—, —C₅H₂N(CH₂NH₂)—, —C₅H₂N(COOH)—, —C₅H₂N(CH₂COOH)—, —C₅H₉N—,

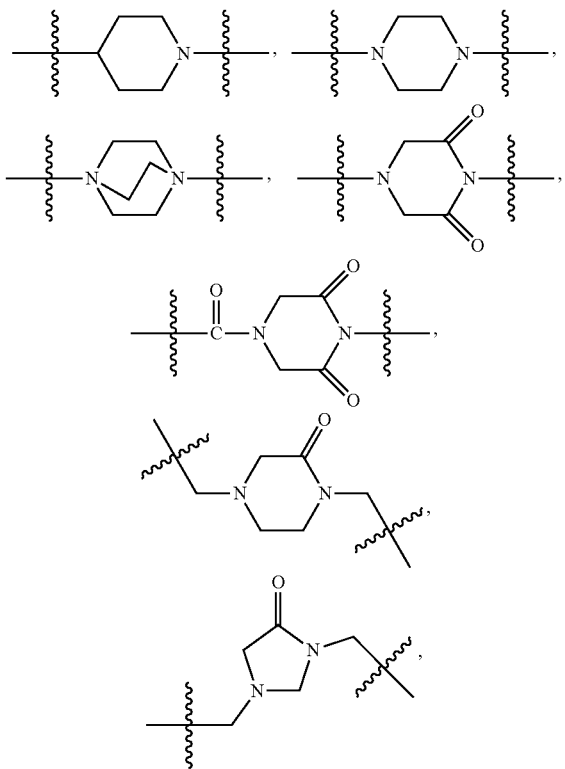

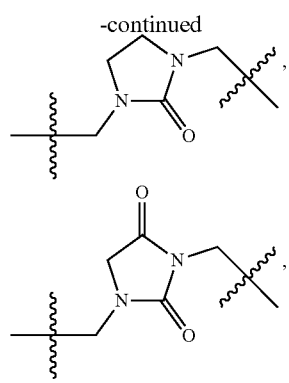

group, a pyrrolyl group, a thienyl group, a pyrazolyl group, an imidazolyl group, an oxazolyl group, a thiazolyl group, a pyridyl group, a piperidinyl group, a pyrimidinyl group, an indolyl group, a quinolinyl group, an isoquinolinyl group, a purinyl group, a pyrimidinyl group, an acridinyl group, a morpholinyl group, or a heterocyclic group containing a substituent.

Preferably, the terminal group Z in formula II is: —H, —CH₃, —C₂H₅, —C₃H₇, —C₄H₉, —C₅H₁₁, —C₆H₁₃, —C₁₂H₂₅, —OCH₃, —OC₂H₅, —OC₃H₇, —OC₄H₉, —OC₅H₁₁, —OC₆H₁₃, —OC₁₂H₂₅, —C₃H₅, —C₄H₇, —C₅H₉, —C₆H₁₁, —C₇H₁₃, —C₆H₅, —OH, —NH₂, —SH, —COOH, —COOCH₃, —COOC₂H₅, —SO₃H, —SO₃CH₃, —SO₃C₂H₅, —PPh₃⁺ (triphenylphosphine) a glycine group, an alanine group, a valine group, a leucine group, an isoleucine group, a phenylalanine group, a proline group, a tryptophan group, a tyrosine group, a serine group, a cysteine group, a methionine group, an aspartate group, a glutamate group, a threonine group, a lysine group, an arginine group, a histidine group, a cystine group, a glutathione group, —C₅H₄N⁺, —C₅H₄N⁺(CH₃), —C₅H₄N⁺(C₂H₅), —C₅H₄N⁺(C₁₂H₂₅), —N⁺(CH₃)₃, —N⁺(C₂H₅)₃, —N⁺(C₃H₇)₃, —N⁺(C₄H₉)₃, —N⁺(C₆H₁₃)₃, —N⁺(CH₃)₂(C₂H₅), —N⁺(CH₃)₂(C₃H₇), —N⁺(CH₃)₂(C₄H₉), —N⁺(CH₃)₂(C₆H₁₃), —N⁺(CH₃)₂(C₁₂H₂₅), —N⁺(C₂H₅)₂(C₃H₇), —N⁺(C₂H₅)₂(C₆H₁₃), —N⁺(C₂H₅)₂(C₁₂H₂₅), or a quaternary ammonium salt having a terminal group containing a hydroxyl group, a carboxylic acid group, a sulfonic acid group, or a carboxylic acid ester.

In the above formulas I-a to I-d, the substituents R₁ and R₂ respectively connected to the amino group can be identical or different.

Specifically, the substituents R₁ and R₂ can be respectively: hydrogen, an alkyl group, a phenyl group, or a substituted phenyl group, such as —H, —CH₃, —C₂H₅, —C₃H₇, —C₄H₉, —C₅H₁₁, —C₆H₁₃, —C₁₂H₂₅, —C₆H₅, —CH₂C₆H₅, —CH₂CH₂C₆H₅, —CH₂(CH₂)₅C₆H₅, —C₆H₄(COOH), —CH₂C₆H₄(COOH), —CH₂C₆H₄(OH), —C₆H₄(CH₂COOH), and —CH₂C₆H₄(CH₂COOH).

Preferably, the substituents R₁ and R₂ are respectively: a cycloalkyl group or a cycloalkyl group containing a substituent, such as —C₃H₅ (a cyclopropyl group), —C₃H₄(CH₃) (a methylcyclopropyl group), —C₃H₄(OH)— (a hydroxylcyclopropyl group), —C₃H₄(CH₂OH)— (a hydroxymethylcyclopropyl group), —C₃H₄(COOH)— (a carboxylcyclopropyl group), —C₄H₇ (a cyclobutyl group), —C₄H₆(CH₃) (a methylcyclobutyl group), —C₄H₆(OH) (a hydroxylcyclobutyl group), —C₄H₆(COOH) (a carboxyl cyclobutyl group), —CH₂C₄H₆(COOH), —C₅H₉ (a cyclopentyl group), —C₅H₈(CH₃) (a methylcyclopentyl group), —C₅H₈(OH) (a hydroxylcyclopentyl group), —C₅H₈(NH₂)

(an aminocyclopentyl group), —C$_5$H$_8$(COOH) (a carboxylcyclopentyl group), —C$_6$Hu (a cyclohexyl group), —C$_6$H$_{10}$(CH$_3$) (a methylcyclohexyl group), —C$_6$H$_{10}$(C$_2$H$_5$) (an ethylcyclohexyl group), —C$_6$H$_{10}$(C$_3$H$_7$) (a propylcyclohexyl group), —C$_6$H$_{10}$(OH) (a hydroxylcyclohexyl group), —C$_6$H$_{10}$(NH$_2$) (an aminocyclohexyl group), —C$_6$H$_{10}$(COOH) (a carboxylcyclohexyl group), —C$_6$H$_{10}$(CH$_2$COOH) (a carboxylmethylcyclohexyl group), —C$_6$H$_9$(COOH)$_2$ (a dicarboxylcyclohexyl group), —CH$_2$C$_6$H$_{10}$(COOH), —CH$_2$C$_6$H$_{10}$(OH), —C$_7$H$_{13}$ (a cycloheptyl group), —C$_7$H$_{12}$(COOH) (a carboxylcycloheptyl group), —C$_7$H$_{12}$(OH) (a hydroxylcycloheptyl group), and —C$_7$H$_{12}$(CH$_3$) (a methylcycloheptyl group).

Preferably, the substituents $R_1$ and $R_2$ are respectively: carboxylic acids, carboxylic acid esters, or carboxylic acid salts of different chain lengths, such as —CH$_2$COOH, —CH$_2$CH$_2$COOH, —CH$_2$(CH$_2$)$_2$COOH, —CH$_2$(CH$_2$)$_3$COOH, —CH$_2$(CH$_2$)$_4$COOH, —CH$_2$(CH$_2$)$_5$COOH, —CH$_2$(CH$_2$)$_6$COOH, —CH$_2$(CH$_2$)$_{10}$COOH, —CH$_2$COOCH$_3$, —CH$_2$CH$_2$COOC$_6$H$_{13}$, —CH$_2$(CH$_2$)$_2$COOCH$_3$, —CH$_2$(CH$_2$)$_2$COOC$_2$H$_5$, —CH$_2$(CH$_2$)$_2$COOC$_6$H$_{13}$, —CH$_2$(CH$_2$)$_4$COOCH$_3$, —CH$_2$(CH$_2$)$_6$COOC$_6$H$_{13}$, —CH$_2$COONa$^+$, —CH$_2$(CH$_2$)$_2$COONa$^+$, and —CH$_2$(CH$_2$)$_4$COONa$^+$.

Preferably, the substituents $R_1$ and $R_2$ are respectively: sulfonic acids, sulfonic acid esters, or sulfonic acid salts of different chain lengths, such as —CH$_2$SO$_3$H, —CH$_2$CH$_2$SO$_3$H, —CH$_2$(CH$_2$)$_2$SO$_3$H, —CH$_2$(CH$_2$)$_3$SO$_3$H, —CH$_2$(CH$_2$)$_4$SO$_3$H, —CH$_2$(CH$_2$)$_5$SO$_3$H, —CH$_2$(CH$_2$)$_{11}$SO$_3$H, —CH$_2$SO$_3$CH$_3$, —CH$_2$SO$_3$C$_6$H$_{13}$, —CH$_2$CH$_2$SO$_3$CH$_3$, —CH$_2$(CH$_2$)$_2$SO$_3$CH$_3$, —CH$_2$(CH$_2$)$_2$SO$_3$C$_6$H$_{13}$, —CH$_2$(CH$_2$)$_4$SO$_3$C$_4$H$_9$, —CH$_2$(CH$_2$)$_{11}$SO$_3$C$_6$H$_{13}$, —CH$_2$SO$_3$Na, and —CH$_2$CH$_2$SO$_3$K.

Preferably, the substituents $R_1$ and $R_2$ are respectively: a hydroxyl group, an alkoxy group, a substituted or unsubstituted amino group, a substituted or unsubstituted pyridyl group, such as —OH, —OCH$_3$, —OC$_2$H$_5$, —OC$_6$H$_{13}$, —NH$_2$, —NHC$_2$H$_5$, —NHC$_6$H$_{13}$, —NHC$_{12}$H$_{25}$, —NHC$_6$H$_5$, —NHC$_5$H$_4$N, —C$_5$H$_4$N, —CH$_2$C$_5$H$_4$N, —(CH$_2$)$_2$C$_5$H$_4$N, —(CH$_2$)$_6$C$_5$H$_4$N, —C$_5$H$_3$N(CH$_3$), —C$_5$H$_3$N(OH), —C$_5$H$_3$N(NH$_2$), —C$_5$H$_3$N(COOH), —C$_5$H$_3$N(CH$_2$COOH), and —CH$_2$C$_5$H$_3$N(CH$_2$COOH).

Preferably, the substituents $R_1$ and $R_2$ are respectively: various polyethylene glycols, polyethylene glycol ethers, or polyethylene glycol esters of different chain lengths, such as —CH$_2$CH$_2$—(OCH$_2$CH$_2$)$_n$—OH, —CH$_2$CH$_2$—(OCH$_2$CH$_2$)$_n$—OCH$_3$, —CH$_2$CH$_2$—(OCH$_2$CH$_2$)$_n$—OC$_6$H$_{13}$, —CH$_2$CH$_2$—(OCH$_2$CH$_2$)$_n$—OC$_{12}$H$_{25}$, —CH$_2$CH$_2$—(OCH$_2$CH$_2$)$_n$—O—COCH$_3$, and —CH$_2$CH$_2$—(OCH$_2$CH$_2$)$_n$—O—COC$_6$H$_{13}$ (n is an integer between 0 and 50).

Preferably, the substituents $R_1$ and $R_2$ are respectively: two polyethylene glycols of different chain lengths connected by a carboxylate group, such as —CH$_2$CH$_2$—O—CO—CH$_2$CH$_2$—(OCH$_2$CH$_2$)$_n$—OH, —CH$_2$CH$_2$—O—CO—CH$_2$CH$_2$—(OCH$_2$CH$_2$)$_n$—OCH$_3$, —CH$_2$CH$_2$—OCH$_2$CH$_2$—O—CO—CH$_2$CH$_2$—(OCH$_2$CH$_2$)$_n$—OH, —CH$_2$CH$_2$—OCH$_2$CH$_2$—O—CO—CH$_2$CH$_2$—(OCH$_2$CH$_2$)$_n$—OCH$_3$, —CH$_2$CH$_2$—OCH$_2$CH$_2$—OCH$_2$CH$_2$—O—CO—CH$_2$CH$_2$—(OCH$_2$CH$_2$)$_n$—OH, and —CH$_2$CH$_2$—OCH$_2$CH$_2$—OCH$_2$CH$_2$—O—CO—CH$_2$CH$_2$—(OCH$_2$CH$_2$)$_n$—OCH$_3$ (n is an integer between 0 and 50).

Preferably, the substituents $R_1$ and $R_2$ in formula II are respectively: polyethylene glycols of different chain lengths connected to triphenylphosphine by a carboxylate group, such as —CH$_2$CH$_2$—O—CO—CH$_2$CH$_2$—PPh$_3^+$, —CH$_2$CH$_2$—O—CO—(CH$_2$)$_3$—PPh$_3^+$, —CH$_2$CH$_2$—O—CO—(CH$_2$)$_5$—PPh$_3^+$, —CH$_2$CH$_2$—OCH$_2$CH$_2$—O—CO—CH$_2$CH$_2$—PPh$_3^+$, —CH$_2$CH$_2$—OCH$_2$CH$_2$—O—CO—(CH$_2$)$_3$—PPh$_3^+$, and —CH$_2$CH$_2$—OCH$_2$CH$_2$—O—CO—(CH$_2$)$_5$—PPh$_3^+$.

Preferably, the substituents $R_1$ and $R_2$ are respectively: alcohols with different numbers of carbon atoms and the alcohols connected to polyethylene glycols of different chain lengths by a carboxylate group, such as —(CH$_2$)$_3$—OH, —(CH$_2$)$_3$—OCH$_3$, —(CH$_2$)$_3$—OC$_2$H$_5$, —(CH$_2$)$_3$—OCOCH$_3$, —(CH$_2$)$_3$—OCOC$_2$H$_5$, —(CH$_2$)$_3$—O—COCH$_2$CH$_2$—(OCH$_2$CH$_2$)$_n$—OCH$_3$, —(CH$_2$)$_4$—OH, —(CH$_2$)$_4$—OCH$_3$, —(CH$_2$)$_4$—OCOCH$_3$, —(CH$_2$)$_4$—OCOC$_2$H$_5$, —(CH$_2$)$_4$—O—COCH$_2$CH$_2$—(OCH$_2$CH$_2$)$_n$—OCH$_3$, —(CH$_2$)$_6$—OH, —(CH$_2$)$_6$—OCH$_3$, —(CH$_2$)$_6$—OCOCH$_3$, and —(CH$_2$)$_6$—O—COCH$_2$CH$_2$—(OCH$_2$CH$_2$)$_n$—OCH$_3$ (n is an integer between 0 and 50).

Preferably, the substituents $R_1$ and $R_2$ are respectively: azapolyethylene glycols or thiopolyethylene glycols of different chain lengths, or polyethylene diamines of different chain lengths connected to polyethylene glycols by an amide group, such as —CH$_2$CH$_2$—NH—CH$_2$CH$_2$—(OCH$_2$CH$_2$)$_n$—OH, —CH$_2$CH$_2$—NH—CH$_2$CH$_2$—(OCH$_2$CH$_2$)$_n$—OCH$_3$, —CH$_2$CH$_2$—(NHCH$_2$CH$_2$)$_n$—NH$_2$, —CH$_2$CH$_2$—(NHCH$_2$CH$_2$)$_n$—N(CH$_3$)$_2$, —CH$_2$CH$_2$—NHCH$_2$CH$_2$—NH—COCH$_2$CH$_2$—(OCH$_2$CH$_2$)$_n$—OCH$_3$, and —CH$_2$CH$_2$—S—CH$_2$CH$_2$—(OCH$_2$CH$_2$)$_n$—OH (n is an integer between 0 and 50).

Preferably, the substituents $R_1$ and $R_2$ are respectively: various aminocarboxylic acids, amino acid esters, or amino acid salts, such as —CH(CH$_3$)—COOH, —CH(CH(CH$_3$)$_2$)—COOH, —CHCH$_2$(CH(CH$_3$)$_2$)—COOH, —CH(CH$_2$CH$_2$SCH$_3$)—COOH, —CHCH(CH$_3$)(C$_2$H$_5$)—COOH, —CH(CH$_2$OH)—COOH, —CHCH(OH)(CH$_3$)—COOH, —CH(CH$_2$SH)—COOH, —CH(CH$_2$CONH$_2$)—COOH, —CH(CH$_2$CH$_2$CONH$_2$)—COOH, —CH(CH$_2$C$_6$H$_5$)—COOH, —CH(CH$_2$C$_6$H$_5$OH)—COOH, —CH(CH$_2$CH$_2$CH$_2$CH$_2$NH$_3^+$)—COOH, —CH(COOH)—CH$_2$COOH, —CH(COOH)—CH$_2$CH$_2$COOH,

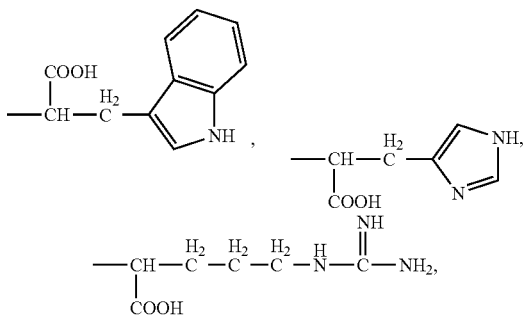

—CH(CH$_3$)—COOCH$_3$, —CH(CH(CH$_3$)$_2$)—COOCH$_3$, —CHCH$_2$(CH(CH$_3$)$_2$)—COOCH$_3$, —CH(CH$_2$CH$_2$SCH$_3$)—COOCH$_3$, —CH(CH$_3$)—COONa$^+$, —CH(CH(CH$_3$)$_2$)—COONa$^+$, —CHCH$_2$(CH(CH$_3$)$_2$)—COOK$^+$, —CH(CH$_2$CH$_2$SCH$_3$)—COOK$^+$.

Preferably, the substituents $R_1$ and $R_2$ are respectively: carboxylic acids with different numbers of carbon atoms connected to polyethylene glycols of different chain lengths by a carboxyl group, such as —CH$_2$CO—(OCH$_2$CH$_2$)$_n$—OH, —CH$_2$CO—(OCH$_2$CH$_2$)$_n$—OCH$_3$, —CH$_2$CH$_2$CO—(OCH$_2$CH$_2$)$_n$—OH, —CH$_2$CH$_2$CO—(OCH$_2$CH$_2$)$_n$—OCH$_3$, —CH$_2$(CH$_2$)$_2$CO—(OCH$_2$CH$_2$)$_n$—OH, —CH$_2$ $(CH_2)_2CO-(OCH_2CH_2)_n-OCH_3$, $-CH_2(CH_2)_4CO-(OCH_2CH_2)_n-OH$, and $-CH_2(CH_2)_4CO-(OCH_2CH_2)_n-OCH_3$ (n is an integer between 0 and 50).

Preferably, the substituents $R_1$ and $R_2$ are respectively: carboxylic acids with different numbers of carbon atoms connected to polyethylene glycols of different chain lengths by an amide bond, such as $-CH_2-CO-NH-CH_2CH_2-(OCH_2CH_2)_n-OH$, $-CH_2-CO-NH-CH_2CH_2-(OCH_2CH_2)_n-OCH_3$, $-(CH_2)_2-CO-NH-CH_2CH_2-(OCH_2CH_2)_n-OH$, $-(CH_2)_2-CO-NH-CH_2CH_2-(OCH_2CH_2)_n-OCH_3$, $-(CH_2)_3-CO-NH-CH_2CH_2-(OCH_2CH_2)_n-OH$, $-(CH_2)_3-CO-NH-CH_2CH_2-(OCH_2CH_2)_n-OCH_3$, $-(CH_2)_4-CO-NH-CH_2CH_2-(OCH_2CH_2)_n-OH$, $-(CH_2)_4-CO-NH-CH_2CH_2-(OCH_2CH_2)_n-OCH_3$, $-(CH_2)_5-CO-NH-CH_2CH_2-(OCH_2CH_2)_n-OH$, and $-(CH_2)_5-CO-NH-CH_2CH_2-(OCH_2CH_2)_n-OCH_3$ (n is an integer between 0 and 50).

Preferably, the substituents $R_1$ and $R_2$ are respectively: sulfonic acids with different numbers of carbon atoms connected to polyethylene glycols of different chain lengths by a sulfonic acid ester group, such as $-CH_2-SO_2-(OCH_2CH_2)_n-OH$, $-CH_2-SO_2-(OCH_2CH_2)_n-OCH_3$, $-(CH_2)_2-SO_2-(OCH_2CH_2)_n-OH$, $-(CH_2)_2-SO_2-(OCH_2CH_2)_n-OCH_3$, $-(CH_2)_3-SO_2-(OCH_2CH_2)_n-OH$, $-(CH_2)_3-SO_2-(OCH_2CH_2)_n-OCH_3$, $-(CH_2)_4-SO_2-(OCH_2CH_2)_n-OH$, $-(CH_2)_4-SO_2-(OCH_2CH_2)_n-OCH_3$, $-(CH_2)_5-SO_2-(OCH_2CH_2)_n-OH$, $-(CH_2)_5-SO_2-(OCH_2CH_2)_n-OCH_3$, $-(CH_2)_6-SO_2-(OCH_2CH_2)_n-OH$, and $-(CH_2)_6-SO_2-(OCH_2CH_2)_n-OCH_3$ (n is an integer between 0 and 50).

Preferably, the substituents $R_1$ and $R_2$ are respectively: sulfonic acids with different numbers of carbon atoms connected to polyethylene glycols of different chain lengths by a sulfonamide group, such as $-CH_2-SO_2-NHCH_2CH_2-(OCH_2CH_2)_n-OH$, $-CH_2-SO_2-NHCH_2CH_2-(OCH_2CH_2)_n-OCH_3$, $-(CH_2)_2-SO_2-NHCH_2CH_2-(OCH_2CH_2)_n-OH$, $-(CH_2)_2-SO_2-NHCH_2CH_2-(OCH_2CH_2)_n-OCH_3$, $-(CH_2)_3-SO_2-NHCH_2CH_2-(OCH_2CH_2)_n-OCH_3$, $-(CH_2)_4-SO_2-NHCH_2CH_2-(OCH_2CH_2)_n-OCH_3$, $-(CH_2)_5-SO_2-NHCH_2CH_2-(OCH_2CH_2)_n-OCH_3$, and $-(CH_2)_6-SO_2-NHCH_2CH_2-(OCH_2CH_2)_n-OCH_3$ (n is an integer between 0 and 50).

Preferably, the substituents $R_1$ and $R_2$ are respectively: quaternary ammonium salts of different chain lengths, such as $-CH_2CH_2-N^+(CH_3)_3$, $-(CH_2)_3-N^+(CH_3)_3$, $-(CH_2)_4-N^+(CH_3)_3$, $-(CH_2)_5-N^+(CH_3)_3$, $-(CH_2)_6-N^+(CH_3)_3$, $-(CH_2)_{12}-N^+(CH_3)_3$, $-CH_2CH_2-N^+(C_2H_5)_3$, $-(CH_2)_4-N^+(C_2H_5)_3$, $-(CH_2)_6-N^+(C_2H_5)_3$, $-(CH_2)_{12}-N^+(C_2H_5)_3$, $-CH_2CH_2-N^+(C_3H_7)_3$, $(CH_2)_4-N^+(C_3H_7)_3$, $-(CH_2)_6-N^+(C_3H_7)_3$, $-CH_2CH_2-N^+(C_4H_9)_3$, $-(CH_2)_6-N^+(C_4H_9)_3$, $-CH_2CH_2-N^+(CH_3)_2(C_2H_5)$, $-CH_2CH_2-N^+(CH_3)_2(C_4H_9)$, $-CH_2CH_2-N^+(CH_3)_2(C_6H_{13})$, $-CH_2CH_2-N^+(CH_3)_2(C_{12}H_{25})$, $-(CH_2)_3-N^+(CH_3)_2(C_4H_9)$, $-(CH_2)_3-N^+(CH_3)_2(C_6H_{13})$, $-(CH_2)_3-N^+(CH_3)_2(C_{12}H_{25})$, $-(CH_2)_4-N^+(CH_3)_2(C_6H_{13})$, $-(CH_2)_4-N^+(CH_3)_2(C_{12}H_{25})$, $-(CH_2)_5-N^+(CH_3)_2(C_2H_5)$, $-(CH_2)_5-N^+(CH_3)_2(C_6H_{13})$, $-(CH_2)_5-N^+(CH_3)_2(C_{12}H_{25})$, $-(CH_2)_6-N^+(CH_3)_2(C_2H_5)$, $-(CH_2)_6-N^+(CH_3)_2(C_6H_{13})$, and $-(CH_2)_6-N^+(CH_3)_2(C_{12}H_{25})$.

Preferably, the substituents $R_1$ and $R_2$ are respectively: carboxylic acids of different chain lengths connected to quaternary ammonium salts of different chain lengths by a carboxylic acid ester bond, such as $-CH_2CO-OCH_2CH_2-N^+(CH_3)_3$, $-CH_2CH_2CO-OCH_2CH_2-N^+(CH_3)_3$, $-CH_2(CH_2)_2CO-OCH_2CH_2-N^+(CH_3)_3$, $-CH_2(CH_2)_6CO-OCH_2CH_2-N^+(CH_3)_3$, $-CH_2CO-O-(CH_3)_3-N^+(CH_3)_3$, $-CH_2(CH_2)_2CO-O-(CH_3)_3-N^+(CH_3)_3$, and $-CH_2COOCH_2CH_2-N^+(CH_3)_2(C_6H_{13})$.

Preferably, the substituents $R_1$ and $R_2$ are respectively: carboxylic acids of different numbers of carbon atoms connected to quaternary ammonium salts of different chain lengths by an amide bond, such as $-CH_2CONH-CH_2CH_2-N^+(CH_3)_3$, $-CH_2CH_2CONH-CH_2CH_2-N^+(CH_3)_3$, $-CH_2(CH_2)_4CONH-CH_2CH_2-N^+(CH_3)_3$, $-CH_2CONH-(CH_2)_3-N^+(CH_3)_3$, $-CH_2CH_2CONH-(CH_2)_3-N^+(CH_3)_3$, $-CH_2(CH_2)_4CONH-(CH_2)_3-N^+(CH_3)_3$, $-CH_2CONH-(CH_2)_4-N^+(CH_3)_3$, $-CH_2CH_2CONH-(CH_2)_4-N^+(CH_3)_3$, $-CH_2(CH_2)_4CONH-(CH_2)_4-N^+(CH_3)_3$, $-CH_2CONH-(CH_2)_5-N^+(CH_3)_3$, $-CH_2CH_2CONH-(CH_2)_5-N^+(CH_3)_3$, $-CH_2(CH_2)_4CONH-(CH_2)_5-N^+(CH_3)_3$, $-CH_2CONH-(CH_2)_6-N^+(CH_3)_3$, $-CH_2CH_2CONH-(CH_2)_6-N^+(CH_3)_3$, $-CH_2(CH_2)_4CONH-(CH_2)_6-N^+(CH_3)_3$, $-CH_2CONH-CH_2CH_2-N^+(CH_3)_2(C_6H_{13})$, and $-CH_2CONH-CH_2CH_2-N^+(CH_3)_2(C_{12}H_{25})$.

Preferably, the substituents $R_1$ and $R_2$ are respectively: various substituted or unsubstituted pyridiniums, such as $-C_5H_4N^+(CH_3)$, $-CH_2C_5H_4N^+(CH_3)$, $-CH_2C_5H_4N^+(C_6H_{13})$, $-CH_2C_5H_4N^+(CH_2COOH)$, $-CH_2CH_2C_5H_4N^+(CH_3)$, $-CH_2CH_2C_5H_4N^+(C_6H_{13})$, and $-CH_2CH_2C_5H_4N^+(CH_2COOH)$.

Preferably, the substituents $R_1$ and $R_2$ are respectively: a methylenecyclohexanoic acid connected to polyethylene glycols of different chain lengths by a carboxylic acid ester bond, such as

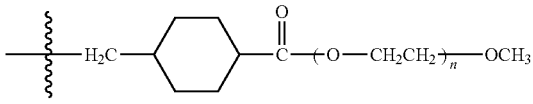

(n is an integer between 0 and 50), wherein specific structures are as follows:

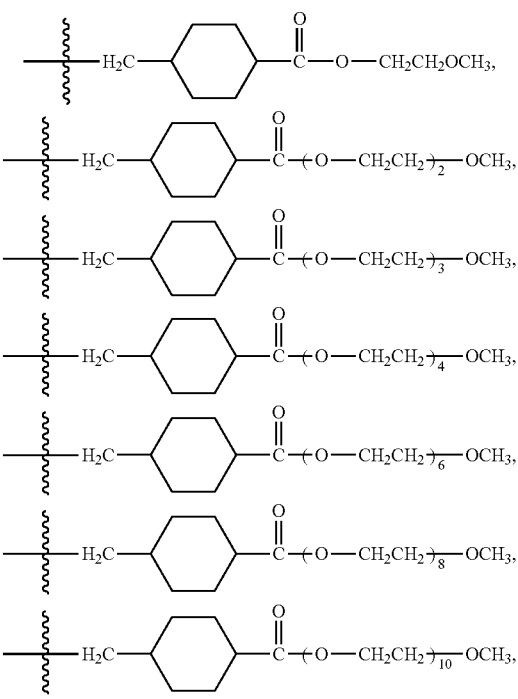

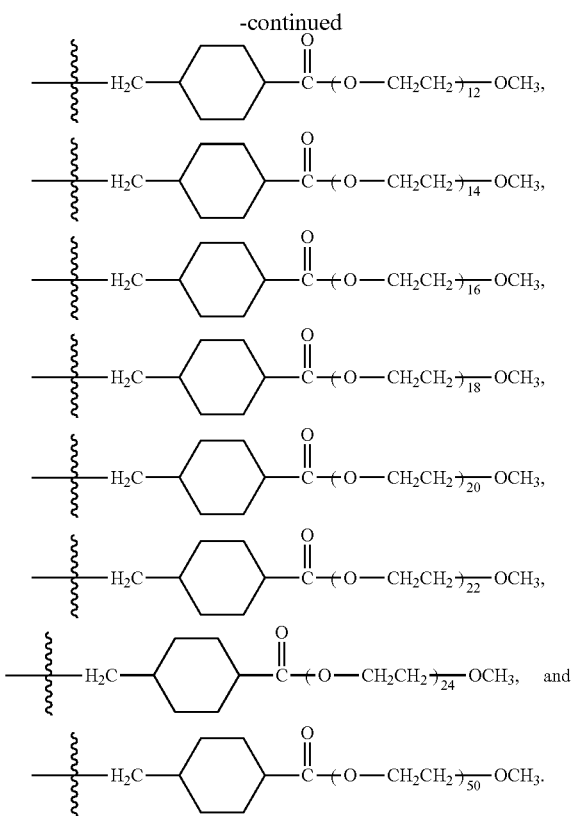

Preferably, the substituents $R_1$ and $R_2$ in formula II are respectively: a methylenecyclohexanoic acid connected to polyethylene glycols of different chain lengths by a carboxylic acid ester bond, with a hydroxyl group as a terminal group, such as

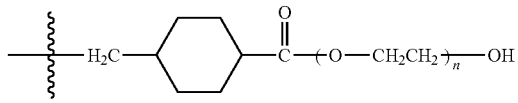

(n is an integer between 0 and 50).

Preferably, the substituents $R_1$ and $R_2$ are respectively: a methylenecyclohexanoic acid connected to polyethylene glycols of different chain lengths by an amide bond, such as

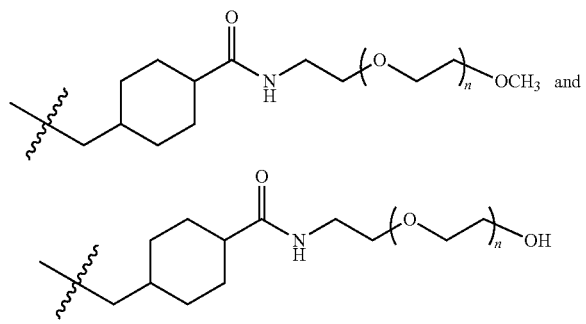

(n is an integer between 0 and 50).

Preferably, the substituents $R_1$ and $R_2$ are respectively: a methylenecyclohexylacetic acid connected to polyethylene glycols of different chain lengths by a carboxylic acid ester bond, with an alkoxy group or a hydroxyl group as a terminal group, such as

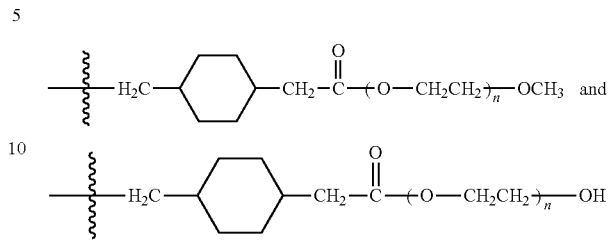

(n is an integer between 0 and 50).

Preferably, the substituents $R_1$ and $R_2$ are respectively: a methylenecyclohexylacetic acid connected to polyethylene glycols of different chain lengths by an amide bond, with an alkoxy group or a hydroxyl group as a terminal group, such as

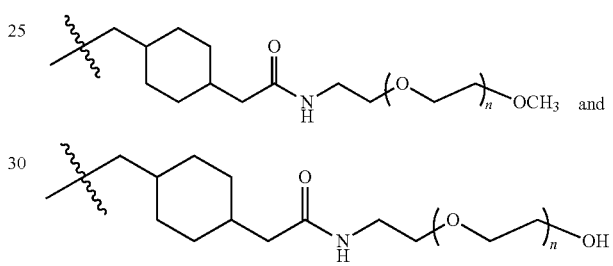

(n is an integer between 0 and 50).

Preferably, the substituents $R_1$ and $R_2$ are respectively: a para-position cyclohexanoic acid connected to polyethylene glycols of different chain lengths by a carboxylic acid ester bond, such as

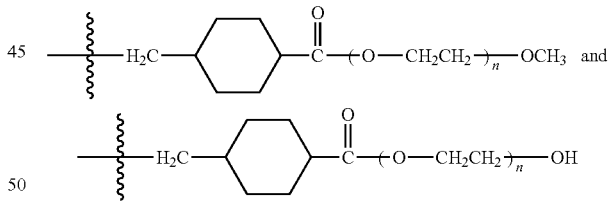

(n is an integer between 0 and 50); or an ortho- or meta-position cyclohexanoic acid connected to polyethylene glycols of different chain lengths by a carboxylic acid ester bond, with an alkoxy group or a hydroxyl group as a terminal group, such as

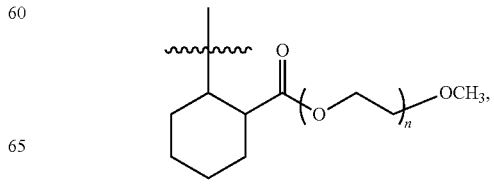

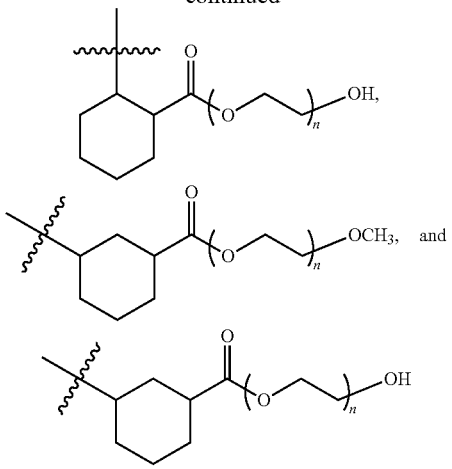

(n is an integer between 0 and 50).

Preferably, the substituents $R_1$ and $R_2$ are respectively: a cyclohexylacetic acid connected to polyethylene glycols of different chain lengths by a carboxylic acid ester bond, such as

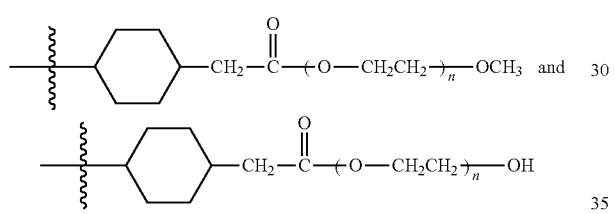

(n is an integer between 0 and 50).

Preferably, the substituents $R_1$ and $R_2$ are respectively: a cyclohexylpropionic acid connected to polyethylene glycols of different chain lengths by a carboxylic acid ester bond, such as

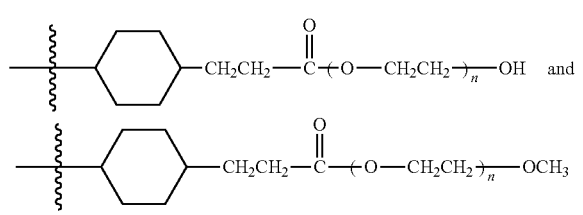

(n is an integer between 0 and 50).

Preferably, the substituents $R_1$ and $R_2$ are respectively: a meta- or ortho-position cyclopentanecarboxylic acid connected to polyethylene glycols of different chain lengths by a carboxylic acid ester bond, with an alkoxy group or a hydroxyl group as a terminal group, such as

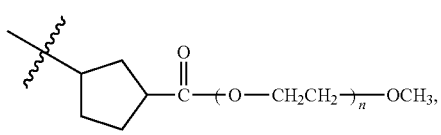

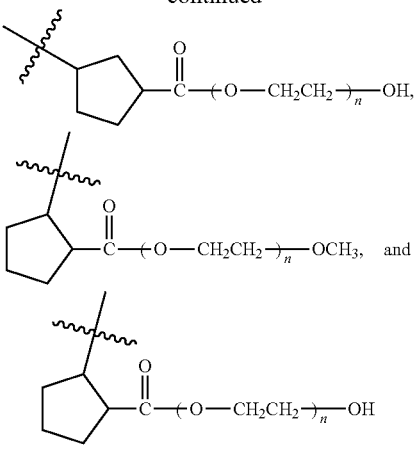

(n is an integer between 0 and 50).

Preferably, the substituents $R_1$ and $R_2$ are respectively: methylenepiperidine directly connected to polyethylene glycols of different chain lengths or connected to polyethylene glycols of different chain lengths by an amide bond, such as

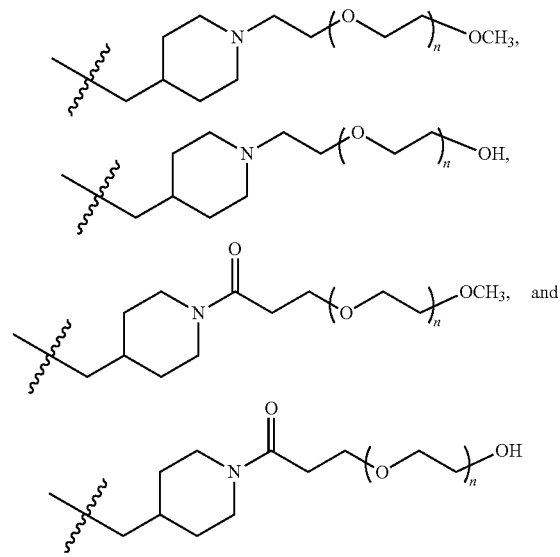

(n is an integer between 0 and 50).

Preferably, the substituents $R_1$ and $R_2$ are respectively: hydroxymethylcyclopropane or carboxylcyclopropane directly connected to polyethylene glycols of different chain lengths by a carboxylic acid ester bond or by an amide bond, such as

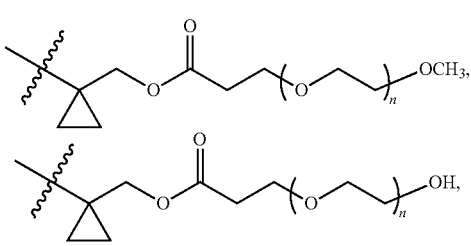

17

-continued

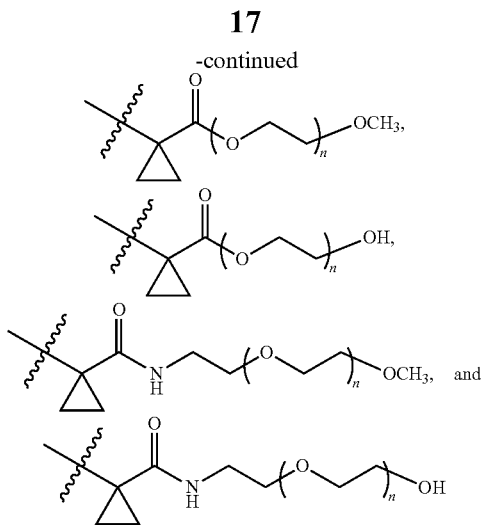

(n is an integer between 0 and 50).

Preferably, the substituents $R_1$ and $R_2$ are respectively: a methylenecyclohexanoic acid connected to triphenylphosphine by a carboxylic acid ester bond or an amide bond, such as

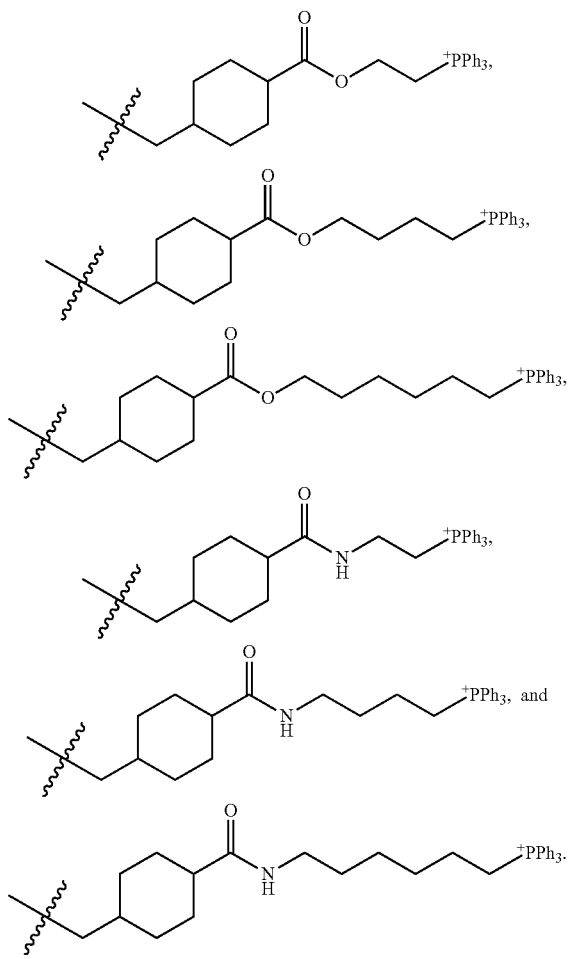

In addition, the substituents $R_1$ and $R_2$ can also respectively be various heterocyclic substituents, such as

18

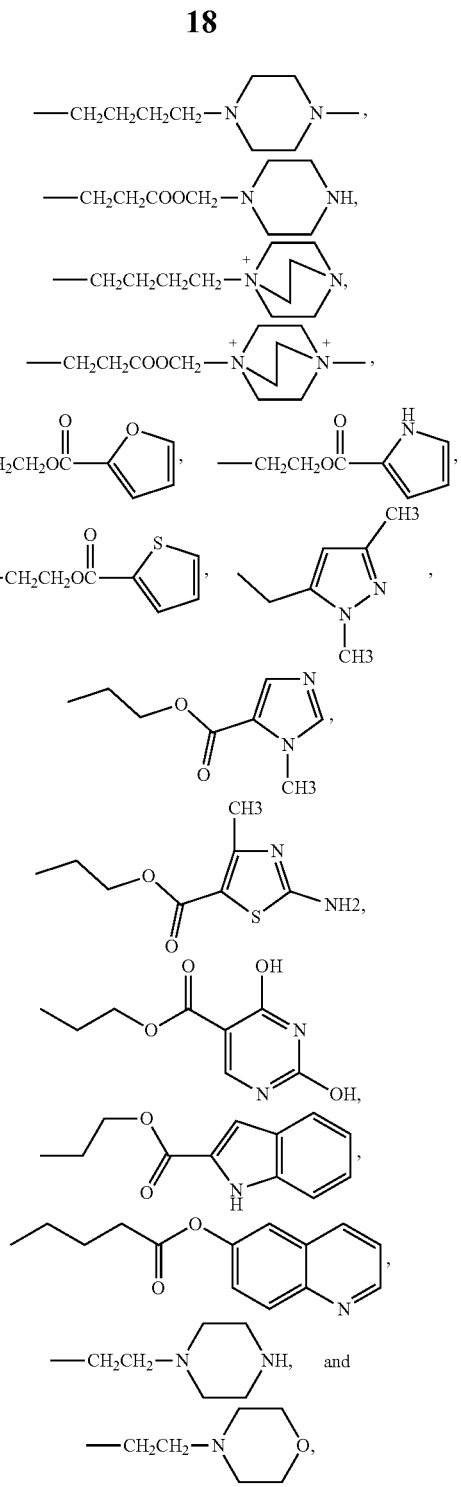

or a heterocyclic group containing a substituent.

In order to achieve the above second objective, the present invention employs the following technical solution.

A method for preparing the above-described derivative having a peri-position and a 2-position both substituted by an amino group comprises the following step:

dissolving hypocrellin and a substituted amine derivative in a solvent for a reaction, to obtain the derivative having a peri-position and a 2-position both substituted by an amino group.

Preferably, the reaction is performed under the protection of a protective gas in a lucifugous condition, and the protective gas is preferably argon or nitrogen.

Preferably, the hypocrellin is hypocrellin B (HB) or deacetyl hypocrellin (HG).

Preferably, a general structural formula of the substituted amine derivative is $R_1$—$NH_2$ or $R_2$—$NH_2$, and general structural formulas of amino substituents $R_1$ and $R_2$ are as presented by formula II.

Preferably, a feeding molar ratio of the hypocrellin and the amino substituted derivative is 1:5-1:100, specifically 1:5, 1:10, 1:20, 1:40, 1:60, 1:80, or 1:100, and more preferably 1:60.

Preferably, a temperature of the reaction is 20-150° C., more preferably 60° C.

Preferably, a time of the reaction is 6-18 hours, more preferably 10 hours.

Preferably, the solvent is an organic solvent, or a mixed solvent of an organic solvent and water. The mass fraction of water in the mixed solvent of an organic solvent and water is 5 wt %-95 wt %; and the organic solvent is one or more of acetonitrile, tetrahydrofuran, pyridine, N,N-dimethylformamide, dimethylsulfoxide, methanol, and ethanol.

More preferably, the mixed solvent of the organic solvent and water is a mixed solvent of N,N-dimethylformamide and water, wherein a volume ratio of the N,N-dimethylformamide and water is 1:1.

Preferably, the reaction can also be performed in an alkaline condition, wherein the alkaline condition is indicated by pH=9-14.

Preferably, a reagent used in the alkaline condition is a 1% potassium hydroxide aqueous solution, a 1% sodium hydroxide aqueous solution, a 5% potassium carbonate aqueous solution, or an ammonia aqueous solution of pH=11.

More preferably, the reaction is performed in the 1% sodium hydroxide aqueous solution or 5% potassium carbonate aqueous solution or ammonia aqueous solution having a pH value of about 11.

Preferably, the separation and purification process is as follows: the reacting organic solvent is removed to obtain a blue black solid residue, which is dissolved by using dichloromethane, washing is performed with the same volume of a 5% dilute aqueous hydrochloric acid solution three times and with water once, and an organic layer is dried by using anhydrous magnesium sulfate, filtered, and subject to solvent-removal, to obtain a crude product. The obtained crude product is subject to further separation by means of silica gel plate chromatography, wherein a developing agent is a mixed solution with a preferred volume ratio of ethyl acetate, diethylamine, and ethanol=20:1:2, thereby obtaining a hypocrellin derivative substituted both in a peri-position and in a 2-position by an amino, with a yield of 3-20%, and a product of a blue black solid.

In the present invention, the developing agent used for silica gel column chromatography or silica gel plate chromatography is a conventional reagent, which is obtained by adding 1% sodium tartrate, sodium citrate, or potassium dihydrogen phosphate to a stationary phase. Preferably, the developing agent used for silica gel plate chromatography is a mixed solution containing ethyl acetate, diethylamine, and ethanol, and the volume ratio of the ethyl acetate, diethylamine, and ethanol in the mixed solution is 20:1:1-20:1:3.

In order to achieve the above third objective, the present invention employs the following technical solution.

The hypocrellin derivative substituted both in a peri-position and in a 2-position by an amino is used as a photosensitizer drug in photodynamic therapy.

The general structural formula of the hypocrellin derivative substituted both in a peri-position and in a 2-position by an amino involved in the present invention is as shown in FIG. 1. During the reaction between the hypocrellin (hypocrellin B HB or deacetyl hypocrellin HG) and the amino substituted derivative, in addition to the 2-position in the hypocrellin, amino substitution can also occur at one of the four peri-positions (3-, 4-, 9-, and 10-positions in FIG. 1) in the hypocrellin, ultimately obtaining the hypocrellin derivative substituted both in a peri-position and in a 2-position by an amino. The ratio of products of amino substitution at different peri-positions in the hypocrellin can be adjusted by controlling different reaction conditions (acidity and alkalinity of the solution, the reaction temperature, the reaction time, steric hindrance of the raw material amine, the feeding molar ratio, etc.). For example, in weakly alkaline conditions such as potassium carbonate and ammonium hydroxide, derivatives I-b and I-d of peri-position amino substitution at positions 9 and 10 are primarily produced; and in strongly alkaline conditions such as sodium hydroxide, derivatives I-a and I-c of peri-position amino substitution at positions 3 and 4 are primarily produced. For example, if the raw material amine has large steric hindrance, since amino substitution has occurred at the 2-position in the hypocrellin, peri-position amino substitution is not easy to occur at a 3-position (FIG. 1). In addition, the ratio of the products I-a to I-d of amino substitution at different peri-positions in the hypocrellin can also be adjusted by controlling different reaction temperatures and different feeding molar ratios.

For example, during a reaction between the hypocrellin B and 2-(2-aminoethoxy)ethanol, hypocrellin derivatives HB-1a-HB-1d having a peri-position and a 2-position both substituted by an amino group are primarily produced, and the obtained products are further esterified with polyethylene glycol having a carboxyl group, to obtain HB-1a-PEGn-HB-1d-PEGn, wherein a synthetic method and a corresponding product are as shown in FIG. 2 and examples 2 and 3. During a reaction between the deacetyl hypocrellin and 2-(2-aminoethoxy)ethanol, deacetyl hypocrellin derivatives HC-1a-HC-1d having a peri-position and a 2-position both substituted by an amino group are primarily produced, and the obtained products are further esterified with polyethylene glycol having a carboxyl group, to obtain HC-1a-PEGn-HC-1d-PEGn, wherein a synthetic method and a corresponding product are as shown in FIG. 3 and examples 5 and 6.

During a reaction between deacetyl hypocrellin B and an aminobutyric acid, deacetyl hypocrellin derivatives HC-8a-HC-8d having a peri-position and a 2-position both substituted by an amino group are primarily produced, and the obtained products are further esterified with polyethylene glycol having a hydroxyl group, to obtain HC-8a-PEGn-HC-8d-PEGn, wherein a synthetic method and a corresponding product are as shown in FIG. 4 and examples 22 and 23.

Most of photosensitizer molecules disclosed in this patent contain a large number of hydrophilic groups, such as a polyethylene glycol chain, a quaternary ammonium salt, a carboxyl group, and a sulfonic acid group, etc., making the photosensitizer molecules have very high water solubility in a physiological condition; and experiments indicate that each milliliter of normal saline or glucose injection can dissolve more than 5 mg of such the photosensitizer molecules, presenting excellent water solubility. Therefore, the photosensitive drug can be well transported in blood vessels during intravenous injection, without causing a vascular blockage. HB-1c-C2-N+ prepared in example 4 contains two quaternary ammonium salts, and each milliliter of normal saline can dissolve more than 20 mg of photosensitizer molecules; HC-1c-PEG6 prepared in example 6 contains two 6-PEG chains, and each milliliter of normal saline can dissolve more than 20 mg of photosensitizer molecules; HB-8c prepared in example 19 contains two carboxyl groups, and each milliliter of normal saline can dissolve more than 10 mg of photosensitizer molecules; HB-13c prepared in example 35 contains two carboxyl groups, and each milliliter of normal saline can dissolve more than 10 mg of photosensitizer molecules; and HB-13c-PEG8 prepared in example 37 contains two 8-PEG chains, and each milliliter of normal saline can dissolve more than 20 mg of photosensitizer molecules. These photosensitizer molecules all present excellent water solubility.

As shown in FIG. 5(a) and FIG. 5(b), the hypocrellin derivative substituted both in a peri-position and in a 2-position by an amino of the present invention has very wide and strong absorption performance in a phototherapy window, has a maximum absorption spectrum wavelength of about 600-650 nm, with the maximum reaching 650 nm, which is redshifted by about 200 nm relative to a maximum absorption peak of the parent hypocrellin, and has a molar extinction coefficient of about 20000-40000 $M^{-1}$ $cm^{-1}$, presenting a very high absorptivity in the phototherapy window. In FIG. 5(a), the unmodified hypocrellin B HB has a maximum absorption wavelength of 450 nm (line a); the di-2-(2-aminoethoxy)ethanol-substituted hypocrellin B derivative HB-1c prepared in example 2 has wide absorption performance at 550 nm-700 nm and has a maximum absorption wavelength of 630 nm (line b); and the di-2-(2-aminoethoxy)ethanol-substituted deacetyl hypocrellin derivative HC-1c prepared in example 5 has wide absorption performance at 550 nm-700 nm and has a maximum absorption wavelength of 650 nm (line c). In FIG. 5(b), a commercialized porphyrin photosensitizer PpIX has multi-band narrow absorption performance, wherein maximum absorption wavelengths available for phototherapy are 570 nm and 630 nm, both cases having a molar extinction coefficient less than 10000 $M^{-1}cm^{-1}$; a commercialized porphin photosensitizer Ce6 has a maximum absorption wavelength of 650 nm and a molar extinction coefficient less than 20000 $M^{-1}cm^{-1}$, and also haa narrow absorption performance in the phototherapy window. Therefore, the hypocrellin derivatives HB-1c and HC-1c having a peri-position and a 2-position both substituted by an amino group synthesized in this patent have an absorption wavelength and an absorptivity in the phototherapy window both far greater than that of the commercial porphyrin photosensitizer PpIX and porphin photosensitizer Ce6, presenting more outstanding photodynamic performance.

The ability of the above di-2-(2-aminoethoxy)ethanol-substituted hypocrellin B derivative HB-1c to produce reactive oxygen is shown in FIGS. 6(a) and 6(b): the experiments indicate that, it is measured by using singlet oxygen and superoxide radical scavengers that, such the hypocrellin derivative having a peri-position substituted by an amino group can efficiently produce photosensitive reactive species, primarily producing singlet oxygen, as shown in FIG. 6(a), also producing a small amount of superoxide radicals, as shown in FIG. 6(b). FIGS. 7(a)-7(d) show efficiency curves of measuring singlet oxygen of HB-1c and HC-1c. From the comparison with a reference rose bengal RB, it can be seen that the singlet oxygen efficiencies of HB-1c and HC-1c are respectively 0.40 and 0.38.

As shown in FIG. 8, the pH value of the hypocrellin derivative prepared in the present invention is in the range of 6.2-8.0, without an obvious change in an absorption spectrum thereof, indicating that the hypocrellin derivative substituted both in a peri-position and in a 2-position by an amino has a higher pH stability. Curve b shows that, in the pH range of 6.2-8.0, there is no obvious change in an absorption spectrum of the di-2-(2-aminoethoxy)ethanol-substituted deacetyl hypocrellin B derivative HC-1c in example 5; and HC-1c-PEG6 (curve c) formed by HC-1c and six units of polyethylene glycol generally has a good pH stability in this range, for the reason that two phenolic hydroxyl groups of the hypocrellin are not prone to deprotonation in this acid-base condition. However, the commercial hematoporphyrin HpD contains two carboxyl groups, which can be deprotonated in the pH range of 6.2-8.0, resulting in an obvious change in the absorption spectrum, thus presenting an instability of the HpD photosensitizer (curve a). Therefore, the hypocrellin derivative prepared in the present invention has a better pH stability than the commercial hematoporphyrin HpD in the pH range of 6.2-8.0.

FIG. 9 is a comparison diagram of photostabilities of the hypocrellin derivative prepared in the present invention and a commercial photosensitizer. As can be seen from the figure, after being irradiated with a 635 nm laser for 30 min at a light intensity of 20 mW/cm$^2$, an absorption spectrum of the aminoethanol-substituted deacetyl hypocrellin derivative HC-2c in example 9 is not obviously decreased, and an absorption intensity at the maximum wavelength is decreased by less than 10% (curve a). In the same condition, in an absorption spectrum of the esterification product HC-2c-PEG6 of HC-2c and polyethylene glycol in example 10, an absorption intensity at the maximum wavelength is also decreased by less than 10%, likewise having a good photostability (curve b). However, in the same condition, after being irradiated with a 635 nm laser for 30 min at a light intensity of 20 mW/cm$^2$, maximum absorption performance of the commercial porphin photosensitizer Ce6 is decreased by 30% (curve c); and an absorption spectrum of the commercial hematoporphyrin photosensitizer HpD is decreased more, reaching about 50% (curve d). Therefore, in the same condition, the hypocrellin derivative prepared in the present invention has a better photostability than the commercial photosensitizers.

Results of confocal fluorescence imaging experiments shown in FIGS. 10(a)-10(c) indicate that the phototherapy drug micromolecule HB-1c-PEG6 has good biocompatibility and is able to enter a lysosome of a Hela cell and generate an excellent red-light fluorescence image in the cell. DCFH-DA is used to detect singlet oxygen in a cell. As shown in FIG. 11, the photosensitizer HC-1c-PEG6 and the fluorescence probe DCFH-DA are co-incubated in the cell, with increase of an irradiation time to 60 s, a green fluorescence intensity is gradually increased, indicating that the amount of the singlet oxygen in the cell is increased.

HB-1c-PEG6 and Hela cells are co-incubated, as shown in FIG. 12(a), a cytotoxicity (dark toxicity) research test indicates that the polyethylene glycol-di-2-(2-aminoethoxy)ethanol-substituted hypocrellin B derivative HB-1c-PEG6 synthesized in example 3 has a smaller cytotoxicity, which is similar to that of the hypocrellin B HB and commercial photosensitive drug hematoporphyrin HpD. After the Hela cells are incubated by using the photosensitizer HB-1c-PEG6 with the concentration of 10 μM for a half hour, death of many Hela cells is not observed, indicating that such the photosensitizer is basically non-cytotoxic. A cell phototoxicity experiment as shown in FIG. 12(b) indicates that HB-1c-PEG6 presents very strong lethality to the Hela cells under irradiation of a 635 nm laser. HB-1c-PEG6 with a concentration range of 160 nM can kill more than 90% of the Hela cells, while in the same condition, the hypocrellin B HB or commercial photosensitizer hematoporphyrin derivative HpD can kill only about 30% of the Hela cells, indicating that a photodynamic effect of the hypocrellin derivative substituted both in a peri-position and in a 2-position by an amino is significantly better than that of the hypocrellin B HB and commercial photosensitizer hematoporphyrin HpD.

FIGS. 13(a) and 13(b) list experimental results of dark cytotoxicity and phototoxicity of the polyethylene glycol-di-2-(2-aminoethoxy)ethanol-substituted deacetyl hypocrellin derivative HB-1c-PEG6 synthesized in example 6. It can be seen that HC-1c-PEG6 has almost no cytotoxicity when not exposed to light. After exposure to 635 nm light, HC-1c-PEG6 with a concentration range of 140 nM can kill more than 90% of the Hela cells, while in the same condition, the deacetyl hypocrellin HC can kill only 40% of the Hela cells, and the commercial photosensitizer hematoporphyrin derivative HpD can kill only about 10% of the Hela cells, indicating that a photodynamic effect of HB-1c-PEG6 is significantly better than that of the deacetyl hypocrellin HC and commercial photosensitizer hematoporphyrin HpD.

FIGS. 14(a) and 14(b) show effect diagrams of dark toxicity and phototoxicity of diaminobutyric acid-substituted deacetyl hypocrellin HC-8c synthesized in example 22 to Hela cells. It can be seen that HC-8c containing two carboxyl groups has almost no cytotoxicity when not exposed to light. After exposure to 635 nm light, HC-8c with a concentration range of 200 nM can kill more than 85% of the Hela cells, while in the same condition, the deacetyl hypocrellin HC can kill 50% of the Hela cells, and the commercial photosensitizer hematoporphyrin derivative HpD can kill only about 10% of the Hela cells, indicating that a photodynamic effect of HC-8c is significantly better than that of the deacetyl hypocrellin HC and commercial photosensitizer hematoporphyrin HpD. Similarly, FIGS. 15(a) and 15(b) show effect diagrams of dark toxicity and phototoxicity for killing tumor cells of a polyethylene glycol-diaminobutyric acid-modified deacetyl hypocrellin derivative HC-8c-PEG6 synthesized in example 23, indicating that a photodynamic effect of HC-8c-PEG6 is significantly better than that of the deacetyl hypocrellin HC and commercial photosensitizer hematoporphyrin HpD.

FIGS. 16(a) and 16(b) show effect diagrams of dark toxicity and phototoxicity for killing tumor cells of a 4-aminomethylcyclohexanoic acid-substituted hypocrellin B derivative HB-13c synthesized in example 35. It can be seen from the figures that HB-13c containing two carboxyl groups has almost no cytotoxicity when not exposed to light. After exposure to 635 nm red light, HB-13c with a concentration range of 240 nM can kill more than 85% of the Hela cells, while in the same condition, the hypocrellin B HB can kill 30% of the Hela cells, and the commercial photosensitizer hematoporphyrin derivative HpD can kill only about 10% of the Hela cells, indicating that a photodynamic effect of HB-13c is significantly better than that of the hypocrellin B HB and commercial photosensitizer hematoporphyrin HpD. The compound HB-13c and two 8-PEG chains are connected by a carboxylic acid ester bond, to obtain HB-13c-PEG8 (example 37) with dark toxicity and phototoxicity effects of killing tumor cells as shown in FIGS. 17(a) and 17(b). Under red light irradiation, HB-13c-PEG8 with a concentration range of 160 nM can kill more than 90% of the Hela cells, while in the same condition, the hypocrellin B HB can kill 30% of the Hela cells. The compound HC-13c and two 8-PEG chains are connected by an amide bond, to obtain HC-13c-NH-PEG8 (example 41) with dark toxicity and phototoxicity effects of killing tumor cells as shown in FIGS. 18(a) and 18(b). Under red light irradiation, HC-13c-NH-PEG8 with a concentration range of 200 nM can kill more than 85% of the Hela cells, while in the same condition, the hypocrellin B HB can kill 60% of the Hela cells, and the commercial photosensitizer hematoporphyrin derivative HpD can kill only about 10% of the Hela cells. The above-described results indicate that photodynamic effects of HB-13c-PEG8 and HC-13c-NH-PEG8 are significantly better than that of the deacetyl hypocrellin and commercial photosensitizer hematoporphyrin.

All of the above phototoxicity experiment results indicate that a photodynamic effect of such the hypocrellin derivatives having a peri-position and a 2-position both substituted by an amino group is significantly better than that of the hypocrellin B HB and commercial photosensitizer hematoporphyrin HpD.

The present invention discloses a method for preparing a hypocrellin derivative substituted both in a peri-position and in a 2-position by an amino, and a use thereof. Such the compounds have a maximum absorption wavelength in the range of 600-650 nm, a molar extinction coefficient reaching 20000-40000 $M^{-1} cm^{-1}$, and a very high absorptivity in the phototherapy window. Studies indicate that such the derivatives can efficiently produce reactive oxygen species such as singlet oxygen in a photosensitive condition, have an excellent photodynamic effect, and can be used as phototherapy drugs to treat diseases such as tumors and various microangiopathies. Compared with the parent hypocrellin B, the hypocrellin derivative substituted both in a peri-position and in a 2-position by an amino of the present invention has a significantly improved absorptivity in the phototherapy window. In the prior art, there is no research on the preparation of a hypocrellin derivative having a peri-position substituted by an amino group, and the synthesis method of such the compound is disclosed for the first time.

It should also be noted that the hypocrellin derivatives involved in this patent that require the protection all have two enol tautomers. For example, the compounds represented by formula I-a and formula I-a', formula I-b and formula I-b', formula I-c and formula I-c', or formula I-d and formula I-d' are tautomers, and chemical structures of both the tautomers certainly fall within the protection scope. In addition, unless otherwise specified, any range recorded in the present invention comprises the end values and any value between the end values, and any sub-range formed by the end values or any value between the end values.

The present invention has the following beneficial effects:

1) The hypocrellin raw material in the present invention is extracted from natural products. The raw material is easy to be obtained, has a low cost, can be prepared in large quantities, has little toxic and side effects, and is easy to be metabolized. The synthesis and separation methods are simple, without expensive reaction raw materials and complicated separation means.

2) Compared with the parent hypocrellin, the prepared the hypocrellin derivative substituted both in a peri-position and in a 2-position by an amino has a significantly red-shifted absorption spectrum and a significantly increased molar extinction coefficient, and can efficiently produce reactive oxygen (primarily singlet oxygen, and secondly reactive oxygen species such as superoxide radicals) in the photosensitive condition.

3) Compared with the first-generation porphyrin photosensitizer and second-generation phthalocyanine photosensitizer used clinically, the absorption wavelength and the absorptivity of the photosensitizer, that is, the hypocrellin derivative substituted both in a peri-position and in a 2-position by an amino in the present invention, are obviously improved. The important thing is that the product is easy to be separated and purified and has a clear structure, overcoming the problems that the porphyrin and phthalocyanine photosensitizers are not easy to be separated and have a complex composition and a structure difficult to be determined. More importantly, in the same condition, the hypocrellin derivative substituted both in a peri-position and in a 2-position by an amino involved in the present invention, when used as a photosensitizer, has a stronger ability to photo-dynamically inactivate tumor cells than the first and second generation commercial photosensitizers.

BRIEF DESCRIPTION OF THE DRAWINGS

The specific embodiments of the present invention will be further described in detail below with reference to the accompanying drawings.

FIG. 7(a) shows a photodegradation curve of the di-2-(2-aminoethoxy)ethanol-substituted hypocrellin B derivative HB-1c in example 2 of the present invention;

FIG. 7(b) shows a photodegradation curve of the di-2-(2-aminoethoxy)ethanol-substituted deacetyl hypocrellin derivative HC-1c in example 5 of the present invention;

FIG. 7(c) shows a photodegradation curve of a standard reference rose bengal (RB);

FIG. 7(d) is a comparison diagram of photodegradation of HB-1c, HC-1c, and RB;

FIG. 10(a) shows a dark field image;

FIG. 10(b) shows a light field image;

FIG. 10(c) shows an image of superimposed dark field and bright field;

DETAILED DESCRIPTION OF THE PREFERRED EMBODIMENTS

In order to describe the present invention more clearly, the present invention is further described below with reference to the preferred embodiments and the accompanying drawings. Those skilled in the art should understand that the contents specifically described below is for illustration, instead of limitation, and the protection scope of the present invention shall not be limited thereto.

In the present invention, the experimental methods are conventional methods unless otherwise specified. Unless otherwise specified, the raw materials used can be obtained from publicly available commercial channels; the percentages are mass percentages unless otherwise specified; and M represents mol/L unless otherwise specified.

Example 1

Extraction of hypocrellin A (HA): 100 g of *Hypocrella bambusae* was pulverized by suing a pulverizer and placed in a Soxhlet extractor, continuous extraction was performed for a day with 1000 mL of acetone as a solvent until an extracting solution was nearly colorless, the extracting solution was filtered to remove a small amount of infiltrated insoluble solid and then spin-dried to remove acetone, 500 mL of dichloromethane was used for dissolution, 3×400 mL of distilled water was used for washing, an organic layer was separated out and spin-dried, a solid residue was washed with 3×100 mL of petroleum ether, the solid was spontaneously combusted and air-dried in air and then recrystallized twice by using chloroform-petroleum ether, and an obtained crystal was the target product hypocrellin A (HA), with a purity of above 98%, and MS (ESI+): 546.8. Further purification can be performed by means of thin-layer silica gel plate chromatography using petroleum ether:ethyl acetate: anhydrous ethanol (30:10:1) as a developing agent, to obtain hypocrellin A with a higher purity.

Figure 5:
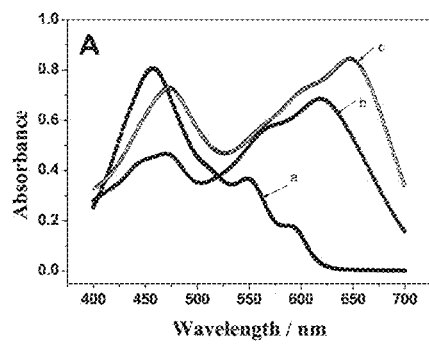
FIG. 5(a) shows a comparison diagram of absorption spectra of hypocrellin and the derivative thereof, in which line a represents hypocrellin B HB extracted in example 1 of the present invention; line b represents a di-2-(2-aminoethoxy)ethanol-substituted hypocrellin B derivative HB-1c prepared in example 2; and line c represents a di-2-(2-aminoethoxy)ethanol-substituted deacetyl hypocrellin derivative HC-1c prepared in example 5.
FIG. 5(b) shows a comparison diagram of absorption spectra of a commercial porphyrin photosensitizer PpIX and a porphyrin photosensitizer Ce6, respectively.
Figure 5:
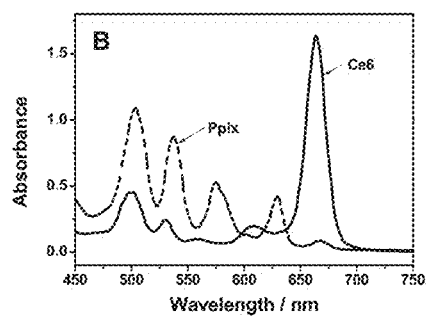

Preparation of hypocrellin B (HB): hypocrellin B was obtained by dehydrating hypocrellin A in an alkaline condition, and for a preparation method, reference is made to Zhao Kaihong, 1989, Organic Chemistry, volume 9, pages 252-254, with appropriate modifications. The specific method was as follows: 1 g of hypocrellin A was dissolved in 1000 mL of 1.5% KOH aqueous solution, the solution was stirred in a lucifugous condition for a reaction for 24 hours and neutralized by using slightly excessive dilute hydrochloric acid, chloroform was used for production extraction, and 0.98 g of hypocrellin B was obtained after separation and purification, with a yield of 98%, and MS (ESI+): 529.3. An absorption spectrum of the extracted hypocrellin A is as shown in FIG. 5(a).

Preparation of deacetyl hypocrellin (HG): 200 mg of hypocrellin B was dissolved in 100 mL of 1.5% KOH aqueous solution, a reflux reaction was performed for 8 hours in a lucifugous condition, the solution was neutralized by using dilute hydrochloric acid after cooling, dichloromethane was used for production extraction, and 110 mg of deacetyl hypocrellin (HG) was obtained after separation and purification, with a yield of 56%, and MS (ESI+): 487.2. $^1$H NMR (CDCl$_3$, δ, ppm): 16.0 (s, —OH, 1H), 15.9 (s, —OH, 1H), 6.62 (d, 1H), 6.35 (s, 2H), 4.14, 4.12 (s, —OCH$_3$, 6H), 4.02 (s, —OCH$_3$, 3H), 3.1 (d, 2H), 2.25 (s, —OCH$_3$, 3H).

Preparation of bromo-hypocrellin B HB-Br and bromo-deacetyl hypocrellin HC-Br: 100 mg of hypocrellin HB or deacetyl hypocrellin HC was dissolved in 100 mL of tetrahydrofuran solvent, and 2 mL of liquid bromine was added dropwise for a reaction at room temperature which was terminated after 6 hours. The reaction solution was treated by adding sodium thiosulfate, extracted by using an organic matter dichloromethane, washed, and dried, and a crude product was separated out by means of thin-layer chromatography, with a developing agent being a mixed solution of acetone:ethyl acetate=1:1 in volume ratio, to respectively obtain 5-bromo-hypocrellin derivatives HB-Br and HC-Br, with yields of 15% and 18%, respectively, and MS (ESI+): 607.5. Structural formulas of the above hypocrellin A (HA), hypocrellin B (HB), deacetyl hypocrellin (HG), and 5-bromo-hypocrellin derivatives HB-Br and HC—Br are as follows:

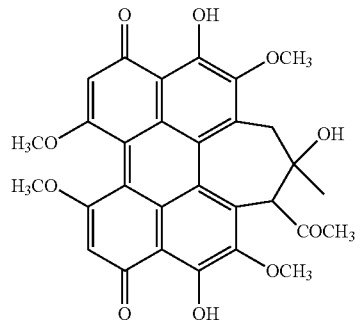

HA

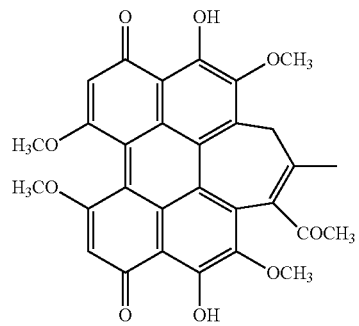

HB

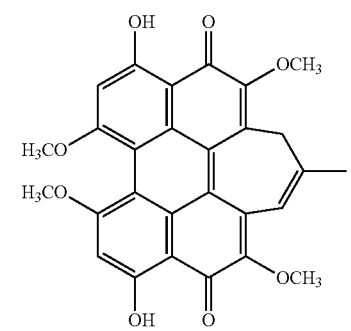

HC

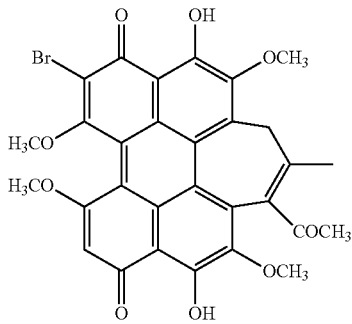

HB-Br

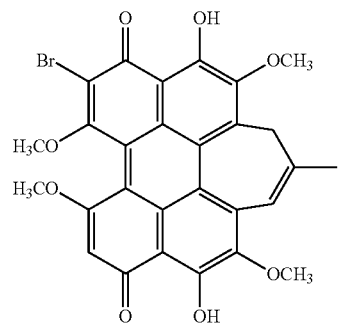

HC-Br

Example 2

Figure 1:
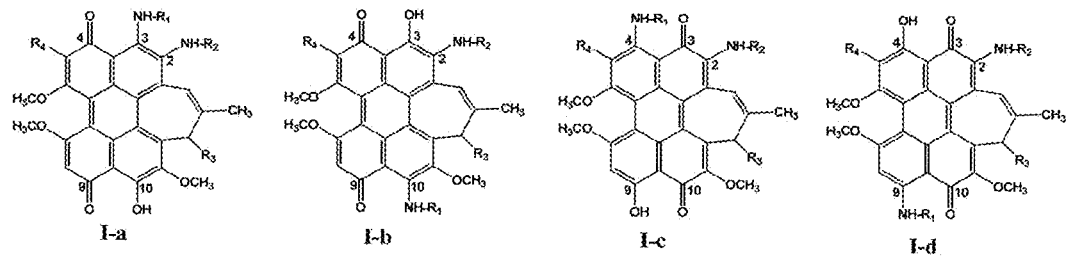
FIG. 1 shows a general structural formula of a hypocrellin derivative substituted both in a peri-position and in a 2-position by an amino of the present invention.
Figure 2:
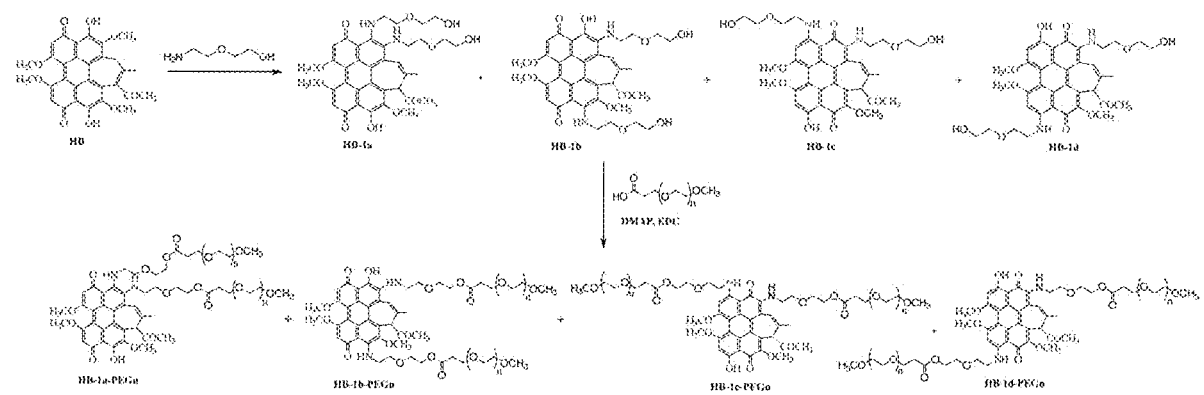
FIG. 2 shows a diagram of a synthetic route of hypocrellin B derivatives HB-1a-PEGn-HB-1d-PEGn having a peri-position and a 2-position both substituted by a polyethylene glycol-2-(2-aminoethoxy)ethanol group in examples 2 and 3 (n is the number of units of the polyethylene glycol)

Preparation of a di-2-(2-aminoethoxy)ethanol-substituted hypocrellin B derivative ($R_1=R_2=$—$CH_2CH_2$—$OCH_2CH_2$—OH, $R_3=$—$COCH_3$, $R_4=$—H): a synthetic route is as shown in FIG. 2, and specifically includes the following steps: hypocrellin B HB (100 mg, 0.18 mmol) and 2-(2-aminoethoxy)ethanol (2 mmol) were dissolved in 100 mL of anhydrous acetonitrile, after fully mixed, a mixture was heated to 100° C. under the protection of nitrogen and stirred in a lucifugous condition for a reaction for 12 h, a solvent was distilled off after the reaction, a blue black solid was dissolved in 100 mL of dichloromethane, a solution was washed once with 100 mL of a dilute hydrochloric acid and then washed with distilled water three times, an organic layer was dried by using anhydrous magnesium sulfate and filtered, and an organic phase was spin-dried to obtain a crude product. The obtained crude product was separated out by means of thin-layer chromatography, with a developing agent being a mixed solution of acetone:ethyl acetate=1:1 (volume ratio), to obtain four blue black solid products HB-1a-HB-1d, respectively. HB-1a: yield: 4.1%, $R_f$: 0.35; MS (ESI+): 688.3; maximum absorption wavelength: 630 nm; molar extinction coefficient: 30,000 $M^{-1}cm^{-1}$; and singlet oxygen yield: 35%. HB-1b: yield: 5.2%, $R_f$: 0.30; MS (ESI+): 688.3; maximum absorption wavelength: 622 nm; molar extinction coefficient: 28,000 $M^{-1}cm^{-1}$; and singlet oxygen yield: 36%. HB-1c: yield: 13.1%, $R_f$: 0.28; MS (ESI+): 688.3; maximum absorption wavelength: 621 nm; molar extinction coefficient: 30,000 $M^{-1}cm^{-1}$; and singlet oxygen yield: 40%. HB-1d: yield: 3.8%, $R_f$: 0.32; MS (ESI+): 688.3; maximum absorption wavelength: 622 nm; molar extinction coefficient: 30,000 $M^{-1}cm^{-1}$; and singlet oxygen yield: 35%. Structural formulas of the above amino-substituted products are as follows:

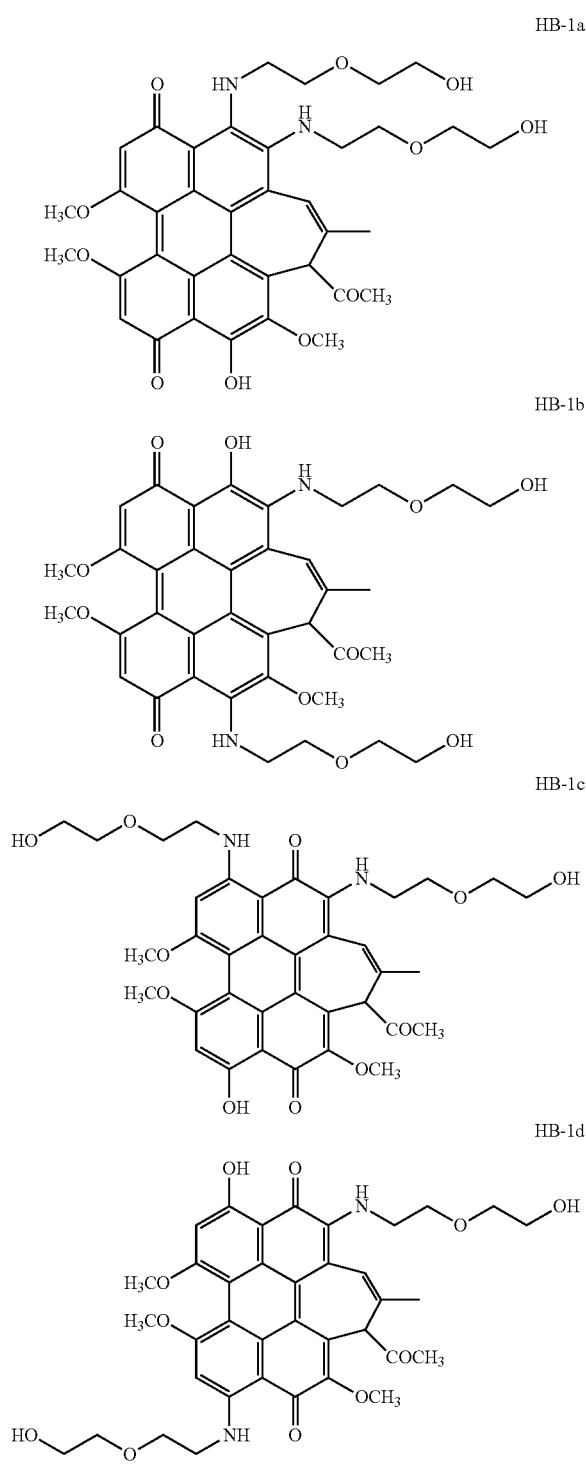

Figure 6:
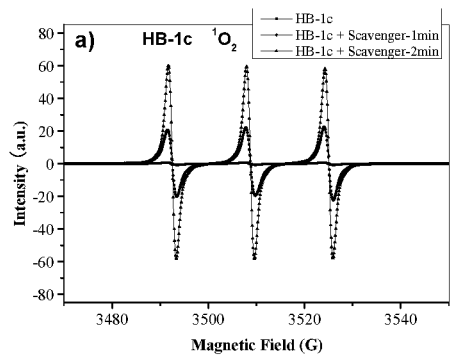
FIG. 6(a) shows a function diagram of the di-2-(2-aminoethoxy)ethanol-substituted hypocrellin B derivative HB-1c in example 2 of the present invention and a singlet oxygen scavenger.
FIG. 6(b) shows a function diagram of the di-2-(2-aminoethoxy)ethanol-substituted hypocrellin B derivative HB-1c in example 2 of the present invention and a superoxide radical scavenger.
Figure 6:
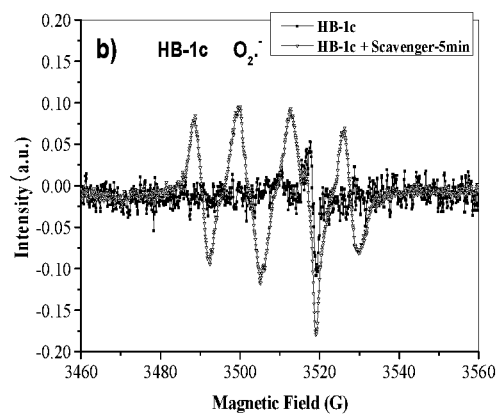
Figure 7:
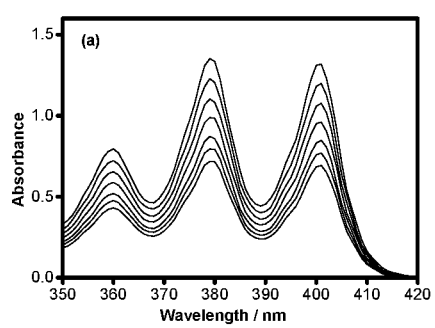
FIGS. 7(a)-7(d) show a singlet oxygen efficiency test.
Figure 7:
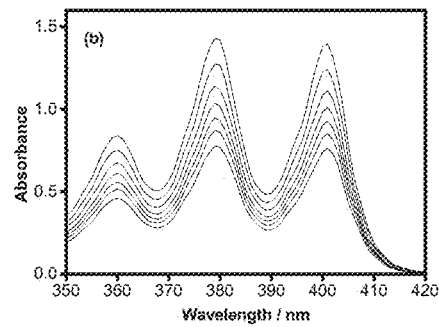
Figure 7:
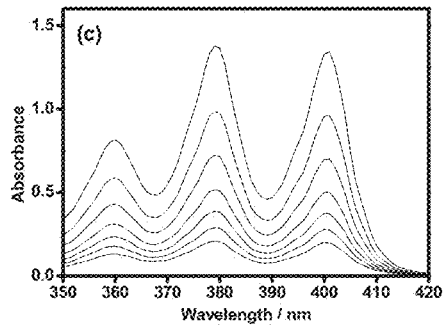
Figure 7:
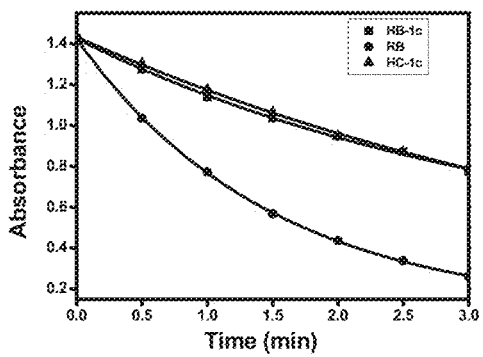
Figure 10:
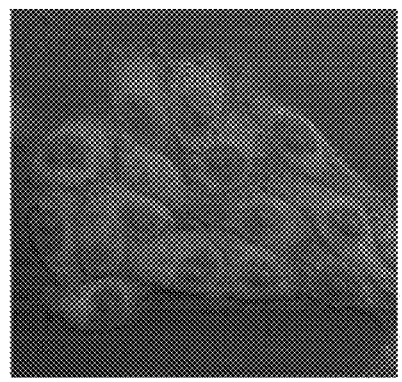
FIGS. 10(a)-10(c) show confocal fluorescence images in Hela cells of the di-2-(2-aminoethoxy)ethanol-substituted hypocrellin B derivative HB-1c in example 2 of the present invention.
Figure 10:
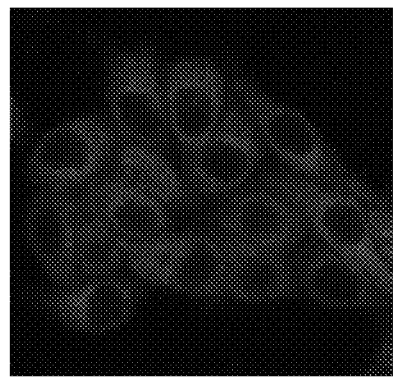
Figure 10:

An absorption spectrum of the di-2-(2-aminoethoxy)ethanol-substituted hypocrellin B derivative HB-1c is as shown by curve a in FIG. 5(a), and HB-1c has very wide and strong absorption performance in a phototherapy window, has a maximum absorption spectrum wavelength of about 630 nm, which is redshifted by about 180 nm relative to a maximum absorption peak of the parent hypocrellin, and has a molar extinction coefficient of about 30000 $M^{-1}$ $cm^{-1}$, presenting a very high absorptivity in the phototherapy window. The ability of HB-1c to produce reactive oxygen is shown in FIGS. 6(a) and 6(b): the experiments indicate that, it is measured by using singlet oxygen and superoxide radical scavenger that, such the hypocrellin derivative having a peri-position substituted by an amino group can efficiently produce photosensitive reactive species, primarily producing singlet oxygen, as shown in FIG. 6(a), also producing a small amount of superoxide radicals, as shown in FIG. 6(b), and the efficiency of producing singlet oxygen being about 40%. Results of confocal fluorescence imaging experiments shown in FIG. 10 indicate that the phototherapy drug micromolecule HB-1c has good biocompatibility and is able to enter a lysosome of a Hela cell and generate an excellent red-light fluorescence image in the cell.

Example 3

Preparation of a di-2-(2-aminoethoxy)ethanol-polyethylene glycol (of different chain lengths)-substituted hypocrellin derivative ($R_1$=$R_2$=—$CH_2CH_2$—$OCH_2CH_2$—OCO-PEGn-$OCH_3$, $R_3$=—$COCH_3$, $R_4$=—H) (PEG is polyethylene glycol, n is the number of ethylene glycol units, and n=1, 6, 16): hypocrellin B HB (100 mg, 0.18 mmol) and 2-(2-aminoethoxy)ethanol (2 mmol) were dissolved in 100 mL of anhydrous acetonitrile, after fully mixed, a mixture was heated to 80° C. under the protection of nitrogen and stirred in a lucifugous condition for a reaction for 20 h, a solvent was distilled off after the reaction, a blue black solid was dissolved in 100 mL of dichloromethane, a solution was washed with distilled water three times, an organic layer was dried and filtered, and an organic phase was spin-dried to obtain a crude product. Add DCC (200 mg) to the obtained crude product and dissolved in 50 mL of anhydrous dichloromethane, to react with polyethylene glycol methyl esters (HOOC-PEGn-$OCH_3$, 2 g) of different chain lengths, respectively, and a reaction solution was stirred in a lucifugous condition at room temperature for a reaction for 8 h. After the reaction, added 100 mL of dichloromethane to the reaction solution, a mixed solution was washed once with 100 mL of a dilute hydrochloric acid aqueous solution and then washed with distilled water three times, an organic layer was dried by using anhydrous magnesium sulfate and filtered, and the crude product was separated out by means of thin-layer chromatography, with a developing agent being a mixed solution of ethyl acetate:ethanol=5:1, to obtain blue black solid products HB-1a-PEGn, HB-1b-PEGn, HB-1c-PEGn, and HB-1d-PEGn (n=1, 6, 16), respectively. HB-1a-PEG1 (n=1): yield: 17.2%, $R_f$: 0.36; MS (ESI+): 948.4; maximum absorption wavelength: 625 nm; molar extinction coefficient: 31,000 $M^{-1}$ $cm^{-1}$; and singlet oxygen yield: 35%. HB-1b-PEG6 (n=6): yield: 12.5%, $R_f$: 0.32; MS (ESI+): 1388.6; maximum absorption wavelength: 622 nm; molar extinction coefficient: 30,000 $M^{-1}$ $cm^{-1}$; and singlet oxygen yield: 32%. HB-1c-PEG1 (n=1): yield: 21.2%, $R_f$: 0.31; MS (ESI+): 948.4; maximum absorption wavelength: 626 nm; molar extinction coefficient: 33,000 $M^{-1}cm^{-1}$; and singlet oxygen yield: 38%. HB-1c-PEG6 (n=6): yield: 32.2%, $R_f$: 0.25; MS (ESI+): 1388.6; maximum absorption wavelength: 628 nm; molar extinction coefficient: 34,500 $M^{-1}$ $cm^{-1}$; and singlet oxygen yield: 34%. HB-1c-PEG16 (n=16): yield: 35.1%, $R_f$: 0.18; MS (ESI+): 2268.9; maximum absorption wavelength: 624 nm; molar extinction coefficient: 31500 $M^{-1}$ $cm^{-1}$; and singlet oxygen yield: 30%. HB-1d-PEG6 (n=6): yield: 32.2%, $R_f$: 0.25; MS (ESI+): 1388.6; maximum absorption wavelength: 628 nm; molar extinction coefficient: 34,500 $M^{-1}$ $cm^{-1}$; and singlet oxygen yield: 34%. Structural formulas of the above amino-substituted products are as follows:

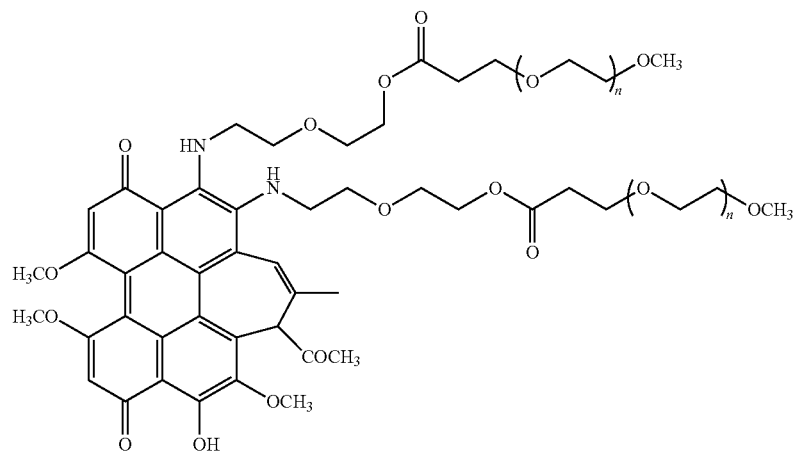
HB-1a-PEG1: n = 1
HB-1a-PEG6: n = 6
HB-1a-PEG12: n = 12
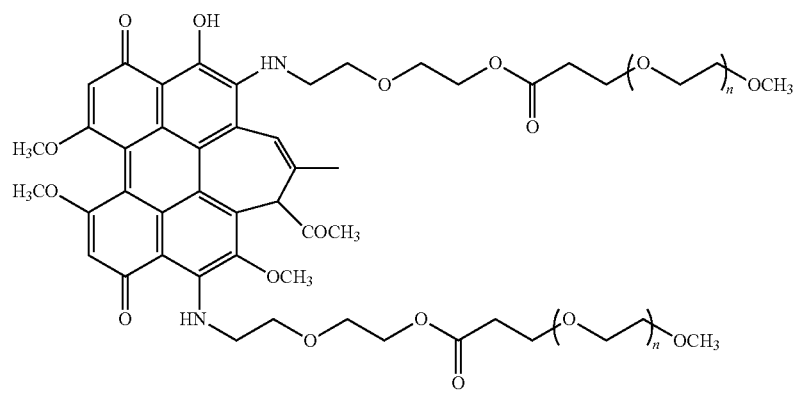
HB-1b-PEG1: n = 1
HB-1b-PEG6: n = 6
HB-1b-PEG12: n = 12
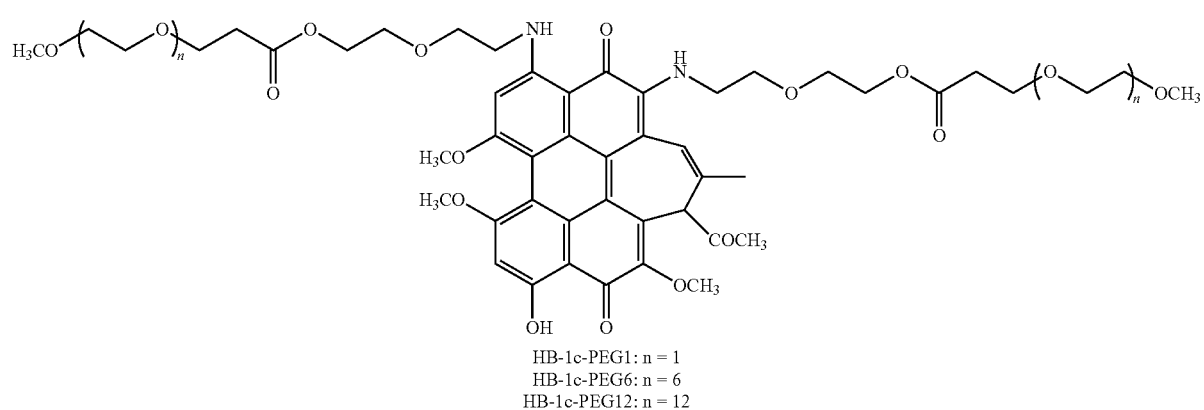
HB-1c-PEG1: n = 1
HB-1c-PEG6: n = 6
HB-1c-PEG12: n = 12

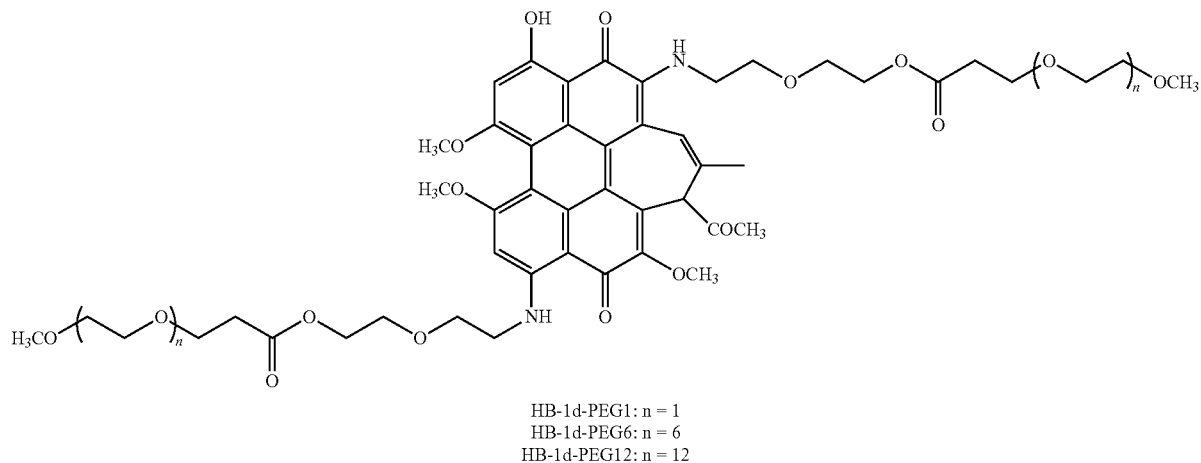

HB-1d-PEG1: n = 1
HB-1d-PEG6: n = 6
HB-1d-PEG12: n = 12

Figure 11:
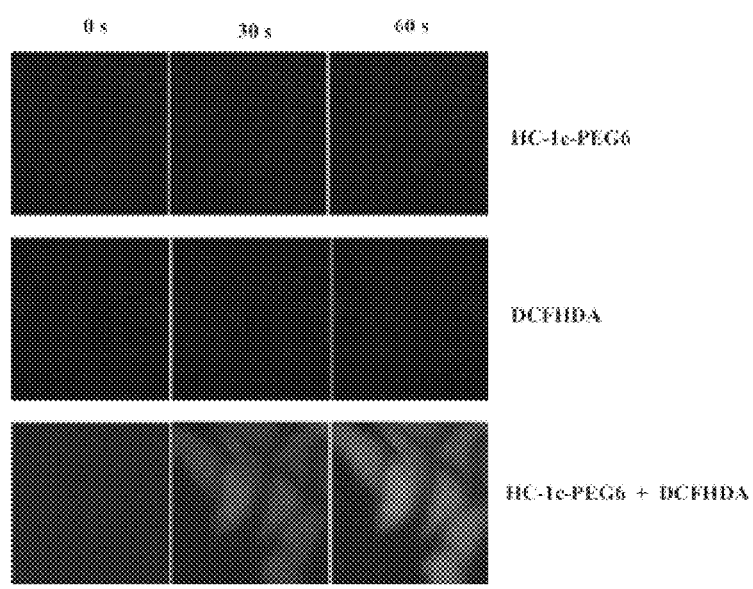
FIG. 11 shows detection of reactive oxygen in a cell for photosensitizer incubation by using a singlet oxygen fluorescence probe DCFH-DA, wherein the first row shows fluorescence images of a cell for incubation of only the photosensitizer HC-1c-PEG6 at different times; the second row shows fluorescence images of a cell for incubation of only the singlet oxygen fluorescence probe DCFH-DA at different times; and the third row shows fluorescence images of a cell for co-incubation of the photosensitizer HC-1c-PEG6 and fluorescence probe DCFH-DA at different times.

Results of confocal fluorescence imaging experiments shown in FIGS. 10(a)-10(c) indicate that the phototherapy drug micromolecule HB-1c-PEG6 has good biocompatibility and is able to enter a lysosome of a Hela cell and generate an excellent red-light fluorescence image in the cell. DCFH-DA is used to detect singlet oxygen in a cell. As shown in FIG. 11, the photosensitizer HC-1c-PEG6 and the fluorescence probe DCFH-DA are co-incubated in the cell, with increase of an irradiation time to 60 s, a green fluorescence intensity is gradually increased, indicating that the amount of the singlet oxygen in the cell is increased.

Figure 12:
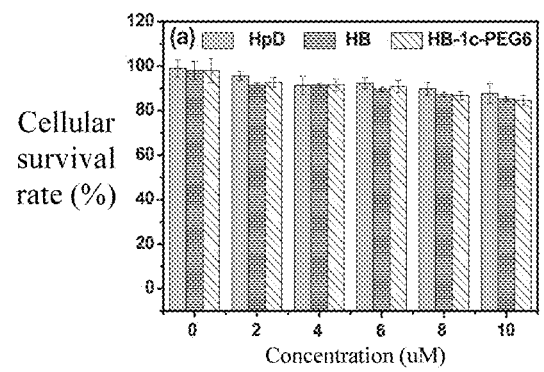
FIG. 12(a) shows dark toxicities, to Hela cells, of the hematoporphyrin derivative HpD, the hypocrellin B HB, and the polyethylene glycol-di-2-(2-aminoethoxy)ethanol-substituted hypocrellin derivative HB-1c-PEG6 in example 3 of the present invention at different concentrations.
FIG. 12(b) shows phototoxicities, to Hela cells, of the hematoporphyrin derivative HpD, the hypocrellin B HB, and the polyethylene glycol-di-2-(2-aminoethoxy)ethanol-substituted hypocrellin derivative HB-1c-PEG6 in example 3 of the present invention at different concentrations.
Figure 12:
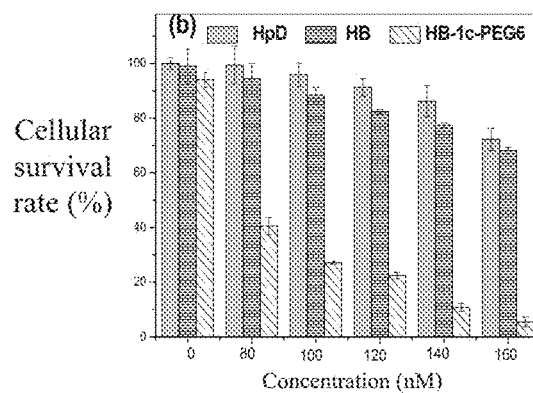

HB-1c-PEG6 and Hela cells are co-incubated, as shown in FIG. 12(a), a cytotoxicity (dark toxicity) research test indicates that HB-1c-PEG6 has a smaller cytotoxicity, which is similar to that of the hypocrellin B HB and commercial photosensitive drug hematoporphyrin HpD. After the Hela cells are incubated by using the photosensitizer HB-1c-PEG6 with the concentration of M for a half hour, death of many Hela cells is not observed, indicating that such the photosensitizer is basically non-cytotoxic. A cell phototoxicity experiment as shown in FIG. 12(b) indicates that HB-1c-PEG6 presents very strong lethality to the Hela cells under irradiation of a 635 nm laser. HB-1c-PEG6 with a concentration range of 160 nM can kill more than 90% of the Hela cells, while in the same condition, the hypocrellin B HB or commercial photosensitizer hematoporphyrin derivative HpD can kill only about 30% of the Hela cells, indicating that a photodynamic effect of HB-1c-PEG6 is significantly better than that of the hypocrellin B HB and commercial photosensitizer hematoporphyrin HpD.

Example 4

Preparation of a di-2-(2-aminoethoxy)ethanol-quaternary ammonium salt-substituted hypocrellin derivative ($R_1=R_2=-CH_2CH_2-OCH_2CH_2-OCO-(CH_2)_n-N^+(CH_3)_3$, $R_3=-COCH_3$, $R_4=-H$) (n=2, 4, 6): the product HB-1c (20 mg, 0.03 mmol) in example 2 is used as a raw material, added DCC (100 mg), and dissolved in 20 mL of anhydrous dichloromethane, to react with carboxytrimethylamine ($HOOC-(CH_2)_n-N^+(CH_3)_3$, 2 g) of different chain lengths, respectively, and a reaction solution was stirred in a lucifugous condition at room temperature for a reaction for 8 h. After the reaction, add 100 mL of dichloromethane to the reaction solution, a mixed solution was washed once with 100 mL of a dilute hydrochloric acid aqueous solution and then washed with distilled water three times, an organic layer was dried by using anhydrous magnesium sulfate and filtered, and a crude product was separated out by means of thin-layer chromatography, with a developing agent being a mixed solution of ethyl acetate:ethanol=5:1, to obtain blue black solid products HB-1a-PEGn, HB-1b-PEGn, HB-1c-PEGn, and HB-1d-PEGn (n=2, 4, 6). HB-1c-C2-N+ (n=2): yield: 27.2%, $R_f$: 0.36; MS (ESI+): 948.4; maximum absorption wavelength: 625 nm; molar extinction coefficient: 33,000 $M^{-1}cm^{-1}$; and singlet oxygen yield: 35%. HB-1c-C4-N+ (n=4): yield: 17.2%, $R_f$: 0.32; MS (ESI+): 1124.1; maximum absorption wavelength: 622 nm; molar extinction coefficient: 31,000 $M^{-1}$ $cm^{-1}$; and singlet oxygen yield: 32%. HB-1c-C6-N+ (n=6): yield: 25.2%, $R_f$: 0.31; MS (ESI+): 1212.6; maximum absorption wavelength: 626 nm; molar extinction coefficient: 33,000 $M^{-1}$ $cm^{-1}$; and singlet oxygen yield: 38%. Structural formulas of the above amino-substituted products are as follows:

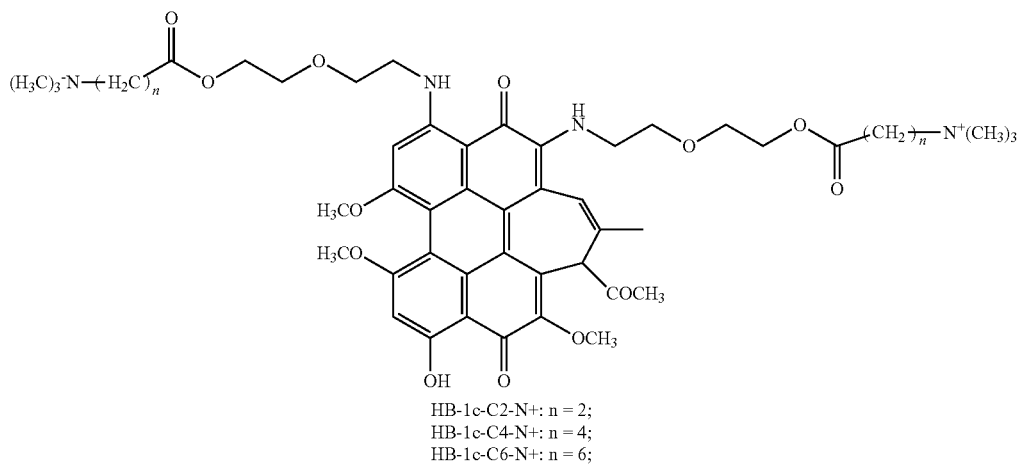

HB-1c-C2-N+: n = 2;
HB-1c-C4-N+: n = 4;
HB-1c-C6-N+: n = 6;

The above prepared compound HB-1c-C2-N+ contains two quaternary ammonium salts and two ethylene glycol units, making the photosensitizer molecules have very high water solubility in a physiological condition; and each milliliter of normal saline can dissolve more than 20 mg of photosensitizer molecules, presenting excellent water solubility. Therefore, the photosensitive drug can be well transported in blood vessels during intravenous injection, without causing a vascular blockage.

Example 5

Figure 3:
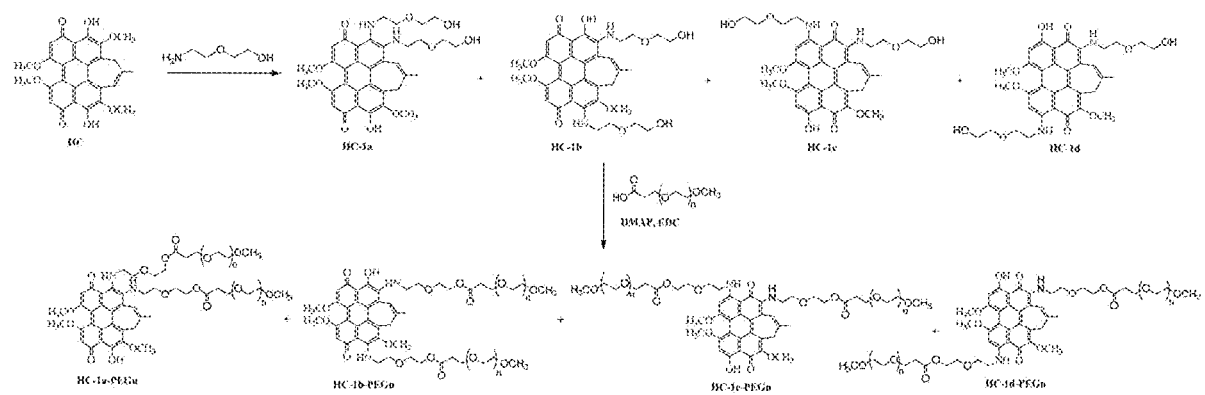
FIG. 3 shows a diagram of a synthetic route of deacetyl hypocrellin derivatives HC-1a-PEGn-HC-1d-PEGn having a peri-position and a 2-position both substituted by a polyethylene glycol-2-(2-aminoethoxy)ethanol group in examples 5 and 6 (n is the number of units of the polyethylene glycol)

Preparation of a di-2-(2-aminoethoxy)ethanol-substituted deacetyl hypocrellin derivative ($R_1$=$R_2$=—$CH_2CH_2$—$OCH_2CH_2$—OH, $R_3$=$R_4$=—H): a synthetic method is as shown in FIG. 3, and specifically includes the following steps: deacetyl hypocrellin HC (100 mg, 0.20 mmol) and 2-(2-aminoethoxy)ethanol (2 mmol) were dissolved in 100 mL of anhydrous acetonitrile, after fully mixed, a mixture was heated to 100° C. under the protection of nitrogen and stirred in a lucifugous condition for a reaction for 15 h, after the reaction, a solvent was removed by means of rotary evaporation, a blue black solid was dissolved in 100 mL of dichloromethane, a solution was washed once with 100 mL of a dilute hydrochloric acid aqueous solution and then washed with distilled water three times, an organic layer was dried and filtered, and an organic phase was spin-dried to obtain a crude product. The obtained crude product was separated out by means of thin-layer chromatography, with a developing agent being a mixed solution of acetone:ethyl acetate=2:1 in volume ratio, to obtain four blue black solid products HC-1a-HC-1d, respectively. HC-1a: yield: 5.6%, $R_f$: 0.30; MS (ESI+): 646.8; maximum absorption wavelength: 628 nm; molar extinction coefficient: 28,000 $M^{-1}cm^{-1}$; and singlet oxygen yield: 36%. HC-1b: yield: 4.2%, $R_f$: 0.28; MS (ESI+): 646.8; maximum absorption wavelength: 624 nm; molar extinction coefficient: 27,000 $M^{-1}cm^{-1}$; and singlet oxygen yield: 33%. HC-1c: yield: 13.1%, $R_f$: 0.26; MS (ESI+): 646.8; maximum absorption wavelength: 6351 nm; molar extinction coefficient: 30,000 $M^{-1} cm^{-1}$; and singlet oxygen yield: 38%. HC-1d: yield: 4.8%, $R_f$: 0.24; MS (ESI+): 646.8; maximum absorption wavelength: 626 nm; molar extinction coefficient: 28,500 $M^{-1}cm^{-1}$; and singlet oxygen yield: 32%. Structural formulas of the above amino-substituted products are as follows:

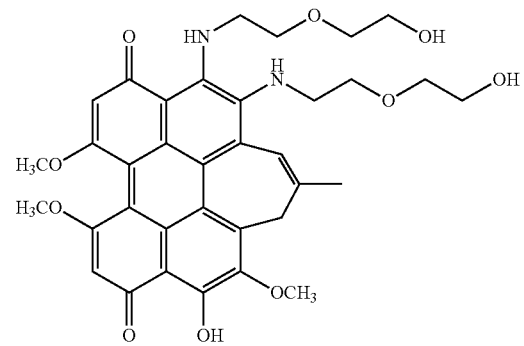

HC-1a

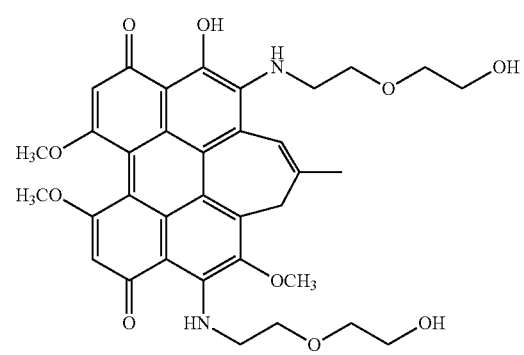

HC-1b

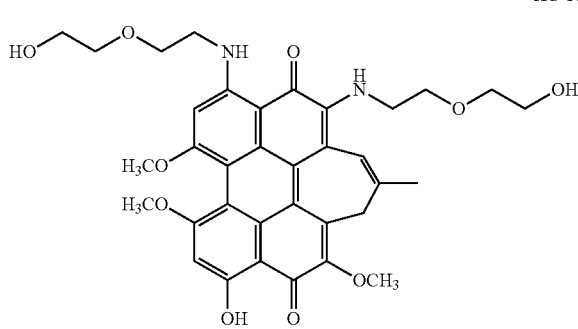

HC-1c

HC-1d

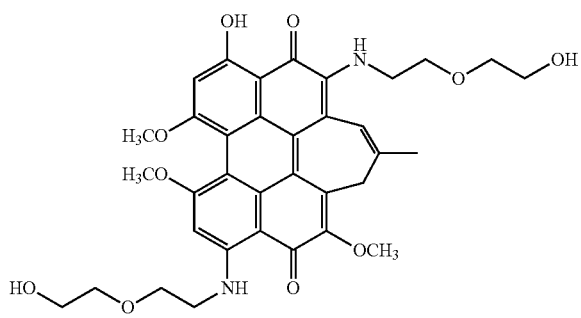

Figure 8:
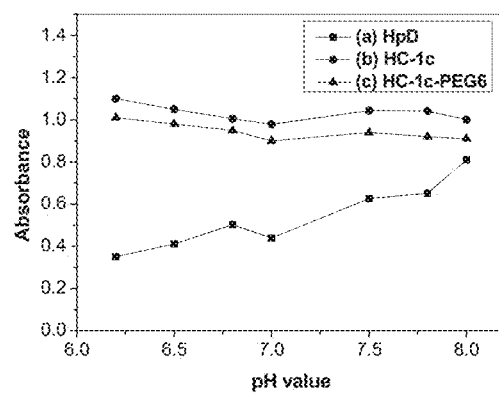
FIG. 8 shows a comparison diagram of pH stabilities of the hypocrellin derivative prepared in the present invention and commercial hematoporphyrin, in which curve (a) shows the pH stability of the commercial hematoporphyrin photosensitizer HpD; curve (b) shows the pH stability of the di-2-(2-aminoethoxy)ethanol-substituted deacetyl hypocrellin derivative HC-1c in example 5; and curve (c) shows the pH stability of polyethylene glycol-di-2-(2-aminoethoxy)ethanol-substituted deacetyl hypocrellin derivative HC-1c-PEG6 in example 6.

An absorption spectrum of the di-2-(2-aminoethoxy)ethanol-substituted deacetyl hypocrellin derivative He-1c is as shown by curve b in FIG. 5(a), and HB-1c has very wide and strong absorption performance in a phototherapy window, has a maximum absorption spectrum wavelength of about 640 nm, which is redshifted by about 190 nm relative to a maximum absorption peak of the parent hypocrellin, and has a molar extinction coefficient of about 30000 $M^{-1}cm^{-1}$, presenting a very high absorptivity in the phototherapy window. In addition, as shown in FIG. 8, HC-1c has an excellent pH stability, and there is no obvious change in an absorption spectrum thereof in the pH range of 6.2-8.0.

Example 6

Preparation of a di-2-(2-aminoethoxy)ethanol-polyethylene glycol (of different chain lengths)-substituted deacetyl hypocrellin derivative ($R_1$=$R_2$=—$CH_2CH_2$—OCO-PEGn-$OCH_3$, $R_3$=—H) (PEG is polyethylene glycol, n is the number of ethylene glycol units, and n=1, 6, 12): deacetyl hypocrellin HC (100 mg, 0.20 mmol) and 2-(2-aminoethoxy)ethanol (2 mmol) were dissolved in 100 mL of anhydrous acetonitrile, after fully mixed, a mixture was heated to 80° C. under the protection of nitrogen and stirred in a lucifugous condition for a reaction for 20 h, a solvent was distilled off after the reaction, a blue black solid was dissolved in 100 mL of dichloromethane, a solution was washed with distilled water three times, an organic layer was dried and filtered, and an organic phase was spin-dried to obtain a crude product. Add DCC (200 mg) to the obtained crude product and dissolved in 50 mL of anhydrous dichloromethane, to react with polyethylene glycol methyl esters (HOOC-PEGn-$OCH_3$, 2 g) of different chain lengths, respectively, and a reaction solution was stirred in a lucifugous condition at room temperature for a reaction for 8 h. After the reaction, the reaction solution was added to 100 mL of dichloromethane, a mixed solution was washed once with 100 mL of a dilute hydrochloric acid aqueous solution and then washed with distilled water three times, an organic layer was dried by using anhydrous magnesium sulfate and filtered, and the crude product was separated out by means of thin-layer chromatography, with a developing agent being a mixed solution of ethyl acetate:ethanol=5:1, to obtain blue black solid products HC-1a-PEGn, HC-1b-PEGn, HC-1c-PEGn, and HC-1d-PEGn (n=1, 6, 12), respectively. HC-1a-PEG1 (n=1): yield: 13.2%, $R_f$: 0.35; MS (ESI+): 906.4; maximum absorption wavelength: 622 nm; molar extinction coefficient: 30,500 $M^{-1}cm^{-1}$; and singlet oxygen yield: 32%. HC-1b-PEG6 (n=6): yield: 10.5%, $R_f$: 0.31; MS (ESI+): 1346.6; maximum absorption wavelength: 624 nm; molar extinction coefficient: 30,000 $M^{-1}cm^{-1}$; and singlet oxygen yield: 30%. HC-1c-PEG1 (n=1): yield: 16.2%, $R_f$: 0.30; MS (ESI+): 906.4; maximum absorption wavelength: 625 nm; molar extinction coefficient: 32,500 $M^{-1}cm^{-1}$; and singlet oxygen yield: 34%. HC-1c-PEG6 (n=6): yield: 18.2%, $R_f$: 0.26; MS (ESI+): 1346.6; maximum absorption wavelength: 628 nm; molar extinction coefficient: 33,500 $M^{-1}cm^{-1}$; and singlet oxygen yield: 34%. HC-1c-PEG12 (n=12): yield: 17.1%, $R_f$: 0.18; MS (ESI+): 1874.9; maximum absorption wavelength: 626 nm; molar extinction coefficient: 32,500 $M^{-1}$ $cm^{-1}$; and singlet oxygen yield: 35%. HC-1d-PEG6 (n=6): yield: 13.2%, $R_f$: 0.22; MS (ESI+): 1346.6; maximum absorption wavelength: 622 nm; molar extinction coefficient: 34,500 $M^{-1}$ $cm^{-1}$; and singlet oxygen yield: 34%. Structural formulas of the above amino-substituted products are as follows:

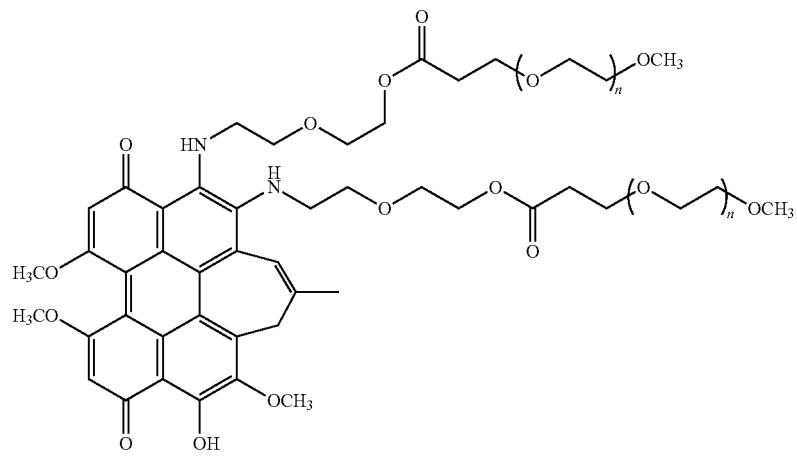

HC-1a-PEG1: n = 1
HC-1a-PEG6: n = 6
HC-1a-PEG12: n = 12

-continued

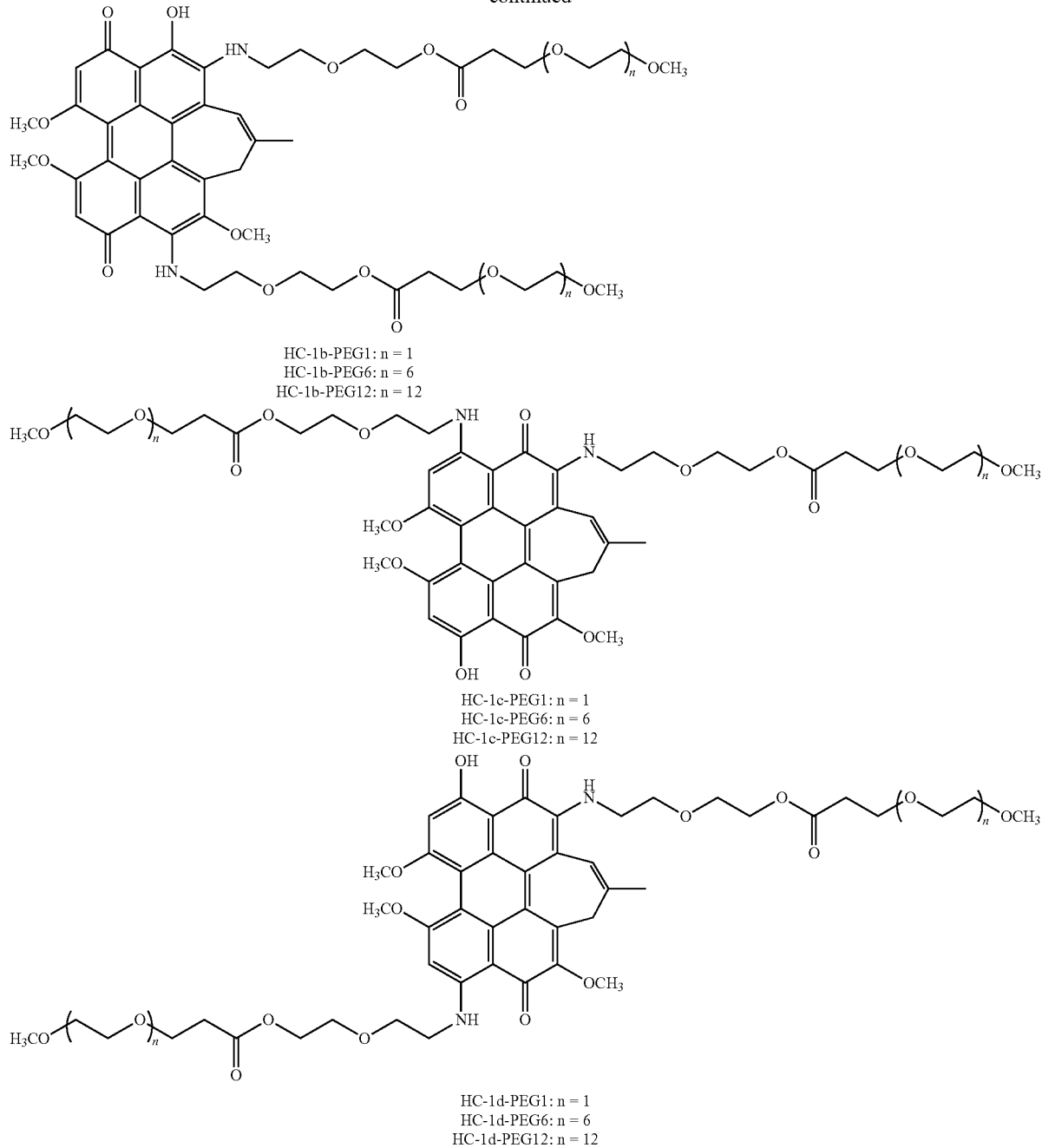

HC-1b-PEG1: n = 1
HC-1b-PEG6: n = 6
HC-1b-PEG12: n = 12

HC-1c-PEG1: n = 1
HC-1c-PEG6: n = 6
HC-1c-PEG12: n = 12

HC-1d-PEG1: n = 1
HC-1d-PEG6: n = 6
HC-1d-PEG12: n = 12

The above prepared compound HC-1c-PEG6 (n=6) contains two 6-PEG long-chains, making the photosensitizer molecules have very high water solubility in a physiological condition; and each milliliter of normal saline can dissolve more than 20 mg of photosensitizer molecules, presenting excellent water solubility. Therefore, the photosensitive drug can be well transported in blood vessels during intravenous injection, without causing a vascular blockage. In addition, as shown in FIG. 8, HC-1c-PEG6 also has an excellent pH stability, and there is no obvious change in an absorption spectrum thereof in the pH range of 6.2-8.0, for the reason that two phenolic hydroxyl groups of the hypocrellin are not prone to deprotonation in this acid-base condition. However, the commercial hematoporphyrin HpD contains two carboxyl groups, which can be deprotonated in the pH range of 6.2-8.0, resulting in an obvious change in the absorption spectrum, thus presenting an instability of the HpD photosensitizer.

Figure 13:
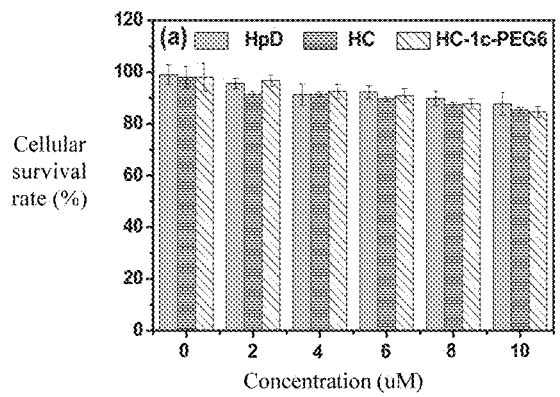
FIG. 13(a) shows dark toxicities, to Hela cells, of the hematoporphyrin derivative HpD, the deacetyl hypocrellin HC, and the polyethylene glycol-di-2-(2-aminoethoxy)ethanol-substituted deacetyl hypocrellin derivative HC-1c-PEG6 in example 6 of the present invention at different concentrations.
FIG. 13(b) shows phototoxicities, to Hela cells, of the hematoporphyrin derivative HpD, the deacetyl hypocrellin HC, and the polyethylene glycol-di-2-(2-aminoethoxy)ethanol-substituted deacetyl hypocrellin derivative HC-1c-PEG6 in example 6 of the present invention at different concentrations.
Figure 13:
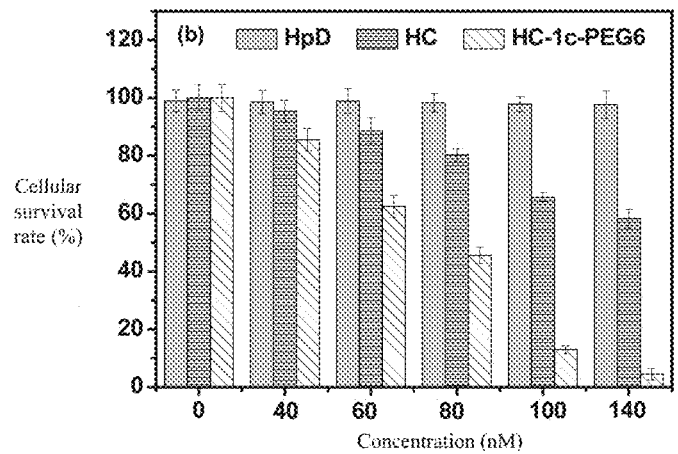

FIGS. 13(*a*) and 13(*b*) show experimental results of dark cytotoxicity and phototoxicity of HB-1c-PEG6. It can be seen that HC-1c-PEG6 has almost no cytotoxicity when not exposed to light. After exposure to 635 nm light, HC-1c-PEG6 with a concentration range of 140 nM can kill more than 90% of the Hela cells, while in the same condition, the deacetyl hypocrellin HC can kill 40% of the Hela cells, and the commercial photosensitizer hematoporphyrin derivative HpD can kill only about 10% of the Hela cells, indicating that a photodynamic effect of HB-1c-PEG6 is significantly better than that of the deacetyl hypocrellin HC and commercial photosensitizer hematoporphyrin HpD.

Example 7

Preparation of an aminoethanol-substituted hypocrellin derivative ($R_1=R_2=$—$CH_2CH_2$—OH, $R_3=$—$COCH_3$, $R_4=$—H): a substituted amino raw material is $NH_2$—$CH_2CH_2$—OH, a synthetic method is similar to the preparation of the di-2-(2-aminoethoxy)ethanol-substituted hypocrellin B derivative in example 2, and four blue black solid products HB-2a-HB-2d are obtained, respectively. HB-2a: yield: 4.2%, $R_f$: 0.36; MS (ESI+): 600.1; maximum absorption wavelength: 625 nm; molar extinction coefficient: 30,500 $M^{-1}$ $cm^{-1}$; and singlet oxygen yield: 28%. HB-2b: yield: 4.7%, $R_f$: 0.32; MS (ESI+): 600.1; maximum absorption wavelength: 627 nm; molar extinction coefficient: 31.500 $M^{-1}$ $cm^{-1}$; and singlet oxygen yield: 25%. HB-2c: yield: 12.7%, $R_f$: 0.39; MS (ESI+): 600.1; maximum absorption wavelength: 628 nm; molar extinction coefficient: 31,000 $M^{-1}cm^{-1}$; and singlet oxygen yield: 30%. HB-2d: yield: 4.6%, $R_f$: 0.29; MS (ESI+): 600.1; maximum absorption wavelength: 629 nm; molar extinction coefficient: 30,000 $M^{-1}$ $cm^{-1}$; and singlet oxygen yield: 26%. Structural formulas of the above amino-substituted products are as follows:

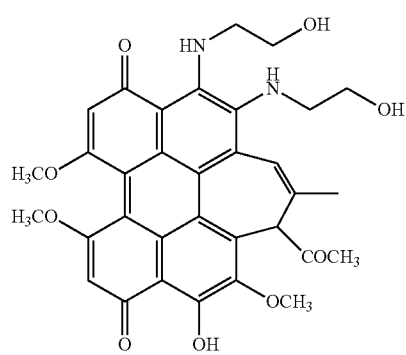

HB-2a

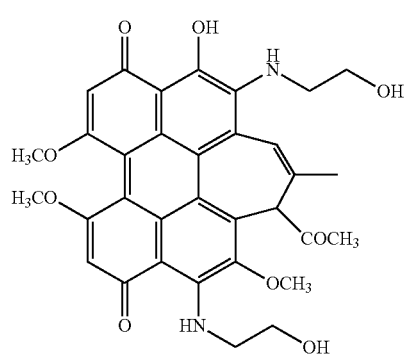

HB-2b

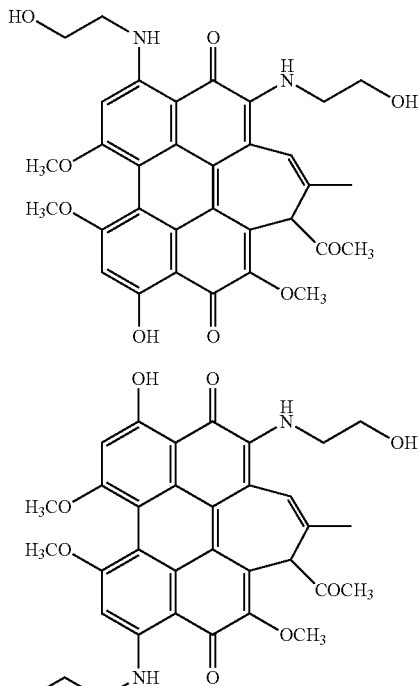

HB-2c

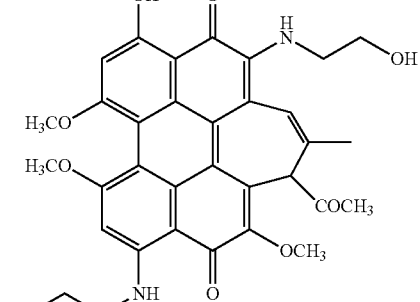

HB-2d

Example 8

Preparation of an aminoethanol-polyethylene glycol (of different chain lengths)-substituted hypocrellin derivative ($R_1=R_2=$—$CH_2CH_2$—OCO— PEGn-OCH$_3$, $R_3=$—COCH$_3$, $R_4=$—H) (PEG is polyethylene glycol, n is the number of ethylene glycol units, and n=1, 6, 12): hypocrellin B HB (100 mg, 0.18 mmol) and 2-(2-aminoethoxy)ethanol (2 mmol) were dissolved in 100 mL of anhydrous acetonitrile, after fully mixed, a mixture was heated to 100° C. under the protection of nitrogen and stirred in a lucifugous condition for a reaction for 12 h, a solvent was distilled off after the reaction, a blue black solid was dissolved in 100 mL of dichloromethane, a solution was washed with distilled water three times, an organic layer was dried and filtered, and an organic phase was spin-dried to obtain a crude product. The obtained crude product was added to DCC (200 mg) and dissolved in 50 mL of anhydrous dichloromethane, to react with polyethylene glycol methyl esters (HOOC-PEGn-OCH$_3$, 2 g) of different chain lengths, respectively, and a reaction solution was stirred in a lucifugous condition at room temperature for a reaction for 8 h. After the reaction, the reaction solution was added to 100 mL of dichloromethane, a mixed solution was washed once with 100 mL of a dilute hydrochloric acid aqueous solution and then washed with distilled water three times, an organic layer was dried by using anhydrous magnesium sulfate and filtered, and the crude product was separated out by means of thin-layer chromatography, with a developing agent being a mixed solution of ethyl acetate:ethanol=5:1, to obtain blue black solid products HB-2a-PEGn, HB-2b-PEGn, HB-2c-PEGn, and HB-2d-PEGn (n=1, 6, 12), respectively. HB-2a-PEG1 (n=1): yield: 12.2%, $R_f$: 0.34; MS (ESI+): 860.3; maximum absorption wavelength: 620 nm; molar extinction coefficient: 30,500 $M^{-1}cm^{-1}$; and singlet oxygen yield: 30%. HB-2b-PEG6 (n=6): yield: 8.5%, $R_f$: 0.32; MS (ESI+):

1300.6; maximum absorption wavelength: 622 nm; molar extinction coefficient: 31,000 $M^{-1}cm^{-1}$; and singlet oxygen yield: 32%. HB-2c-PEG6 (n=6): yield: 18.4%, $R_f$: 0.26; MS (ESI+): 1300.6; maximum absorption wavelength: 628 nm; molar extinction coefficient: 33,000 $M^{-1}cm^{-1}$; and singlet oxygen yield: 35%. HB-2c-PEG12 (n=12): yield: 17.1%, $R_f$: 0.18; MS (ESI+): 1828.9; maximum absorption wavelength: 626 nm; molar extinction coefficient: 32,500 $M^{-1}cm^{-1}$; and singlet oxygen yield: 36%. HB-2c-PEG6 (n=6): yield: 12.2%, $R_f$: 0.20; MS (ESI+): 1300.6; maximum absorption wavelength: 624 nm; molar extinction coefficient: 31500 $M^{-1}cm^{-1}$; and singlet oxygen yield: 30%. HB-1d-PEG6 (n=6): yield: 12.2%, $R_f$: 0.20; MS (ESI+): 1300.6; maximum absorption wavelength: 622 nm; molar extinction coefficient: 32,500 $M^{-1}cm^{-1}$; and singlet oxygen yield: 30%. Structural formulas of the above amino-substituted products are as follows:

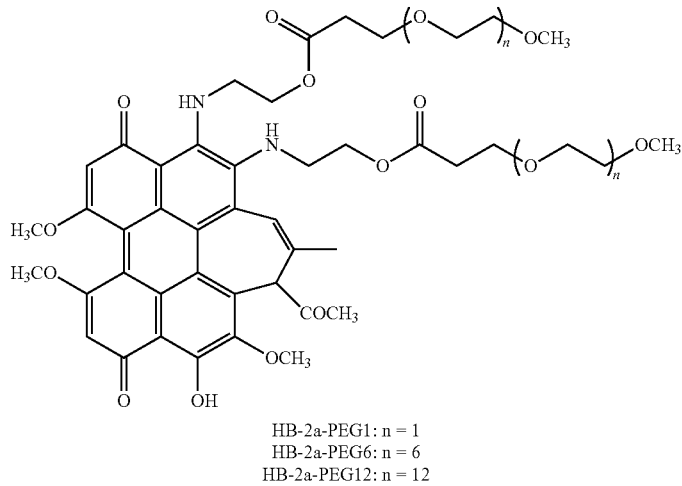

HB-2a-PEG1: n = 1
HB-2a-PEG6: n = 6
HB-2a-PEG12: n = 12

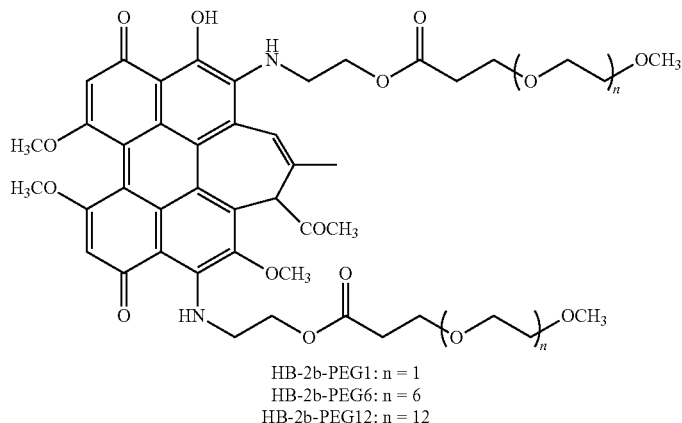

HB-2b-PEG1: n = 1
HB-2b-PEG6: n = 6
HB-2b-PEG12: n = 12

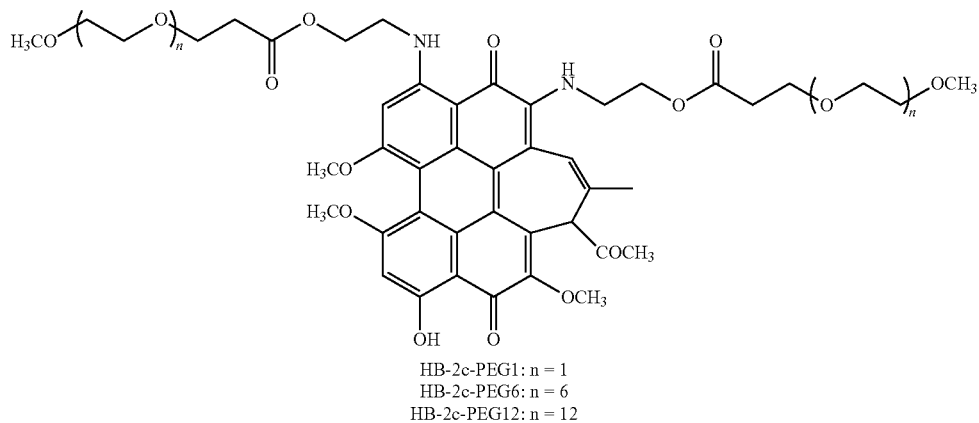

HB-2c-PEG1: n = 1
HB-2c-PEG6: n = 6
HB-2c-PEG12: n = 12

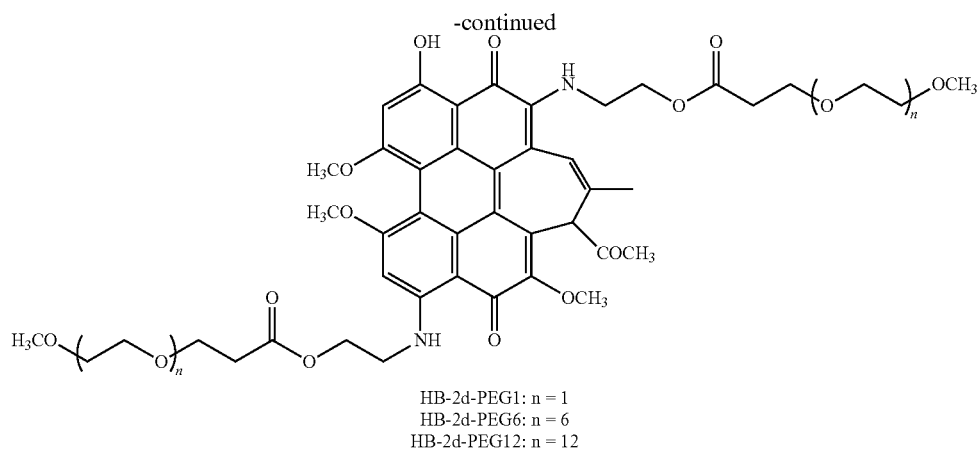

HB-2d-PEG1: n = 1
HB-2d-PEG6: n = 6
HB-2d-PEG12: n = 12

Example 9

Preparation of an aminoethanol-substituted deacetyl hypocrellin derivative ($R_1=R_2=$—$CH_2CH_2$—OH, $R_3=R_4=$—H): a substituted amino raw material is $NH_2$—$CH_2CH_2$—OH, a synthetic method is similar to the preparation of the di-2-(2-aminoethoxy)ethanol-substituted deacetyl hypocrellin B derivative in example 5, and four blue black solid products HC-2a-HC-2d are obtained, respectively. HC-2a: yield: 5.8%, $R_f$: 0.28; MS (ESI+): 558.8; maximum absorption wavelength: 627 nm; molar extinction coefficient: 28.500 $M^{-1}$ $cm^{-1}$; and singlet oxygen yield: 32%. HC-2b: yield: 3.8%, $R_f$: 0.26; MS (ESI+): 558.8; maximum absorption wavelength: 624 nm; molar extinction coefficient: 27.500 $M^{-1}$ $cm^{-1}$; and singlet oxygen yield: 33%. HC-2c: yield: 12.1%, $R_f$: 0.24; MS (ESI+): 558.8; maximum absorption wavelength: 636 nm; molar extinction coefficient: 31,000 $M^{-1}$ $cm^{-1}$; and singlet oxygen yield: 40%. HC-2d: yield: 5.2%, $R_f$: 0.20; MS (ESI+): 558.8; maximum absorption wavelength: 625 nm; molar extinction coefficient: 28,500 $M^{-1}cm^{-1}$; and singlet oxygen yield: 34%. Structural formulas of the above amino-substituted products are as follows:

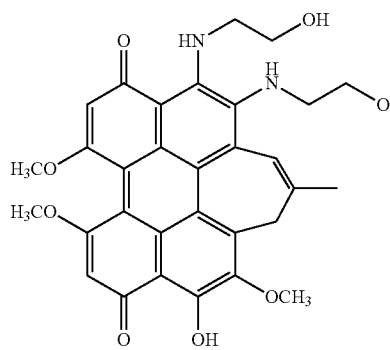

HC-2a

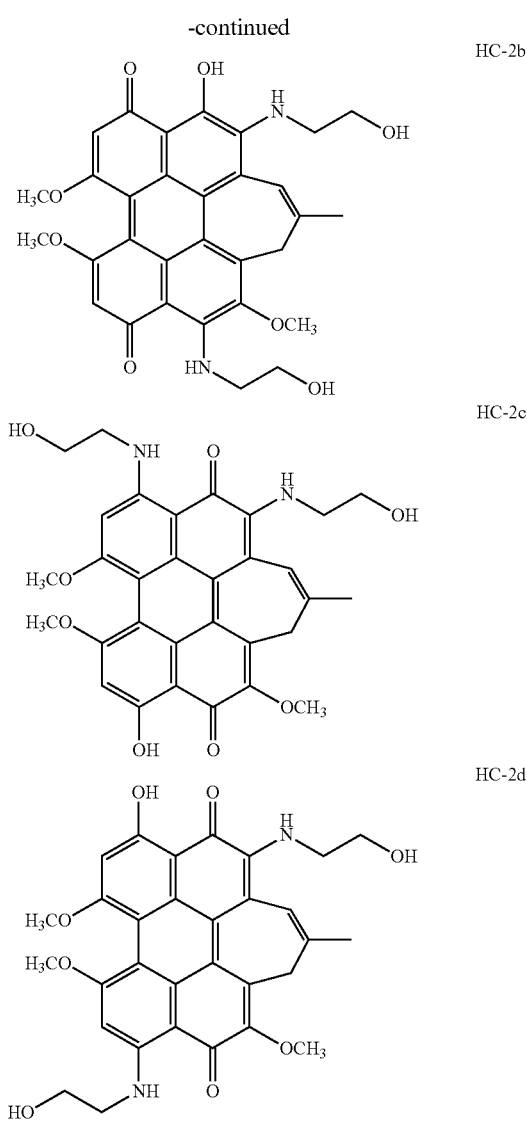

Figure 9:
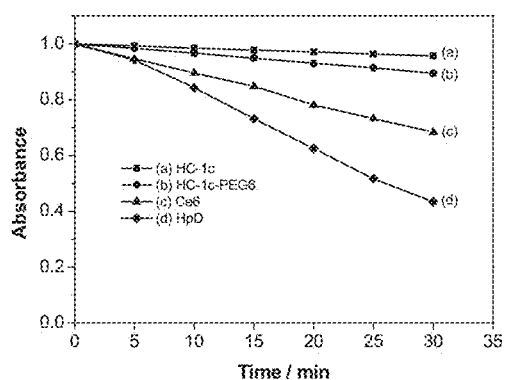
FIG. 9 shows a comparison diagram of photostabilities of the hypocrellin derivative prepared in the present invention and a commercial photosensitizer under irradiation with a laser for 30 min at a light intensity of 20 mW/cm$^2$, in which curve (a) shows the photostability of a diaminoethanol-substituted deacetyl hypocrellin B derivative HC-2c in example 9; curve (b) shows the photostability of a polyethylene glycol-diaminoethanol-substituted deacetyl hypocrellin B derivative HC-2c-PEG6 in example 10; curve (c) shows the photostability of a commercial porphin photosensitizer Ce6; and curve (d) shows the photostability of the commercial hematoporphyrin photosensitizer HpD.

As shown in FIG. 9, after being irradiated with a 635 nm laser for 30 min at a light intensity of 20 mW/cm², an absorption spectrum of the above prepared compound HC-2c is not obviously decreased, and an absorption intensity at the maximum wavelength is decreased by less than 10%, indicating that HC-2c has a good light stability, and the photosensitizer does not lose efficacy under continuous laser irradiation.

Example 10

Preparation of an aminoethanol-polyethylene glycol (of different chain lengths)-substituted deacetyl hypocrellin derivative ($R_1=R_2=$—$CH_2CH_2$—$OCO$-$PEGn$-$OCH_3$, $R_3=R_4=$—H) (PEG is polyethylene glycol, n is the number of ethylene glycol units, and n=1, 6, 12): deacetyl hypocrellin HC (100 mg, 0.201 mmol) and 2-(2-aminoethoxy)ethanol (2 mmol) were dissolved in 100 mL of anhydrous acetonitrile, after fully mixed, a mixture was heated to 100° C. under the protection of nitrogen and stirred in a lucifugous condition for a reaction for 12 h, a solvent was distilled off after the reaction, a blue black solid was dissolved in 100 mL of dichloromethane, a solution was washed with distilled water three times, an organic layer was dried and filtered, and an organic phase was spin-dried to obtain a crude product. The obtained crude product was added to DCC (200 mg) and dissolved in 50 mL of anhydrous dichloromethane, to react with polyethylene glycol methyl esters (HOOC-PEGn-OCH$_3$, 2 g) of different chain lengths, respectively, and a reaction solution was stirred in a lucifugous condition at room temperature for a reaction for 8 h. After the reaction, the reaction solution was added to 100 mL of dichloromethane, a mixed solution was washed once with 100 mL of dilute hydrochloric acid aqueous solution and then washed with distilled water three times, an organic layer was dried by using anhydrous magnesium sulfate and filtered, and the crude product was separated out by means of thin-layer chromatography, with a developing agent being a mixed solution of ethyl acetate:ethanol=5:1, to obtain blue black solid products HC-2a-PEGn, HC-2b-PEGn, HC-2c-PEGn, and HC-2d-PEGn (n=1, 6, 12), respectively. HC-2a-PEG1 (n=1): yield: 11.2%, $R_f$: 0.34; MS (ESI+): 818.4; maximum absorption wavelength: 622 nm; molar extinction coefficient: 30,000 $M^{-1}cm^{-1}$; and singlet oxygen yield: 30%. HC-2b-PEG6 (n=6): yield: 10.8%, $R_f$: 0.31; MS (ESI+): 1258.6; maximum absorption wavelength: 625 nm; molar extinction coefficient: 30,500 $M^{-1}$ $cm^{-1}$; and singlet oxygen yield: 31%. HC-2c-PEG6 (n=6): yield: 18.6%, $R_f$: 0.25; MS (ESI+): 1258.6; maximum absorption wavelength: 628 nm; molar extinction coefficient: 33,000 $M^{-1}$ $cm^{-1}$; and singlet oxygen yield: 35%. HC-2c-PEG12 (n=12): yield: 18.1%, $R_f$: 0.20; MS (ESI+): 1786.9; maximum absorption wavelength: 630 nm; molar extinction coefficient: 32,500 $M^{-1}$ $cm^{-1}$; and singlet oxygen yield: 34%. HC-2d-PEG6 (n=6): yield: 12.2%, $R_f$: 0.24; MS (ESI+): 1258.6; maximum absorption wavelength: 624 nm; molar extinction coefficient: 31,500 $M^{-1}$ $cm^{-1}$; and singlet oxygen yield: 32%. Structural formulas of the above amino-substituted products are as follows:

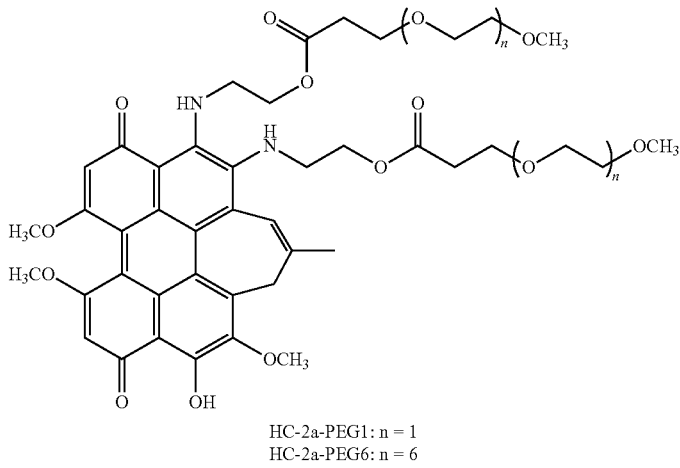

HC-2a-PEG1: n = 1
HC-2a-PEG6: n = 6
HC-2a-PEG8: n = 12

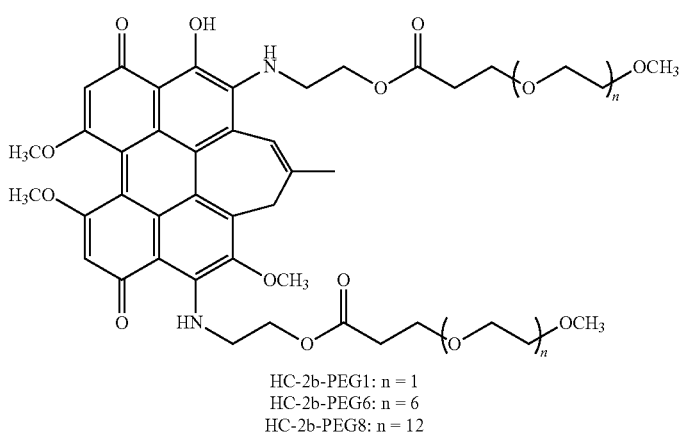

HC-2b-PEG1: n = 1
HC-2b-PEG6: n = 6
HC-2b-PEG8: n = 12

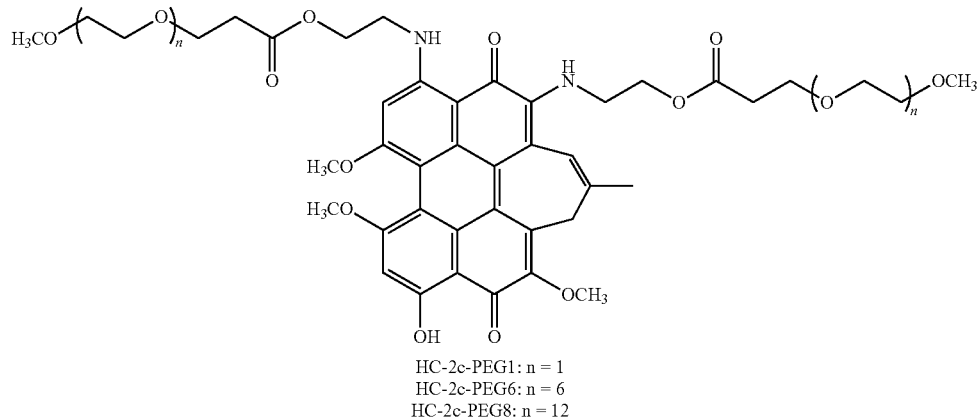

HC-2c-PEG1: n = 1
HC-2c-PEG6: n = 6
HC-2c-PEG8: n = 12

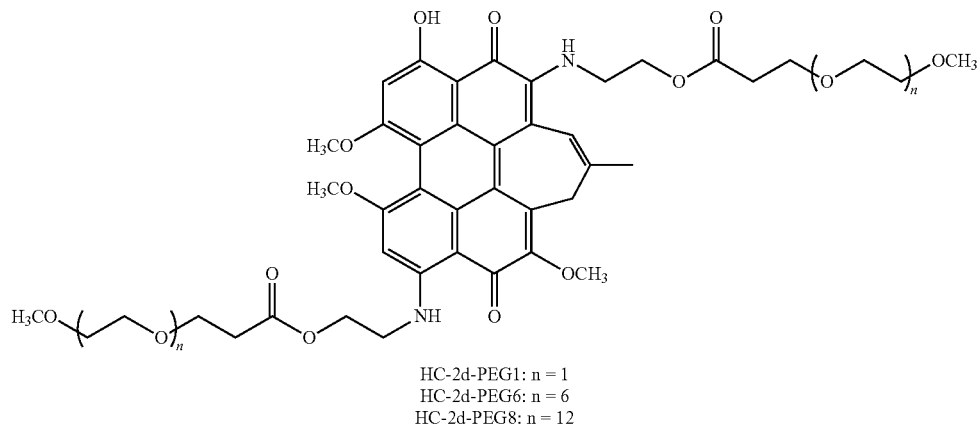

HC-2d-PEG1: n = 1
HC-2d-PEG6: n = 6
HC-2d-PEG8: n = 12

As shown in FIG. 9, after being irradiated with a 635 nm laser for 30 min at a light intensity of 20 mW/cm$^2$, an absorption spectrum of the above prepared compound HC-2d-PEG6 is not obviously decreased, and an absorption intensity at the maximum wavelength is decreased by less than 10%, indicating that HC-2d-PEG6 has a good light stability, and the photosensitizer does not lose efficacy under continuous laser irradiation. However, in the same condition, after being irradiated with a 635 nm laser for 30 min at a light intensity of 20 mW/cm$^2$, maximum absorption performance of the commercial porphin photosensitizer Ce6 is decreased by 30%; and an absorption spectrum of the commercial hematoporphyrin photosensitizer HpD is decreased more, reaching about 50%. Therefore, in the same condition, HC-2d-PEG6 has a better photostability than the commercial photosensitizers.

Example 11

Preparation of a diaminoethyl-polyethylene glycol monomethyl ether (of different chain lengths)-substituted hypocrellin derivative ($R_1=R_2=$—$CH_2CH_2$—PEGn-OH, $R_3=$—$COCH_3$, $R_4=$—H) (PEG is polyethylene glycol, n is the number of ethylene glycol units, and n=4, 8, 12): a substituted amino group is $NH_2$—$CH_2CH_2$—PEGn-OH, a synthetic method is similar to the preparation of the di-2-(2-aminoethoxy)ethanol-substituted hypocrellin B derivative in example 2, and four blue black solid products HB-3a-PEGn, HB-3b-PEGn, HB-3c-PEGn, and HB-3d-PEGn (n=4, 8, 12) are obtained, respectively. HB-3a-PEG4 (n=4): yield: 6.2%, $R_f$: 0.24; MS (ESI+): 980.3; maximum absorption wavelength: 622 nm; molar extinction coefficient: 29,500 M$^{-1}$cm$^{-1}$; and singlet oxygen yield: 28%. HB-3b-PEG6 (n=8): yield: 7.5%, $R_f$: 0.22; MS (ESI+): 1332.6; maximum absorption wavelength: 624 nm; molar extinction coefficient: 29,000 M$^{-1}$ cm$^{-1}$; and singlet oxygen yield: 30%. HB-3c-PEG6 (n=8): yield: 10.4%, $R_f$: 0.16; MS (ESI+): 1332.6; maximum absorption wavelength: 628 nm; molar extinction coefficient: 30,000 M$^{-1}$ cm$^{-1}$; and singlet oxygen yield: 33%. HB-3c-PEG12 (n=12): yield: 10.1%, $R_f$: 0.12; MS (ESI+): 1684.9; maximum absorption wavelength: 626 nm; molar extinction coefficient: 31,000 M$^{-1}$ cm$^{-1}$; and singlet oxygen yield: 35%. HB-3d-PEG6 (n=8): yield: 5.2%, $R_f$: 0.10; MS (ESI+): 1332.6; maximum absorption wavelength: 621 nm; molar extinction coefficient: 30,500 M$^{-1}$ cm$^{-1}$; and singlet oxygen yield: 30%. Structural formulas of the above amino-substituted products are as follows:

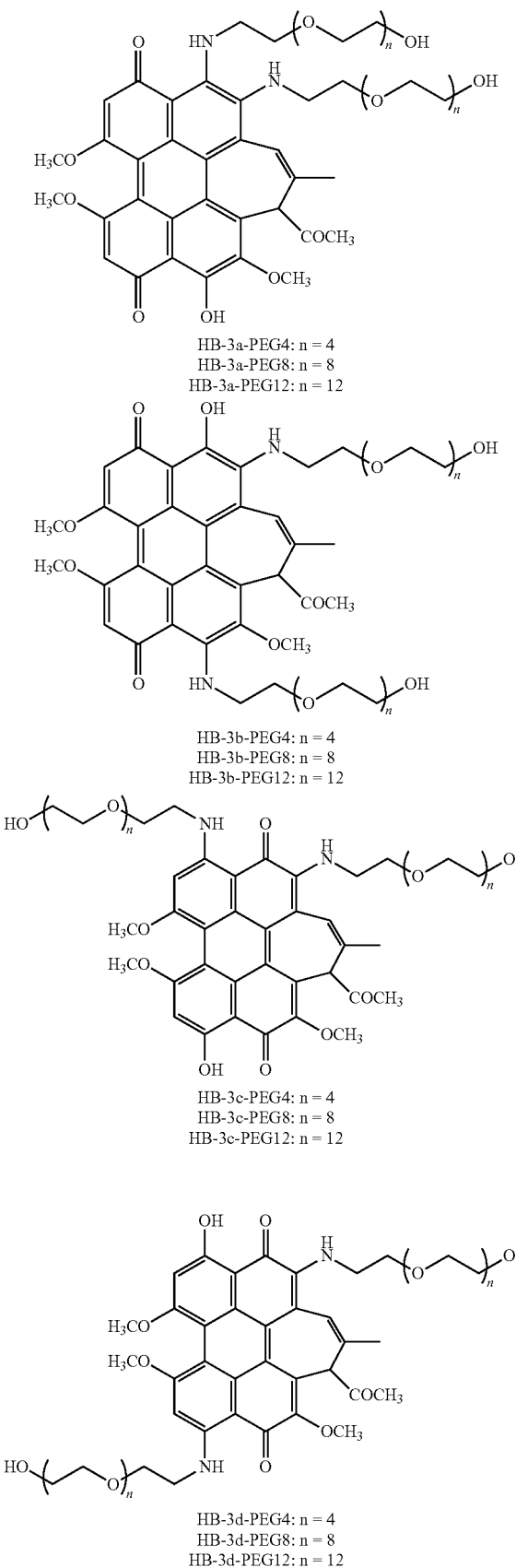

Example 12

Preparation of a diaminoethyl-polyethylene glycol monomethyl ether (of different chain lengths)-substituted deacetyl hypocrellin derivative ($R_1=R_2=$—$CH_2CH_2$—PEGn-OH, $R_3=R_4=$—H) (PEG is polyethylene glycol, n is the number of ethylene glycol units, and n=4, 8, 12): a substituted amino group is $NH_2$—$CH_2CH_2$-PEGn-OH, a synthetic method is similar to the preparation of the di-2-(2-aminoethoxy)ethanol-substituted hypocrellin B derivative in example 2, and four blue black solid products HC-3a-PEGn, HC-3b-PEGn, HC-3c-PEGn, and HC-3d-PEGn (n=4, 8, 12) are obtained, respectively. HC-3a-PEG4 (n=4): yield: 5.4%, $R_f$: 0.25; MS (ESI+): 938.3; maximum absorption wavelength: 622 nm; molar extinction coefficient: 29,000 $M^{-1}cm^{-1}$; and singlet oxygen yield: 28%. HC-3b-PEG6 (n=8): yield: 7.1%, $R_f$: 0.22; MS (ESI+): 1290.6; maximum absorption wavelength: 623 nm; molar extinction coefficient: 29,500 $M^{-1}cm^{-1}$; and singlet oxygen yield: 32%. HC-3c-PEG6 (n=8): yield: 11.2%, $R_f$: 0.18; MS (ESI+): 1290.6; maximum absorption wavelength: 630 nm; molar extinction coefficient: 30,500 $M^{-1}$ $cm^{-1}$; and singlet oxygen yield: 33%. HC-3d-PEG12 (n=12): yield: 8.1%, $R_f$: 0.15; MS (ESI+): 1642.9; maximum absorption wavelength: 628 nm; molar extinction coefficient: 31,500 $M^{-1}$ $cm^{-1}$; and singlet oxygen yield: 36%. HC-3d-PEG6 (n=8): yield: 4.8%, $R_f$: 0.12; MS (ESI+): 1290.6; maximum absorption wavelength: 621 nm; molar extinction coefficient: 30,000 $M^{-1}$ $cm^{-1}$; and singlet oxygen yield: 32%. Structural formulas of the above amino-substituted products are as follows:

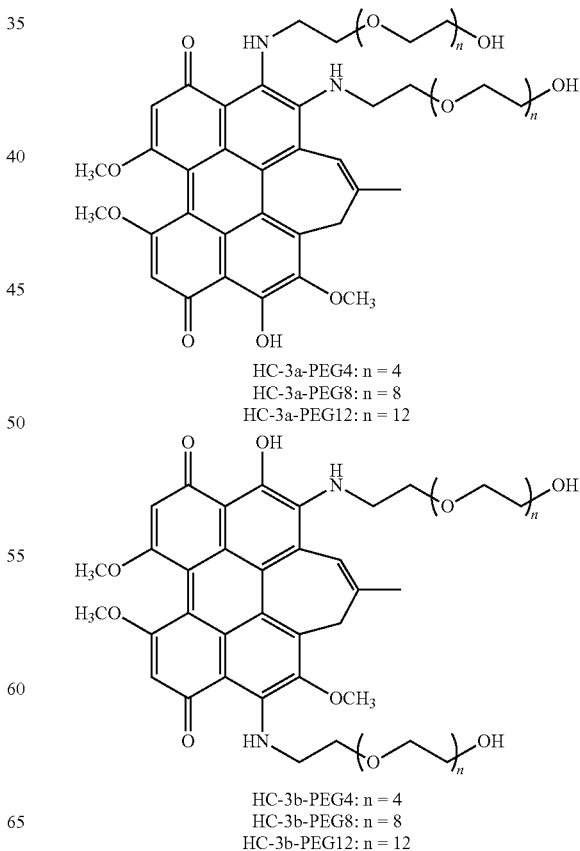

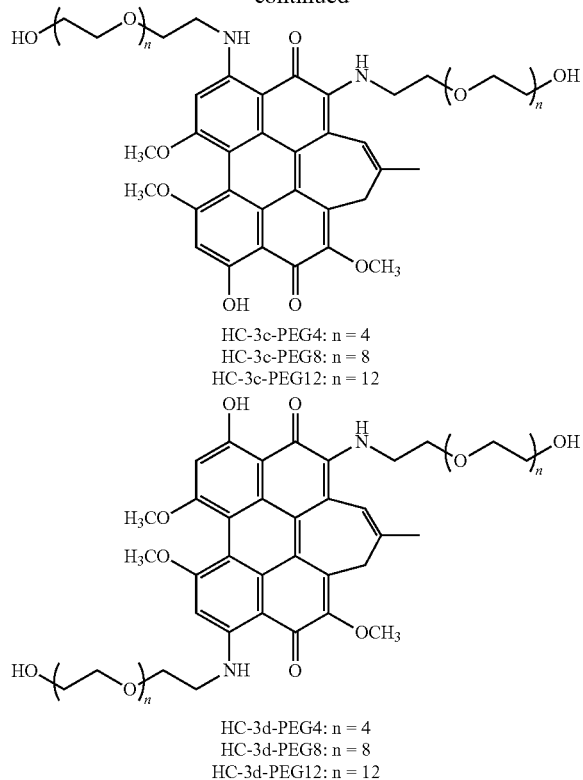

HC-3c-PEG4: n = 4
HC-3c-PEG8: n = 8
HC-3c-PEG12: n = 12

HC-3d-PEG4: n = 4
HC-3d-PEG8: n = 8
HC-3d-PEG12: n = 12

Example 13

Preparation of a diaminoethyl-polyethylene glycol monomethyl ether (of different chain lengths)-substituted hypocrellin derivative ($R_1=R_2=-CH_2CH_2$-PEGn-$OCH_3$, $R_3=R_4=-H$) (PEG is polyethylene glycol, n is the number of ethylene glycol units, and n=4, 8, 16): a substituted amino group is $NH_2-CH_2CH_2-$PEGn-$OCH_3$, a synthetic method is similar to the preparation of the di-2-(2-aminoethoxy)ethanol-substituted hypocrellin B derivative in example 2, and four blue black solid products HC-4a-PEGn, HC-4b-PEGn, HC-4c-PEGn, and HC-4d-PEGn (n=4, 8, 16) are obtained, respectively. HC-4a-PEGn (n=4): yield: 5.4%, $R_f$: 0.25; MS (ESI+): 924.3; maximum absorption wavelength: 622 nm; molar extinction coefficient: 29,000 $M^{-1}$ $cm^{-1}$; and singlet oxygen yield: 28%. HC-4b-PEG6 (n=8): yield: 7.1%, $R_f$: 0.22; MS (ESI+): 1276.6; maximum absorption wavelength: 623 nm; molar extinction coefficient: 29,500 $M^{-1}$ $cm^{-1}$; and singlet oxygen yield: 32%. HC-4c-PEG6 (n=8): yield: 11.2%, $R_f$: 0.18; MS (ESI+): 1276.6; maximum absorption wavelength: 630 nm; molar extinction coefficient: 30,500 $M^{-1}$ $cm^{-1}$; and singlet oxygen yield: 33%. HC-4c-PEG16 (n=16): yield: 8.1%, $R_f$: 0.15; MS (ESI+): 1978.9; maximum absorption wavelength: 628 nm; molar extinction coefficient: 31,500 $M^{-1}cm^{-1}$; and singlet oxygen yield: 36%. HC-4d-PEG6 (n=8): yield: 4.8%, $R_f$: 0.12; MS (ESI+): 1276.6; maximum absorption wavelength: 621 nm; molar extinction coefficient: 30,000 $M^{-1}cm^{-1}$; and singlet oxygen yield: 32%. Structural formulas of the above amino-substituted products are as follows:

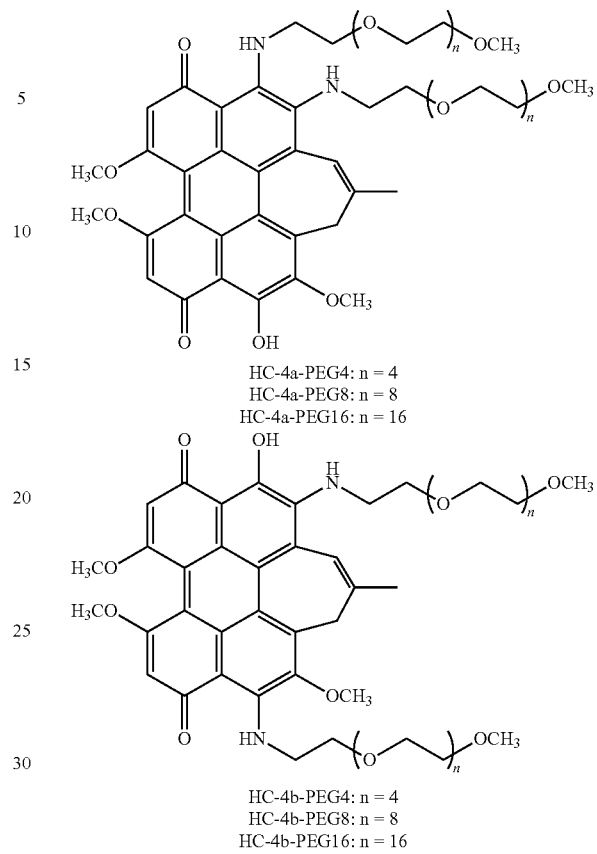

HC-4a-PEG4: n = 4
HC-4a-PEG8: n = 8
HC-4a-PEG16: n = 16

HC-4b-PEG4: n = 4
HC-4b-PEG8: n = 8
HC-4b-PEG16: n = 16

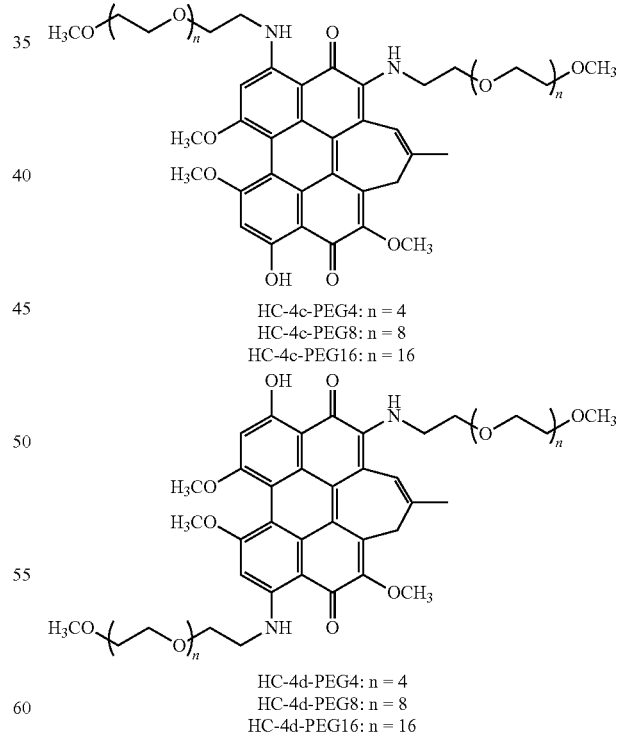

HC-4c-PEG4: n = 4
HC-4c-PEG8: n = 8
HC-4c-PEG16: n = 16

HC-4d-PEG4: n = 4
HC-4d-PEG8: n = 8
HC-4d-PEG16: n = 16

Example 14

Preparation of an ethylene diamine-polyethylene glycol (of different chain lengths)-substituted hypocrellin derivative ($R_1=R_2=$—$CH_2CH_2$—NH—$CH_2CH_2$-PEGn-OH, $R_3=$—$COCH_3$, $R_4=$—H) (PEG is polyethylene glycol, n is the number of ethylene glycol units, and n=1, 4): a substituted amino raw material is $NH_2$—$CH_2CH_2$—NH—$CH_2CH_2$—PEGn-OH, a synthetic method is similar to the preparation of the di-2-(2-aminoethoxy)ethanol-substituted hypocrellin B derivative in example 2, and four blue black solid products HB-5a-PEGn, HB-5b-PEGn, HB-5c-PEGn, and HB-5d-PEGn (n=1, 4) are obtained, respectively. HB-5a-PEG1 (n=1): yield: 6.4%, $R_f$: 0.24; MS (ESI+): 774.3; maximum absorption wavelength: 622 nm; molar extinction coefficient: 29,500 $M^{-1}cm^{-1}$; and singlet oxygen yield: 28%. HB-5b-PEG4 (n=4): yield: 8.1%, $R_f$: 0.28; MS (ESI+): 1038.6; maximum absorption wavelength: 625 nm; molar extinction coefficient: 30,500 $M^{-1}cm^{-1}$; and singlet oxygen yield: 31%. HB-5c-PEG4 (n=4): yield: 10.2%, $R_f$: 0.30; MS (ESI+): 1038.6; maximum absorption wavelength: 628 nm; molar extinction coefficient: 31,500 $M^{-1}cm^{-1}$; and singlet oxygen yield: 35%. HB-5d-PEG1 (n=1): yield: 4.6%, Rf: 0.15; MS (ESI+): 774.6; maximum absorption wavelength: 625 nm; molar extinction coefficient: 30,500$M^{-1}$ $cm^{-1}$; and singlet oxygen yield: 32%. Structural formulas of the above amino-substituted products are as follows:

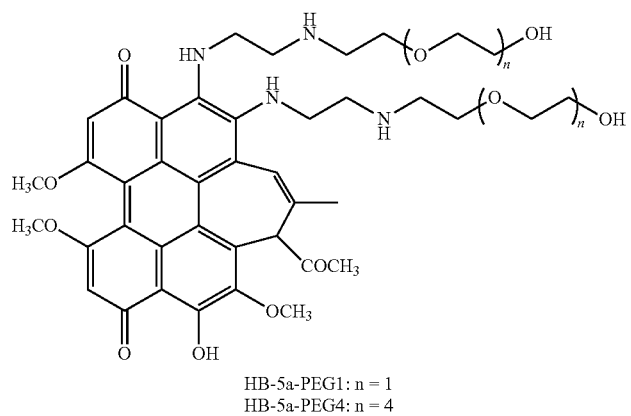

HB-5a-PEG1: n = 1
HB-5a-PEG4: n = 4

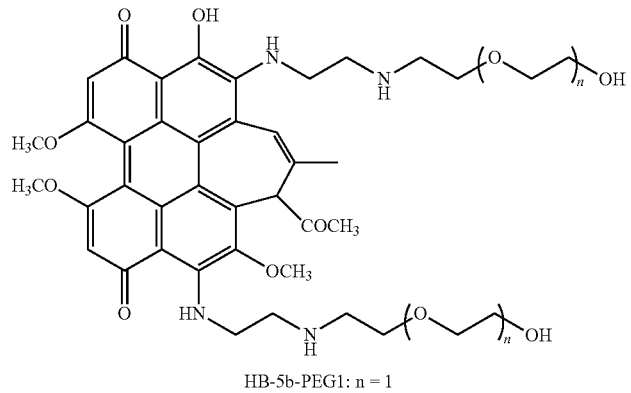

HB-5b-PEG1: n = 1
HB-5b-PEG4: n = 4

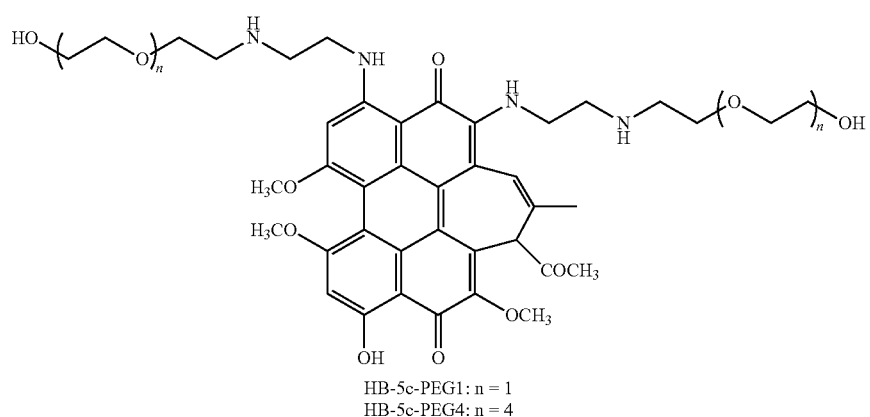

HB-5c-PEG1: n = 1
HB-5c-PEG4: n = 4

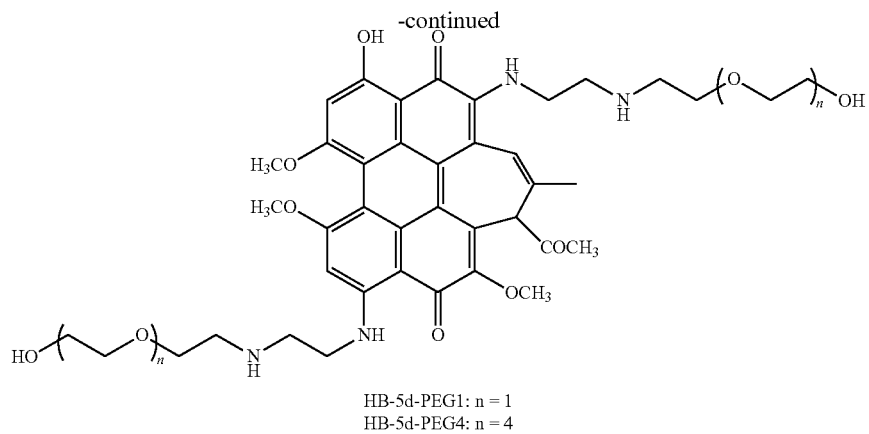

HB-5d-PEG1: n = 1
HB-5d-PEG4: n = 4

Example 15

Preparation of an ethylene diamine-polyethylene glycol (of different chain lengths)-substituted bromo-hypocrellin derivative ($R_1$=$R_2$=—$CH_2CH_2$—NH—$CH_2CH_2$—PEGn-OH, $R_3$=—H, $R_4$=—Br) (PEG is polyethylene glycol, n is the number of ethylene glycol units, and n=1, 4): a substituted amino raw material is $NH_2$—$CH_2CH_2$—NH—$CH_2CH_2$-PEGn-OH, a synthetic method is similar to the preparation of the di-2-(2-aminoethoxy)ethanol-substituted hypocrellin B derivative in example 2, and four blue black solid products HB-5a-Br-PEGn, HB-5b-Br-PEGn, HB-5c-Br-PEGn, and HB-5d-Br-PEGn (n=1, 4) are obtained, respectively. HB-5a-Br-PEG1 (n=1): yield: 7.4%, $R_f$: 0.22; MS (ESI+): 854.3; maximum absorption wavelength: 622 nm; molar extinction coefficient: 30,500 $M^{-1}cm^{-1}$; singlet oxygen yield: 28%. HB-5b-Br-PEG4 (n=4): yield: 8.5%, $R_f$: 0.25; MS (ESI+): 1118.6; maximum absorption wavelength: 625 nm; molar extinction coefficient: 30,000 $M^{-1}cm^{-1}$; singlet oxygen yield: 30%. HB-5c-Br-PEG4 (n=4): yield: 10.5%, $R_f$: 0.33; MS (ESI+): 1118.6; maximum absorption wavelength: 630 nm; molar extinction coefficient: 31,500 $M^{-1}cm^{-1}$; singlet oxygen yield: 36%. HB-5d-Br-PEG1 (n=1): yield: 6.6%, $R_f$: 0.18; MS (ESI+): 854.6; maximum absorption wavelength: 624 nm; molar extinction coefficient: 29,500 $M^{-1}cm^{-1}$; singlet oxygen yield: 32%. Structural formulas of the above amino-substituted products are as follows:

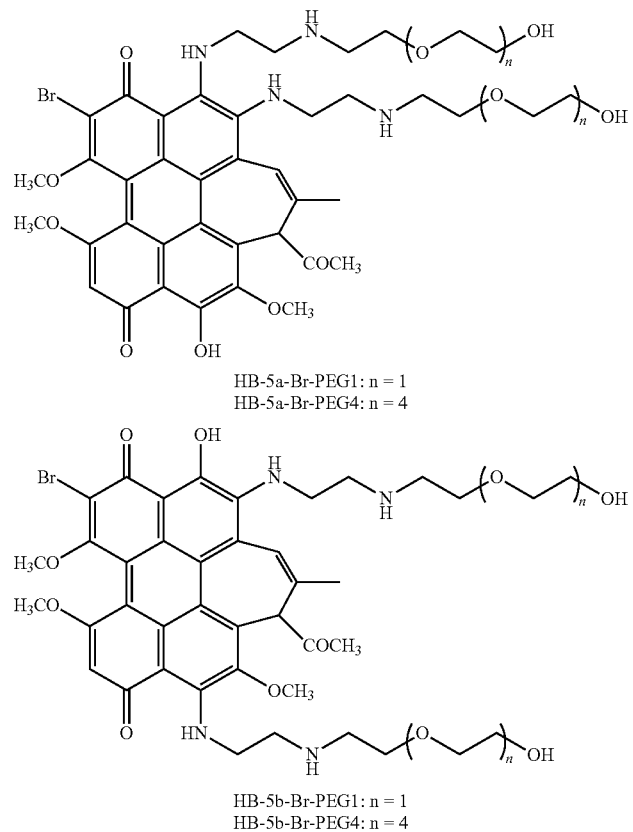

HB-5a-Br-PEG1: n = 1
HB-5a-Br-PEG4: n = 4

HB-5b-Br-PEG1: n = 1
HB-5b-Br-PEG4: n = 4

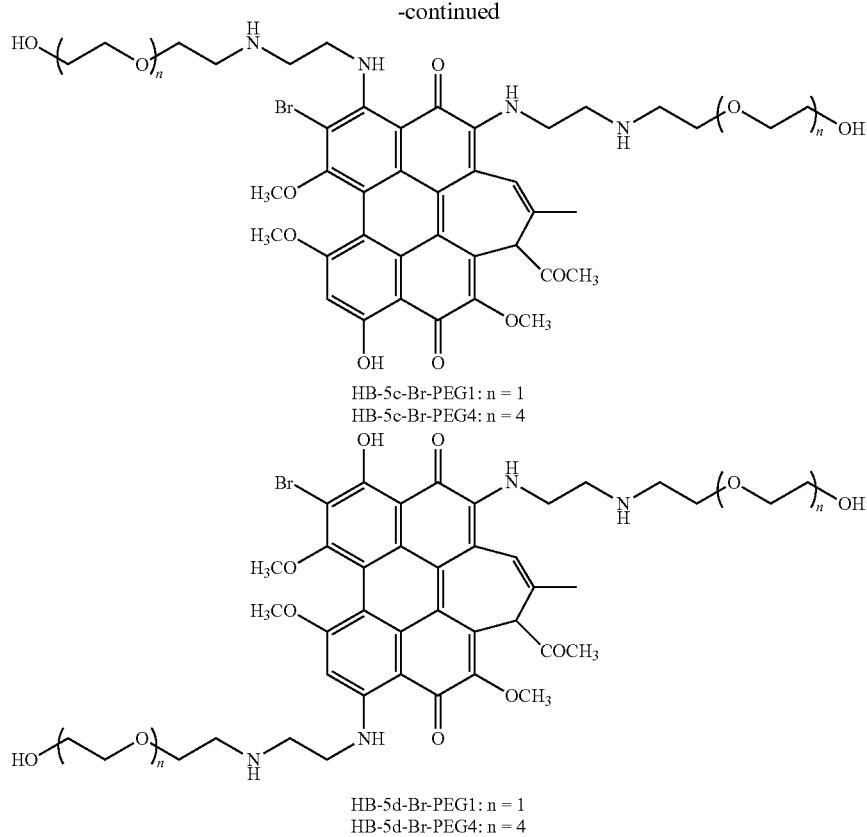

HB-5c-Br-PEG1: n = 1
HB-5c-Br-PEG4: n = 4

HB-5d-Br-PEG1: n = 1
HB-5d-Br-PEG4: n = 4

Example 16

Preparation of a diamino-thiopolyethylene glycol-substituted hypocrellin B derivative ($R_1=R_2=$—$CH_2CH_2$—$SCH_2CH_2$-PEGn-OH, $R_3=$—$COCH_3$, $R_4=$—H) (PEG is polyethylene glycol, n is the number of ethylene glycol units, and n=1, 4): a substituted amino raw material is $NH_2$—$SCH_2CH_2$—PEGn-OH, a synthetic method is similar to the preparation of the di-2-(2-aminoethoxy)ethanol-substituted hypocrellin B derivative in example 2, and four blue black solid products HB-6a-PEGn, HB-6b-PEGn, HB-6c-PEGn, and HB-6d-PEGn (n=1, 4) are obtained, respectively. HB-6a-PEG1 (n=1): yield: 7.4%, $R_f$: 0.26; MS (ESI+): 791.3; maximum absorption wavelength: 622 nm; molar extinction coefficient: 30,500 $M^{-1}$ $cm^{-1}$; singlet oxygen yield: 28%. HB-6b-PEG4 (n=4): yield: 9.1%, $R_f$: 0.28; MS (ESI+): 1055.6; maximum absorption wavelength: 624 nm; molar extinction coefficient: 30,500 $M^{-1}cm^{-1}$; singlet oxygen yield: 32%. HB-6c-PEG4 (n=4): yield: 12.2%, $R_f$: 0.30; MS (ESI+): 1055.6; maximum absorption wavelength: 630 nm; molar extinction coefficient: 32,500 $M^{-1}$ $cm^{-1}$; singlet oxygen yield: 36%. HB-6d-PEG1 (n=1): yield: 5.6%, $R_f$: 0.12; MS (ESI+): 791.6; maximum absorption wavelength: 625 nm; molar extinction coefficient: 30,500 $M^{-1}$ $cm^{-1}$; singlet oxygen yield: 32%. Structural formulas of the above amino-substituted products are as follows:

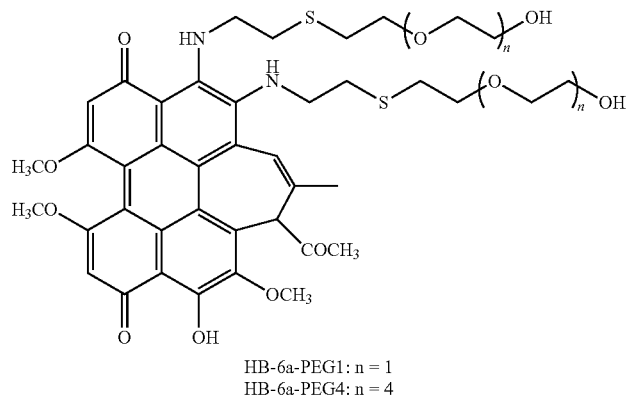

HB-6a-PEG1: n = 1
HB-6a-PEG4: n = 4

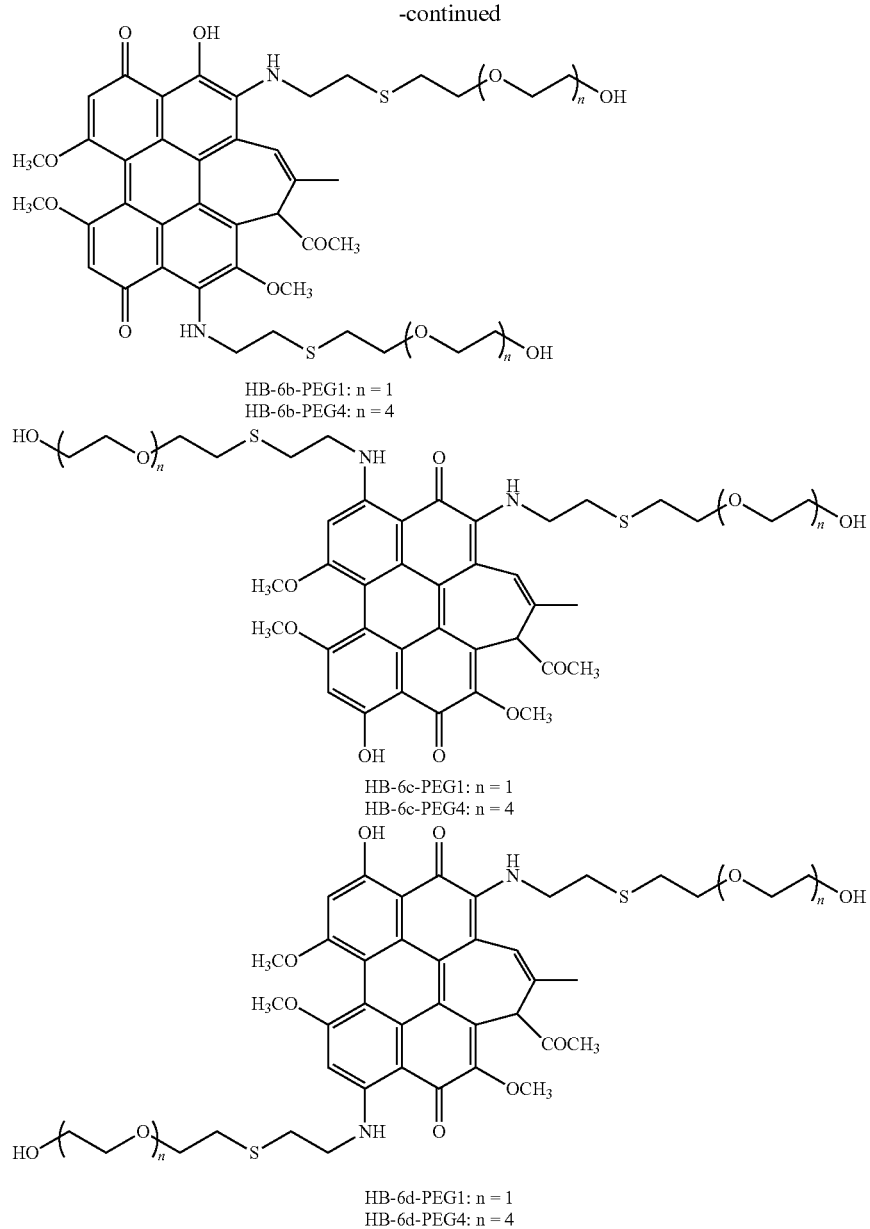

HB-6b-PEG1: n = 1
HB-6b-PEG4: n = 4

HB-6c-PEG1: n = 1
HB-6c-PEG4: n = 4

HB-6d-PEG1: n = 1
HB-6d-PEG4: n = 4

Example 17

Preparation of a diaminoacetic acid-substituted hypocrellin B derivative ($R_1=R_2=$—$CH_2COOH$, $R_3=$—$COCH_3$, $R_4=$—H): hypocrellin B HB (100 mg, 0.18 mmol), aminoacetic acid (10 mmol), and NaOH (2 g) were dissolved in 100 mL of a mixed solution of DMF and water (at a volume ratio of 1:1), and after fully mixed, a mixed solution was heated to 120° C. under the protection of nitrogen and stirred in a lucifugous condition for a reaction for 10 h. After the reaction, dilute hydrochloric acid was added to adjust the pH to weak acidity, and filtration was performed to collect a precipitate. A blue black solid was dissolved in 200 mL of dichloromethane, a solution was washed once with 100 mL of a dilute hydrochloric acid aqueous solution and then washed twice with distilled water, an organic layer was dried by using anhydrous magnesium sulfate and filtered, and an organic phase was spin-dried to obtain a crude product. The obtained crude product was separated out by means of thin-layer chromatography, with a developing agent being a mixed solution of ethyl acetate, diethylamine, and ethanol (at a volume ratio of 20:1:2), to obtain four blue black solid products HB-7a-HB-7d, respectively. HB-7a: yield: 7.4%, $R_f$: 0.32; MS (ESI+): 628.9; maximum absorption wavelength: 620 nm; molar extinction coefficient: 26,500 $M^{-1}cm^{-1}$; singlet oxygen yield: 28%. HB-7b: yield: 6.2%, $R_f$: 0.35; MS (ESI+): 628.9; maximum absorption wavelength: 622 nm; molar extinction coefficient: 28,000 $M^{-1}cm^{-1}$; singlet oxygen yield: 25%. HB-7c: yield: 15.8%, $R_f$: 0.24; MS (ESI+): 628.9; maximum absorption wavelength: 618 nm; molar extinction coefficient: 27,500 $M^{-1}cm^{-1}$; singlet oxygen yield: 27%. HB-7d: yield: 4.8%, $R_f$: 0.28; MS (ESI+): 628.9; maximum absorption wavelength: 623 nm; molar extinction coefficient: 25,000 $M^{-1}cm^{-1}$; singlet oxygen yield: 25%. Structural formulas of the above amino-substituted products are as follows:

HB-7a

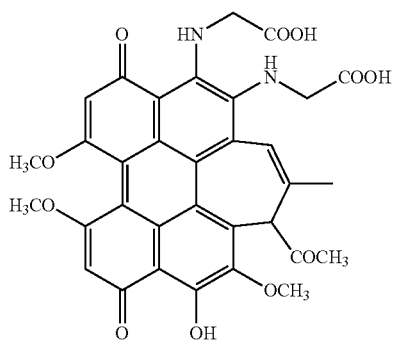

HB-7b

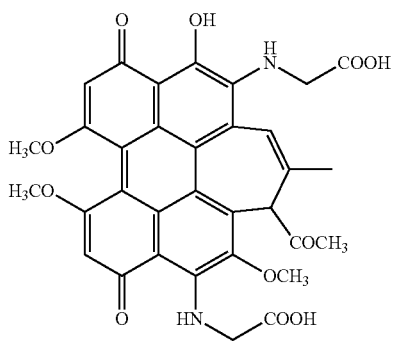

HB-7c

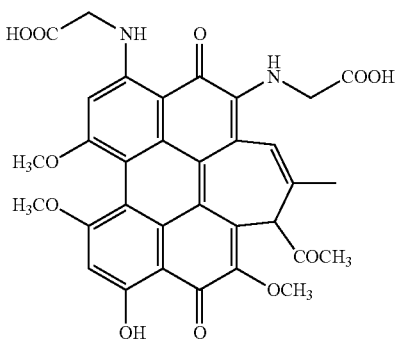

HB-7d

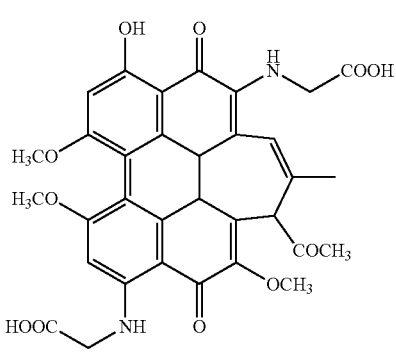

Example 18

Preparation of a diaminoacetic acid-substituted deacetyl hypocrellin derivative ($R_1$=$R_2$=—$CH_2COOH$, $R_3$=$R_4$=—H): deacetyl hypocrellin HC was used as a raw material, a synthetic method is similar to the preparation of the diaminoacetic acid-substituted hypocrellin B derivative in example 17, and four blue black solid products are obtained, respectively. HC-7a: yield: 5.8%, $R_f$: 0.30; MS (ESI+): 586.9; maximum absorption wavelength: 620 nm; molar extinction coefficient: 27,500 $M^{-1}$ $cm^{-1}$; singlet oxygen yield: 28%. HC-7b: yield: 6.6%, $R_f$: 0.33; MS (ESI+): 586.9; maximum absorption wavelength: 622 nm; molar extinction coefficient: 28,500 $M^{-1}cm^{-1}$; singlet oxygen yield: 25%. HC-7c: yield: 12.8%, $R_f$: 0.22; MS (ESI+): 586.9; maximum absorption wavelength: 630 nm; molar extinction coefficient: 29,500 $M^{-1}cm^{-1}$; singlet oxygen yield: 27%. HC-7d: yield: 3.8%, $R_f$: 0.26; MS (ESI+): 586.9; maximum absorption wavelength: 626 nm; molar extinction coefficient: 26,000 $M^{-1}$ $cm^{-1}$; singlet oxygen yield: 25%. Structural formulas of the above amino-substituted products are as follows:

HC-7a

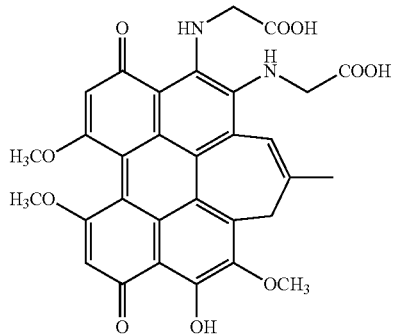

HC-7b

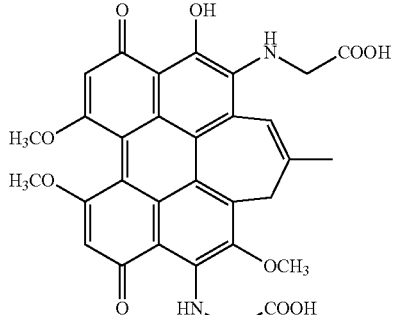

HC-7c

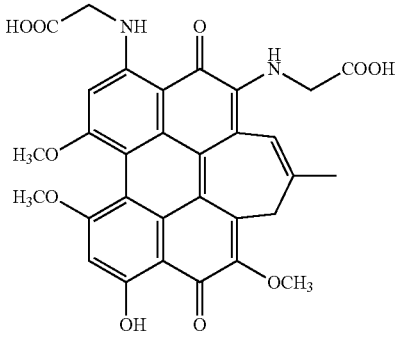

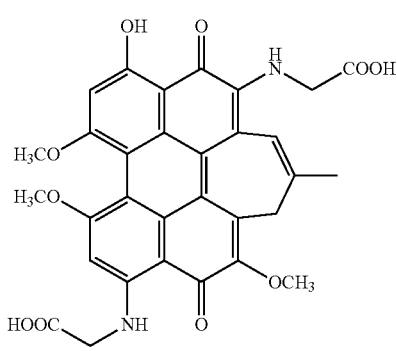

HC-7d

Example 19

Figure 4:
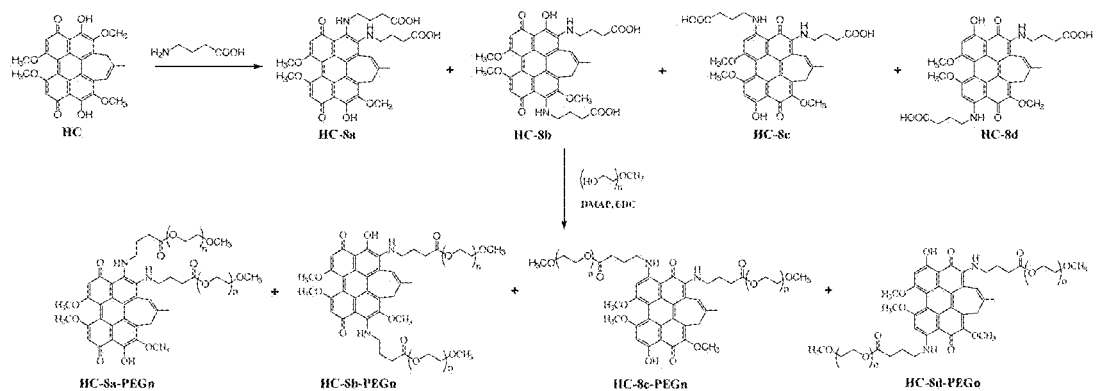
FIG. 4 shows a diagram of a synthetic route of deacetyl hypocrellin derivatives HC-8a-PEGn-HC-8d-PEGn having a peri-position and a 2-position both substituted by a polyethylene glycol-aminobutyric acid group in examples 22 and 23 (n is the number of units of the polyethylene glycol)

Preparation of a diaminobutyric acid-substituted hypocrellin B derivative ($R_1=R_2=$—$CH_2CH_2CH_2COOH$, $R_3=$—$COCH_3$, $R_4=$—H): a synthetic route is as shown in FIG. 4, a substituted amino raw material is an aminobutyric acid, a synthetic method is similar to the preparation of the diaminoacetic acid-substituted hypocrellin B derivative in example 17, and four blue black solid products HB-8a-HB-8d are obtained, respectively. HB-8a: yield: 4.4%, $R_f$: 0.36; MS (ESI+): 684.6; maximum absorption wavelength: 622 nm; molar extinction coefficient: 27,500 $M^{-1}cm^{-1}$; singlet oxygen yield: 25%. HB-8b: yield: 6.2%, $R_f$: 0.32; MS (ESI+): 684.6; maximum absorption wavelength: 618 nm; molar extinction coefficient: 28,500 $M^{-1}cm^{-1}$; singlet oxygen yield: 26%. HB-8c: yield: 5.4%, $R_f$: 0.22; MS (ESI+): 684.6; maximum absorption wavelength: 620 nm; molar extinction coefficient: 29,500 $M^{-1}cm^{-1}$; singlet oxygen yield: 30%. HB-8d: yield: 4.6%, $R_f$: 0.20; MS (ESI+): 684.6; maximum absorption wavelength: 624 nm; molar extinction coefficient: 29,000 $M^{-1}cm^{-1}$; singlet oxygen yield: 26%.

As shown in FIGS. 5(a) and 5(b), the hypocrellin derivative having a peri-position substituted by an amino group (HB-2a) of the present invention has very wide and strong absorption performance in the phototherapy window, has a maximum absorption spectrum wavelength reaching about 650 nm, which is redshifted by about 200 nm relative to a maximum absorption peak (450 nm) of the parent hypocrellin, and has a molar extinction coefficient of about 30000 $M^{-1}cm^{-1}$, presenting an extremely strong red-light absorption capability.

As shown in FIGS. 6(a) and 6(b): the experiments indicate that, it is measured by using singlet oxygen and superoxide radical scavengers that, the hypocrellin derivative having a peri-position substituted by an amino group can efficiently produce photosensitive reactive species, primarily producing singlet oxygen, and also producing a small amount of superoxide radicals. The photosensitizer molecule HB-8a contains two water-soluble carboxyl groups, making the photosensitizer molecules have very high water solubility in a physiological condition; and experiments indicate that each milliliter of normal saline can dissolve more than 5 mg of the photosensitizer molecules, presenting excellent water solubility. Therefore, the photosensitive drug HB-8a can be well transported in blood vessels during intravenous injection, without causing a vascular blockage. Structural formulas of the above amino-substituted products are as follows:

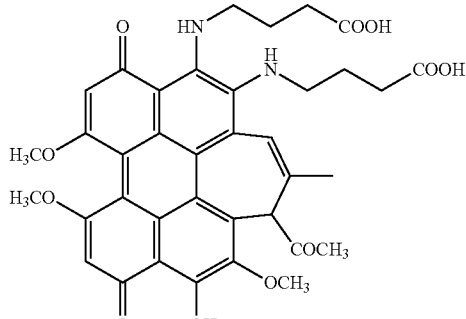

HB-8a

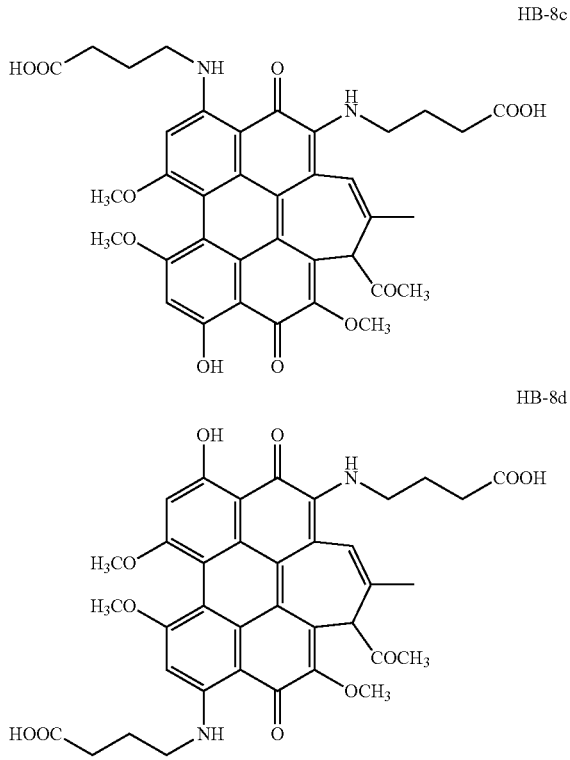

HB-8b

HB-8c

HB-8d

The above prepared compound HB-8c contains two carboxylic acid groups, making the photosensitizer molecules have good water solubility in a physiological condition; and each milliliter of normal saline can dissolve more than 10 mg of photosensitizer molecules. Therefore, the photosensitive drug can be well transported in blood vessels during intravenous injection, without causing a vascular blockage.

Example 20

Preparation of an aminobutyric acid-polyethylene glycol (of different chain lengths)-substituted hypocrellin derivative ($R_1=R_2=$—$CH_2CH_2CH_2COO$—$PEGn$, $R_3=$—$COCH_3$, $R_4=$—H): hypocrellin B HB (100 mg, 0.18 mmol), aminobutyric acid (10 mmol), and NaOH (2 g) were dissolved in 100 mL of a mixed solution of DMF and water (at a volume ratio of 1:1), and after fully mixed, a mixed solution was heated to 120° C. under the protection of nitrogen and stirred in a lucifugous condition for a reaction for 10 h. After the reaction, dilute hydrochloric acid was added to adjust the pH to weak acidity, and filtration was performed to collect a precipitate. A blue black solid was dissolved in 200 mL of dichloromethane, a solution was washed once with 100 mL of a dilute hydrochloric acid aqueous solution and then washed twice with distilled water, an organic layer was dried by using anhydrous magnesium sulfate, filtered, and spin-dried. Add DCC (200 mg) to the obtained crude product and dissolved in 50 mL of anhydrous dichloromethane, to react with polyethylene glycol methyl esters (HOOC-PEGn-OCH₃, 2 g) of different chain lengths, respectively, and a reaction solution was stirred in a lucifugous condition at room temperature for a reaction for 8 h. After the reaction, the reaction solution was added to 100 mL of dichloromethane, a mixed solution was washed once with 100 mL of dilute hydrochloric acid aqueous solution and then washed with distilled water three times, an organic layer was dried by using anhydrous magnesium sulfate and filtered, and the crude product was separated out by means of thin-layer chromatography, with a developing agent being a mixed solution of ethyl acetate:ethanol=5:1, to obtain blue black solid products HB-8a-PEGn, HB-8b-PEGn, HB-8c-PEGn, and HB-8d-PEGn (n=1, 6, 12), respectively. HB-8a-PEG1 (n=1): yield: 12.8%, $R_f$: 0.34; MS (ESI+): 800.3; maximum absorption wavelength: 621 nm; molar extinction coefficient: 30,500 $M^{-1}cm^{-1}$; singlet oxygen yield: 28%. HB-8b-PEG6 (n=6): yield: 8.9%, $R_f$: 0.36; MS (ESI+): 1240.6; maximum absorption wavelength: 622 nm; molar extinction coefficient: 30,000 $M^{-1}$ $cm^{-1}$; singlet oxygen yield: 30%. HB-8c-PEG6 (n=6): yield: 16.4%, $R_f$: 0.28; MS (ESI+): 1240.6; maximum absorption wavelength: 630 nm; molar extinction coefficient: 32,500 $M^{-1}$ $cm^{-1}$; singlet oxygen yield: 34%. HB-8c-PEG12 (n=12): yield: 15.1%, $R_f$: 0.18; MS (ESI+): 1768.9; maximum absorption wavelength: 628 nm; molar extinction coefficient: 33,000 $M^{-1}cm^{-1}$; singlet oxygen yield: 36%. HB-8d-PEG6 (n=6): yield: 13.2%, $R_f$: 0.22; MS (ESI+): 1240.6; maximum absorption wavelength: 620 nm; molar extinction coefficient: 31,500 $M^{-1}$ $cm^{-1}$; singlet oxygen yield: 32%. Structural formulas of the above amino-substituted products are as follows:

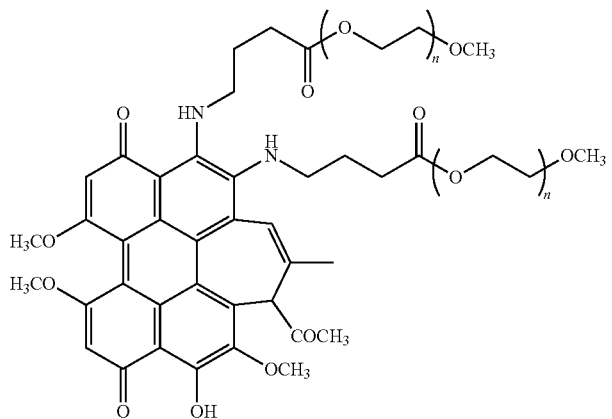

HB-8a-PEG1: n = 1
HB-8a-PEG6: n = 6
HB-8a-PEG12: n = 12

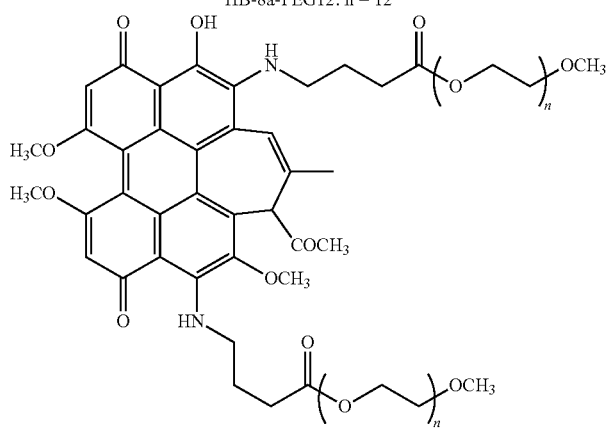

HB-8b-PEG1: n = 1
HB-8b-PEG6: n = 6
HB-8b-PEG12: n = 12

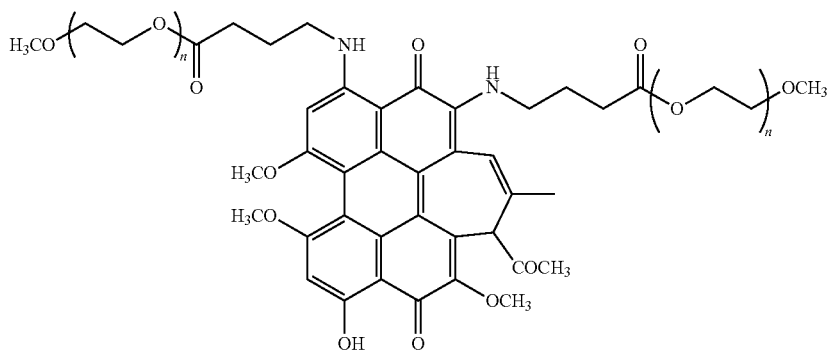

HB-8c-PEG1: n = 1
HB-8c-PEG6: n = 6
HB-8c-PEG12: n = 12

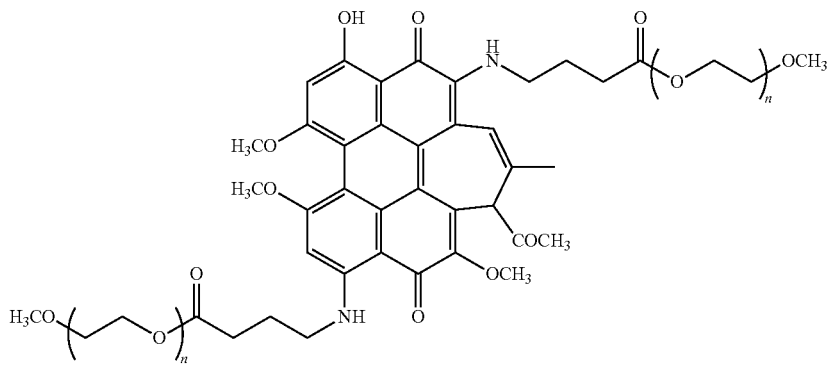

HB-8d-PEG1: n = 1
HB-8d-PEG6: n = 6
HB-8d-PEG12: n = 12

Example 21

Preparation of a diaminobutyric acid-amino PEG (of different chain lengths)-substituted hypocrellin B derivative ($R_1=R_2=-(CH_2)_3CO-NH-PEGn$, $R_3=-COCH_3$, $R_4=-H$) (PEG is polyethylene glycol, n is the number of ethylene glycol units, and n=1, 6, 12): a synthetic route is similar to the preparation of the diaminobutyric acid-substituted polyethylene glycol-modified hypocrellin B derivative in example 20, and four blue black solid products HB-8a-NH-PEGn, HB-8b-NH-PEGn, HB-8c-NH-PEGn, and HB-8d-NH-PEGn (n=1, 6, 12) are obtained, respectively. HB-8a-NH-PEG1 (n=1): yield: 10.8%, $R_f$: 0.34; MS (ESI+): 844.3; maximum absorption wavelength: 621 nm; molar extinction coefficient: 30,500 $M^{-1} cm^{-1}$; singlet oxygen yield: 28%. HB-8b-NH-PEG6 (n=6): yield: 8.0%, $R_f$: 0.38; MS (ESI+): 1284.6; maximum absorption wavelength: 624 nm; molar extinction coefficient: 31,000 $M^{-1}cm^{-1}$; singlet oxygen yield: 30%. HB-8c-NH-PEG6 (n=6): yield: 15.4%, $R_f$: 0.29; MS (ESI+): 1284.6; maximum absorption wavelength: 632 nm; molar extinction coefficient: 32,000 $M^{-1} cm^{-1}$; singlet oxygen yield: 35%. HB-8c-NH-PEG12 (n=12): yield: 14.1%, $R_f$: 0.18; MS (ESI+): 1812.9; maximum absorption wavelength: 628 nm; molar extinction coefficient: 33,500 $M^{-1}cm^{-1}$; singlet oxygen yield: 38%. HB-8d-NH-PEG6 (n=6): yield: 13.5%, $R_f$: 0.24; MS (ESI+): 1284.6; maximum absorption wavelength: 622 nm; molar extinction coefficient: 31,000 $M^{-1}cm^{-1}$; singlet oxygen yield: 34%. Structural formulas of the above amino-substituted products are as follows:

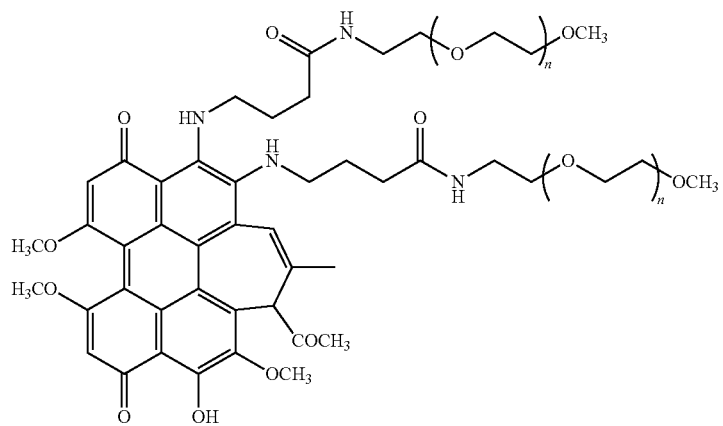
HB-8a-NH-PEG1: n = 1
HB-8a-NH-PEG6: n = 6
HB-8a-NH-PEG12: n = 12
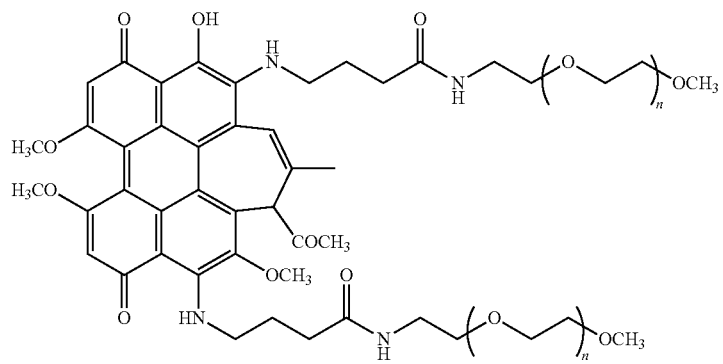
HB-8b-NH-PEG1: n = 1
HB-8b-NH-PEG6: n = 6
HB-8b-NH-PEG12: n = 12
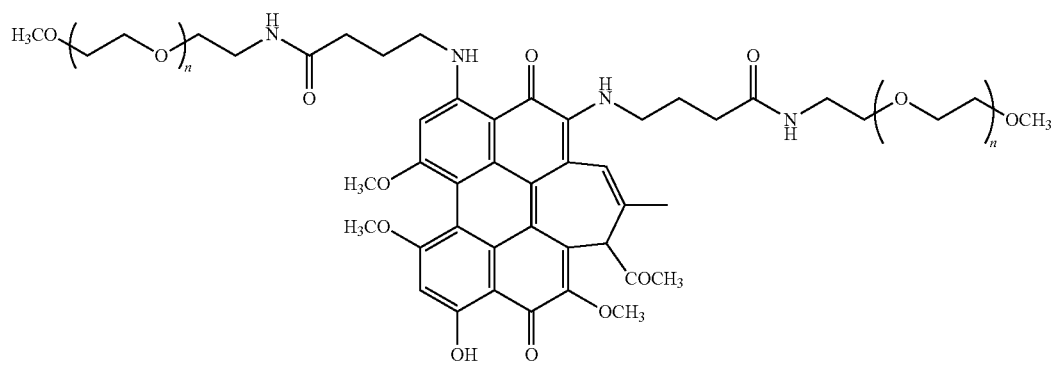
HB-8c-NH-PEG1: n = 1
HB-8c-NH-PEG6: n = 6
HB-8c-NH-PEG12: n = 12

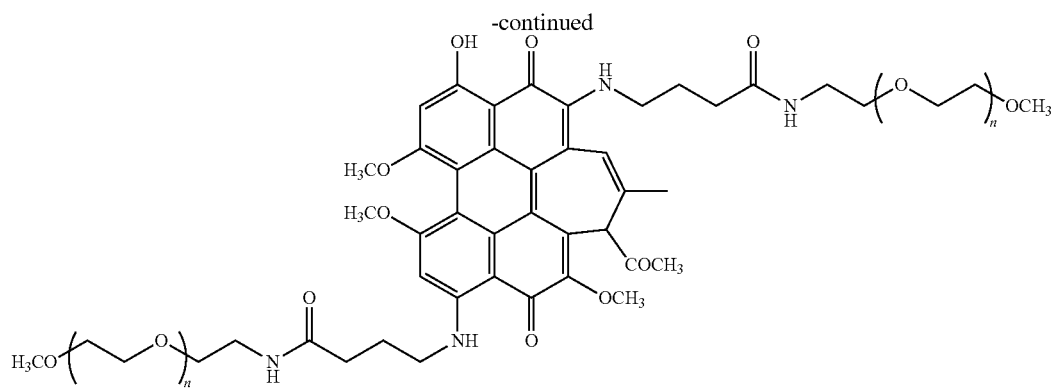

HB-8d-NH-PEG1: n = 1
HB-8d-NH-PEG6: n = 6
HB-8d-NH-PEG12: n = 12

Example 22

Preparation of a diaminobutyric acid-substituted deacetyl hypocrellin derivative ($R_1=R_2=$—CH$_2$(CH$_2$)$_2$COOH, $R_3=R_4=$—H): a synthetic method is as shown in FIG. 4, deacetyl hypocrellin HC is used as a raw material, the synthetic method is similar to the preparation of the diaminoacetic acid-substituted hypocrellin derivative in example 17, and four blue black solid products HC-8a-HC-8d are obtained, respectively. HC-8a: yield: 5.4%, $R_f$: 0.30; MS (ESI+): 642.9; maximum absorption wavelength: 620 nm; molar extinction coefficient: 28,500 M$^{-1}$ cm$^{-1}$; singlet oxygen yield: 26%. HC-8b: yield: 5.2%, $R_f$: 0.34; MS (ESI+): 642.9; maximum absorption wavelength: 622 nm; molar extinction coefficient: 28,000 M$^{-1}$cm$^{-1}$; singlet oxygen yield: 25%. HC-8c: yield: 16.8%, $R_f$: 0.24; MS (ESI+): 642.9; maximum absorption wavelength: 618 nm; molar extinction coefficient: 28,500 M$^{-1}$ cm$^{-1}$; singlet oxygen yield: 27%. HC-8d: yield: 4.2%, $R_f$: 0.25; MS (ESI+): 642.9; maximum absorption wavelength: 623 nm; molar extinction coefficient: 27,000 M$^{-1}$cm$^{-1}$; singlet oxygen yield: 26%. Structural formulas of the above amino-substituted products are as follows:

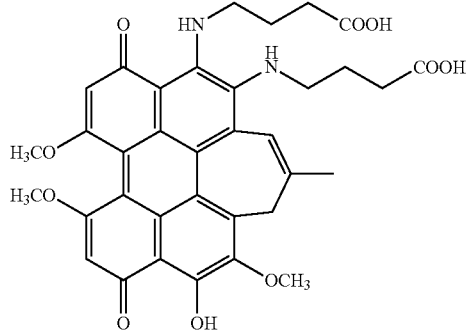
HC-8a

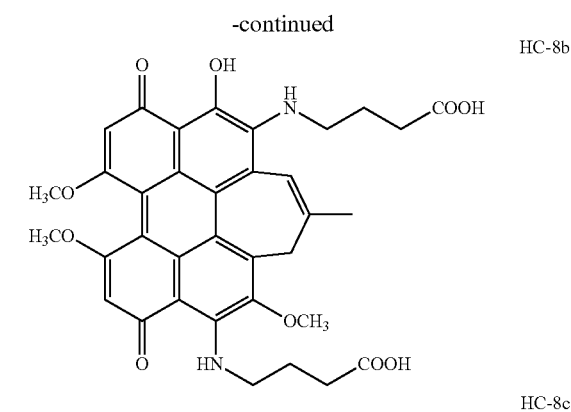
HC-8b

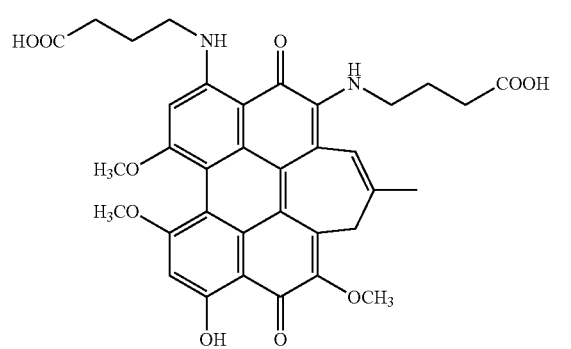
HC-8c

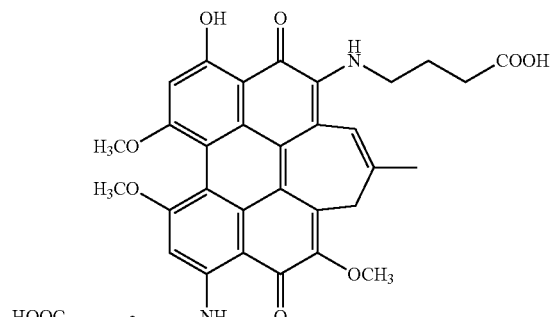
HC-8d

Figure 14:
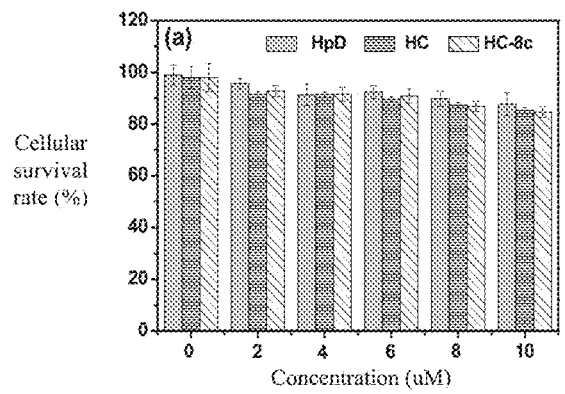
FIG. 14(a) shows dark toxicities, to Hela cells, of the hematoporphyrin derivative HpD, the deacetyl hypocrellin HC, and the diaminobutyric acid-substituted deacetyl hypocrellin HC-8c synthesized in example 22 of the present invention at different concentrations.
FIG. 14(b) shows phototoxicities, to Hela cells, of the hematoporphyrin derivative HpD, the deacetyl hypocrellin HC, and the diaminobutyric acid-substituted deacetyl hypocrellin HC-8c synthesized in example 22 of the present invention at different concentrations.
Figure 14:
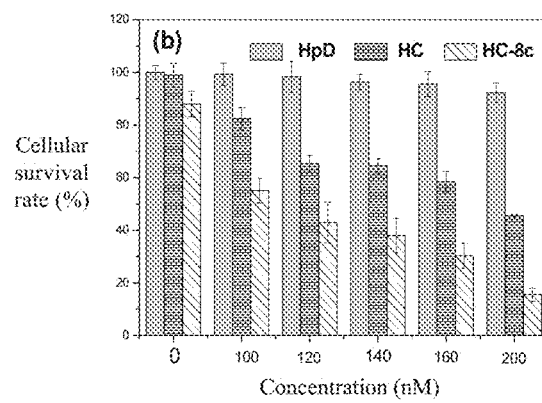

FIGS. 14(a) and 14(b) show effect diagrams of dark toxicity and phototoxicity of HC-8c to Hela cells. It can be seen that HC-8c containing two carboxyl groups has almost no cytotoxicity when not exposed to light. After exposure to 635 nm light, HC-8c with a concentration range of 200 nM can kill more than 85% of the Hela cells, while in the same condition, the deacetyl hypocrellin HC can kill 50% of the Hela cells, and the commercial photosensitizer hematoporphyrin derivative HpD can kill only about 10% of the Hela cells, indicating that a photodynamic effect of HC-8c is significantly better than that of HC and the commercial photosensitizer hematoporphyrin HpD.

Example 23

Preparation of an aminobutyric acid-polyethylene glycol (of different chain lengths)-substituted deacetyl hypocrellin derivative ($R_1$=$R_2$=—$CH_2CH_2CH_2COO$-PEGn, $R_3$=$R_4$=—H) (PEG is polyethylene glycol, n is the number of ethylene glycol units, and n=1, 6, 12): for a synthetic method, reference is made to the preparation of the diaminobutyric acid-PEG (of different chain lengths)-substituted hypocrellin derivative in example 20, and four blue black solid products HC-8a-PEGn, HC-8b-PEGn, HC-8c-PEGn, and HC-8d-PEGn (n=1, 6, 12) are obtained, respectively. HC-8a-PEG1 (n=1): yield: 11.8%, $R_f$: 0.32; MS (ESI+): 758.3; maximum absorption wavelength: 621 nm; molar extinction coefficient: 30,000 $M^{-1}$ $cm^{-1}$; singlet oxygen yield: 28%. HC-8b-PEG6 (n=6): yield: 8.6%, $R_f$: 0.38; MS (ESI+): 1198.6; maximum absorption wavelength: 624 nm; molar extinction coefficient: 30,000 $M^{-1}cm^{-1}$; singlet oxygen yield: 32%. HC-8c-PEG6 (n=6): yield: 16.8%, $R_f$: 0.26; MS (ESI+): 1198.6; maximum absorption wavelength: 632 nm; molar extinction coefficient: 31,500 $M^{-1}cm^{-1}$; singlet oxygen yield: 36%. HC-8c-PEG12 (n=12): yield: 15.6%, $R_f$: 0.20; MS (ESI+): 1726.9; maximum absorption wavelength: 628 nm; molar extinction coefficient: 32,500 $M^{-1}cm^{-1}$; singlet oxygen yield: 38%. HC-8d-PEG6 (n=6): yield: 14.2%, $R_f$: 0.24; MS (ESI+): 1198.6; maximum absorption wavelength: 624 nm; molar extinction coefficient: 31,500 $M^{-1}$ $cm^{-1}$; singlet oxygen yield: 32%. Structural formulas of the above amino-substituted products are as follows:

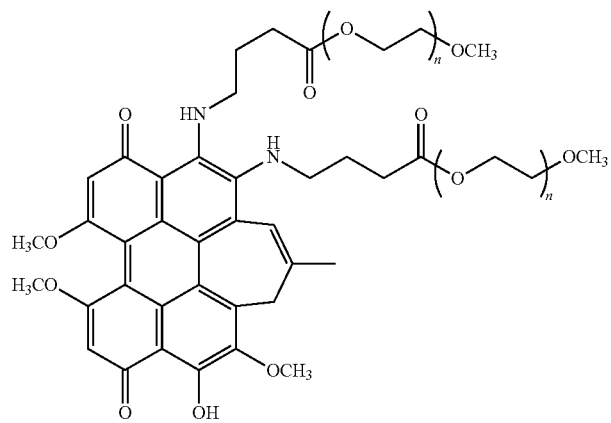

HC-8a-PEG1: n = 1
HC-8a-PEG6: n = 6
HC-8a-PEG12: n = 12

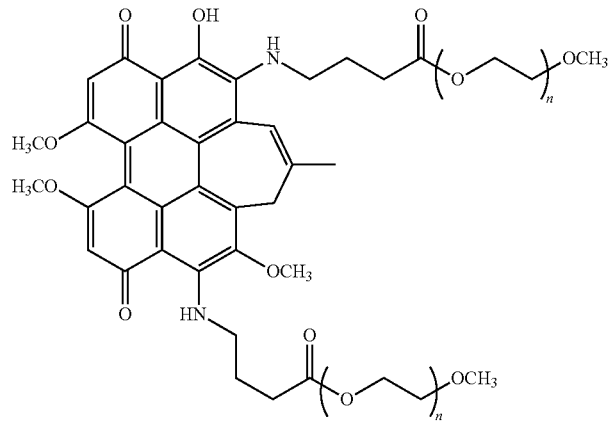

HC-8b-PEG1: n = 1
HC-8b-PEG6: n = 6
HC-8b-PEG12: n = 12

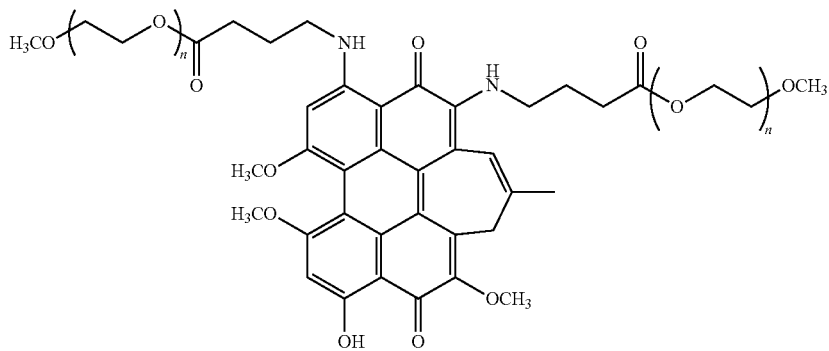

HC-8c-PEG1: n = 1
HC-8c-PEG6: n = 6
HC-8c-PEG12: n = 12

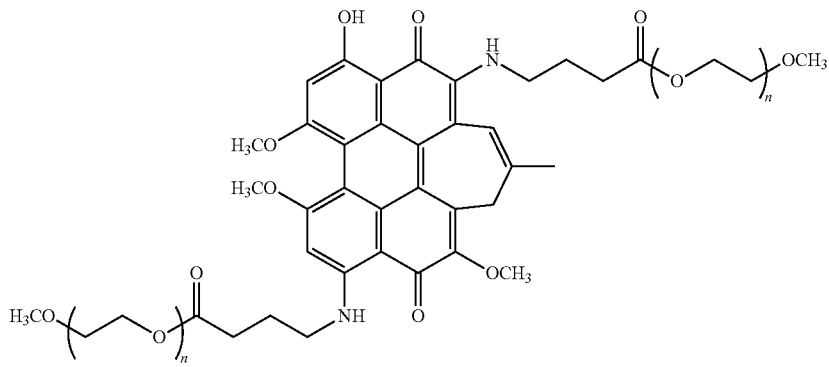

HC-8d-PEG1: n = 1
HC-8d-PEG6: n = 6
HC-8d-PEG12: n = 12

Figure 15:
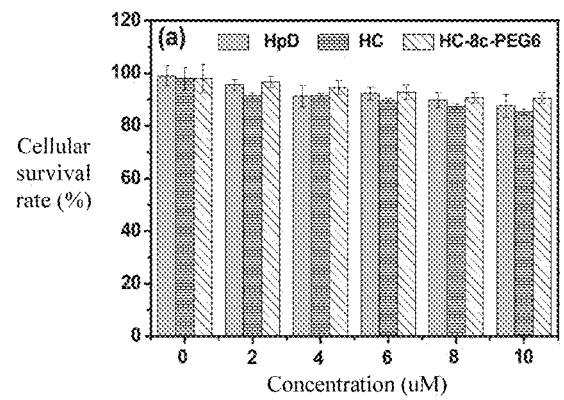
FIG. 15(a) shows dark toxicities, to Hela cells, of the hematoporphyrin derivative HpD, the deacetyl hypocrellin HC, and the polyethylene glycol-diaminobutyric acid-modified deacetyl hypocrellin HC-8c-PEG6 synthesized in example 23 of the present invention at different concentrations.
FIG. 15(b) shows phototoxicities, to Hela cells, of the hematoporphyrin derivative HpD, the deacetyl hypocrellin HC, and the polyethylene glycol-diaminobutyric acid-modified deacetyl hypocrellin HC-8c-PEG6 synthesized in example 23 of the present invention at different concentrations.
Figure 15:
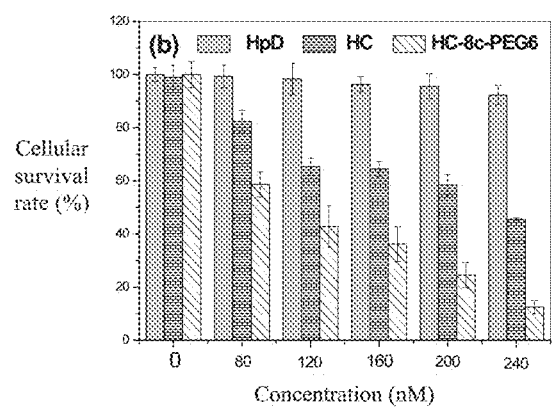

FIGS. 15(a) and 15(b) show effects of dark toxicity and phototoxicity for killing tumor cells of HC-8c-PEG6. HC-8c-PEG6 has almost no cytotoxicity when not exposed to light. After exposure to 635 nm light, HC-8c-PEG6 with a concentration range of 240 nM can kill more than 90% of the Hela cells, while in the same condition, the deacetyl hypocrellin HC can kill 50% of the Hela cells, indicating that a photodynamic effect of HC-8c-PEG6 is significantly better than that of the deacetyl hypocrellin HC and the commercial photosensitizer hematoporphyrin HpD.

Example 24

Preparation of an aminobutyric acid-amino PEG (of different chain lengths)-substituted deacetyl hypocrellin B derivative ($R_1=R_2=-CH_2(CH_2)_4CO-NH-PEGn$, $R_3=R_4=-H$) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HC-8a-NH-PEGn, HC-8b-NH-PEGn, HC-8c-NH-PEGn, and HC-8d-NH-PEGn (n=1, 6, 12) are obtained, respectively. HC-8a-NH-PEG1 (n=1): yield: 12.6%, $R_f$: 0.32; MS (ESI+): 844.3; maximum absorption wavelength: 621 nm; molar extinction coefficient: 30,500 $M^{-1}cm^{-1}$; singlet oxygen yield: 30%. HC-8b-NH-PEG6 (n=6): yield: 8.5%, $R_f$: 0.36; MS (ESI+): 1244.6; maximum absorption wavelength: 622 nm; molar extinction coefficient: 30,000 $M^{-1}$ $cm^{-1}$; singlet oxygen yield: 31%. HC-8c-NH-PEG6 (n=6): yield: 17.8%, $R_f$: 0.28; MS (ESI+): 1244.6; maximum absorption wavelength: 630 nm; molar extinction coefficient: 32,500 $M^{-1}$ $cm^{-1}$; singlet oxygen yield: 35%. HC-8c-NH-PEG12 (n=12): yield: 14.6%, $R_f$: 0.20; MS (ESI+): 1772.9; maximum absorption wavelength: 628 nm; molar extinction coefficient: 32,000 $M^{-1}cm^{-1}$; singlet oxygen yield: 36%. HC-8d-NH-PEG6 (n=6): yield: 12.2%, $R_f$: 0.25; MS (ESI+): 1244.6; maximum absorption wavelength: 625 nm; molar extinction coefficient: 31,000 $M^{-1}cm^{-1}$; singlet oxygen yield: 32%. Structural formulas of the above amino-substituted products are as follows:

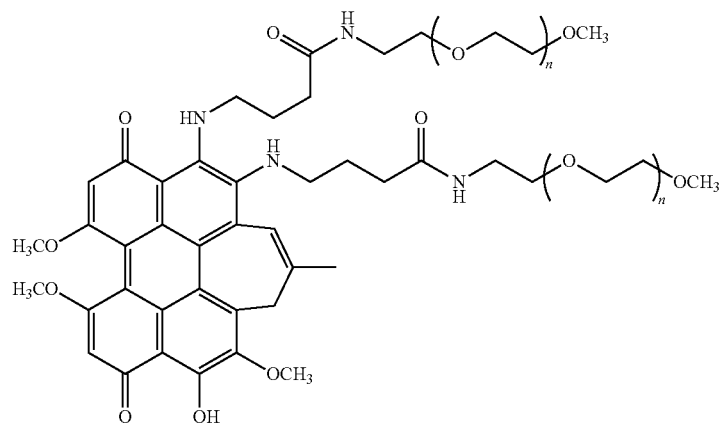
HC-8a-NH-PEG1: n = 1
HC-8a-NH-PEG6: n = 6
HC-8a-NH-PEG12: n = 12
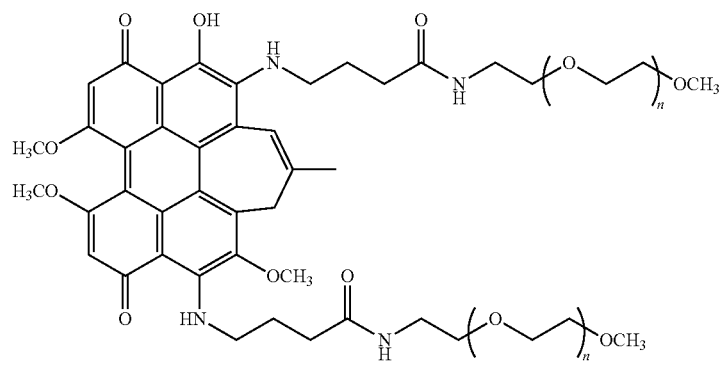
HC-8b-NH-PEG1: n = 1
HC-8b-NH-PEG6: n = 6
HC-8b-NH-PEG12: n = 12
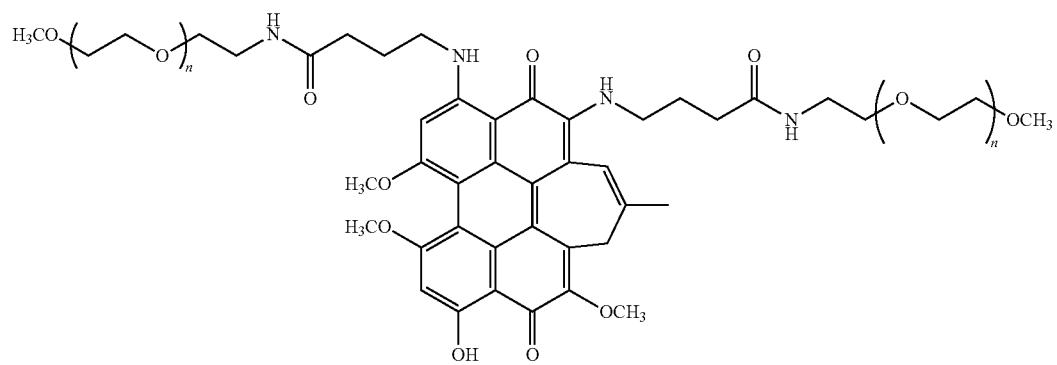
HC-8c-NH-PEG1: n = 1
HC-8c-NH-PEG6: n = 6
HC-8c-NH-PEG12: n = 12

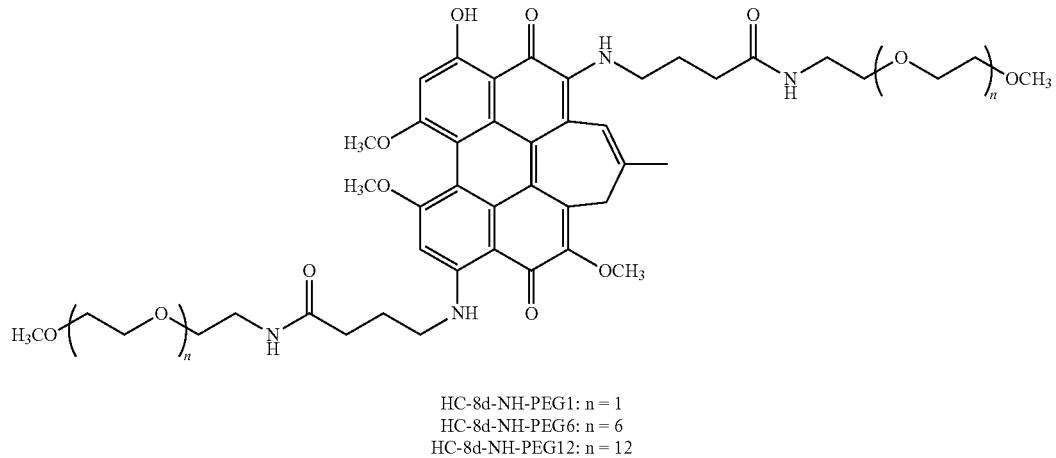

HC-8d-NH-PEG1: n = 1
HC-8d-NH-PEG6: n = 6
HC-8d-NH-PEG12: n = 12

Example 25

Preparation of an aminobutyric acid-sulfonic acid (of different chain lengths)-substituted deacetyl hypocrellin B derivative ($R_1=R_2=-(CH_2)_3CO-NH-(CH_2)_n-SO_3H$, $R_3=R_4=-H$) (n=2, 4, 6): a synthetic route is similar to the preparation of the aminobutyric acid-polyethylene glycol (of different chain lengths)-substituted deacetyl hypocrellin derivative in example 20, and four blue black solid products HC-8a-NH—Cn-SO$_3$H—HC-8d-NH—Cn-SO$_3$H (n=2, 4, 6) are obtained, respectively. HC-8a-NH—C2-SO$_3$H (n=2): yield: 10.6%, $R_f$: 0.30; MS (ESI+): 856.3; maximum absorption wavelength: 620 nm; molar extinction coefficient: 31,000 $M^{-1}$ $cm^{-1}$; singlet oxygen yield: 32%. HC-8b-NH—C4-SO$_3$H (n=4): yield: 9.5%, $R_f$: 0.34; MS (ESI+): 912.6; maximum absorption wavelength: 624 nm; molar extinction coefficient: 31,500 $M^{-1}$ $cm^{-1}$; singlet oxygen yield: 33%. HC-8c-NH—C6-SO$_3$H (n=6): yield: 18.8%, $R_f$: 0.30; MS (ESI+): 968.6; maximum absorption wavelength: 632 nm; molar extinction coefficient: 33,500 $M^{-1}$ $cm^{-1}$; singlet oxygen yield: 35%. HC-8d-NH—C4-SO$_3$H (n=4): yield: 13.2%, $R_f$: 0.26; MS (ESI+): 912.6; maximum absorption wavelength: 626 nm; molar extinction coefficient: 30,500 $M^{-1}cm^{-1}$; singlet oxygen yield: 32%. Structural formulas of the above amino-substituted products are as follows:

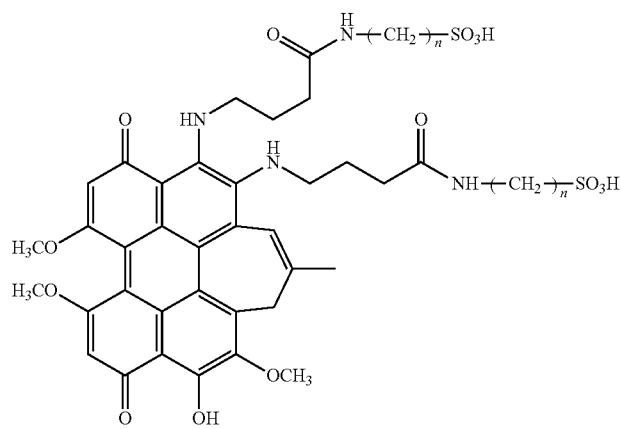

HC-8a-NH-C2-SO$_3$H: n = 2
HC-8a-NH-C4-SO$_3$H: n = 4
HC-8a-NH-C6-SO$_3$H: n = 6

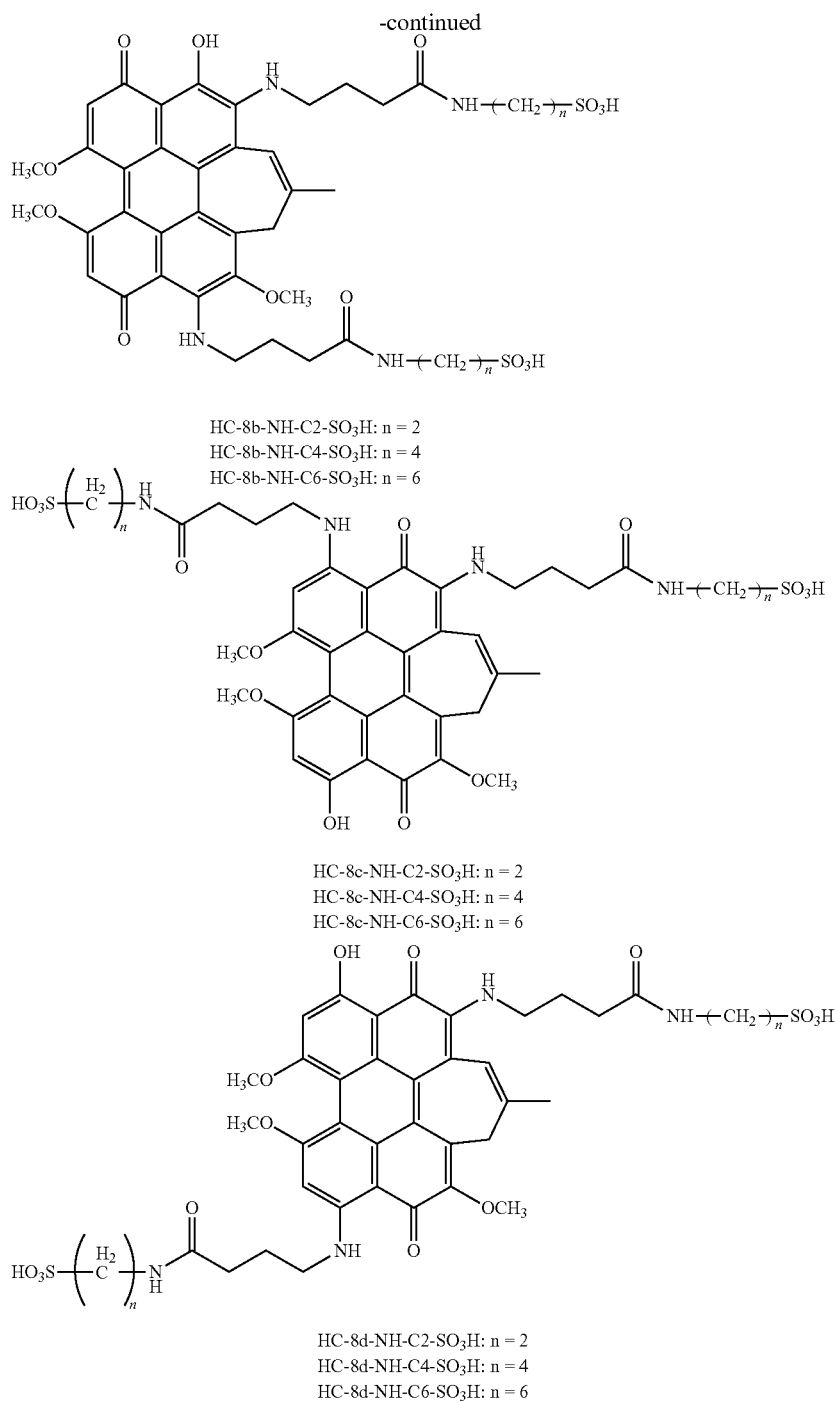

HC-8b-NH-C2-SO₃H: n = 2
HC-8b-NH-C4-SO₃H: n = 4
HC-8b-NH-C6-SO₃H: n = 6

HC-8c-NH-C2-SO₃H: n = 2
HC-8c-NH-C4-SO₃H: n = 4
HC-8c-NH-C6-SO₃H: n = 6

HC-8d-NH-C2-SO₃H: n = 2
HC-8d-NH-C4-SO₃H: n = 4
HC-8d-NH-C6-SO₃H: n = 6

Example 26

Preparation of an aminobutyric acid-quaternary ammonium salt (of different chain lengths)-substituted deacetyl hypocrellin B derivative ($R_1=R_2=$—$(CH_2)_3COO$—$(CH_2)_n$—$N^+(CH_3)_3$, $R_3=R_4=$—H) (n=2, 4, 6): a synthetic route is similar to the preparation of the aminobutyric acid-polyethylene glycol (of different chain lengths)-substituted deacetyl hypocrellin derivative in example 20, and four blue black solid products HC-8a-Cn-N⁺~HC-8d-Cn-N⁺ (n=2, 4, 6) are obtained, respectively. HC-8a-C2-N⁺ (n=2): yield: 9.6%, $R_f$: 0.32; MS (ESI+): 814.3; maximum absorption wavelength: 622 nm; molar extinction coefficient: 30,500 $M^{-1}cm^{-1}$; singlet oxygen yield: 28%. HC-8b-C4-N⁺ (n=4): yield: 9.8%, $R_f$: 0.36; MS (ESI+): 870.6; maximum absorption wavelength: 625 nm; molar extinction coefficient: 31,000 $M^{-1}cm^{-1}$; singlet oxygen yield: 32%. HC-8c-C6-N⁺ (n=6): yield: 19.8%, $R_f$: 0.32; MS (ESI+): 926.6; maximum absorption wavelength: 632 nm; molar extinction coefficient: 32,500 $M^{-1}$ $cm^{-1}$; singlet oxygen yield: 35%. HC-8d-C4-N⁺ (n=4): yield: 15.2%, $R_f$: 0.28; MS (ESI+): 870.6; maximum absorption wavelength: 624 nm; molar extinction coefficient: 31,000 $M^{-1}$ $cm^{-1}$; singlet oxygen yield: 34%. Structural formulas of the above amino-substituted products are as follows:

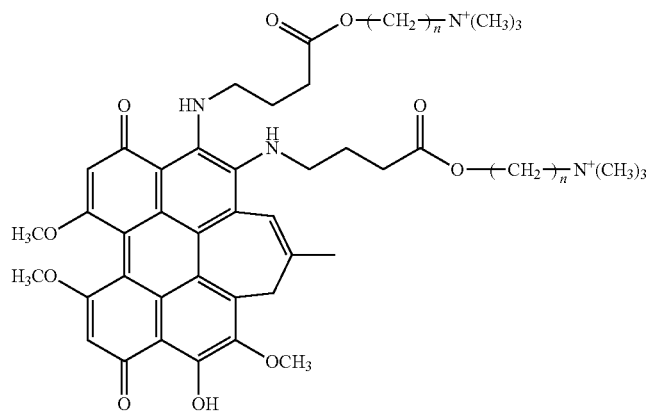
HC-8a-C2-N+: n = 2
HC-8a-C4-N+: n = 4
HC-8a-C6-N+: n = 6
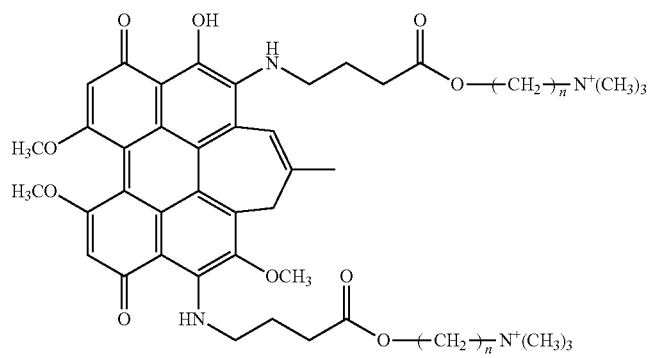
HC-8b-C2-N+: n = 2
HC-8b-C4-N+: n = 4
HC-8b-C6-N+: n = 6
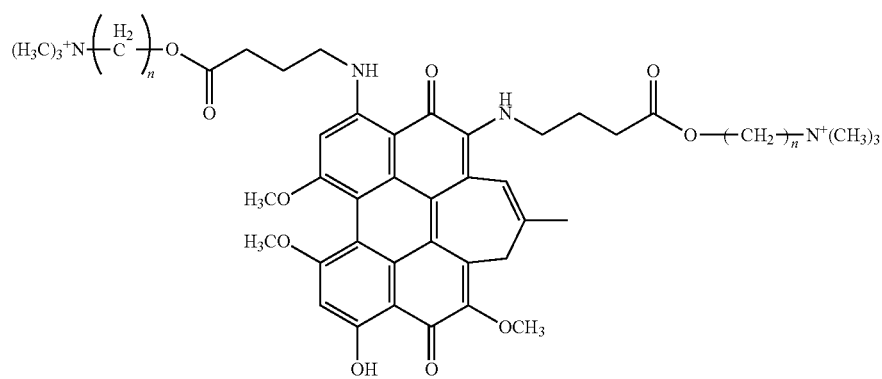
HC-8c-C2-N+: n = 2
HC-8c-C4-N+: n = 4
HC-8c-C6-N+: n = 6

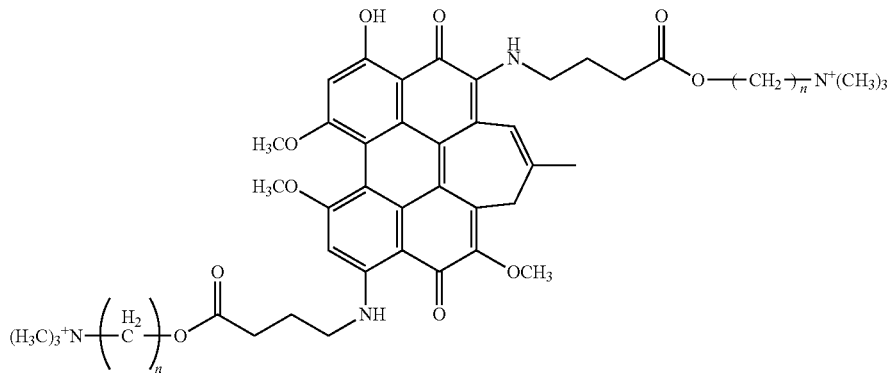

HC-8d-C2-N+: n = 2
HC-8d-C4-N+: n = 4
HC-8d-C6-N+: n = 6

Example 27

Preparation of an aminobutyric acid-amino quaternary ammonium salt (of different chain lengths)-substituted deacetyl hypocrellin B derivative ($R_1=R_2=$ —$(CH_2)_3CO$—NH—$(CH_2)_n$—$N^+(CH_3)_3$, $R_3=R_4=$—H) (n=2, 4, 6): a synthetic route is similar to the preparation of the aminobutyric acid-polyethylene glycol (of different chain lengths)-substituted deacetyl hypocrellin derivative in example 20, and four blue black solid products HC-8a-NH—Cn-N+~HC-8d-NH—Cn-N+ (n=2, 4, 6) are obtained, respectively. HC-8a-NH—C2-N+ (n=2): yield: 8.6%, $R_f$: 0.32; MS (ESI+): 813.3; maximum absorption wavelength: 622 nm; molar extinction coefficient: 30,000 $M^{-1}cm^{-1}$; singlet oxygen yield: 29%. HC-8b-NH—C4-N+ (n=4): yield: 9.5%, $R_f$: 0.35; MS (ESI+): 869.6; maximum absorption wavelength: 626 nm; molar extinction coefficient: 30,500 $M^{-1}$ $cm^{-1}$; singlet oxygen yield: 32%. HC-8c-NH—C6-N+ (n=6): yield: 16.8%, $R_f$: 0.38; MS (ESI+): 925.6; maximum absorption wavelength: 634 nm; molar extinction coefficient: 32,000 $M^{-1}$ $cm^{-1}$; singlet oxygen yield: 36%. HC-8d-NH—C4-N+ (n=4): yield: 13.2%, $R_f$: 0.28; MS (ESI+): 869.6; maximum absorption wavelength: 624 nm; molar extinction coefficient: 30,500 $M^{-1}$ $cm^{-1}$; singlet oxygen yield: 33%. Structural formulas of the above amino-substituted products are as follows:

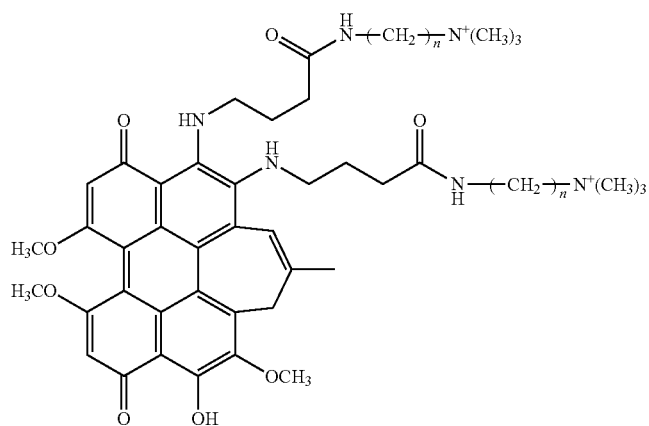

HC-8a-NH-C2-N+: n = 2
HC-8a-NH-C4-N+: n = 4
HC-8a-NH-C6-N+: n = 6

-continued

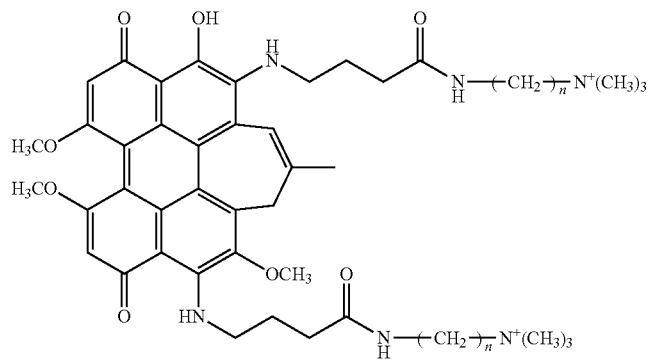

HC-8b-NH-C2-N+: n = 2
HC-8b-NH-C4-N+: n = 4
HC-8b-NH-C6-N+: n = 6

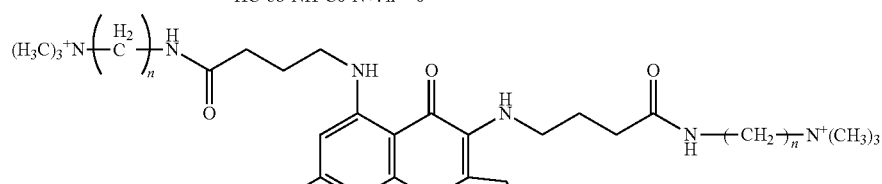

HC-8c-NH-C2-N+: n = 2
HC-8c-NH-C4-N+: n = 4
HC-8c-NH-C6-N+: n = 6

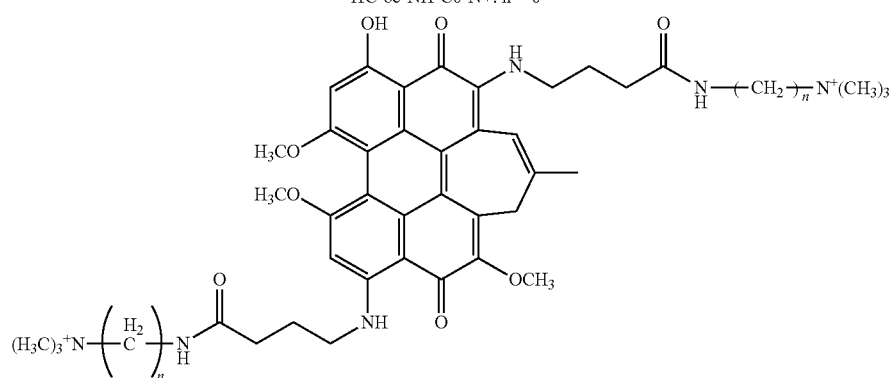

HC-8d-NH-C2-N+: n = 2
HC-8d-NH-C4-N+: n = 4
HC-8d-NH-C6-N+: n = 6

Example 28

Preparation of an aminocaproic acid-substituted deacetyl hypocrellin derivative ($R_1=R_2=$—$CH_2(CH_2)_4COOH$, $R_3=R_4=$—H): a synthetic route is similar to the preparation of the aminoacetic acid-substituted deacetyl hypocrellin derivative in example 17, and four blue black solid products HC-9a-HC-9d are obtained, respectively. HC-9a: yield: 8.4%, $R_f$: 0.30; MS (ESI+): 698.5; maximum absorption wavelength: 620 nm; molar extinction coefficient: 26,500 $M^{-1}$ $cm^{-1}$; singlet oxygen yield: 26%. HC-9b: yield: 7.2%, $R_f$: 0.36; MS (ESI+): 698.6; maximum absorption wavelength: 622 nm; molar extinction coefficient: 27,500 $M^{-1}cm^{-1}$; singlet oxygen yield: 24%. HC-9c: yield: 8.8%, $R_f$: 0.24; MS (ESI+): 698.5; maximum absorption wavelength: 628 nm; molar extinction coefficient: 27,000 $M^{-1}$ $cm^{-1}$; singlet oxygen yield: 29%. HC-9d: yield: 5.8%, $R_f$: 0.25; MS (ESI+): 698.9; maximum absorption wavelength: 624 nm; molar extinction coefficient: 25,000 $M^{-1}cm^{-1}$; singlet oxygen yield: 26%. Structural formulas of the above amino-substituted products are as follows:

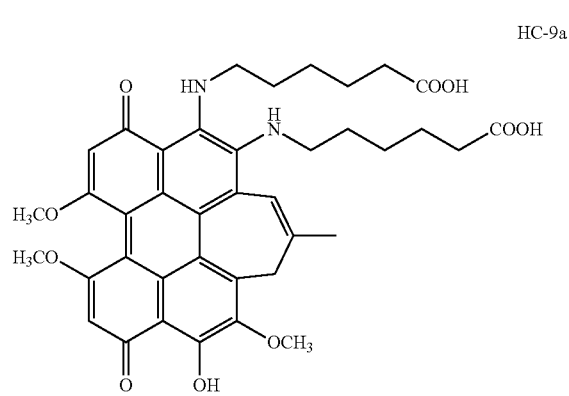

HC-9a

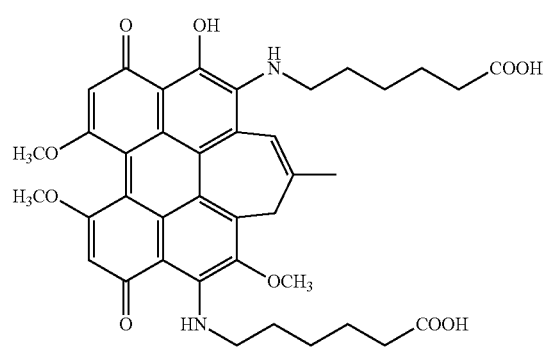

HC-9b

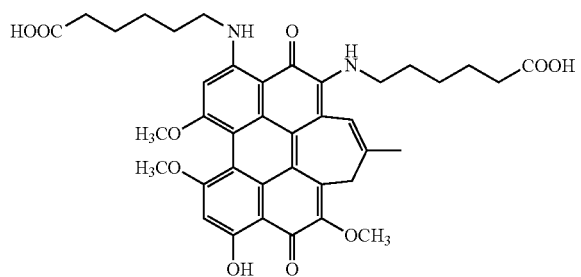

HC-9c

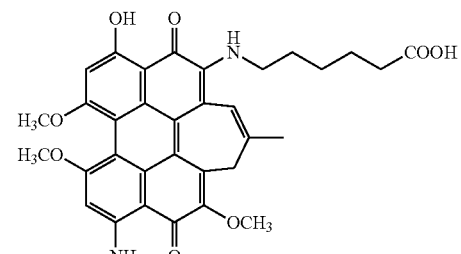

HC-9d

Example 29

Preparation of an aminocaproic acid-PEG (of different chain lengths)-substituted hypocrellin B derivative ($R_1=R_2=$—$CH_2(CH_2)_4COO$-PEGn, $R_3=R_4=$—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HC-9a-PEGn-HC-9d-PEGn (n=1, 6, 12) are obtained, respectively. HC-9a-PEG1 (n=1): yield: 10.6%, $R_f$: 0.32; MS (ESI+): 814.3; maximum absorption wavelength: 621 nm; molar extinction coefficient: 30,000 $M^{-1}cm^{-1}$; singlet oxygen yield: 32%. HC-9b-PEG6 (n=6): yield: 8.7%, $R_f$: 0.38; MS (ESI+): 1254.6; maximum absorption wavelength: 622 nm; molar extinction coefficient: 30,500 $M^{-1}cm^{-1}$; singlet oxygen yield: 30%. HC-9c-PEG6 (n=6): yield: 16.8%, $R_f$: 0.30; MS (ESI+): 1254.6; maximum absorption wavelength: 628 nm; molar extinction coefficient: 33,000 $M^{-1}cm^{-1}$; singlet oxygen yield: 36%. HC-9d-PEG12 (n=12): yield: 11.2%, $R_f$: 0.25; MS (ESI+): 1782.6; maximum absorption wavelength: 625 nm; molar extinction coefficient: 31,500 $M^{-1}cm^{-1}$; singlet oxygen yield: 32%. Structural formulas of the above amino-substituted products are as follows:

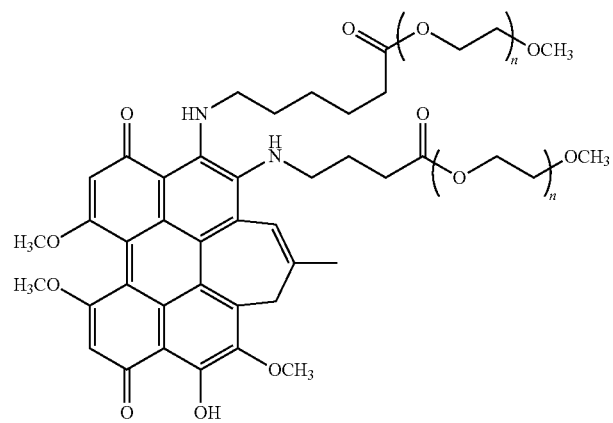

HC-9a-PEG1: n = 1
HC-9a-PEG6: n = 6
HC-9a-PEG12: n = 12

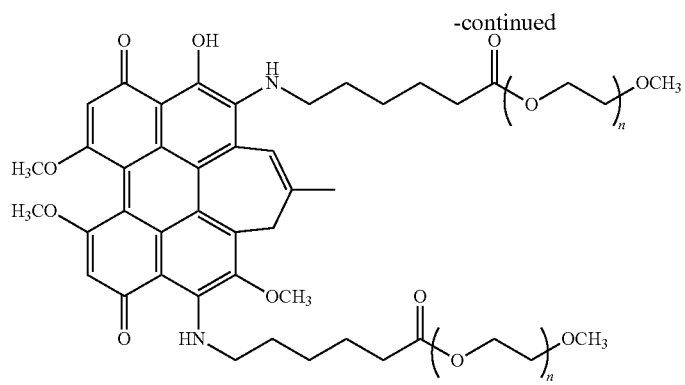

HC-9b-PEG1: n = 1
HC-9b-PEG6: n = 6
HC-9b-PEG12: n = 12

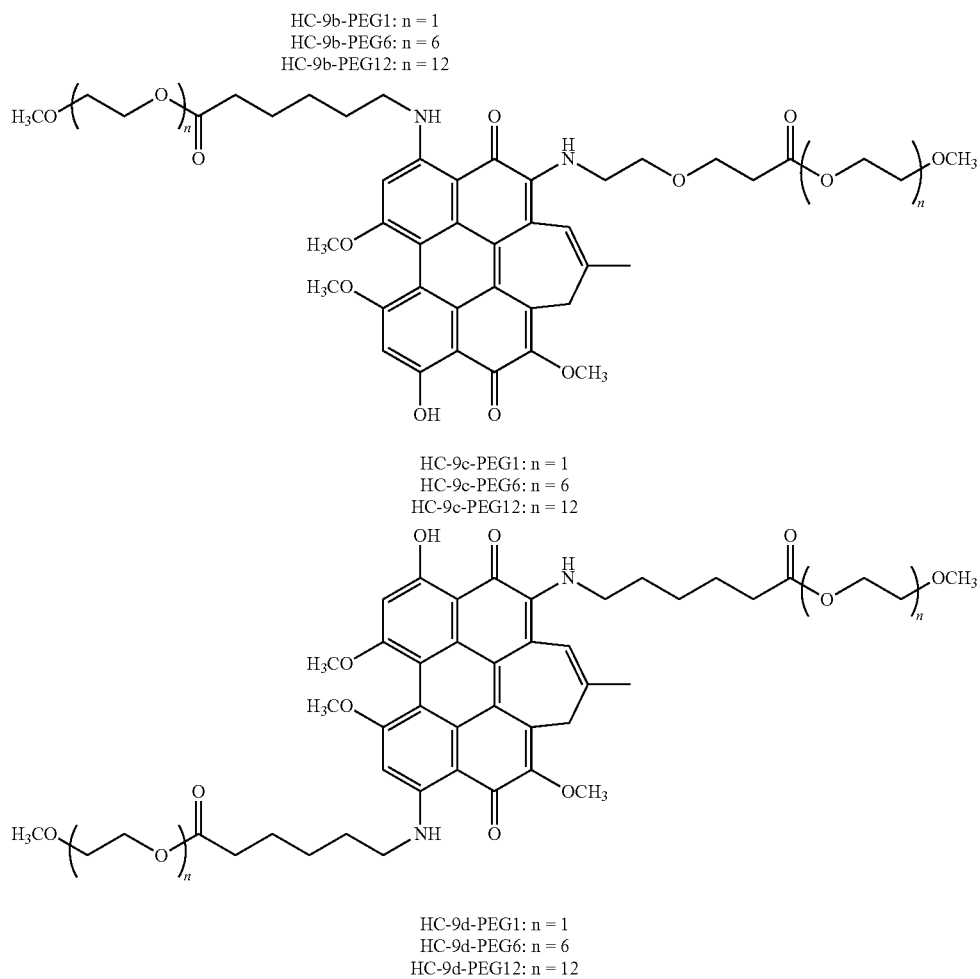

HC-9c-PEG1: n = 1
HC-9c-PEG6: n = 6
HC-9c-PEG12: n = 12

HC-9d-PEG1: n = 1
HC-9d-PEG6: n = 6
HC-9d-PEG12: n = 12

Example 30

Preparation of an aminocaproic acid-quaternary ammonium salt (of different chain lengths)-substituted hypocrellin derivative ($R_1=R_2=-(CH_2)_5COO-(CH_2)_n-N^+(CH_3)_3$, $R_3=R_4=-H$) (n=2, 4, 6): a synthetic route is similar to the preparation of the aminobutyric acid-polyethylene glycol (of different chain lengths)-substituted deacetyl hypocrellin derivative in example 20, and four blue black solid products HC-9a-Cn-N$^+$~ HC-9d-Cn-N$^+$ (n=2, 4, 6) are obtained, respectively. HC-9a-C2-N$^+$ (n=2): yield: 10.6%, $R_f$: 0.32; MS (ESI+): 814.3; maximum absorption wavelength: 622 nm; molar extinction coefficient: 30,000 M$^{-1}$cm$^{-1}$; singlet oxygen yield: 26%. HC-9b-C4-N$^+$ (n=4): yield: 9.2%, $R_f$: 0.38; MS (ESI+): 870.6; maximum absorption wavelength: 625 nm; molar extinction coefficient: 31,500 M$^{-1}$cm$^{-1}$; singlet oxygen yield: 32%. HC-9c-C6-N$^+$ (n=6): yield: 16.8%, $R_f$: 0.30; MS (ESI+): 926.6; maximum absorption wavelength: 630 nm; molar extinction coefficient: 33,500 M$^{-1}$ cm$^{-1}$; singlet oxygen yield: 36%. HC-9d-C4-N$^+$ (n=4): yield: 18.2%, $R_f$: 0.22; MS (ESI+): 870.6; maximum absorption wavelength: 626 nm; molar extinction coefficient: 31,500 M$^{-1}$cm$^{-1}$; singlet oxygen yield: 33%. Structural formulas of the above amino-substituted products are as follows:

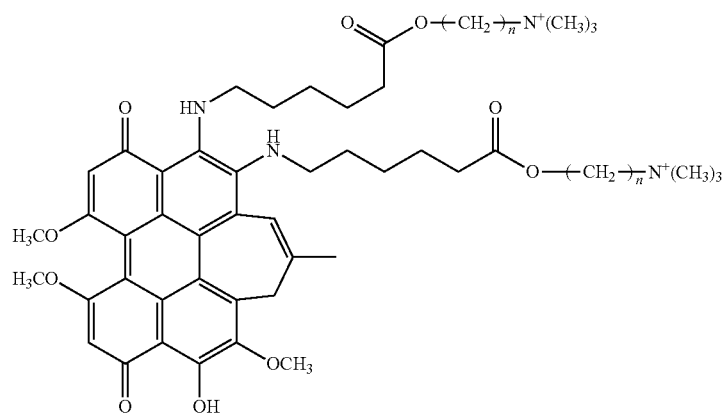
HC-9a-C2-C+: n = 2
HC-9a-C4-C+: n = 4
HC-9a-C6-C+: n = 6
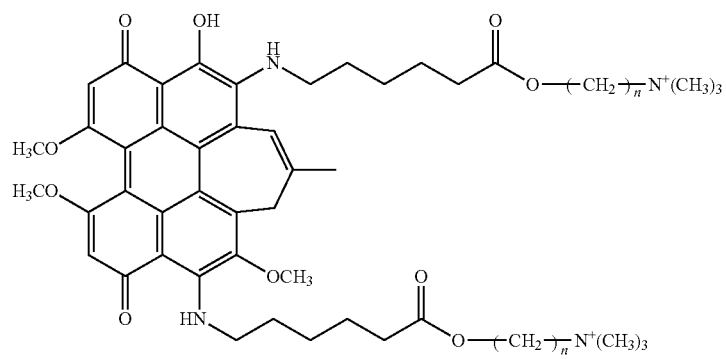
HC-9b-C2-C+: n = 2
HC-9b-C4-C+: n = 4
HC-9b-C6-C+: n = 6
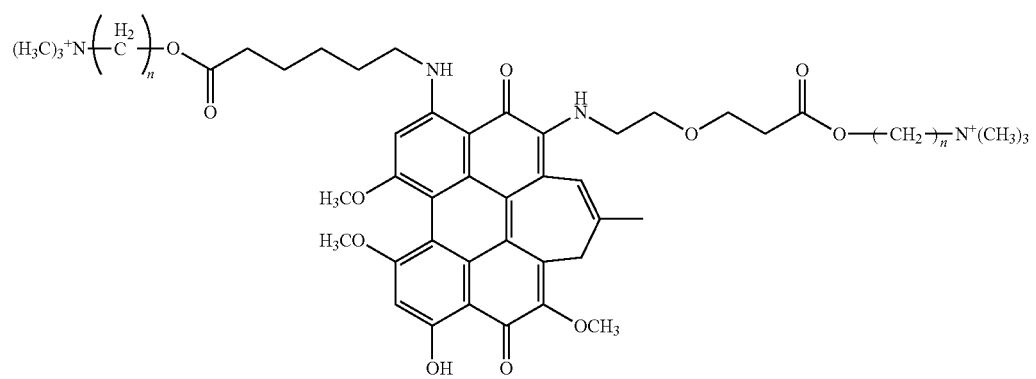
HC-9c-C2-C+: n = 2
HC-9c-C4-C+: n = 4
HC-9c-C6-C+: n = 6

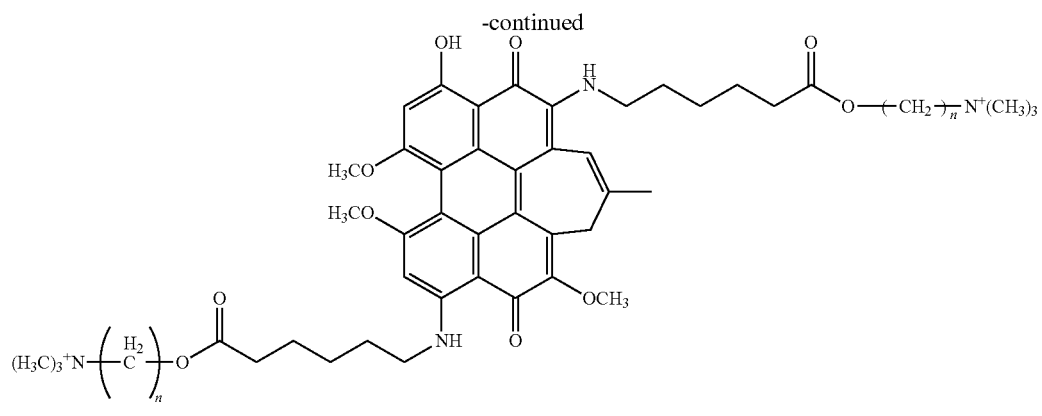

HC-9d-C2-C+: n = 2
HC-9d-C4-C+: n = 4
HC-9d-C6-C+: n = 6

Example 31

Preparation of an aminopropionic acid-substituted hypocrellin B derivative ($R_1=R_2=$—$CH_2CH_2COOH$, $R_3=$—$COCH_3$, $R_4=$—H): a synthetic route is similar to the preparation of the diaminoacetic acid-substituted hypocrellin B derivative in example 17, $NH_2$—$CH_2CH_2COOH$ is used as a raw material, and four blue black solid products HB-10a-HB-10d are obtained, respectively. HB-10a: yield: 8.4%, $R_f$: 0.40; MS (ESI+): 656.6; maximum absorption wavelength: 620 nm; molar extinction coefficient: 31,000 $M^{-1}cm^{-1}$; singlet oxygen yield: 32%. HB-10b: yield: 6.2%, $R_f$: 0.32; MS (ESI+): 656.6; maximum absorption wavelength: 615 nm; molar extinction coefficient: 31,500 $M^{-1}cm^{-1}$; singlet oxygen yield: 34%. HB-10c: yield: 9.4%, $R_f$: 0.24; MS (ESI+): 656.6; maximum absorption wavelength: 622 nm; molar extinction coefficient: 33,000 $M^{-1}cm^{-1}$; singlet oxygen yield: 38%. HB-10d: yield: 4.6%, $R_f$: 0.20; MS (ESI+): 656.6; maximum absorption wavelength: 621 nm; molar extinction coefficient: 32,500 $M^{-1}cm^{-1}$; singlet oxygen yield: 32%.

Results of confocal fluorescence imaging experiments shown in FIGS. 6(a) and 6(c) indicate that HB-10a has good biocompatibility and is able to enter a lysosome of a Hela cell and generate an excellent red-light fluorescence image in the cell. Structural formulas of the above amino-substituted products are as follows:

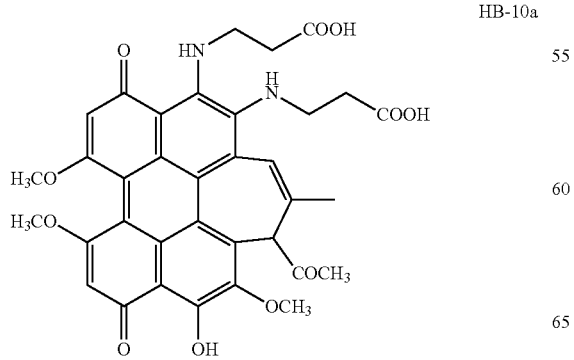

HB-10a

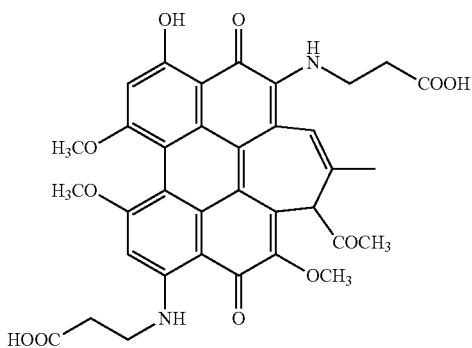

HB-10b

HB-10c

HB-10d

Example 32

Preparation of an aminopropionic acid-amino PEG (of different chain lengths)-substituted hypocrellin B derivative ($R_1$=$R_2$=—$CH_2CH_2CO$—NH-PEGn, $R_3$=—$COCH_3$, $R_4$=—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-10a-NH-PEGn, HB-10b-NH-PEGn, HB-10c-NH-PEGn, and HB-10d-NH-PEGn (n=1, 6, 12) are obtained, respectively. HB-10a-NH-PEG1 (n=1): yield: 10.6%, $R_f$: 0.32; MS (ESI+): 858.3; maximum absorption wavelength: 621 nm; molar extinction coefficient: 31,500 $M^{-1}cm^{-1}$; singlet oxygen yield: 30%. HB-10b-NH-PEG6 (n=6): yield: 9.5%, $R_f$: 0.38; MS (ESI+): 1294.6; maximum absorption wavelength: 622 nm; molar extinction coefficient: 30,500 $M^{-1}cm^{-1}$; singlet oxygen yield: 34%. HB-10c-NH-PEG6 (n=6): yield: 18.8%, $R_f$: 0.24; MS (ESI+): 1294.6; maximum absorption wavelength: 628 nm; molar extinction coefficient: 32,000 $M^{-1}cm^{-1}$; singlet oxygen yield: 38%. HB-10d-NH-PEG12 (n=12): yield: 13.2%, $R_f$: 0.25; MS (ESI+): 1822.6; maximum absorption wavelength: 626 nm; molar extinction coefficient: 31,600 $M^{-1}cm^{-1}$; singlet oxygen yield: 32%. Structural formulas of the above amino-substituted products are as follows:

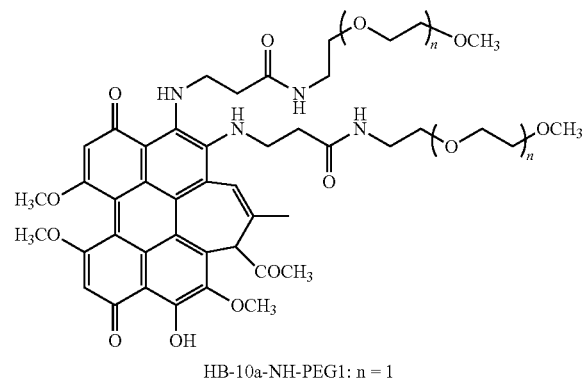

HB-10a-NH-PEG1: n = 1
HB-10a-NH-PEG6: n = 6
HB-10a-NH-PEG12: n = 12

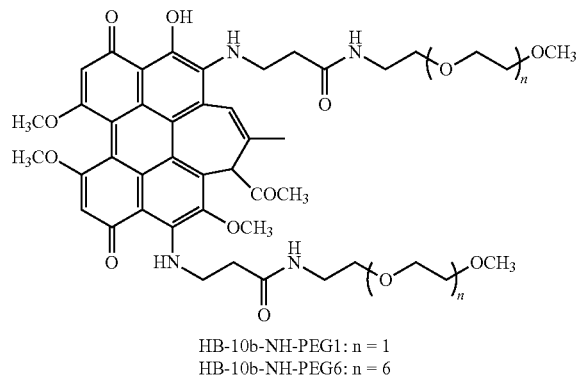

HB-10b-NH-PEG1: n = 1
HB-10b-NH-PEG6: n = 6
HB-10b-NH-PEG12: n = 12

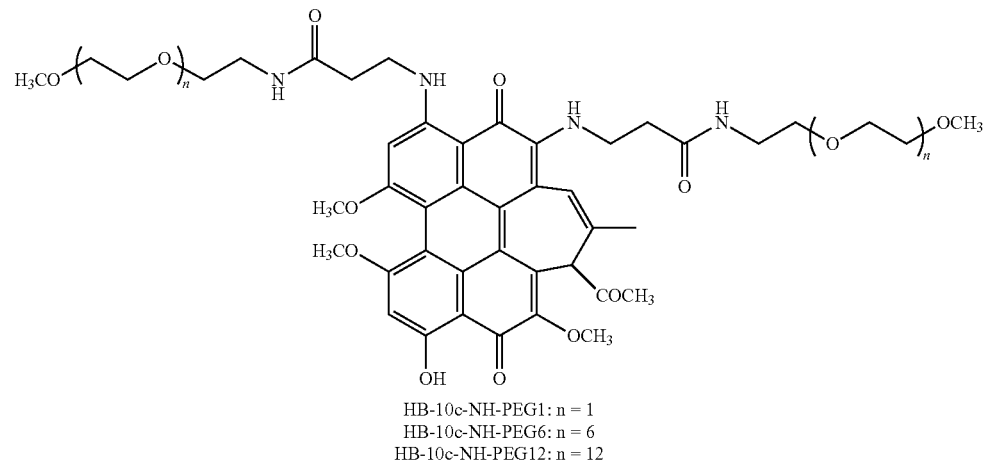

HB-10c-NH-PEG1: n = 1
HB-10c-NH-PEG6: n = 6
HB-10c-NH-PEG12: n = 12

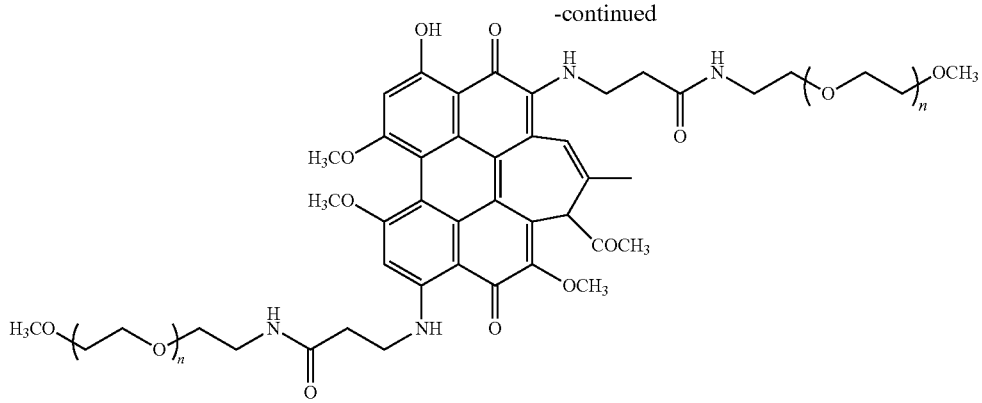

HB-10d-NH-PEG1: n = 1
HB-10d-NH-PEG6: n = 6
HB-10d-NH-PEG12: n = 12

Example 33

Preparation of an aminosulfonic acid-substituted hypocrellin B derivative ($R_1$=$R_2$=—$(CH_2)_m$—$SO_3H$, $R_3$=—$COCH_3$, $R_4$=—H): a substituted amino raw material is $NH_2$—$(CH_2)_m$—$SO_3H$ (m=2, 4, 6), a synthetic route is similar to the preparation of the aminobutyric acid-polyethylene glycol (of different chain lengths)-substituted deacetyl hypocrellin derivative in example 20, and four blue black solid products HB-11a-$C_m$—$SO_3H$, HB-11b-$C_m$—$SO_3H$, HB-11c-$C_m$—$SO_3H$, and HB-11d-$C_m$—$SO_3H$ (n=2, 4, 6) are obtained, respectively. HB-11a-C2-$SO_3H$ (n=2): yield: 8.6%, $R_f$: 0.30; MS (ESI+): 728.3; maximum absorption wavelength: 620 nm; molar extinction coefficient: 30,000 $M^{-1}$ $cm^{-1}$; singlet oxygen yield: 32%. HB-11b-C4-$SO_3H$ (n=4): yield: 10.5%, $R_f$: 0.34; MS (ESI+): 784.6; maximum absorption wavelength: 620 nm; molar extinction coefficient: 30,500 $M^{-1}$ $cm^{-1}$; singlet oxygen yield: 34%. HB-11c-C6-$SO_3H$ (n=6): yield: 16.8%, $R_f$: 0.30; MS (ESI+): 840.6; maximum absorption wavelength: 626 nm; molar extinction coefficient: 31,500 $M^{-1}cm^{-1}$; singlet oxygen yield: 38%. HB-11d-C4-$SO_3H$ (n=4): yield: 11.2%, $R_f$: 0.26; MS (ESI+): 784.6; maximum absorption wavelength: 626 nm; molar extinction coefficient: 30,500 $M^{-1}$ $cm^{-1}$; singlet oxygen yield: 32%. Structural formulas of the above amino-substituted products are as follows:

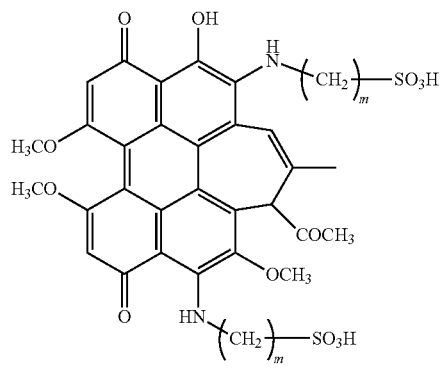

HB-11b-C2-$SO_3H$: m = 2
HB-11b-C4-$SO_3H$: m = 4
HB-11b-C6-$SO_3H$: m = 6

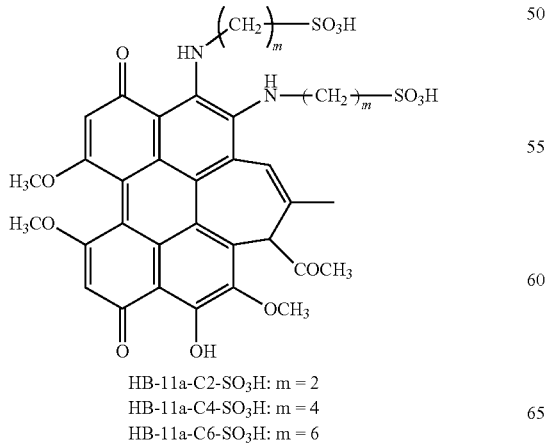

HB-11a-C2-$SO_3H$: m = 2
HB-11a-C4-$SO_3H$: m = 4
HB-11a-C6-$SO_3H$: m = 6

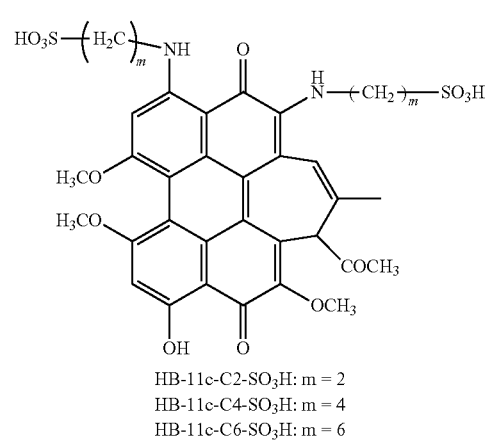

HB-11c-C2-$SO_3H$: m = 2
HB-11c-C4-$SO_3H$: m = 4
HB-11c-C6-$SO_3H$: m = 6

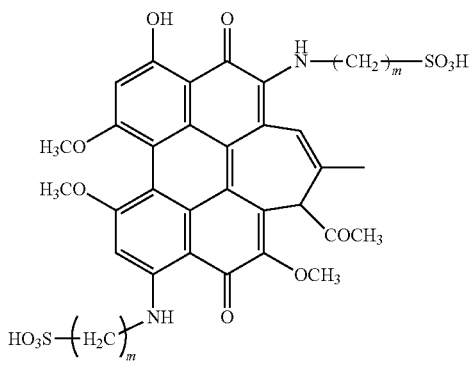

HB-11d-C2-SO₃H: m = 2
HB-11d-C4-SO₃H: m = 4
HB-11d-C6-SO₃H: m = 6

Example 34

Preparation of an aminoethyl methanesulfonate-substituted hypocrellin B derivative ($R_1=R_2=$—$CH_2CH_2SO_3CH_3$, $R_3=$—$COCH_3$, $R_4=$—H): a substituted amino raw material is $NH_2CH_2CH_2SO_3CH_3$, a synthetic route is similar to the preparation of the diaminoacetic acid-substituted hypocrellin B derivative in example 17, and four blue black solid products HB-12a-HB-12d are obtained, respectively. HB-12a: yield: 6.4%, $R_f$: 0.31; MS (ESI+): 756.7; maximum absorption wavelength: 621 nm; molar extinction coefficient: 23,500 $M^{-1}cm^{-1}$; singlet oxygen yield: 20%. HB-12b: yield: 6.2%, $R_f$: 0.33; MS (ESI+): 756.7; maximum absorption wavelength: 621 nm; molar extinction coefficient: 22,500 $M^{-1}cm^{-1}$; singlet oxygen yield: 22%. HB-12c: yield: 5.9%, $R_f$: 0.25; MS (ESI+): 756.7; maximum absorption wavelength: 622 nm; molar extinction coefficient: 23,500 $M^{-1}cm^{-1}$; singlet oxygen yield: 22%. HB-12d: yield: 5.6%, $R_f$: 0.23; MS (ESI+): 756.7; maximum absorption wavelength: 624 nm; molar extinction coefficient: 21,500 $M^{-1}cm^{-1}$; singlet oxygen yield: 21%. Structural formulas of the above amino-substituted products are as follows:

HB-12a

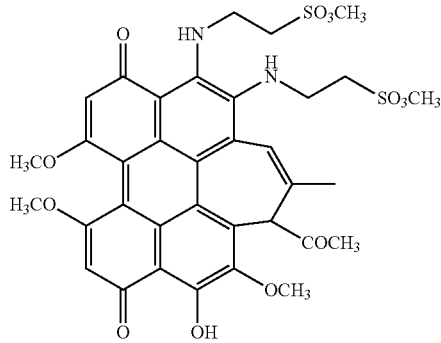

HB-12b

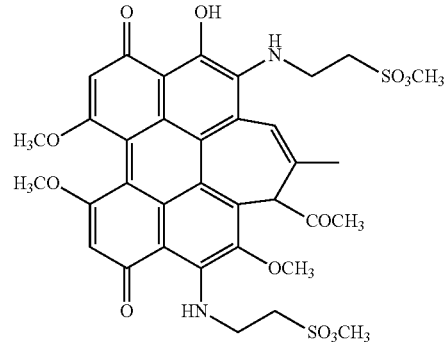

HB-12c

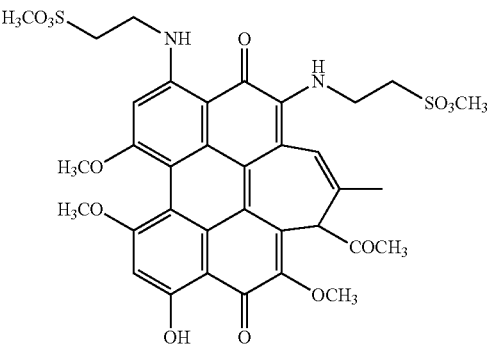

HB-12d

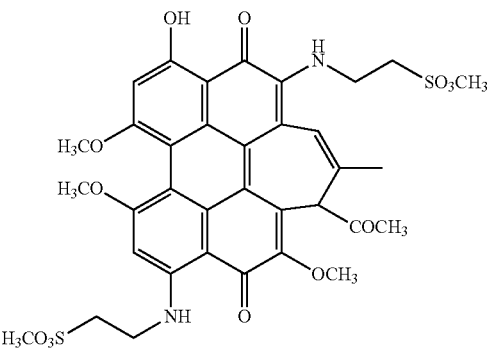

Example 35

Preparation of a 4-tranexamic acid-substituted hypocrellin B derivative ($R_1=R_2=$—$CH_2C_6H_{10}COOH$, $R_3=$—$COCH_3$, $R_4=$—H): a substituted amino raw material is $NH_2$—$CH_2C_6H_{10}COOH$, a synthetic method is similar to the preparation of the diaminoacetic acid-substituted hypocrellin B derivative in example 17, and four blue black solid products HB-13a-HB-13d are obtained, respectively. HB-13a: yield: 7.8%, $R_f$: 0.36; MS (ESI+): 792.1; maximum absorption wavelength: 621 nm; molar extinction coefficient: 28,500 $M^{-1}cm^{-1}$; singlet oxygen yield: 28%. HB-13b: yield: 8.0%, $R_f$: 0.39; MS (ESI+): 792.1; maximum absorption wavelength: 621 nm; molar extinction coefficient: 28,000 $M^{-1}$ $cm^{-1}$; singlet oxygen yield: 26%. HB-13c: yield: 5.8%, $R_f$: 0.36; MS (ESI+): 792.5; maximum absorption wavelength: 621 nm; molar extinction coefficient: 29,500 $M^{-1}$ $cm^{-1}$; singlet oxygen yield: 30%. HB-13d: yield: 5.8%, $R_f$: 0.39; MS (ESI+): 792.9; maximum absorption wavelength: 621 nm; molar extinction coefficient:

28,000 M⁻¹cm⁻¹; singlet oxygen yield: 28%. Structural formulas of the above amino-substituted products are as follows:

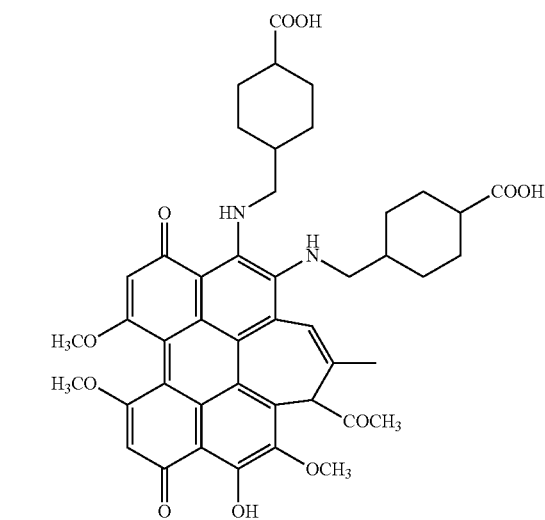

HB-13a

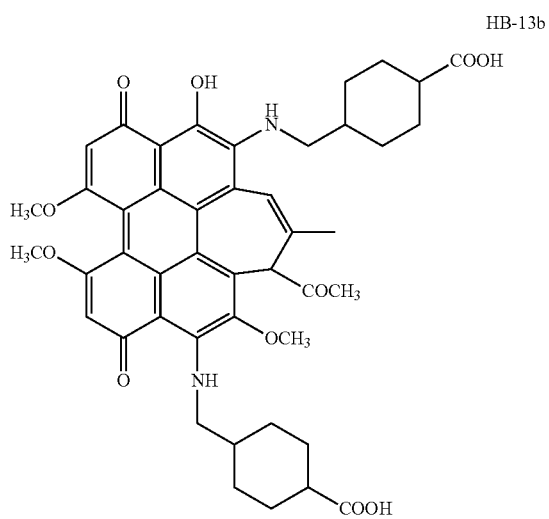

HB-13b

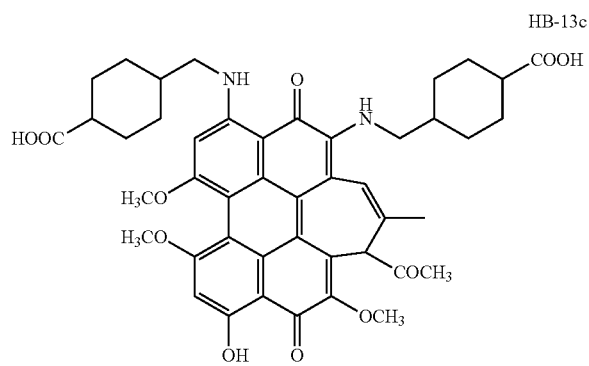

HB-13c

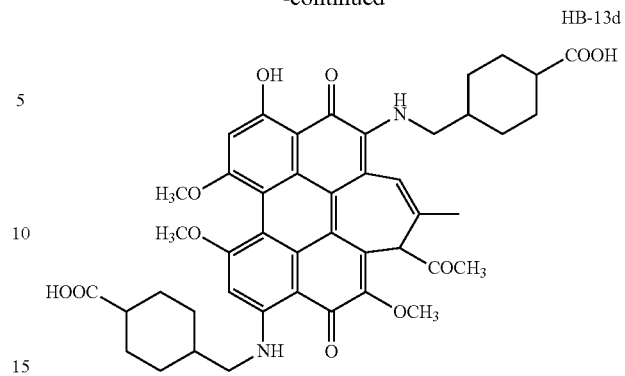

HB-13d

Figure 16:
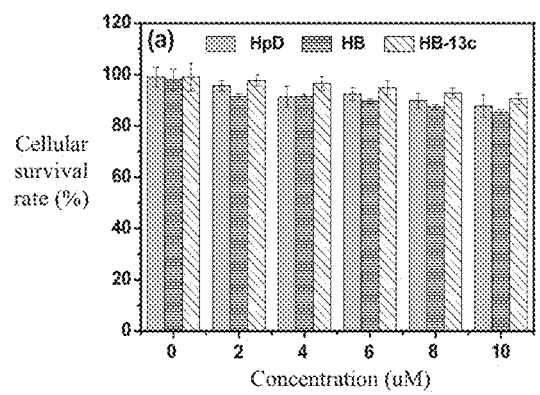
FIG. 16(a) shows dark toxicities, to Hela cells, of the hematoporphyrin derivative HpD, the hypocrellin B HB, and the 4-aminomethylcyclohexanoic acid-substituted hypocrellin B derivative HB-13c synthesized in example 35 of the present invention at different concentrations.
FIG. 16(b) shows phototoxicities, to Hela cells, of the hematoporphyrin derivative HpD, the hypocrellin B HB, and the 4-aminomethylcyclohexanoic acid-substituted hypocrellin B derivative HB-13c synthesized in example 35 of the present invention at different concentrations.
Figure 16:
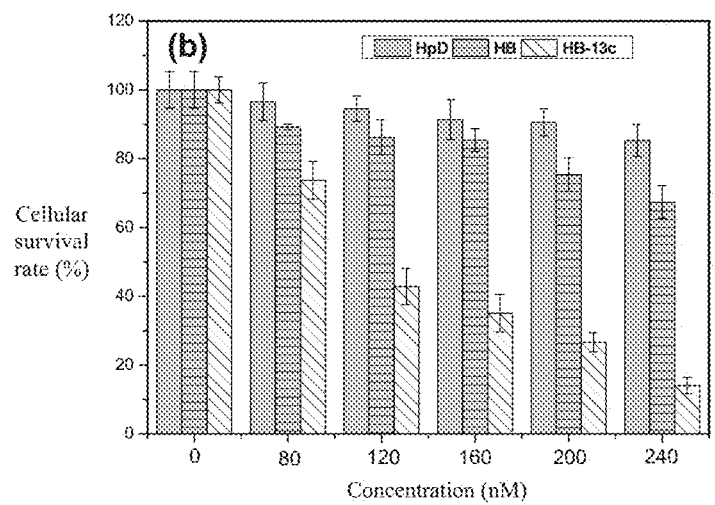

The above prepared compound HB-13c contains two carboxyl groups of a tranexamic acid, making the photosensitizer molecules have good water solubility in a physiological condition; and each milliliter of normal saline can dissolve more than 10 mg of photosensitizer molecules. Therefore, the photosensitive drug can be well transported in blood vessels during intravenous injection, without causing a vascular blockage. FIGS. 16(a) and 16(b) show effects of dark toxicity and phototoxicity for killing tumor cells of HB-13c. As can be seen from the figures, HB-13c containing two carboxyl groups has almost no cytotoxicity in a non-light condition. After exposure to 635 nm red light, HB-13c with a concentration range of 240 nM can kill more than 85% of the Hela cells, while in the same condition, the hypocrellin B HB can kill 30% of the Hela cells, and the commercial photosensitizer hematoporphyrin derivative HpD can kill only about 10% of the Hela cells, indicating that a photodynamic effect of HB-13c is significantly better than that of the hypocrellin B HB and the commercial photosensitizer hematoporphyrin HpD.

Example 36

Preparation of a 4-aminomethyl cyclohexanecarboxylate-substituted hypocrellin B derivative ($R_1=R_2=$—$CH_2C_6H_{10}COOCH_3$, $R_3=$—$COCH_3$, $R_4=$—H): a substituted amino raw material is $NH_2$—$CH_2C_6H_{10}COOCH_3$, a synthetic method is similar to the preparation of the diaminoacetic acid-substituted hypocrellin B derivative in example 17, and four blue black solid products HB-13a-AcE-HB-13d-AcE are obtained, respectively. HB-13a-AcE: yield: 5.8%, $R_f$: 0.38; MS (ESI+): 820.1; maximum absorption wavelength: 625 nm; molar extinction coefficient: 27,000 M⁻¹cm⁻¹; singlet oxygen yield: 25%. HB-13b-AcE: yield: 8.5%, $R_f$: 0.40; MS (ESI+): 820.1; maximum absorption wavelength: 623 nm; molar extinction coefficient: 27,000 M⁻¹cm⁻¹; singlet oxygen yield: 24%. HB-13c-AcE: yield: 5.5%, $R_f$: 0.32; MS (ESI+): 820.8; maximum absorption wavelength: 621 nm; molar extinction coefficient: 28,500 M⁻¹cm⁻¹; singlet oxygen yield: 30%. HB-13d-AcE: yield: 5.9%, $R_f$: 0.45; MS (ESI+): 820.9; maximum absorption wavelength: 623 nm; molar extinction coefficient: 28,000 M⁻¹cm⁻¹; singlet oxygen yield: 25%. Structural formulas of the above amino-substituted products are as follows:

HB-13a-AcE

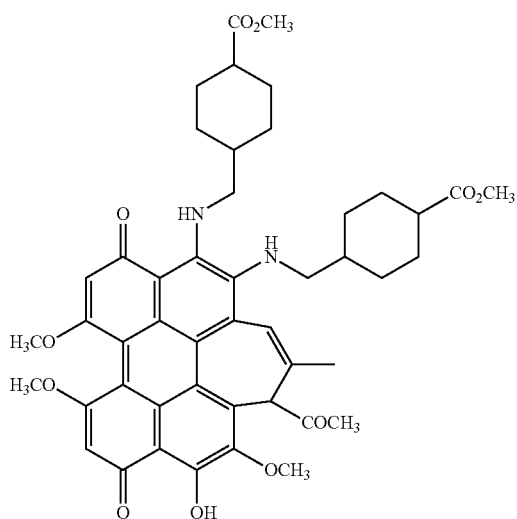

HB-13b-AcE

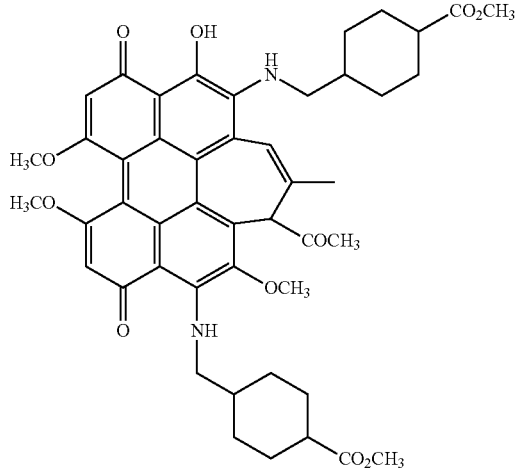

HB-13c-AcE

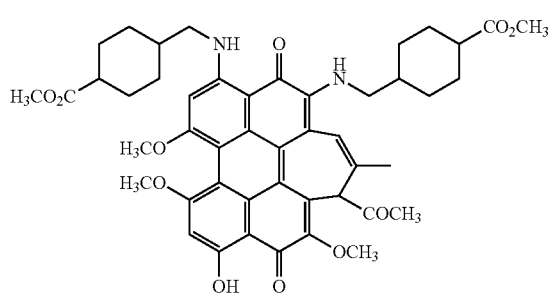

HB-13d-AcE

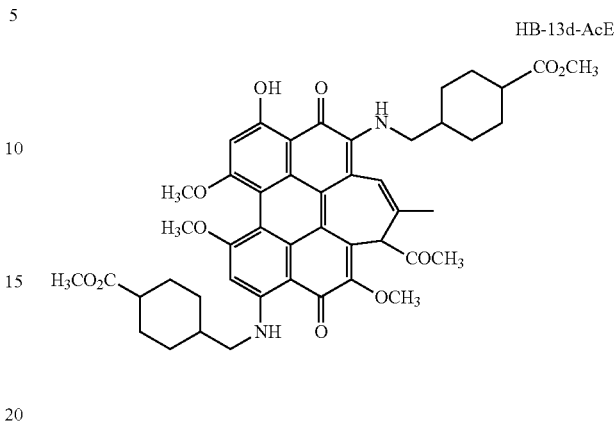

Example 37

Preparation of a 4-tranexamic acid-amino PEG (of different chain lengths)-substituted hypocrellin B derivative ($R_1=R_2=$—$CH_2C_6H_{10}COO$-PEGn, $R_3=$—$COCH_3$, $R_4=$—H) (PEG is polyethylene glycol, n is the number of ethylene glycol units, and n=1, 4, 8, 16): a synthetic route is similar to the preparation of the aminobutyric acid-polyethylene glycol (of different chain lengths)-substituted deacetyl hypocrellin derivative in example 20, and four blue black solid products HB-13a-PEGn, HB-13b-PEGn, HB-13c-PEGn, and HB-13d-PEGn (n=1, 4, 8, 16) are obtained, respectively. HB-13a-PEG1 (n=1): yield: 8.6%, $R_f$: 0.32; MS (ESI+): 908.6; maximum absorption wavelength: 622 nm; molar extinction coefficient: 30,500 $M^{-1}cm^{-1}$; singlet oxygen yield: 30%. HB-13b-PEG4 (n=4): yield: 8.5%, $R_f$: 0.36; MS (ESI+): 1172.6; maximum absorption wavelength: 622 nm; molar extinction coefficient: 30,500 $M^{-1}cm^{-1}$; singlet oxygen yield: 32%. HB-13c-PEG4 (n=4): yield: 18.8%, $R_f$: 0.31; MS (ESI+): 1172.6; maximum absorption wavelength: 630 nm; molar extinction coefficient: 32,500 $M^{-1}cm^{-1}$; singlet oxygen yield: 38%. HB-13c-PEG8 (n=8): yield: 15.2%, $R_f$: 0.38; MS (ESI+): 1524.6; maximum absorption wavelength: 628 nm; molar extinction coefficient: 33,000 $M^{-1}cm^{-1}$; singlet oxygen yield: 38%. HB-13d-PEG16 (n=16): yield: 10.2%, $R_f$: 0.26; MS (ESI+): 2228.6; maximum absorption wavelength: 624 nm; molar extinction coefficient: 30,500 $M^{-1}cm^{-1}$; singlet oxygen yield: 33%. Structural formulas of the above amino-substituted products are as follows:

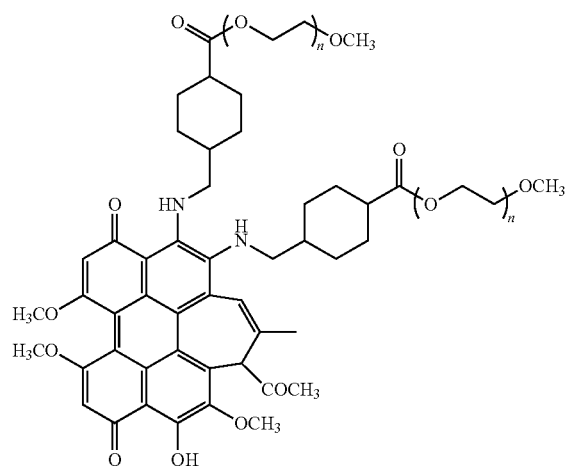

HB-13a-PEG1: n = 1
HB-13a-PEG4: n = 4
HB-13a-PEG8: n = 8
HB-13a-PEG16: n = 16

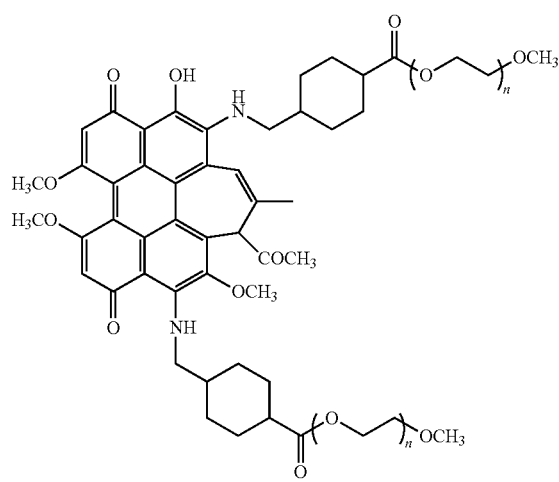

HB-13b-PEG1: n = 1
HB-13b-PEG4: n = 4
HB-13b-PEG8: n = 8
HB-13b-PEG16: n = 16

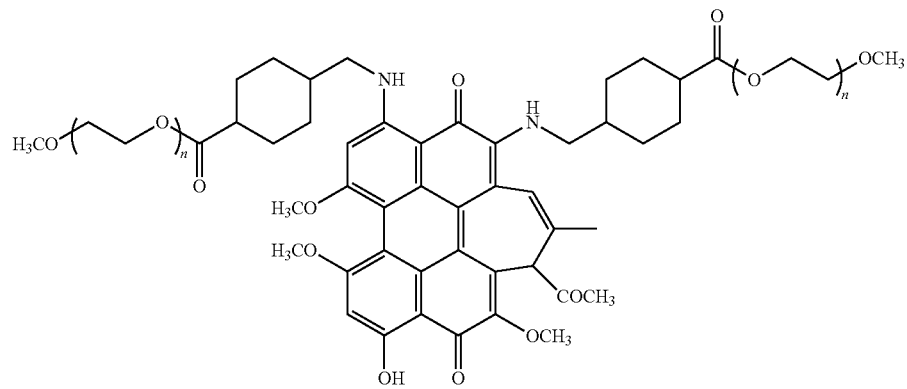

HB-13c-PEG1: n = 1
HB-13c-PEG4: n = 4
HB-13c-PEG8: n = 8
HB-13c-PEG16: n = 16

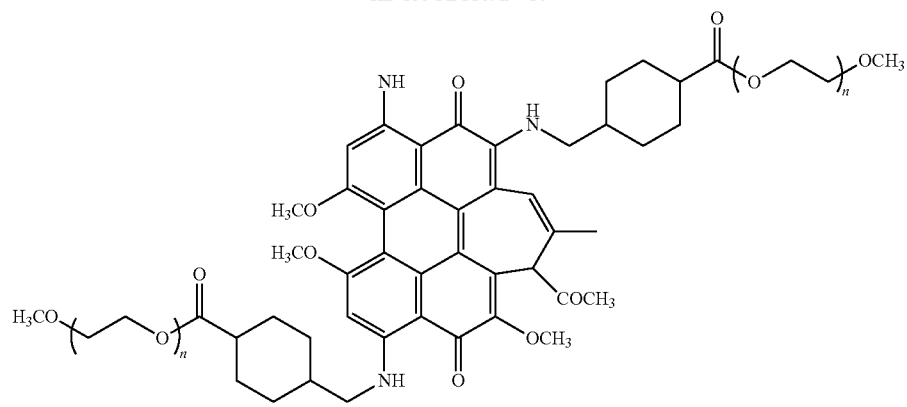

HB-13d-PEG1: n = 1
HB-13d-PEG4: n = 4
HB-13d-PEG8: n = 8
HB-13d-PEG16: n = 16

Figure 17:
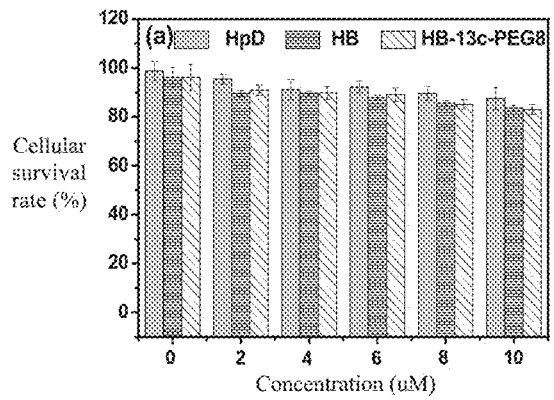
FIG. 17(a) shows dark toxicities, to Hela cells, of the hematoporphyrin derivative HpD, the hypocrellin B HB, and HB-13c-PEG8 synthesized in example 37 of the present invention at different concentrations, wherein HB-13c-PEG8 is obtained by connecting the 4-aminomethylcyclohexanoic acid-substituted hypocrellin B derivative and two 8-PEG chains with a carboxylic acid ester bond.
FIG. 17(b) shows phototoxicities, to Hela cells, of the hematoporphyrin derivative HpD, the hypocrellin B HB, and HB-13c-PEG8 synthesized in example 37 of the present invention at different concentrations, wherein HB-13c-PEG8 is obtained by connecting the 4-aminomethylcyclohexanoic acid-substituted hypocrellin B derivative and two 8-PEG chains with a carboxylic acid ester bond.
Figure 17:
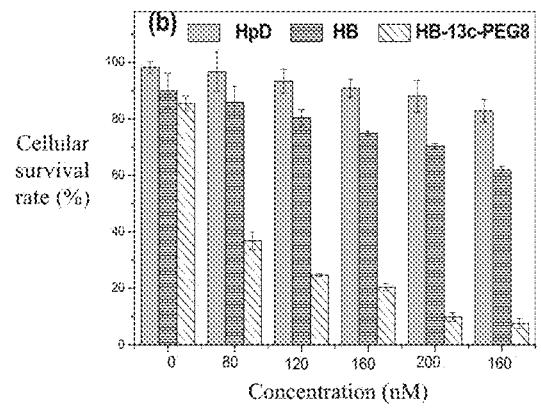

The above prepared compound HB-13c-PEG8 contains two 8-PEG long-chains, making the photosensitizer molecules have very high water solubility in a physiological condition; and each milliliter of normal saline can dissolve more than 20 mg of photosensitizer molecules, presenting excellent water solubility. Therefore, the photosensitive drug can be well transported in blood vessels during intravenous injection, without causing a vascular blockage. FIGS. 17(a) and 17(b) show effects of dark toxicity and phototoxicity for killing tumor cells of HB-13c-PEG8, wherein under irradiation of red light, HB-13c-PEG8 with a concentration range of 160 nM can kill more than 90% of the Hela cells, while in the same condition, the hypocrellin B HB can kill 30% of the Hela cells, Example 38

Preparation of a 4-tranexamic acid-amino PEG (of different chain lengths)-substituted hypocrellin B derivative ($R_1=R_2=$—$CH_2C_6H_{10}CO$—$NH$-$PEGn$, $R_3=$—$COCH_3$, $R_4=$—H) (PEG is polyethylene glycol, n is the number of ethylene glycol units, and n=1, 4, 8, 16): a synthetic route is similar to the preparation of the aminobutyric acid-polyethylene glycol (of different chain lengths)-substituted deacetyl hypocrellin derivative in example 20, and four blue black solid products HB-13a-NH-PEGn, HB-13b-NH-PEGn, HB-13c-NH-PEGn, and HB-13d-NH-PEGn (n=1, 4, 8, 16) are obtained, respectively. HB-13a-NH-PEG1 (n=1): yield: 8.6%, $R_f$: 0.30; MS (ESI+): 996.6; maximum absorption wavelength: 624 nm; molar extinction coefficient: 31,000 $M^{-1}$ $cm^{-1}$; singlet oxygen yield: 32%. HB-13b-NH-PEG4 (n=4): yield: 8.8%, $R_f$: 0.38; MS (ESI+): 1258.6; maximum absorption wavelength: 622 nm; molar extinction coefficient: 31,000 $M^{-1}cm^{-1}$; singlet oxygen yield: 34%. HB-13c-NH-PEG8 (n=8): yield: 19.2%, $R_f$: 0.38; MS (ESI+): 1610.6; maximum absorption wavelength: 630 nm; molar extinction coefficient: 33,500 $M^{-1}cm^{-1}$; singlet oxygen yield: 39%. HB-13d-NH-PEG8 (n=8): yield: 7.8%, $R_f$: 0.32; MS (ESI+): 1610.6; maximum absorption wavelength: 628 nm; molar extinction coefficient: 31,500 $M^{-1}cm^{-1}$; singlet oxygen yield: 32%. Structural formulas of the above amino-substituted products are as follows:

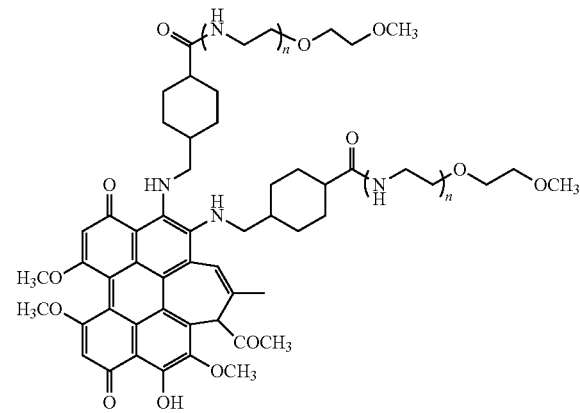

HB-13a-NH-PEG1: n = 1
HB-13a-NH-PEG4: n = 4
HB-13a-NH-PEG8: n = 8
HB-13a-NH-PEG16: n = 16

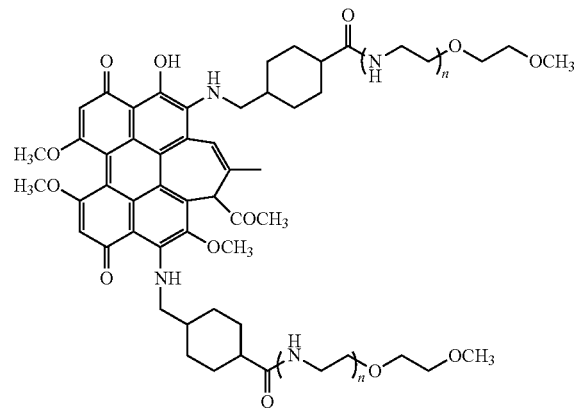

HB-13b-NH-PEG1: n = 1
HB-13b-NH-PEG4: n = 4
HB-13b-NH-PEG8: n = 8
HB-13b-NH-PEG16: n = 16

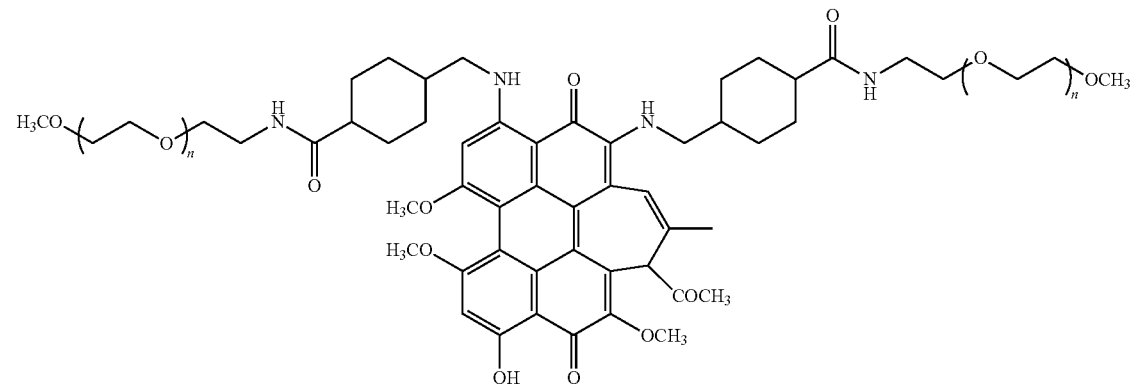

HB-13c-NH-PEG1: n = 1
HB-13c-NH-PEG4: n = 4
HB-13c-NH-PEG8: n = 8
HB-13c-NH-PEG16: n = 16

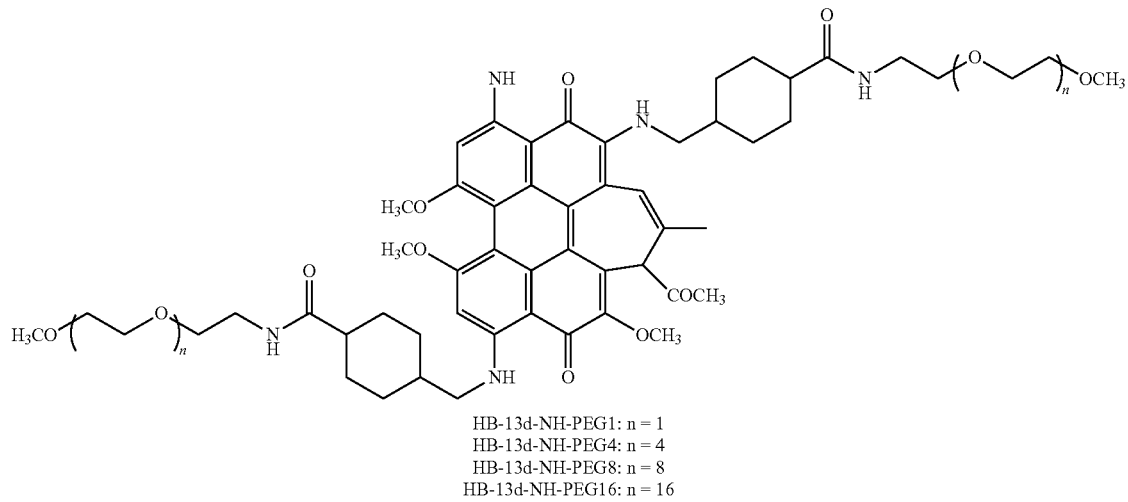

HB-13d-NH-PEG1: n = 1
HB-13d-NH-PEG4: n = 4
HB-13d-NH-PEG8: n = 8
HB-13d-NH-PEG16: n = 16

Example 39

Preparation of a 4-tranexamic acid-PEG (of different chain lengths)-substituted hypocrellin B derivative ($R_1$=$R_2$=—$CH_2C_6H_{10}$COO-PEGn-OH, $R_3$=—$COCH_3$, $R_4$=—H) (PEG is polyethylene glycol, n is the number of ethylene glycol units, and n=1, 4, 8): a synthetic route is similar to the preparation of the aminobutyric acid-polyethylene glycol (of different chain lengths)-substituted deacetyl hypocrellin derivative in example 20, and four blue black solid products HB-13a-PEGn-OH, HB-13b-PEGn-OH, HB-13c-PEGn-OH, and HB-13d-PEGn-OHn (n=1, 4, 8) are obtained, respectively. HB-13a-PEG1 (n=1): yield: 7.6%, $R_f$: 0.32; MS (ESI+): 852.6; maximum absorption wavelength: 624 nm; molar extinction coefficient: 31,000 $M^{-1}$ $cm^{-1}$; singlet oxygen yield: 32%. HB-13b-PEG4 (n=4): yield: 8.6%, $R_f$: 0.36; MS (ESI+): 1116.6; maximum absorption wavelength: 624 nm; molar extinction coefficient: 31,000 $M^{-1}cm^{-1}$; singlet oxygen yield: 34%. HB-13c-PEG8 (n=8): yield: 17.2%, $R_f$: 0.40; MS (ESI+): 1468.6; maximum absorption wavelength: 630 nm; molar extinction coefficient: 32,500 $M^{-1}$ $cm^{-1}$; singlet oxygen yield: 40%. HB-13d-PEG8 (n=8): yield: 8.2%, $R_f$: 0.25; MS (ESI+): 1468.6; maximum absorption wavelength: 625 nm; molar extinction coefficient: 32,500 $M^{-1}$ $cm^{-1}$; singlet oxygen yield: 30%. Structural formulas of the above amino-substituted products are as follows:

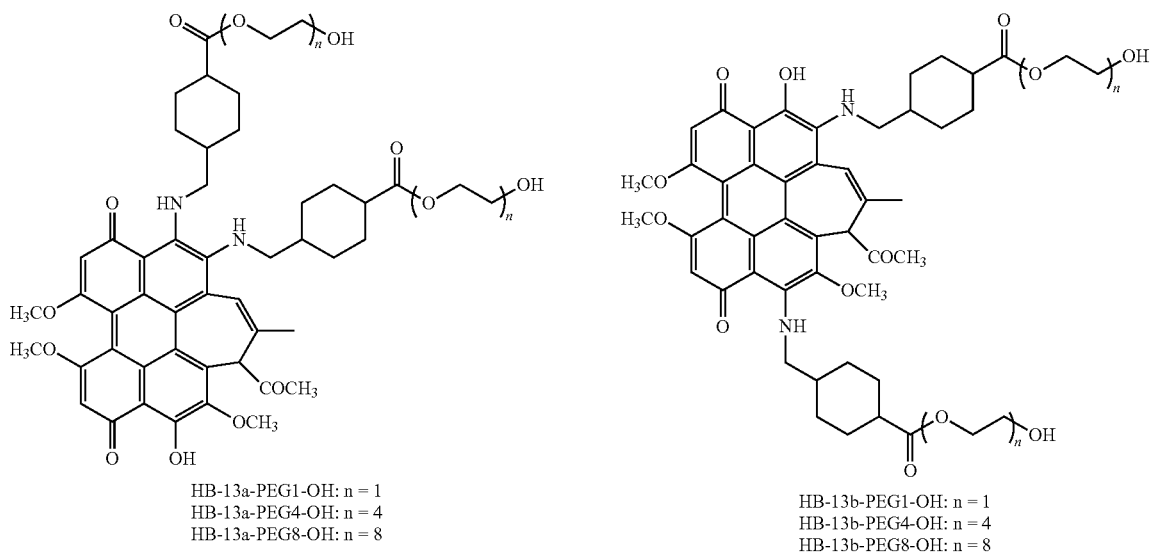

HB-13a-PEG1-OH: n = 1
HB-13a-PEG4-OH: n = 4
HB-13a-PEG8-OH: n = 8

HB-13b-PEG1-OH: n = 1
HB-13b-PEG4-OH: n = 4
HB-13b-PEG8-OH: n = 8

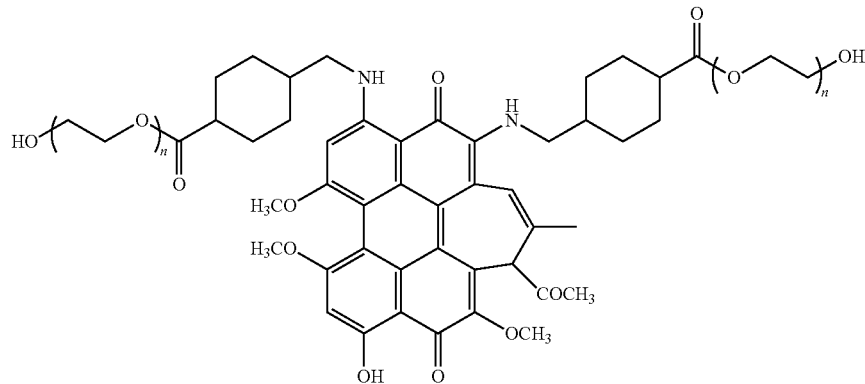

HB-13c-PEG1-OH: n = 1
HB-13c-PEG4-OH: n = 4
HB-13c-PEG8-OH: n = 8

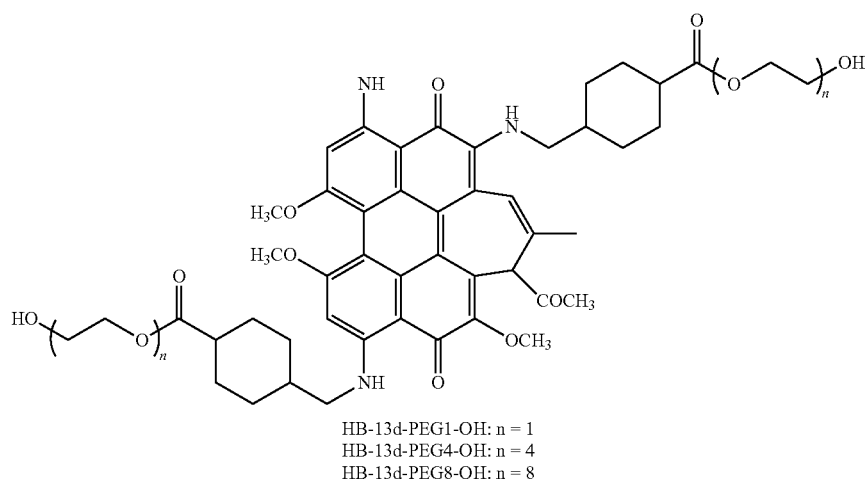

HB-13d-PEG1-OH: n = 1
HB-13d-PEG4-OH: n = 4
HB-13d-PEG8-OH: n = 8

Example 40

Preparation of a 4-tranexamic acid-amino PEG (of different chain lengths)-substituted deacetyl hypocrellin derivative ($R_1=R_2=$—$CH_2C_6H_{10}$ COO-PEGn, $R_3=R_4=$—H) (PEG is polyethylene glycol, n is the number of ethylene glycol units, and n=1, 4, 8): a synthetic route is similar to the preparation of the aminobutyric acid-polyethylene glycol (of different chain lengths)-substituted deacetyl hypocrellin derivative in example 20, and four blue black solid products HC-13a-PEGn, HC-13b-PEGn, HC-13c-PEGn, and HC-13d-PEGn (n=1, 4, 8) are obtained, respectively. HC-13a-PEG1 (n=1): yield: 9.6%, $R_f$: 0.30; MS (ESI+): 866.6; maximum absorption wavelength: 622 nm; molar extinction coefficient: 30,000 $M^{-1}$ $cm^{-1}$; singlet oxygen yield: 32%. HC-13b-PEG4 (n=4): yield: 8.0%, $R_f$: 0.35; MS (ESI+): 1130.6; maximum absorption wavelength: 624 nm; molar extinction coefficient: 30,000 $M^{-1}cm^{-1}$; singlet oxygen yield: 32%. HC-13c-PEG4 (n=4): yield: 17.8%, $R_f$: 0.34; MS (ESI+): 1130.6; maximum absorption wavelength: 632 nm; molar extinction coefficient: 31,500 $M^{-1}cm^{-1}$; singlet oxygen yield: 36%. HC-13c-PEG8 (n=8): yield: 15.2%, $R_f$: 0.40; MS (ESI+): 1482.6; maximum absorption wavelength: 628 nm; molar extinction coefficient: 32,500 $M^{-1}$ $cm^{-1}$; singlet oxygen yield: 38%. HC-13d-PEG16 (n=16): yield: 9.2%, $R_f$: 0.28; MS (ESI+): 2186.6; maximum absorption wavelength: 625 nm; molar extinction coefficient: 31,500 $M^{-1}cm^{-1}$; singlet oxygen yield: 30%. Structural formulas of the above amino-substituted products are as follows:

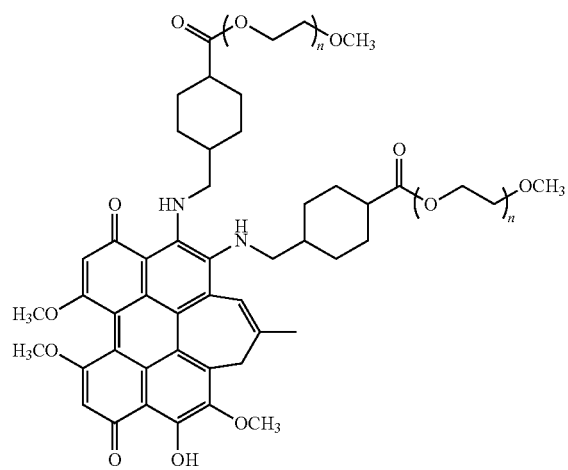

HC-13a-PEG1: n = 1
HC-13a-PEG4: n = 4
HC-13a-PEG8: n = 8
HC-13a-PEG16: n = 16

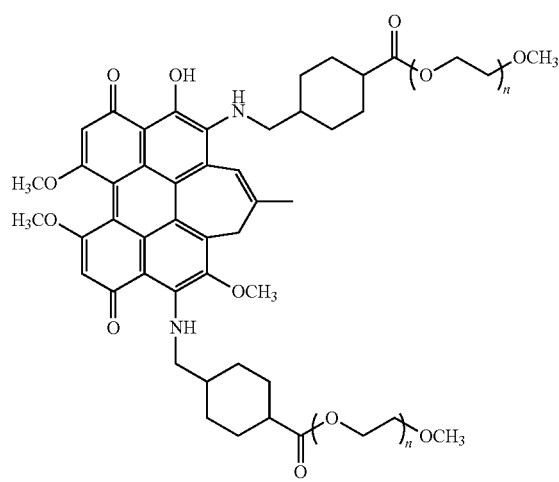

HC-13b-PEG1: n = 1
HC-13b-PEG4: n = 4
HC-13b-PEG8: n = 8
HC-13b-PEG16: n = 16

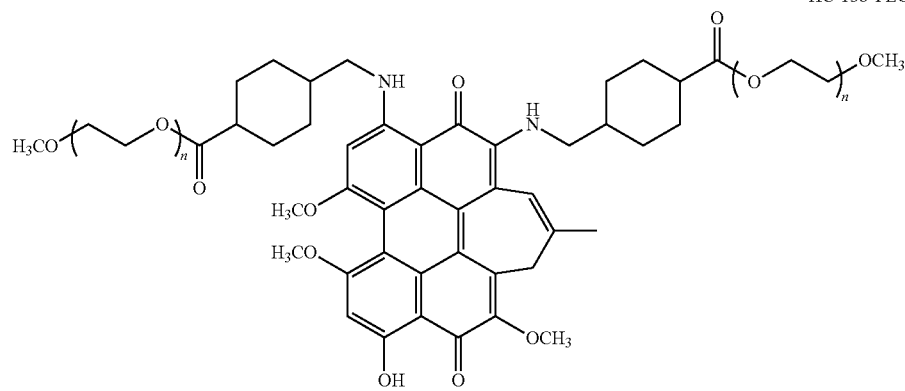

HC-13c-PEG1: n = 1
HC-13c-PEG4: n = 4
HC-13c-PEG8: n = 8
HC-13c-PEG16: n = 16

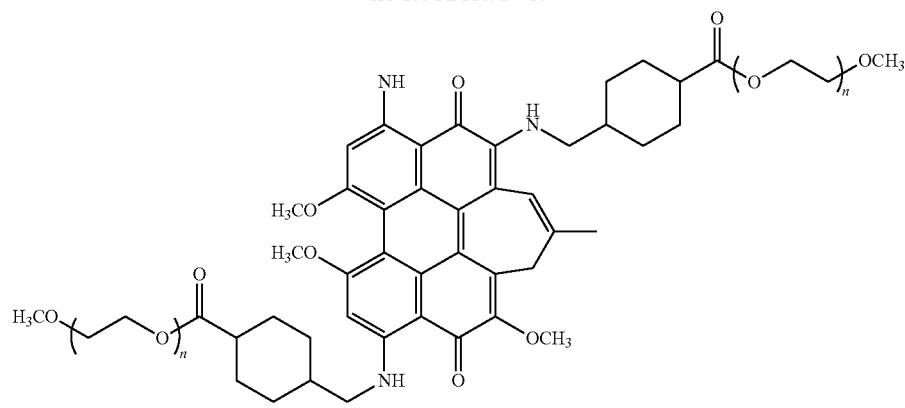

HC-13d-PEG1: n = 1
HC-13d-PEG4: n = 4
HC-13d-PEG8: n = 8
HC-13d-PEG16: n = 16

Example 41

Preparation of a 4-tranexamic acid-amino PEG (of different chain lengths)-substituted deacetyl hypocrellin B derivative ($R_1=R_2=$—$CH_2C_6H_{10}CO$—$NH$-PEGn, $R_3=R_4=$—H) (PEG is polyethylene glycol, n is the number of ethylene glycol units, and n=1, 4, 8): a synthetic route is similar to the preparation of the aminobutyric acid-polyethylene glycol (of different chain lengths)-substituted deacetyl hypocrellin derivative in example 20, and four blue black solid products HC-13a-NH-PEGn, HC-13b-NH-PEGn, HC-13c-NH-PEGn, and HC-13d-NH-PEGn (n=1, 4, 8) are obtained, respectively. HC-13a-NH-PEG1 (n=1): yield: 7.6%, $R_f$: 0.32; MS (ESI+): 952.6; maximum absorption wavelength: 624 nm; molar extinction coefficient: 30,000 $M^{-1}cm^{-1}$; singlet oxygen yield: 32%. HC-13b-NH-PEG4 (n=4): yield: 8.8%, $R_f$: 0.38; MS (ESI+): 1216.6; maximum absorption wavelength: 624 nm; molar extinction coefficient: 30,000 $M^{-1}cm^{-1}$; singlet oxygen yield: 32%. HC-13c-NH-PEG8 (n=8): yield: 17.2%, $R_f$: 0.36; MS (ESI+): 1568.6; maximum absorption wavelength: 630 nm; molar extinction coefficient: 33,500 $M^{-1}$ $cm^{-1}$; singlet oxygen yield: 38%. HC-13d-NH-PEG8 (n=8): yield: 9.8%, $R_f$: 0.30; MS (ESI+): 1568.6; maximum absorption wavelength: 625 nm; molar extinction coefficient: 32,500 $M^{-1}$ $cm^{-1}$; singlet oxygen yield: 30%. Structural formulas of the above amino-substituted products are as follows:

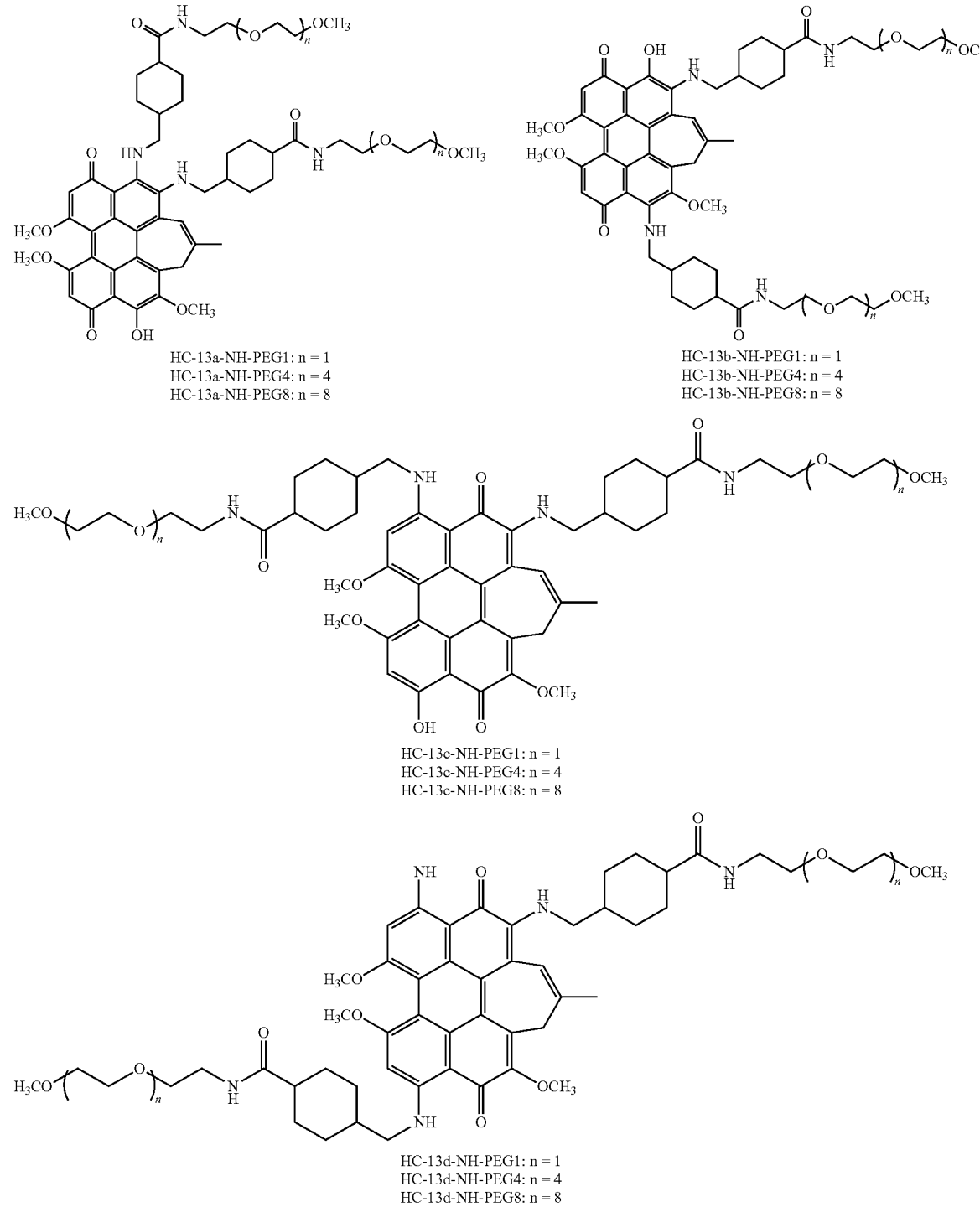

Figure 18:
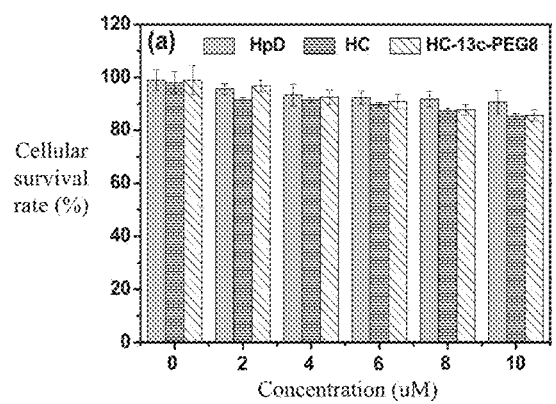
FIG. 18(a) shows dark toxicities, to Hela cells, of the hematoporphyrin derivative HpD, the hypocrellin B HB, and HC-13c-NH-PEG8 synthesized in example 41 of the present invention at different concentrations, wherein HC-13c-NH-PEG8 is obtained by connecting the 4-aminomethylcyclohexanoic acid-substituted hypocrellin B derivative and two 8-PEG chains with an amide bond.
FIG. 18(b) shows phototoxicities, to Hela cells, of the hematoporphyrin derivative HpD, the hypocrellin B HB, and HC-13c-NH-PEG8 synthesized in example 41 of the present invention at different concentrations, wherein HC-13c-NH-PEG8 is obtained by connecting the 4-aminomethylcyclohexanoic acid-substituted hypocrellin B derivative and two 8-PEG chains with an amide bond.
Figure 18:
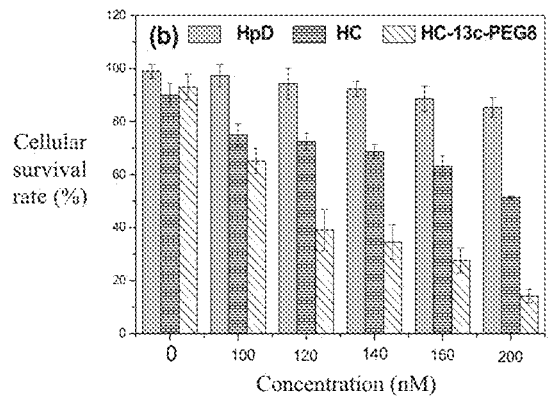

The compound HC-13c and two 8-PEG chains are connected by an amide bond, to obtain HC-13c-NH-PEG8 (example 41) with dark toxicity and phototoxicity effects of killing tumor cells as shown in FIGS. 18(a) and 18(b). Under red light irradiation, HC-13c-NH-PEG8 with a concentration range of 200 nM can kill more than 85% of the Hela cells, while in the same condition, the hypocrellin B HB can kill 60% of the Hela cells, and the commercial photosensitizer hematoporphyrin derivative HpD can kill only about 10% of the Hela cells. The above-described results indicate that A photodynamic effect of HC-13c-NH-PEG8 is significantly better than that of the deacetyl hypocrellin and commercial photosensitizer hematoporphyrin.

Example 42

Preparation of a 4-tranexamic acid-quaternary ammonium salt (of different chain lengths)-substituted hypocrellin B derivative ($R_1=R_2=$—$CH_2C_6H_{10}COO$—$Cn$-$N(CH_3)_3$, $R_3=R_4=$—H) (n is the number of carbon atoms of the quaternary ammonium salt, and n=2, 4, 6): a synthetic route is similar to the preparation of the aminobutyric acid-polyethylene glycol (of different chain lengths)-substituted deacetyl hypocrellin derivative in example 20, and four blue black solid products HC-13a-Cn-N$^+$, HC-13b-Cn-N$^+$, HC-13c-Cn-N$^+$, and HC-13d-Cn-N$^+$ (n=2, 4, 6) are obtained, respectively. HC-13a-C2-N$^+$ (n=2): yield: 11.6%, $R_f$: 0.32; MS (ESI+): 922.3; maximum absorption wavelength: 622 nm; molar extinction coefficient: 30,500 M$^{-1}$ cm$^{-1}$; singlet oxygen yield: 30%. HC-13b-C4-N$^+$ (n=4): yield: 9.2%, $R_f$: 0.38; MS (ESI+): 978.6; maximum absorption wavelength: 624 nm; molar extinction coefficient: 31,500 M$^{-1}$ cm$^{-1}$; singlet oxygen yield: 36%. HC-13c-C6-N$^+$ (n=6): yield: 15.8%, $R_f$: 0.38; MS (ESI+): 1034.6; maximum absorption wavelength: 630 nm; molar extinction coefficient: 33,000 M$^{-1}$ cm$^{-1}$; singlet oxygen yield: 38%. HC-13d-C4-N$^+$ (n=4): yield: 13.2%, $R_f$: 0.32; MS (ESI+): 978.6; maximum absorption wavelength: 630 nm; molar extinction coefficient: 32,500 M$^{-1}$ cm$^{-1}$; singlet oxygen yield: 33%. Structural formulas of the above amino-substituted products are as follows:

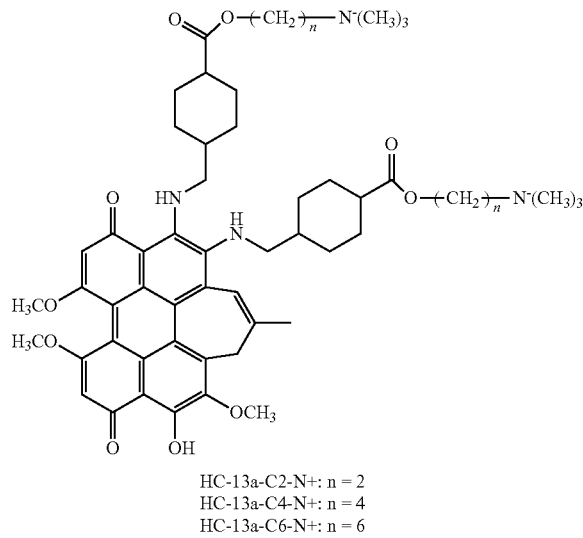

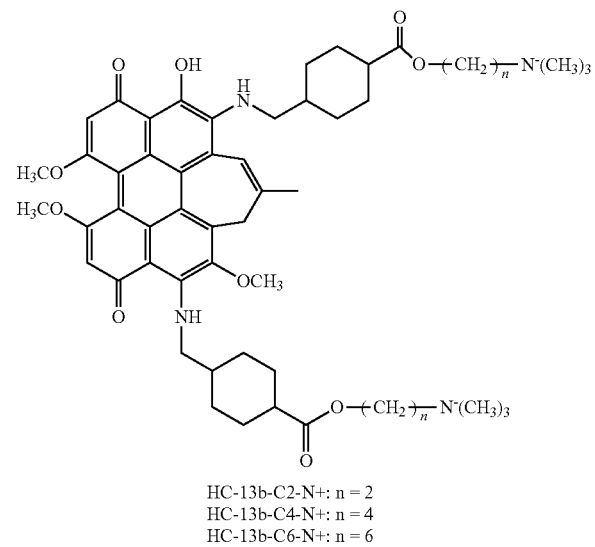

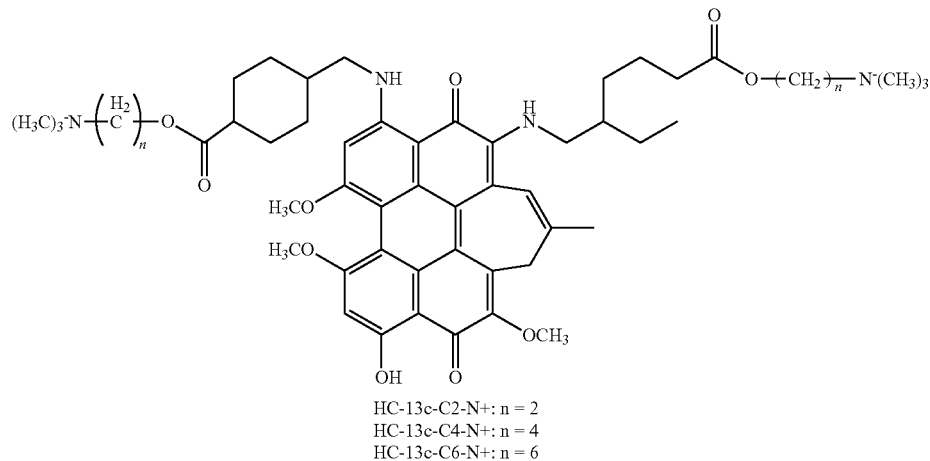

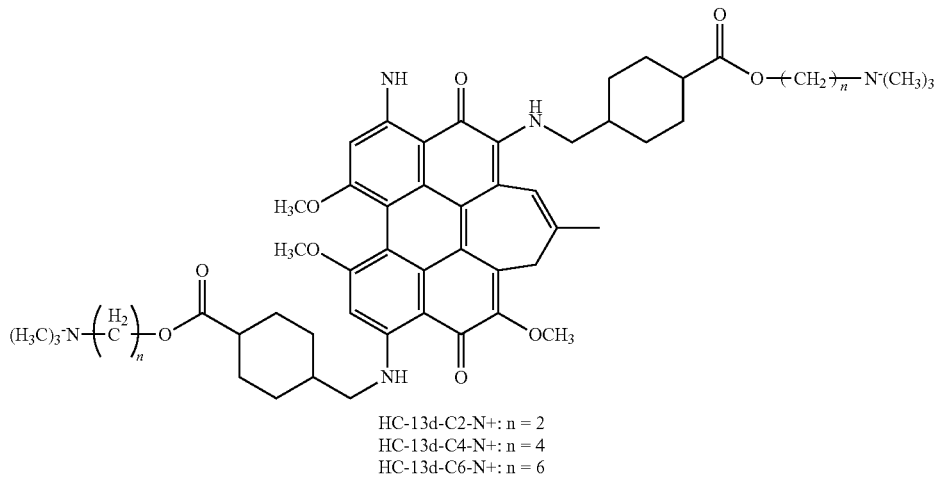

HC-13d-C2-N+: n = 2
HC-13d-C4-N+: n = 4
HC-13d-C6-N+: n = 6

Example 43

Preparation of a 4-tranexamic acid-sulfonic acid group (of different chain lengths)-substituted hypocrellin B derivative ($R_1=R_2=$—$CH_2C_6H_{10}CO$—NH—$Cn$-$SO_3H$, $R_3=R_4=$—H) (n is the number of carbon atoms of the sulfonate, and n=2, 4, 6): a synthetic route is similar to the preparation of the aminobutyric acid-polyethylene glycol (of different chain lengths)-substituted deacetyl hypocrellin derivative in example 20, and four blue black solid products HC-13a-Cn-$SO_3H$, HC-13b-Cn-$SO_3H$, HC-13c-Cn-$SO_3H$, and HC-13d-Cn-$SO_3H$ (n=2, 4, 6) are obtained, respectively. HC-13a-C2-$SO_3H$ (n=2): yield: 8.6%, $R_f$: 0.32; MS (ESI+): 964.3; maximum absorption wavelength: 622 nm; molar extinction coefficient: 31,000 $M^{-1}$ $cm^{-1}$; singlet oxygen yield: 32%. HC-13b-C4-$SO_3H$ (n=4): yield: 11.5%, $R_f$: 0.34; MS (ESI+): 1020.6; maximum absorption wavelength: 622 nm; molar extinction coefficient: 30,000 $M^{-1}$ $cm^{-1}$; singlet oxygen yield: 32%. HC-13c-C6-$SO_3H$ (n=6): yield: 17.8%, $R_f$: 0.36; MS (ESI+): 1076.6; maximum absorption wavelength: 630 nm; molar extinction coefficient: 33,000 $M^{-1}$ $cm^{-1}$; singlet oxygen yield: 36%. HC-13d-C4-$SO_3H$ (n=4): yield: 13.2%, $R_f$: 0.26; MS (ESI+): 1020.6; maximum absorption wavelength: 624 nm; molar extinction coefficient: 31,000 $M^{-1}cm^{-1}$; singlet oxygen yield: 30%. Structural formulas of the above amino-substituted products are as follows:

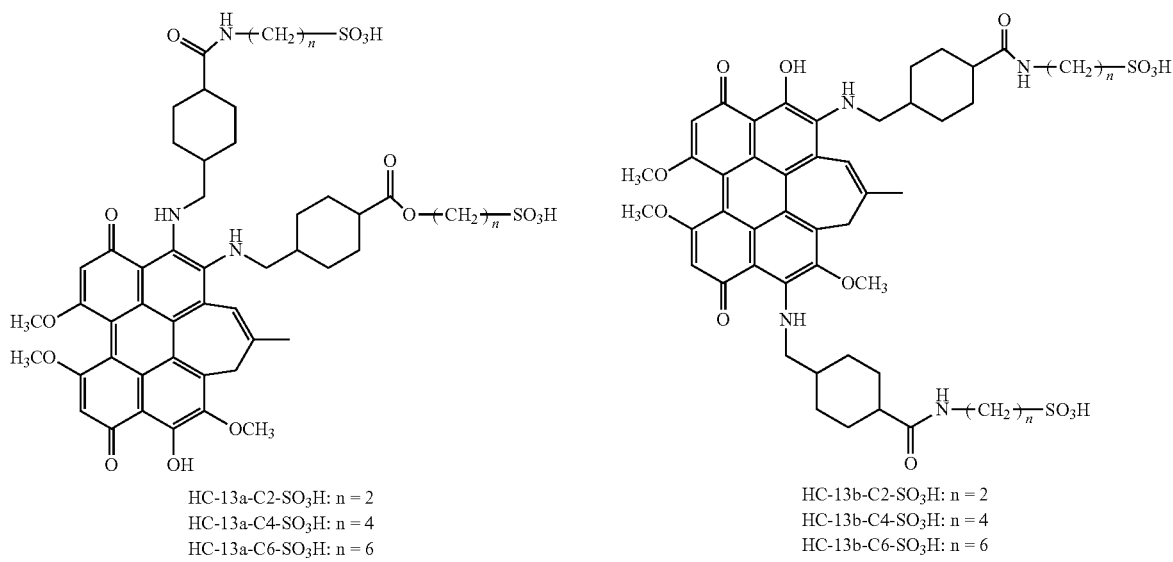

HC-13a-C2-SO₃H: n = 2
HC-13a-C4-SO₃H: n = 4
HC-13a-C6-SO₃H: n = 6

HC-13b-C2-SO₃H: n = 2
HC-13b-C4-SO₃H: n = 4
HC-13b-C6-SO₃H: n = 6

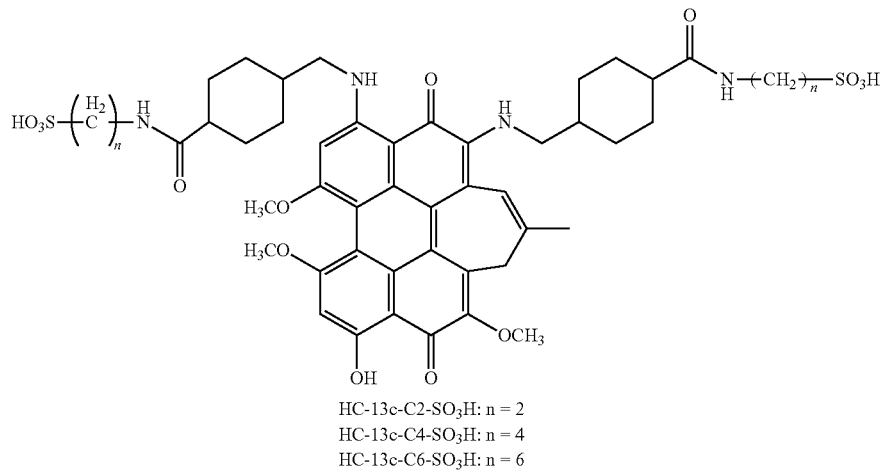

HC-13c-C2-SO₃H: n = 2
HC-13c-C4-SO₃H: n = 4
HC-13c-C6-SO₃H: n = 6

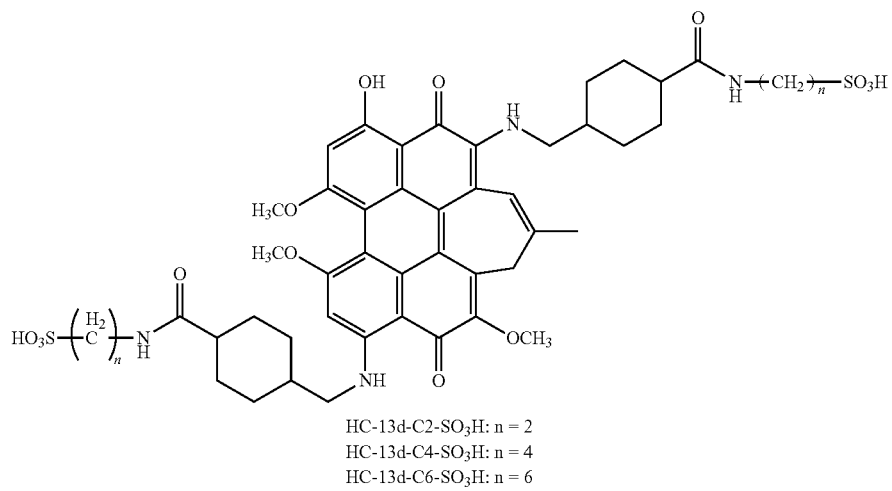

HC-13d-C2-SO₃H: n = 2
HC-13d-C4-SO₃H: n = 4
HC-13d-C6-SO₃H: n = 6

Example 44

Preparation of a 4-tranexamic acid-amino triphenylphosphine (of different chain lengths)-substituted hypocrellin derivative ($R_1=R_2=$—$CH_2C_6H_{10}CO$—$NH$-$Cn$-$PPh_3+$, $R_3=R_4=$—H) (n is the number of carbon atoms of the amino triphenylphosphine, and n=2, 4, 6): a synthetic route is similar to the preparation of the aminobutyric acid-polyethylene glycol (of different chain lengths)-substituted deacetyl hypocrellin derivative in example 20, and four blue black solid products HC-13a-NH—Cn-PPh₃+, HC-13b-NH—Cn-PPh₃+, HC-13c-NH—Cn-PPh₃+, and HC-13d-NH—Cn-PPh₃+(n=2, 4, 6) are obtained, respectively. HC-13a-NH—C2-PPh₃+(n=2): yield: 9.6%, $R_f$: 0.32; MS (ESI+): 1327.3; maximum absorption wavelength: 622 nm; molar extinction coefficient: 31,500 $M^{-1}$ $cm^{-1}$; singlet oxygen yield: 32%. HC-13b-NH—C4-PPh₃+(n=4): yield: 10.5%, $R_f$: 0.38; MS (ESI+): 1383.6; maximum absorption wavelength: 626 nm; molar extinction coefficient: 30,500 $M^{-1}$ $cm^{-1}$; singlet oxygen yield: 34%. HC-13c-NH—C6-PPh₃+(n=6): yield: 18.8%, $R_f$: 0.40; MS (ESI+): 1439.6; maximum absorption wavelength: 632 nm; molar extinction coefficient: 33,500 $M^{-1}cm^{-1}$; singlet oxygen yield: 38%. HC-13d-NH—C4-PPh₃+(n=4): yield: 12.2%, $R_f$: 0.26; MS (ESI+): 1383.6; maximum absorption wavelength: 618 nm; molar extinction coefficient: 31,500 $M^{-1}cm^{-1}$; singlet oxygen yield: 30%. Structural formulas of the above amino-substituted products are as follows:

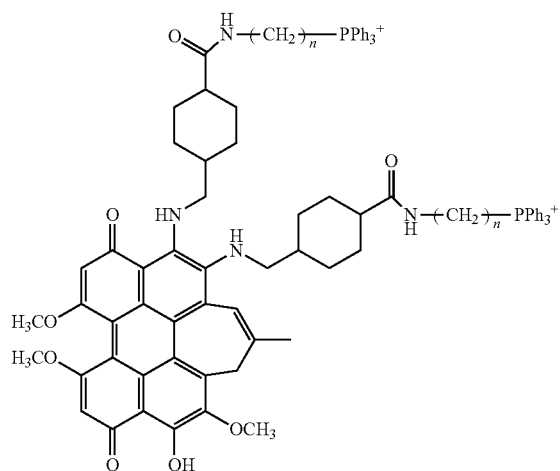

HC-13a-C2-PPh$_3^+$: n = 2
HC-13a-C4-PPh$_3^+$: n = 4
HC-13a-C6-PPh$_3^+$: n = 6

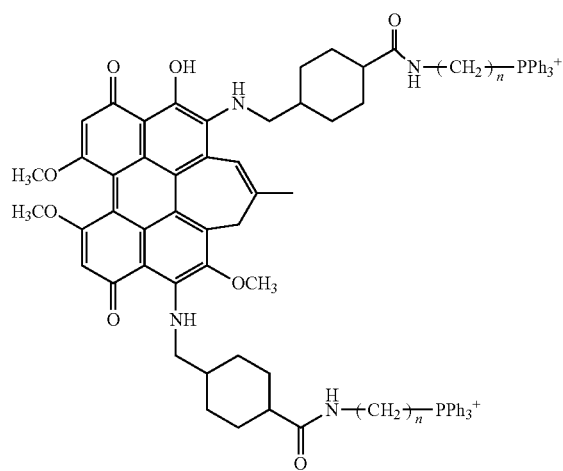

HC-13b-C2-PPh$_3^+$: n = 2
HC-13b-C4-PPh$_3^+$: n = 4
HC-13b-C6-PPh$_3^+$: n = 6

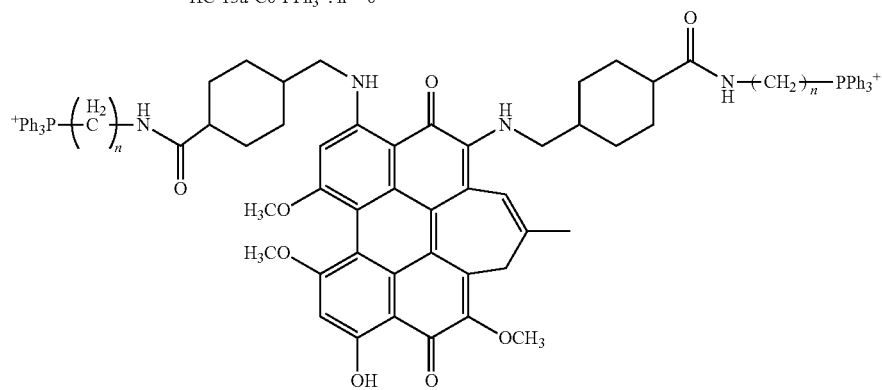

HC-13c-C2-PPh$_3^+$: n = 2
HC-13c-C4-PPh$_3^+$: n = 4
HC-13c-C6-PPh$_3^+$: n = 6

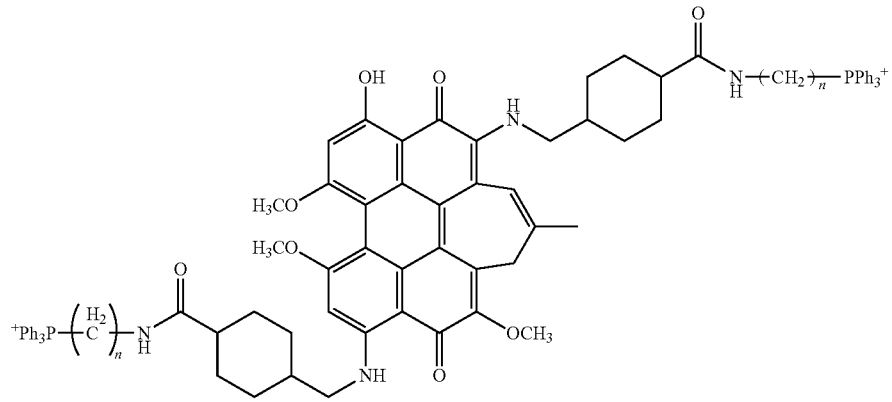

HC-13d-C2-PPh$_3^+$: n = 2
HC-13d-C4-PPh$_3^+$: n = 4
HC-13d-C6-PPh$_3^+$: n = 6

Example 45

Preparation of a 4-aminocyclohexanecarboxylic acid-substituted hypocrellin B derivative (R$_1$=R$_2$=—C$_6$H$_{10}$COOCH$_3$, R$_3$=—COCH$_3$, R$_4$=—H): a substituted amino raw material is NH$_2$—C$_6$H$_{10}$COOH, a synthetic method is similar to the preparation of the diaminoacetic acid-substituted hypocrellin B derivative in example 17, and four blue black solid products HB-14a-HB-14d are obtained, respectively. HB-14a: yield: 5.8%, R$_f$: 0.38; MS (ESI+): 764.1; maximum absorption wavelength: 625 nm; molar extinction coefficient: 27,000 M$^{-1}$cm$^{-1}$; singlet oxygen yield: 25%. HB-14b: yield: 8.5%, R$_f$: 0.40; MS (ESI+): 764.1; maximum absorption wavelength: 623 nm; molar extinction coefficient: 27,000 M$^{-1}$cm$^{-1}$; singlet oxygen yield: 24%. HB-14c: yield: 5.5%, $R_f$: 0.32; MS (ESI+): 764.8; maximum absorption wavelength: 621 nm; molar extinction coefficient: 28,000 $M^{-1}cm^{-1}$; singlet oxygen yield: 26%. HB-14d: yield: 5.9%, $R_f$: 0.45; MS (ESI+): 764.9; maximum absorption wavelength: 623 nm. molar extinction coefficient: 27,000 $M^{-1}cm^{-1}$; singlet oxygen yield: 24%. Structural formulas of the above amino-substituted products are as follows:

HB-14a

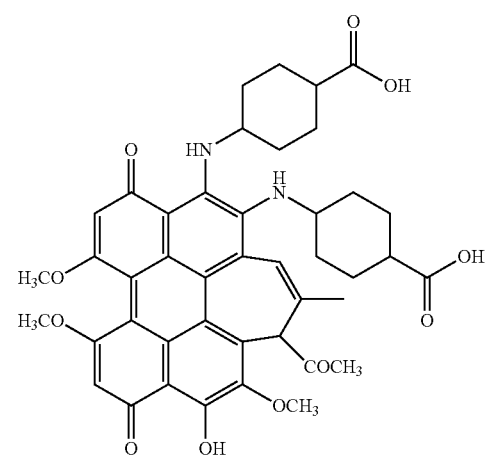

HB-14b

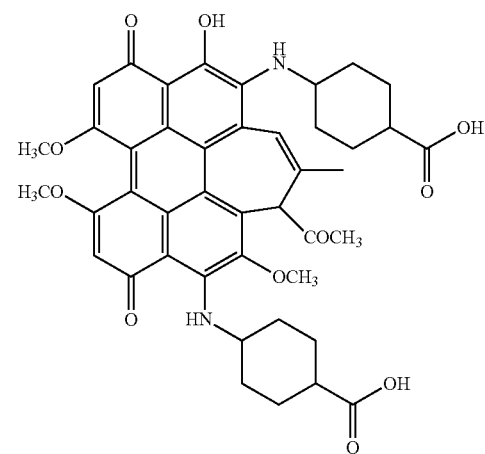

HB-14c

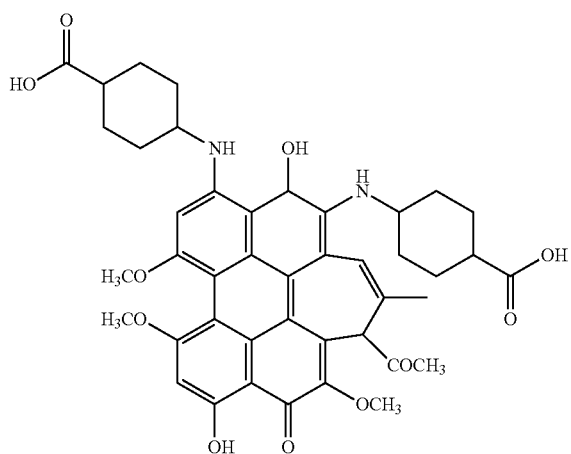

HB-14d

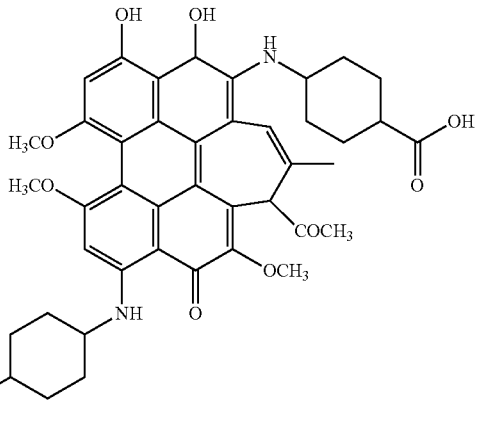

Example 46

Preparation of a 4-aminocyclohexanecarboxylic acid-amino PEG (of different chain lengths)-substituted deacetyl hypocrellin B derivative ($R_1$=$R_2$=—$C_6H_{10}$COO-PEGn, $R_3$=—$COCH_3$, $R_4$=—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-14a-PEGn, HB-14b-PEGn, HB-14c-PEGn, and HB-14d-PEGn (n=1, 6, 12) are obtained, respectively. HB-14a-PEG1 (n=1): yield: 9.6%, $R_f$: 0.32; MS (ESI+): 880.6; maximum absorption wavelength: 622 nm; molar extinction coefficient: 30,500 $M^{-1}cm^{-1}$; singlet oxygen yield: 32%. HB-14b-PEG6 (n=6): yield: 8.2%, $R_f$: 0.36; MS (ESI+): 1320.6; maximum absorption wavelength: 624 nm; molar extinction coefficient: 30,500 $M^{-1}cm^{-1}$; singlet oxygen yield: 34%. HB-14c-PEG12 (n=12): yield: 17.2%, $R_f$: 0.42; MS (ESI+): 1848.6; maximum absorption wavelength: 628 nm; molar extinction coefficient: 33,500 $M^{-1}cm^{-1}$; singlet oxygen yield: 38%. HB-14d-PEG6 (n=6): yield: 9.4%, $R_f$: 0.30; MS (ESI+): 1320.6; maximum absorption wavelength: 630 nm; molar extinction coefficient: 31,500 $M^{-1}cm^{-1}$; singlet oxygen yield: 32%. Structural formulas of the above amino-substituted products are as follows:

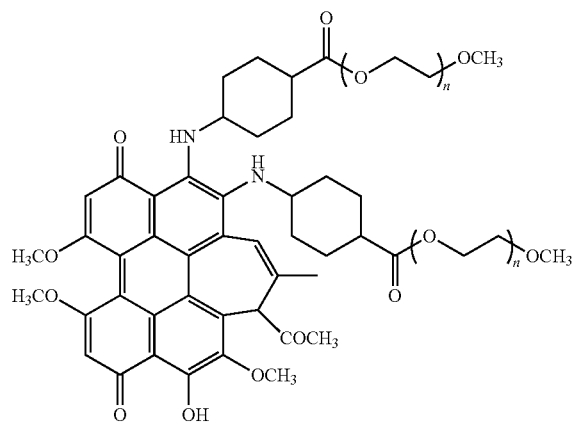

HB-14a-PEG1: n = 1
HB-14a-PEG6: n = 6
HB-14a-PEG12: n = 12

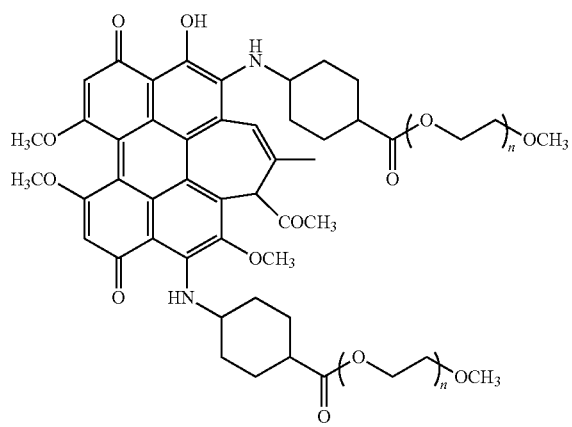

HB-14b-PEG1: n = 1
HB-14b-PEG6: n = 6
HB-14b-PEG12: n = 12

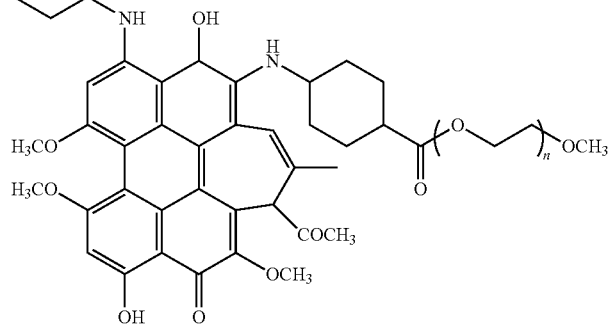

HB-14c-PEG1: n = 1
HB-14c-PEG6: n = 6
HB-14c-PEG12: n = 12

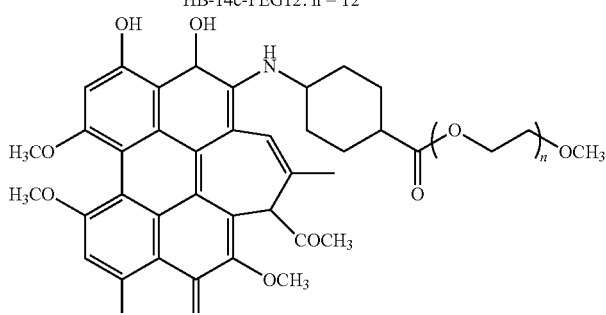

HB-14d-PEG1: n = 1
HB-14d-PEG6: n = 6
HB-14d-PEG12: n = 12

Example 47

Preparation of a 3-aminocyclohexanecarboxylic acid-substituted hypocrellin derivative ($R_1=R_2=C_6H_{10}COOCH_3$, $R_3=$—COCH$_3$, $R_4=$—H): a substituted amino raw material is $NH_2$—$C_6H_{10}COOH$, a synthetic method is similar to the preparation of the diaminoacetic acid-substituted hypocrellin B derivative in example 17, and four blue black solid products HB-15a-HB-15d are obtained, respectively. HB-15a: yield: 5.8%, $R_f$: 0.38; MS (ESI+): 764.1; maximum absorption wavelength: 625 nm; molar extinction coefficient: 27,000 $M^{-1}cm^{-1}$; singlet oxygen yield: 25%. HB-15b: yield: 8.5%, $R_f$: 0.40; MS (ESI+): 764.1; maximum absorption wavelength: 623 nm; molar extinction coefficient: 27,000 $M^{-1}$ $cm^{-1}$; singlet oxygen yield: 24%. HB-15c: yield: 5.5%, $R_f$: 0.32; MS (ESI+): 764.8; maximum absorption wavelength: 621 nm; molar extinction coefficient: 28,000 $M^{-1}cm$; singlet oxygen yield: 26%. HB-15d: yield: 5.9%, $R_f$: 0.45; MS (ESI+): 764.9; maximum absorption wavelength: 623 nm. molar extinction coefficient: 27,000 $M^{-1}cm^{-1}$; singlet oxygen yield: 24%. Structural formulas of the above amino-substituted products are as follows:

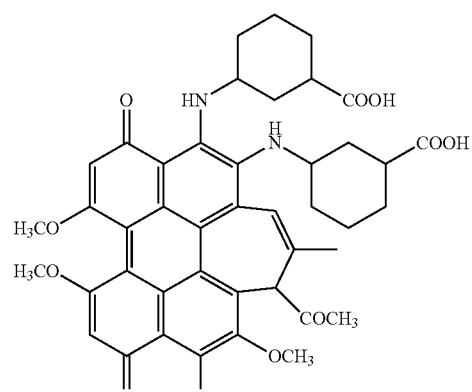

HB-15a

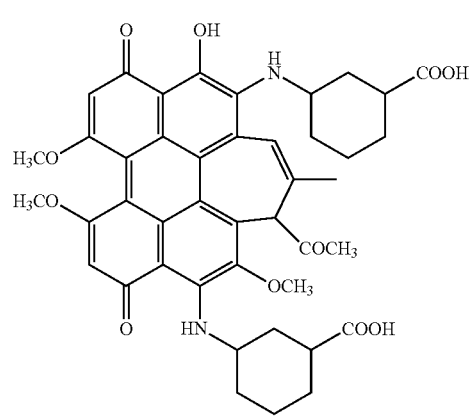

HB-15b

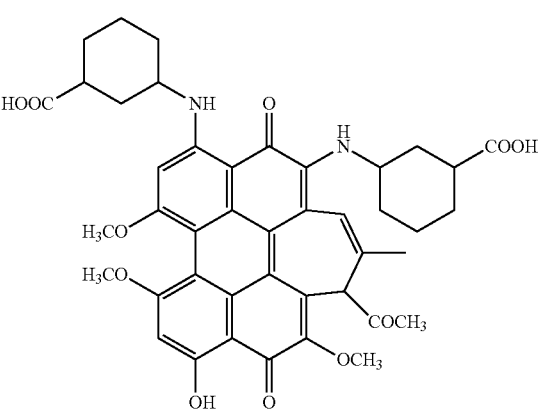

HB-15c

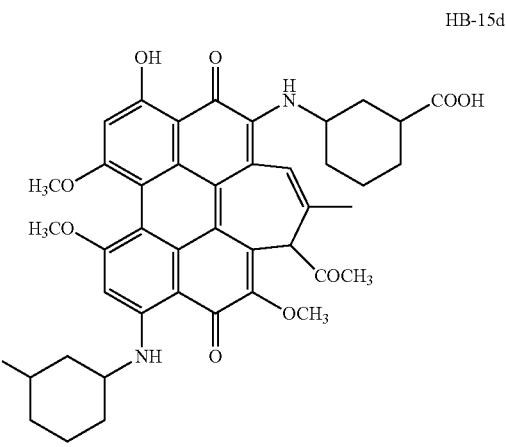

HB-15d

Example 48

Preparation of a 3-aminocyclohexanecarboxylic acid-PEG (of different chain lengths)-substituted hypocrellin B derivative ($R_1$=$R_2$=—$C_6H_{10}$COO-PEGn, $R_3$=—$COCH_3$, $R_4$=—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-15a-PEGn, HB-15b-PEGn, HB-15c-PEGn, and HB-15d-PEGn (n=1, 6, 12) are obtained, respectively. HB-15a-PEG1 (n=1): yield: 9.8%, $R_f$: 0.28; MS (ESI+): 880.6; maximum absorption wavelength: 624 nm; molar extinction coefficient: 30,000 $M^{-1}$ $cm^{-1}$; singlet oxygen yield: 30%. HB-15b-PEG6 (n=6): yield: 8.2%, $R_f$: 0.34; MS (ESI+): 1320.6; maximum absorption wavelength: 624 nm; molar extinction coefficient: 30,000 $M^{-1}cm^{-1}$; singlet oxygen yield: 34%. HB-15c-PEG12 (n=12): yield: 18.2%, $R_f$: 0.42; MS (ESI+): 1848.6; maximum absorption wavelength: 630 nm; molar extinction coefficient: 33,000 $M^{-1}$ $cm^{-1}$; singlet oxygen yield: 35%. HB-15d-PEG6 (n=6): yield: 9.9%, $R_f$: 0.32; MS (ESI+): 1320.6; maximum absorption wavelength: 630 nm; molar extinction coefficient: 32,500 $M^{-1}$ $cm^{-1}$; singlet oxygen yield: 32%. Structural formulas of the above amino-substituted products are as follows:

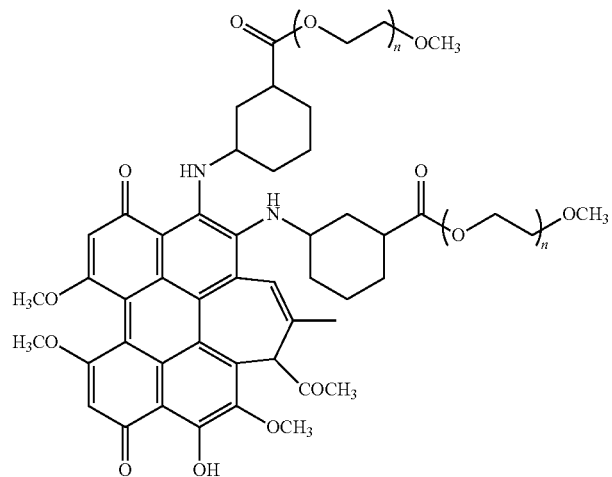
HB-15a-PEG1: n = 1
HB-15a-PEG6: n = 6
HB-15a-PEG12: n = 12
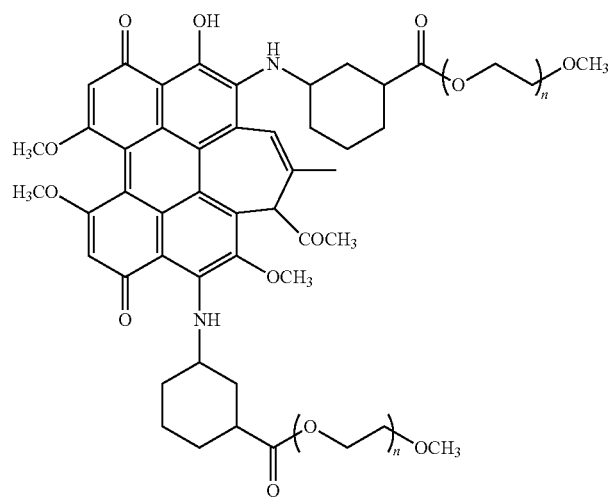
HB-15b-PEG1: n = 1
HB-15b-PEG6: n = 6
HB-15b-PEG12: n = 12
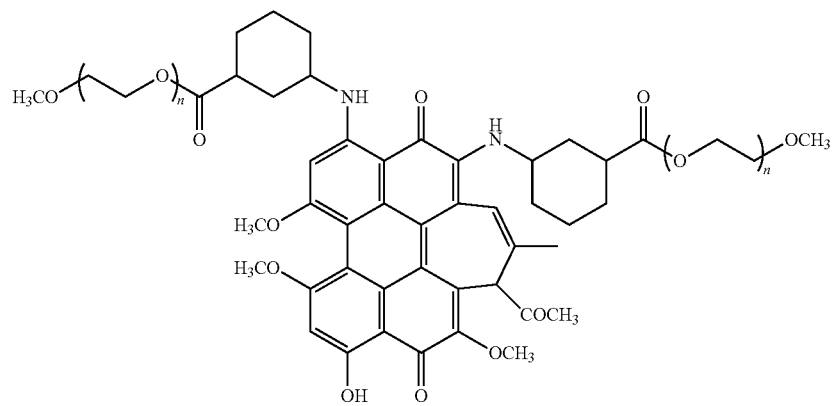
HB-15c-PEG1: n = 1
HB-15c-PEG6: n = 6
HB-15c-PEG12: n = 12

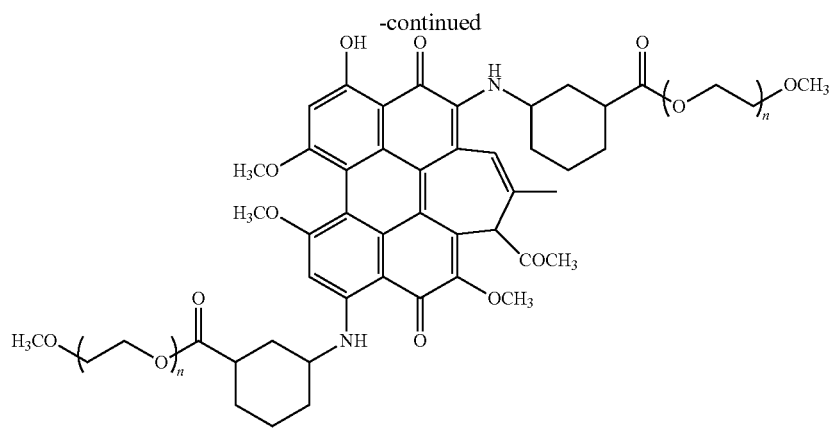

HB-15d-PEG1: n = 1
HB-15d-PEG6: n = 6
HB-15d-PEG12: n = 12

Example 49

Preparation of a 2-aminocyclohexanecarboxylic acid-substituted hypocrellin B derivative ($R_1$=$R_2$=—$C_6H_{10}COOCH_3$, $R_3$=—$COCH_3$, $R_4$=—H): a substituted amino raw material is $NH_2$—$C_6H_{10}COOH$, a synthetic method is similar to the preparation of the diaminoacetic acid-substituted hypocrellin B derivative in example 17, and four blue black solid products HB-16a-HB-16d are obtained, respectively. HB-16a: yield: 4.8%, $R_f$: 0.36; MS (ESI+): 764.1; maximum absorption wavelength: 620 nm; molar extinction coefficient: 25,500 $M^{-1}$ $cm^{-1}$; singlet oxygen yield: 25%. HB-16b: yield: 5.5%, $R_f$: 0.38; MS (ESI+): 764.1; maximum absorption wavelength: 625 nm; molar extinction coefficient: 26,000 $M^{-1}$ $cm^{-1}$; singlet oxygen yield: 26%. HB-16c: yield: 5.5%, $R_f$: 0.34; MS (ESI+): 764.8; maximum absorption wavelength: 628 nm; molar extinction coefficient: 28,000 $M^{-1}$ $cm^{-1}$; singlet oxygen yield: 28%. HB-16d: yield: 6.9%, $R_f$: 0.40; MS (ESI+): 764.9; maximum absorption wavelength: 625 nm; molar extinction coefficient: 26,500 $M^{-1}cm^{-1}$; singlet oxygen yield: 26%. Structural formulas of the above amino-substituted products are as follows:

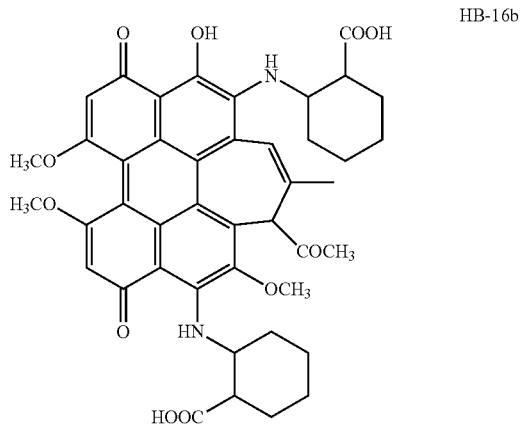

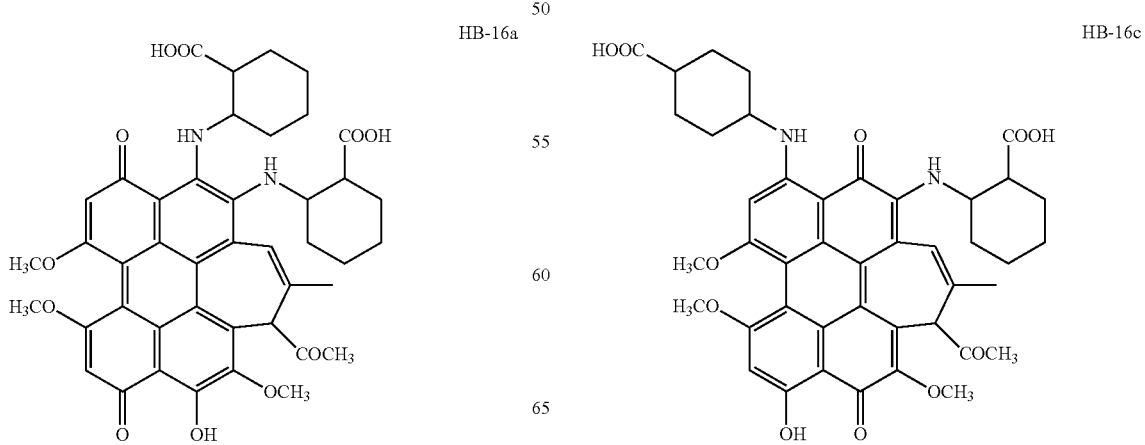

-continued

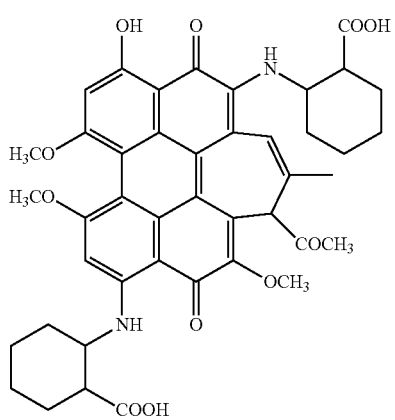

HB-16d

Example 50

Preparation of a 2-aminocyclohexanecarboxylic acid-PEG (of different chain lengths)-substituted hypocrellin B derivative ($R_1=R_2=\!=\!\!-C_6H_{10}CO\!-\!NH\text{-PEGn}$, $R_3=\!\!-COCH_3$, $R_4=\!\!=\!\!H$) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-16a-PEGn, HB-16b-PEGn, HB-16c-PEGn, and HB-16d-PEGn (n=1, 6, 12) are obtained, respectively. HB-16a-PEG1 (n=1): yield: 7.8%, $R_f$: 0.32; MS (ESI+): 880.6; maximum absorption wavelength: 624 nm; molar extinction coefficient: 30,500 $M^{-1}cm^{-1}$; singlet oxygen yield: 32%. HB-16b-PEG6 (n=6): yield: 8.5%, $R_f$: 0.34; MS (ESI+): 1320.6; maximum absorption wavelength: 624 nm; molar extinction coefficient: 30,500 $M^{-1}cm^{-1}$; singlet oxygen yield: 32%. HB-16c-PEG12 (n=12): yield: 16.2%, $R_f$: 0.40; MS (ESI+): 1848.6; maximum absorption wavelength: 628 nm; molar extinction coefficient: 33,500 $M^{-1}cm^{-1}$; singlet oxygen yield: 36%. HB-16d-PEG6 (n=6): yield: 9.9%, $R_f$: 0.34; MS (ESI+): 1320.6; maximum absorption wavelength: 628 nm; molar extinction coefficient: 32,000 $M^{-1}cm^{-1}$; singlet oxygen yield: 33%. Structural formulas of the above amino-substituted products are as follows:

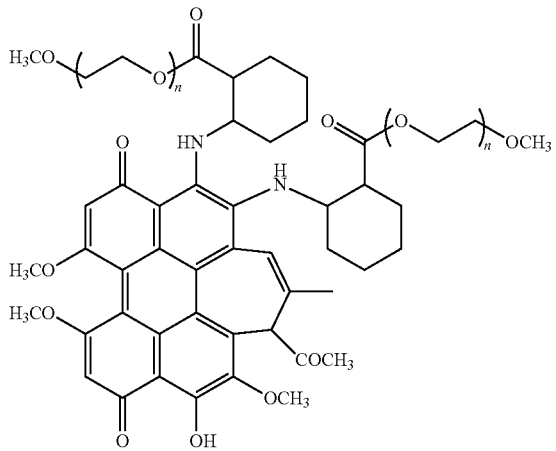

HB-16a-PEG1: n = 1
HB-16a-PEG6: n = 6
HB-16a-PEG12: n = 12

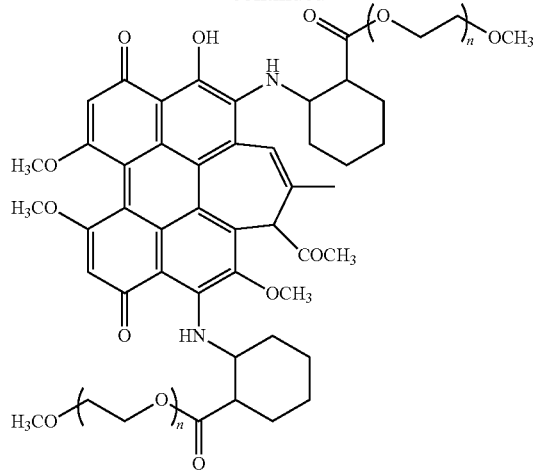

HB-16a-PEG1: n = 1
HB-16a-PEG6: n = 6
HB-16a-PEG12: n = 12

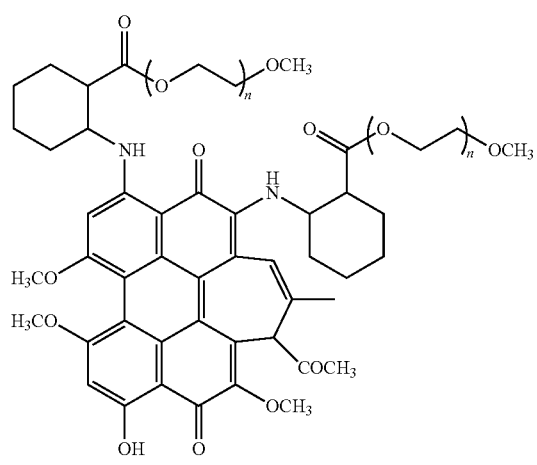

HB-16a-PEG1: n = 1
HB-16a-PEG6: n = 6
HB-16a-PEG12: n = 12

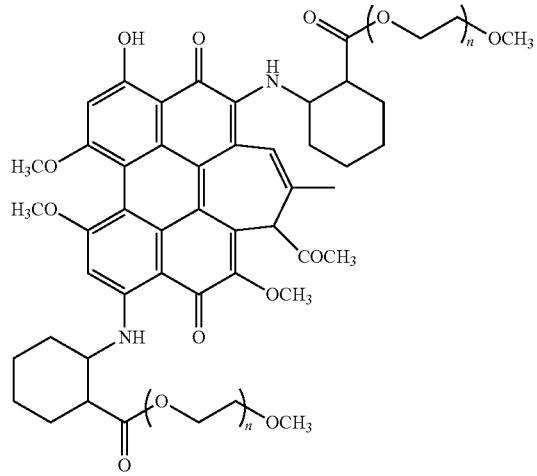

HB-16a-PEG1: n = 1
HB-16a-PEG6: n = 6
HB-16a-PEG12: n = 12

Example 51

Preparation of a 2-aminocyclohexanecarboxylic acid-amino PEG (of different chain lengths)-substituted hypocrellin B derivative ($R_1=R_2=$—$C_6H_{10}CO$—NH-PEGn, $R_3=$—$COCH_3$, $R_4=$—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-16a-NH-PEGn, HB-16b-NH-PEGn, HB-16c-NH-PEGn, and HB-16d-NH-PEGn (n=1, 6, 12) are obtained, respectively. HB-16a-NH-PEG1 (n=1): yield: 8.8%, $R_f$: 0.30; MS (ESI+): 925.6; maximum absorption wavelength: 622 nm; molar extinction coefficient: 30,000 $M^{-1}cm^{-1}$; singlet oxygen yield: 32%. HB-16b-NH-PEG6 (n=6): yield: 7.5%, $R_f$: 0.32; MS (ESI+): 1365.6; maximum absorption wavelength: 622 nm; molar extinction coefficient: 31,500 $M^{-1}cm^{-1}$; singlet oxygen yield: 34%. HB-16c-NH-PEG12 (n=12): yield: 18.2%, $R_f$: 0.38; MS (ESI+): 1893.6; maximum absorption wavelength: 628 nm; molar extinction coefficient: 33,000 $M^{-1}$ $cm^{-1}$; singlet oxygen yield: 38%. HB-16d-NH-PEG6 (n=6): yield: 9.5%, $R_f$: 0.36; MS (ESI+): 1365.6; maximum absorption wavelength: 628 nm; molar extinction coefficient: 32,500 $M^{-1}cm^{-1}$; singlet oxygen yield: 32%. Structural formulas of the above amino-substituted products are as follows:

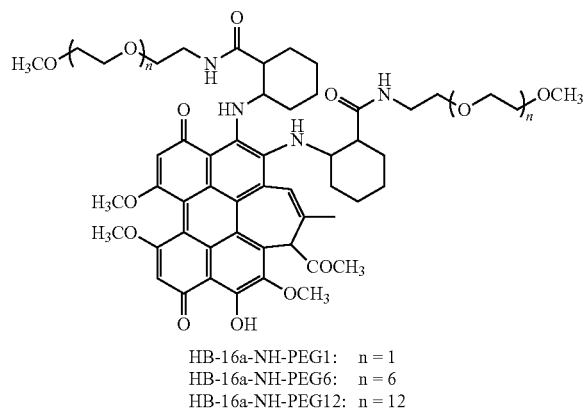

HB-16a-NH-PEG1: n = 1
HB-16a-NH-PEG6: n = 6
HB-16a-NH-PEG12: n = 12

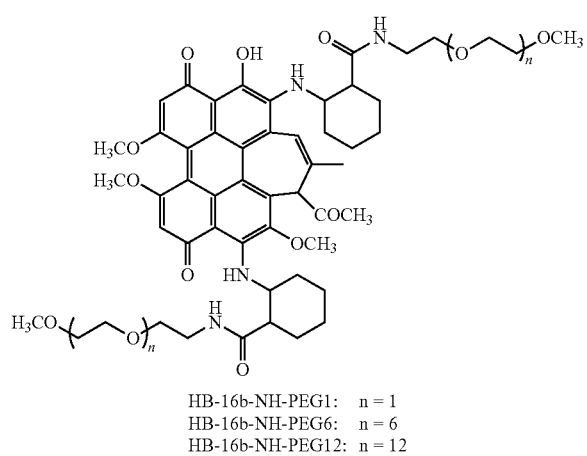

HB-16b-NH-PEG1: n = 1
HB-16b-NH-PEG6: n = 6
HB-16b-NH-PEG12: n = 12

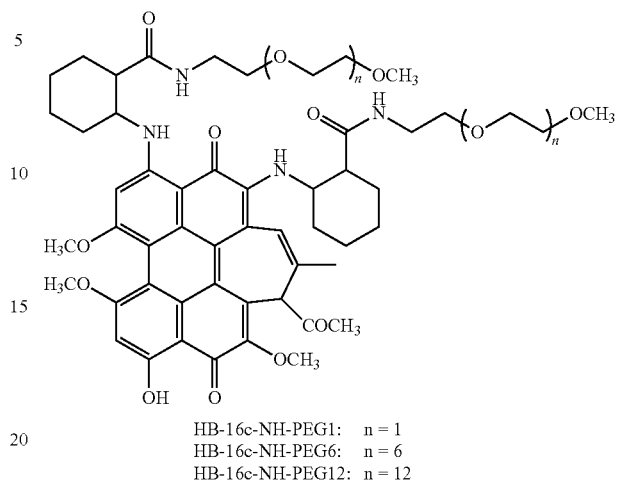

HB-16c-NH-PEG1: n = 1
HB-16c-NH-PEG6: n = 6
HB-16c-NH-PEG12: n = 12

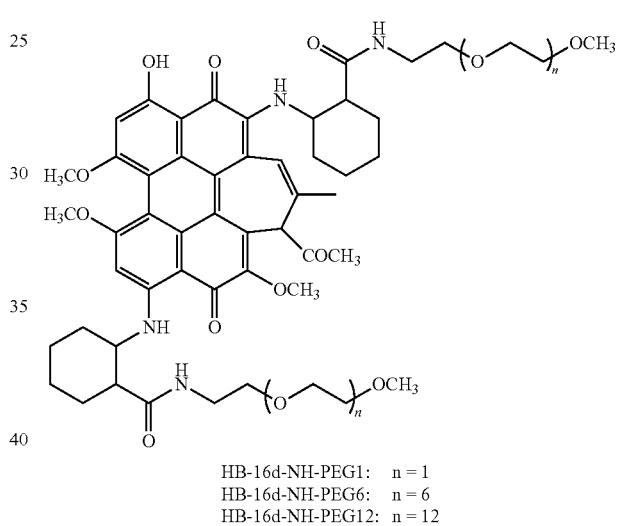

HB-16d-NH-PEG1: n = 1
HB-16d-NH-PEG6: n = 6
HB-16d-NH-PEG12: n = 12

Example 52

Preparation of a 4-hydroxylcyclohexylamine-substituted hypocrellin B derivative ($R_1=R_2=$—$C_6H_{10}OH$, $R_3=$—$COCH_3$, $R_4=$—H): a substituted amino raw material is $NH_2$—$C_6H_{10}OH$, a synthetic method is similar to the preparation of the di-2-(2-aminoethoxy)ethanol-substituted hypocrellin B derivative in example 2, and four blue black solid products HB-17a-HB-17d are obtained, respectively. HB-17a: yield: 6.9%, $R_f$: 0.36; MS (ESI+): 708.3; maximum absorption wavelength: 617 nm; molar extinction coefficient: 25,000 $M^{-1}cm^{-1}$; singlet oxygen yield: 22%. HB-17b: yield: 5.2%, $R_f$: 0.28; MS (ESI+): 708.3; maximum absorption wavelength: 620 nm; molar extinction coefficient: 25,500 $M^{-1}cm^{-1}$; singlet oxygen yield: 20%. HB-17c: yield: 6.9%, $R_f$: 0.35; MS (ESI+): 708.3; maximum absorption wavelength: 622 nm; molar extinction coefficient: 26,000 $M^{-1}cm^{-1}$; singlet oxygen yield: 23%. HB-17d: yield: 5.7%, $R_f$: 0.33; MS (ESI+): 708.3; maximum absorption wavelength: 624 nm; molar extinction coefficient: 25,000 $M^{-1}$ cm$^{-1}$; singlet oxygen yield: 22%. Structural formulas of the above amino-substituted products are as follows:

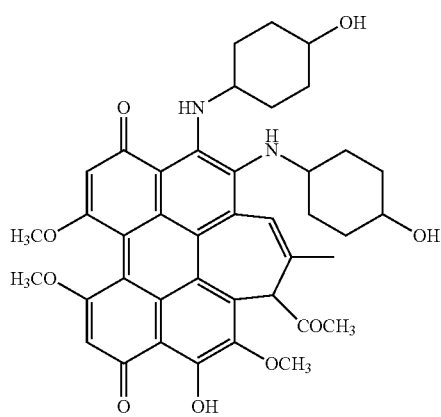

HB-17a

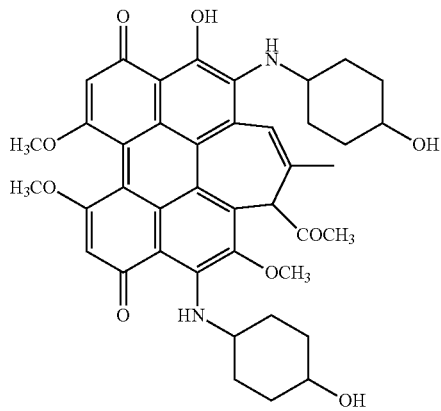

HB-17b

HB-17c

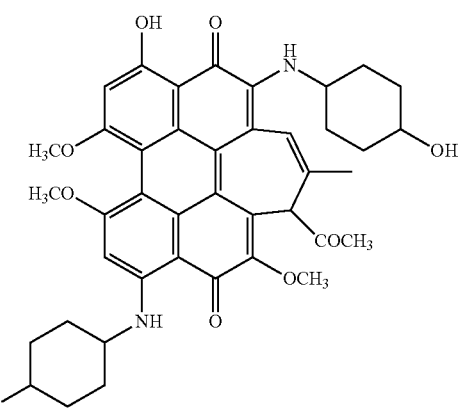

HB-17d

Example 53

Preparation of a 4-aminocyclohexanol-carboxyl PEG (of different chain lengths)-substituted hypocrellin B derivative ($R_1$=$R_2$=—$C_6H_{10}$O—CO-PEGn, $R_3$=—COCH$_3$, $R_4$=—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-17a-PEGn, HB-17b-PEGn, HB-17c-PEGn, HB-17d-PEGn (n=1, 6, 12) are obtained, respectively. HB-17a-PEG1 (n=1): yield: 7.6%, $R_f$: 0.32; MS (ESI+): 968.6; maximum absorption wavelength: 622 nm; molar extinction coefficient: 30,500 M$^{-1}$ cm$^{-1}$; singlet oxygen yield: 30%. HB-17b-PEG6 (n=6): yield: 8.5%, $R_f$: 0.34; MS (ESI+): 1408.6; maximum absorption wavelength: 622 nm; molar extinction coefficient: 31,500 M$^{-1}$cm$^{-1}$; singlet oxygen yield: 32%. HB-17c-PEG12 (n=12): yield: 19.2%, $R_f$: 0.38; MS (ESI+): 1936.6; maximum absorption wavelength: 632 nm; molar extinction coefficient: 33,500 M$^{-1}$ cm$^{-1}$; singlet oxygen yield: 38%. HB-17d-PEG6 (n=6): yield: 8.5%, $R_f$: 0.32; MS (ESI+): 1408.6; maximum absorption wavelength: 632 nm; molar extinction coefficient: 31,500 M$^{-1}$cm$^{-1}$; singlet oxygen yield: 32%. Structural formulas of the above amino-substituted products are as follows:

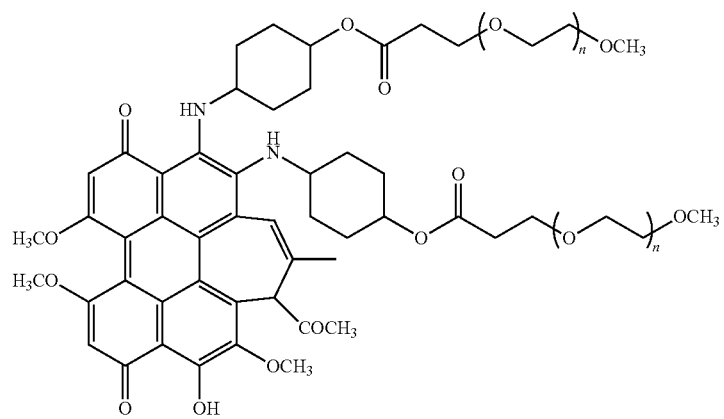
HB-17a-PEG1: n = 1
HB-17a-PEG6: n = 6
HB-17a-PEG12: n = 12
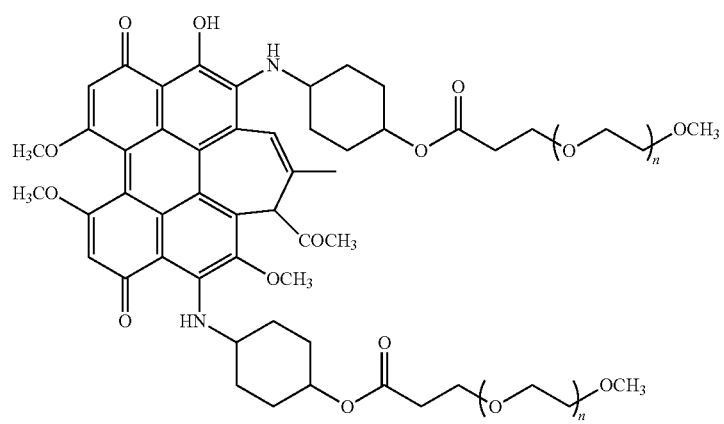
HB-17b-PEG1: n = 1
HB-17b-PEG6: n = 6
HB-17b-PEG12: n = 12
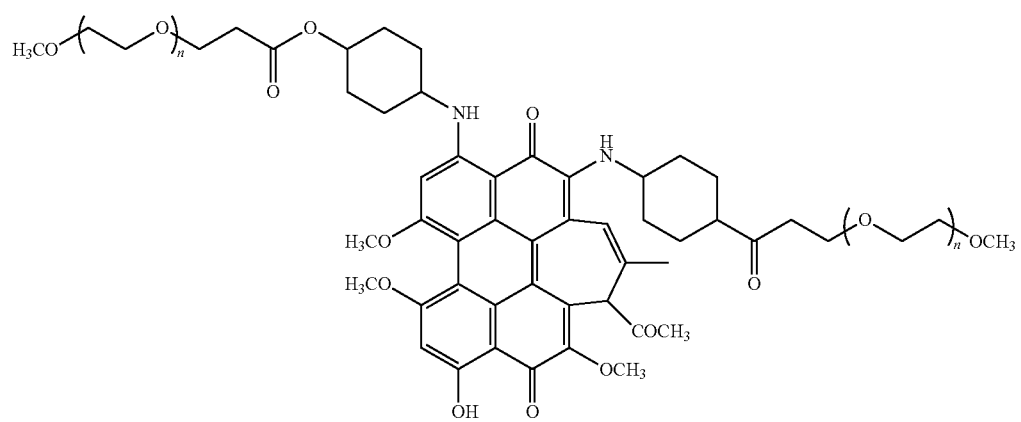
HB-17c-PEG1: n = 1
HB-17c-PEG6: n = 6
HB-17c-PEG12: n = 12

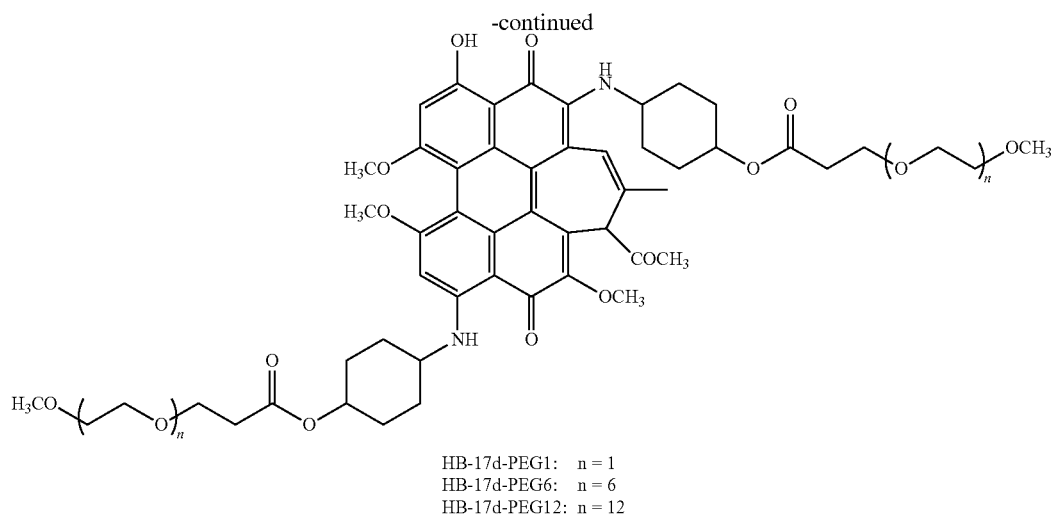

HB-17d-PEG1: n = 1
HB-17d-PEG6: n = 6
HB-17d-PEG12: n = 12

Example 54

Preparation of a 4-aminoethylcyclohexanol-substituted hypocrellin B derivative ($R_1=R_2=$—$CH_2CH_2C_6H_9(OH)$, $R_3=$—$COCH_3$, $R_4=$—H): a substituted amino raw material is $NH_2$—$CH_2CH_2C_6H_9(OH)$, a synthetic method is similar to the preparation of the di-2-(2-aminoethoxy)ethanol-substituted hypocrellin B derivative in example 2, and four blue black solid products HB-18a-HB-18d are obtained, respectively. HB-18a: yield: 6.1%, $R_f$: 0.37; MS (ESI+): 764.2; maximum absorption wavelength: 614 nm; molar extinction coefficient: 24,000 $M^{-1}cm^{-1}$; singlet oxygen yield: 20%. HB-18b: yield: 6.8%, $R_f$: 0.33; MS (ESI+): 764.2; maximum absorption wavelength: 621 nm; molar extinction coefficient: 24,500 $M^{-1}cm^{-1}$; singlet oxygen yield: 21%. HB-18c: yield: 9.8%, $R_f$: 0.35; MS (ESI+): 764.2; maximum absorption wavelength: 624 nm; molar extinction coefficient: 23,500 $M^{-1}$ $cm^{-1}$; singlet oxygen yield: 23%; HC-18d: yield: 4.8%, $R_f$: 0.28; MS (ESI+): 764.2; maximum absorption wavelength: 622 nm; molar extinction coefficient: 23,500 $M^{-1}$ $cm^{-1}$; singlet oxygen yield: 20%; Structural formulas of the above amino-substituted products are as follows:

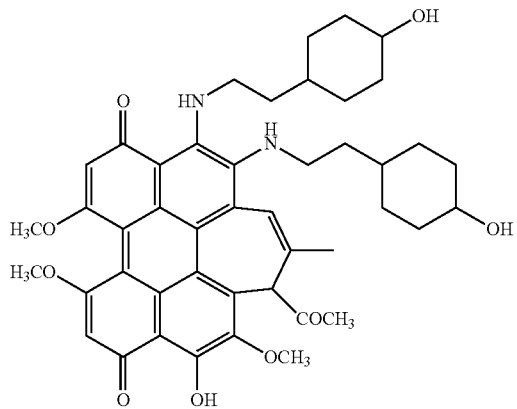
HB-18a

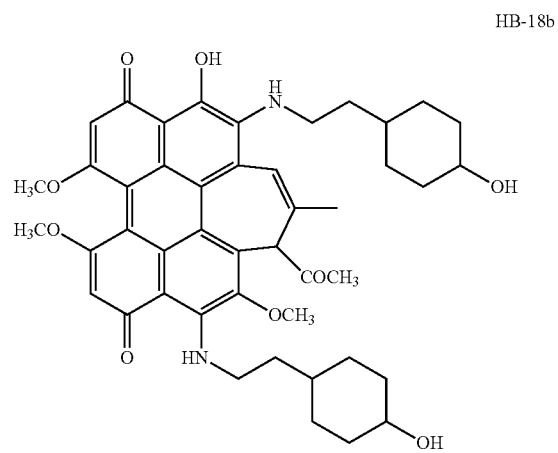
HB-18b

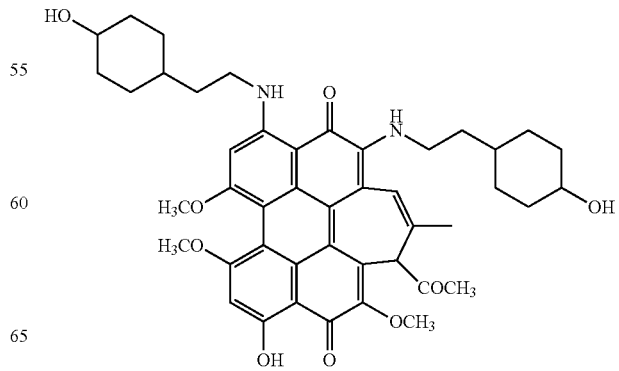
HB-18c

HB-18d

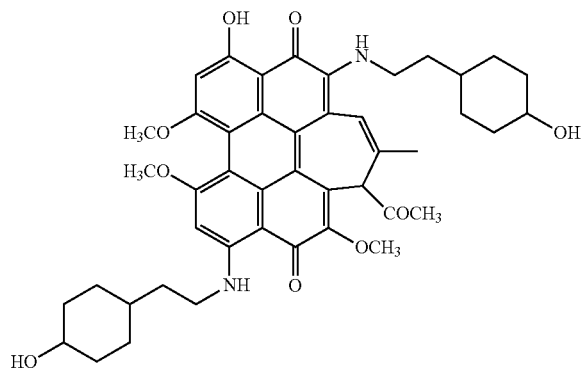

Example 55

Preparation of a 3-aminocyclopentanecarboxylic acid-substituted hypocrellin B derivative ($R_1=R_2=$—$C_5H_8COOH$, $R_3=$—$COCH_3$, $R_4=$—H): a synthetic method is similar to the preparation of the di-2-(2-aminoethoxy)ethanol-substituted hypocrellin B derivative in example 2, and four blue black solid products HB-19a-HB-19d are obtained, respectively. HB-19a: yield: 8.0%, $R_f$: 0.38; MS (ESI+): 736.2; maximum absorption wavelength: 621 nm; molar extinction coefficient: 25,500 $M^{-1}cm^{-1}$; singlet oxygen yield: 21%. HB-19b: yield: 7.0%, $R_f$: 0.33; MS (ESI+): 736.2; maximum absorption wavelength: 620 nm; molar extinction coefficient: 25,000 $M^{-1}$ $cm^{-1}$; singlet oxygen yield: 22%. HB-19c: yield: 6.7%, $R_f$: 0.30; MS (ESI+): 736.2; maximum absorption wavelength: 622 nm; molar extinction coefficient: 25,500 $M^{-1}$ $cm^{-1}$; singlet oxygen yield: 24%. HB-19d: yield: 5.9%, $R_f$: 0.38; MS (ESI+): 736.2; maximum absorption wavelength: 625 nm; molar extinction coefficient: 24,000 $M^{-1}$ $cm^{-1}$; singlet oxygen yield: 20%. Structural formulas of the above amino-substituted products are as follows:

HB-19a

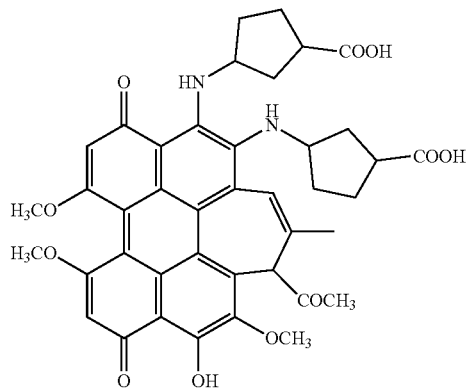

HB-19b

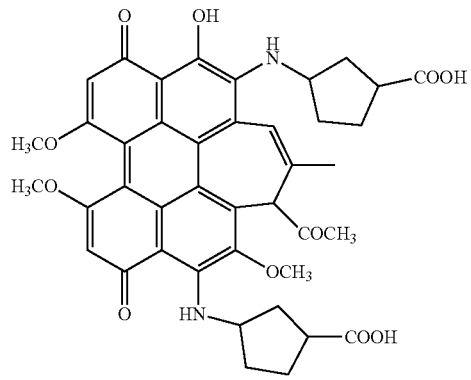

HB-19c

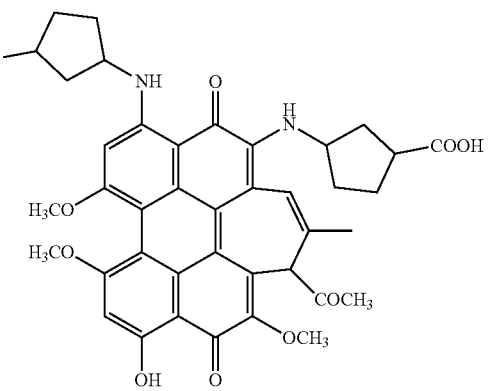

HB-19d

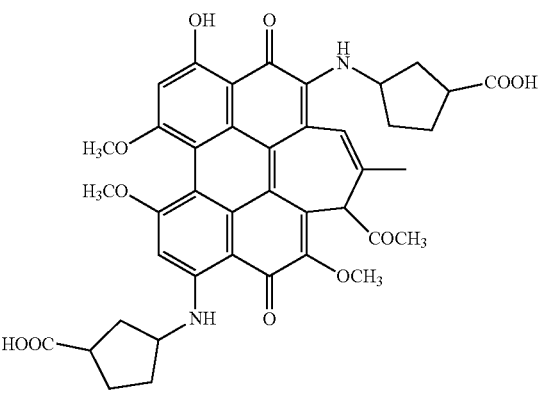

Example 56

Preparation of a 3-aminocyclopentanecarboxylic acid-PEG (of different chain lengths)-substituted hypocrellin B derivative ($R_1=R_2=$—$C_5H_8COO$-PEGn, $R_3=$—$COCH_3$, $R_4=$—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-19a-PEGn, HB-19b-PEGn, HB-19c-PEGn, HB-19d-PEGn (n=1, 6, 12) are obtained, respectively. HB-19a-PEG1 (n=1): yield: 7.5%, $R_f$: 0.32; MS (ESI+): 852.6; maximum absorption wavelength: 624 nm; molar extinction coefficient: 30,500 $M^{-1}$ $cm^{-1}$; singlet oxy gen yield: 32%. HB-19b-PEG6 (n=6): yield: 9.5%, $R_f$: 0.36; MS (ESI+): 1292.6; maximum absorption wavelength: 624 nm; molar extinction coefficient: 30,500 $M^{-1} cm^{-1}$; singlet oxygen yield: 34%. HB-19c-PEG12 (n=12): yield: 18.2%, $R_f$: 0.40; MS (ESI+): 1820.6; maximum absorption wavelength: 636 nm; molar extinction coefficient: 33,500 $M^{-1} cm^{-1}$; singlet oxygen yield: 38%. HB-19d-PEG6 (n=6): yield: 8.4%, $R_f$: 0.34; MS (ESI+): 1292.6; maximum absorption wavelength: 636 nm; molar extinction coefficient: 31,000 $M^{-1} cm^{-1}$; singlet oxygen yield: 32%. Structural formulas of the above amino-substituted products are as follows:

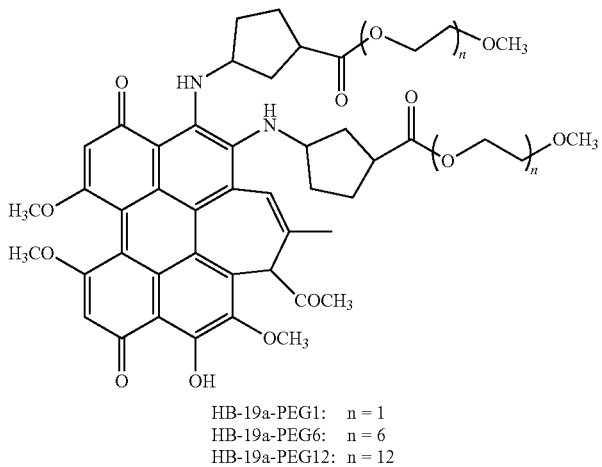

HB-19a-PEG1: n = 1
HB-19a-PEG6: n = 6
HB-19a-PEG12: n = 12

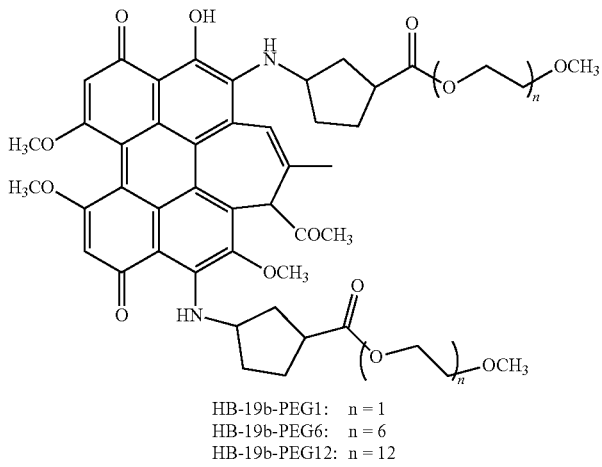

HB-19b-PEG1: n = 1
HB-19b-PEG6: n = 6
HB-19b-PEG12: n = 12

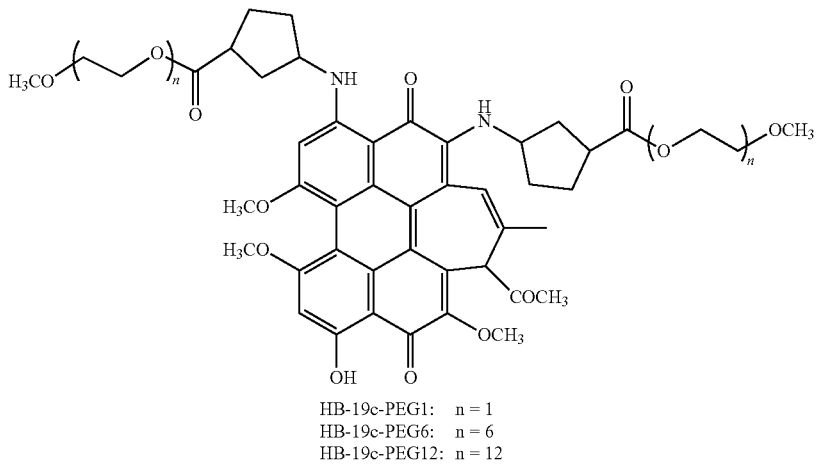

HB-19c-PEG1: n = 1
HB-19c-PEG6: n = 6
HB-19c-PEG12: n = 12

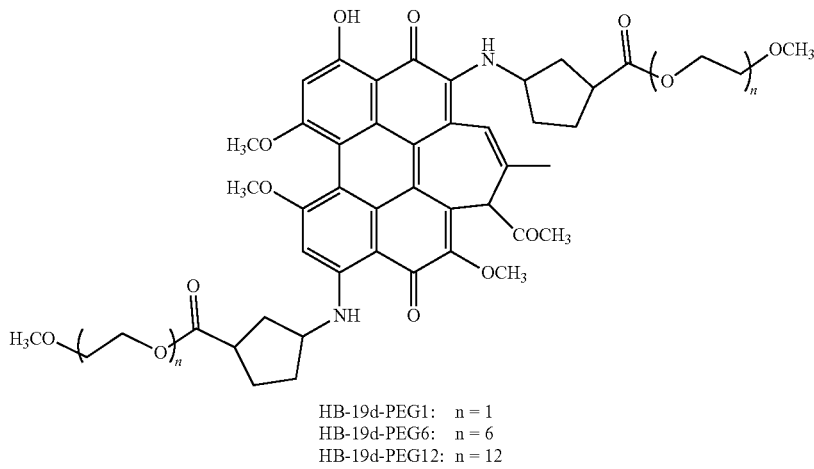

HB-19d-PEG1: n = 1
HB-19d-PEG6: n = 6
HB-19d-PEG12: n = 12

Example 57

Preparation of a 3-aminocyclopentanecarboxylic acid-amino PEG (of different chain lengths)-substituted hypocrellin B derivative ($R_1=R_2=$—$C_5H_8CO$—NH-PEGn, $R_3=$—$COCH_3$, $R_4=$—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-19a-NH-PEGn, HB-19b-NH-PEGn, HB-19c-NH-PEGn, HB-19d-NH-PEGn (n=1, 6, 12) are obtained, respectively. HB-19a-NH-PEG1 (n=1): yield: 8.5%, $R_f$: 0.30; MS (ESI+): 896.6; maximum absorption wavelength: 622 nm; molar extinction coefficient: 30,000 $M^{-1}cm^{-1}$; singlet oxygen yield: 32%. HB-19b-NH-PEG6 (n=6): yield: 10.5%, $R_f$: 0.38; MS (ESI+): 1336.6; maximum absorption wavelength: 622 nm; molar extinction coefficient: 30,000 $M^{-1}cm^{-1}$; singlet oxygen yield: 30%. HB-19c-NH-PEG12 (n=12): yield: 19.2%, $R_f$: 0.42; MS (ESI+): 1864.6; maximum absorption wavelength: 630 nm; molar extinction coefficient: 32,500 $M^{-1}cm^{-1}$; singlet oxygen yield: 36%. HB-19d-NH-PEG6 (n=6): yield: 6.4%, $R_f$: 0.36; MS (ESI+): 1336.6; maximum absorption wavelength: 630 nm; molar extinction coefficient: 31,500 $M^{-1}$ $cm^{-1}$; singlet oxygen yield: 32%. Structural formulas of the above amino-substituted products are as follows:

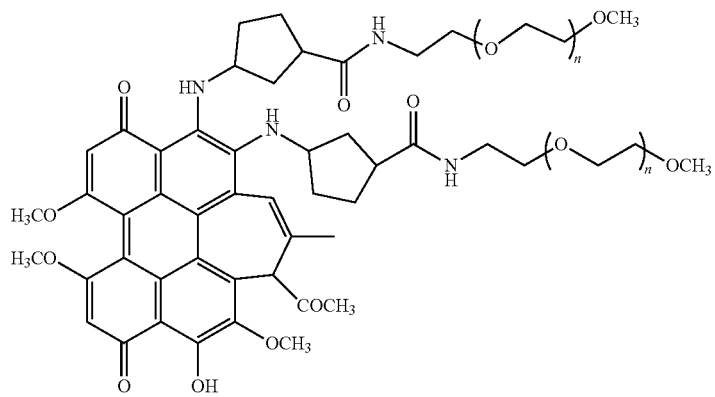

HB-19a-NH-PEG1: n = 1
HB-19a-NH-PEG6: n = 6
HB-19a-NH-PEG12: n = 12

-continued
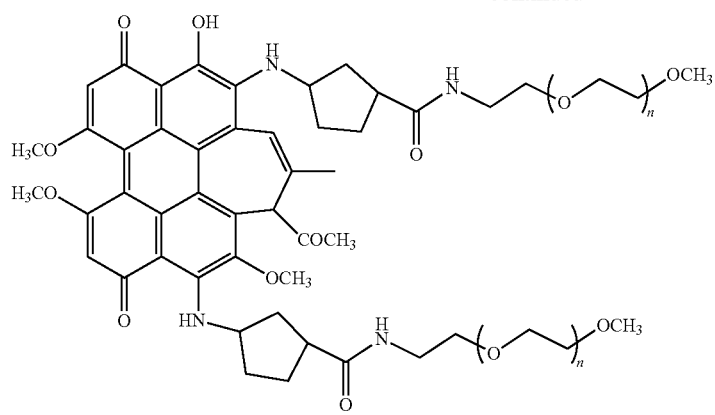
HB-19b-NH-PEG1: n = 1
HB-19b-NH-PEG6: n = 6
HB-19b-NH-PEG12: n = 12
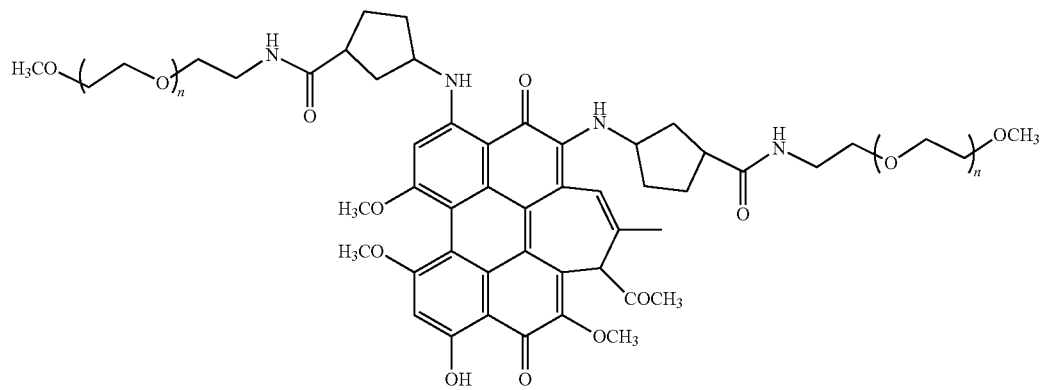
HB-19c-NH-PEG1: n = 1
HB-19c-NH-PEG6: n = 6
HB-19c-NH-PEG12: n = 12
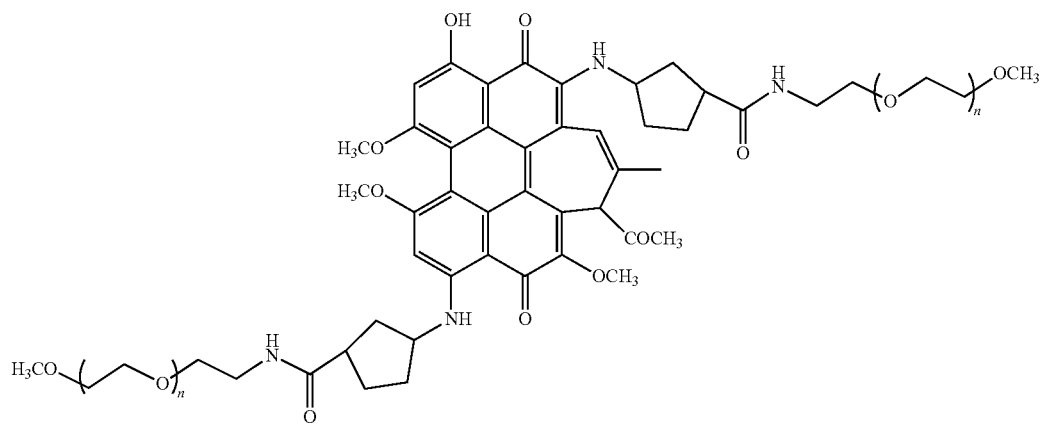
HB-19d-NH-PEG1: n = 1
HB-19d-NH-PEG6: n = 6
HB-19d-NH-PEG12: n = 12

Example 58

Preparation of a 3-aminocyclopentanol-substituted hypocrellin B derivative ($R_1=R_2=$—$C_5H_8OH$, $R_3=$—$COCH_3$, $R_4=$—H): a synthetic method is similar to the preparation of the di-2-(2-aminoethoxy)ethanol-substituted hypocrellin B derivative in example 2, and four blue black solid products HB-20a-HB-20d are obtained, respectively. HB-20a: yield: 5.0%, $R_f$: 0.32; MS (ESI+): 680.2; maximum absorption wavelength: 624 nm; molar extinction coefficient: 24,500 $M^{-1}cm^{-1}$; singlet oxygen yield: 20%. HB-20b: yield: 5.0%, $R_f$: 0.32; MS (ESI+): 680.2; maximum absorption wavelength: 620 nm; molar extinction coefficient: 24,000 $M^{-1}cm^{-1}$; singlet oxygen yield: 22%. HB-20c: yield: 12.7%, $R_f$: 0.30; MS (ESI+): 680.2; maximum absorption wavelength: 622 nm; molar extinction coefficient: 24,500 $M^{-1}cm^{-1}$; singlet oxygen yield: 24%. HB-20d: yield: 3.9%, $R_f$: 0.35; MS (ESI+): 680.2; maximum absorption wavelength: 625 nm; molar extinction coefficient: 24,500 $M^{-1}cm^{-1}$; singlet oxygen yield: 20%. Structural formulas of the above amino-substituted products are as follows:

HB-20a
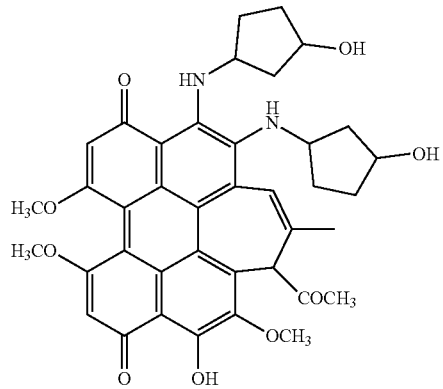

HB-20b
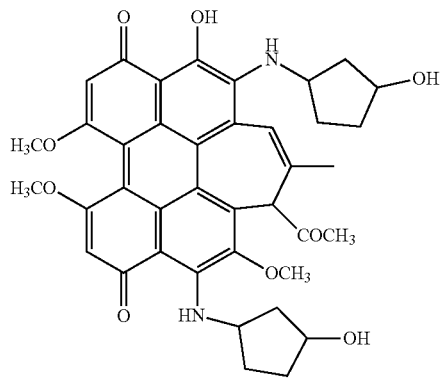

HB-20c
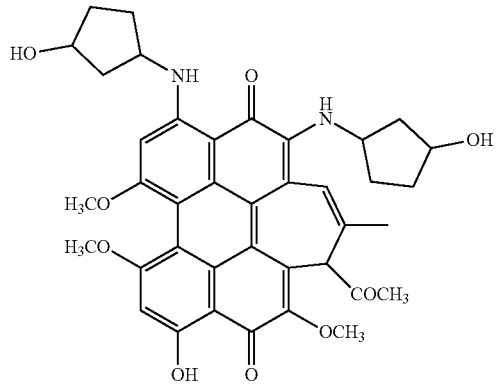

HB-20d
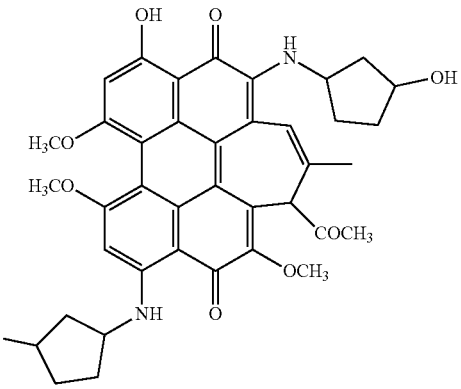

Example 59

Preparation of a 3-aminocyclopentanol-carboxyl PEG (of different chain lengths)-substituted hypocrellin B derivative ($R_1=R_2=$—$C_5H_8$—O—CO-PEGn, $R_3=$—$COCH_3$, $R_4=$—H) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-20a-PEGn, HB-20b-PEGn, HB-20c-PEGn, HB-20d-PEGn (n=1, 6, 12) are obtained, respectively. HB-20a-PEG1 (n=1): yield: 8.1%, $R_f$: 0.32; MS (ESI+): 940.6; maximum absorption wavelength: 624 nm; molar extinction coefficient: 31,000 $M^{-1}cm^{-1}$; singlet oxygen yield: 30%. HB-20b-PEG6 (n=6): yield: 9.5%, $R_f$: 0.38; MS (ESI+): 1380.6; maximum absorption wavelength: 624 nm; molar extinction coefficient: 31,000 $M^{-1}cm^{-1}$; singlet oxygen yield: 28%. HB-20c-PEG12 (n=12): yield: 18.2%, $R_f$: 0.40; MS (ESI+): 1908.6; maximum absorption wavelength: 632 nm; molar extinction coefficient: 32,500 $M^{-1}cm^{-1}$; singlet oxygen yield: 34%. HB-20d-PEG6 (n=6): yield: 6.2%, $R_f$: 0.32; MS (ESI+): 1380.6; maximum absorption wavelength: 630 nm; molar extinction coefficient: 30,500 $M^{-1}cm^{-1}$; singlet oxygen yield: 32%. Structural formulas of the above amino-substituted products are as follows:

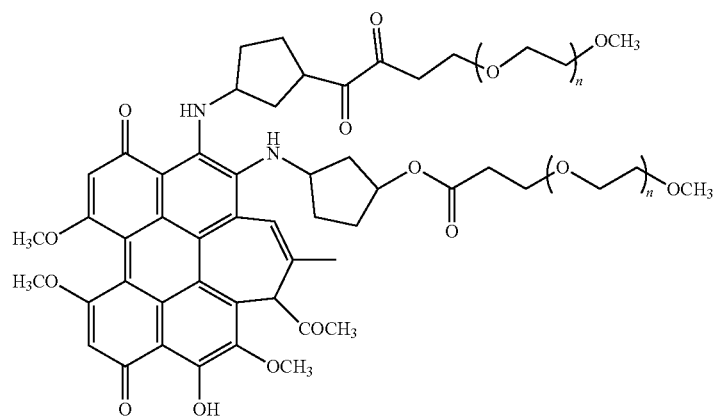
HB-20a-PEG1:  n = 1
HB-20a-PEG6:  n = 6
HB-20a-PEG12: n = 12
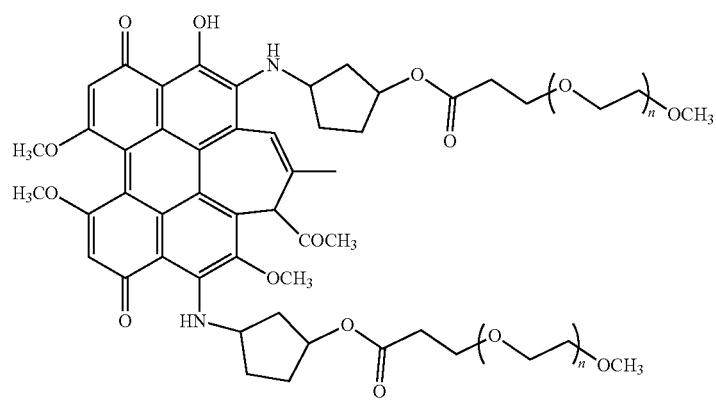
HB-20b-PEG1:  n = 1
HB-20b-PEG6:  n = 6
HB-20b-PEG12: n = 12
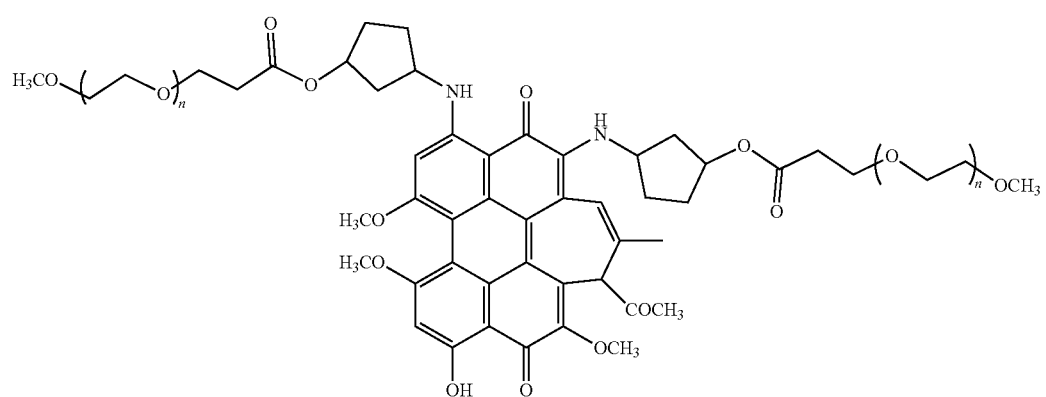
HB-20c-PEG1:  n = 1
HB-20c-PEG6:  n = 6
HB-20c-PEG12: n = 12

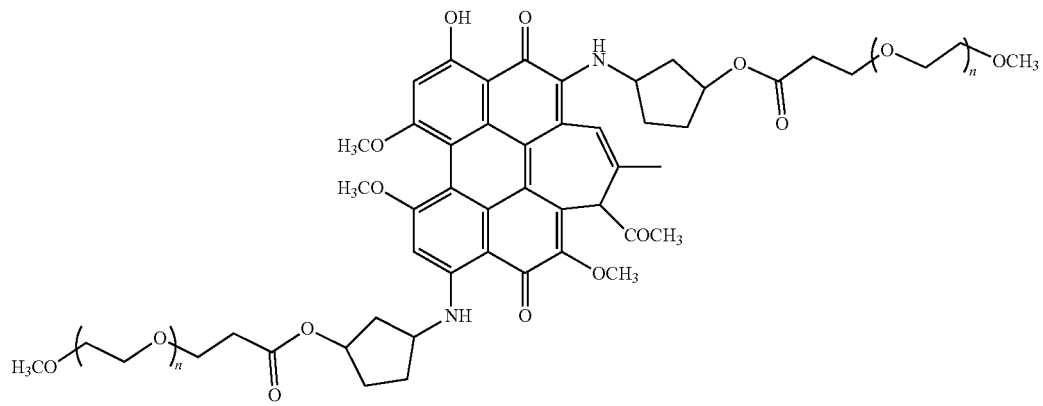

HB-20d-PEG1: n = 1
HB-20d-PEG6: n = 6
HB-20d-PEG12: n = 12

Example 60

Preparation of a 2-aminocyclocarboxylic acid-substituted hypocrellin B derivative ($R_1=R_2=$—$C_5H_8COOH$, $R_3=$—$COCH_3$, $R_4=$—H): a synthetic method is similar to the preparation of the di-2-(2-aminoethoxy)ethanol-substituted hypocrellin B derivative in example 2, and four blue black solid products HB-21a-HB-21d are obtained, respectively. HB-21a: yield: 4.0%, $R_f$: 0.34; MS (ESI+): 736.2; maximum absorption wavelength: 620 nm; molar extinction coefficient: 23,500 $M^{-1}cm^{-1}$; singlet oxygen yield: 20%. HB-20b: yield: 5.0%, $R_f$: 0.35; MS (ESI+): 736.2; maximum absorption wavelength: 622 nm; molar extinction coefficient: 23,000 $M^{-1}$ $cm^{-1}$; singlet oxygen yield: 22%. HB-20c: yield: 12.7%, $R_f$: 0.32; MS (ESI+): 736.2; maximum absorption wavelength: 624 nm; molar extinction coefficient: 24,000 $M^{-1}$ $cm^{-1}$; singlet oxygen yield: 24%. HB-20d: yield: 3.9%, $R_f$: 0.35; MS (ESI+): 736.2; maximum absorption wavelength: 620 nm; molar extinction coefficient: 23,500 $M^{-1}cm^{-1}$; singlet oxygen yield: 20%. Structural formulas of the above amino-substituted products are as follows:

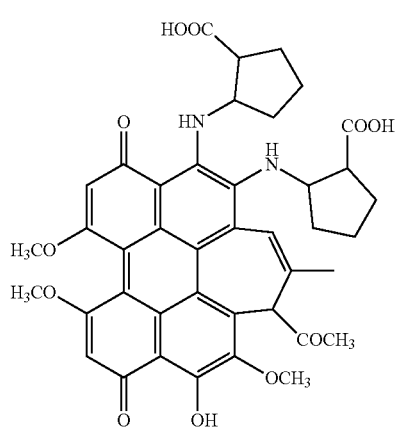

HB-21a

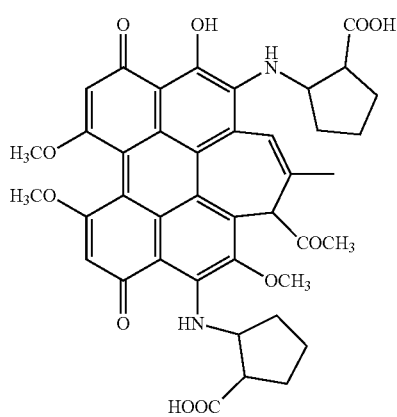

HB-21b

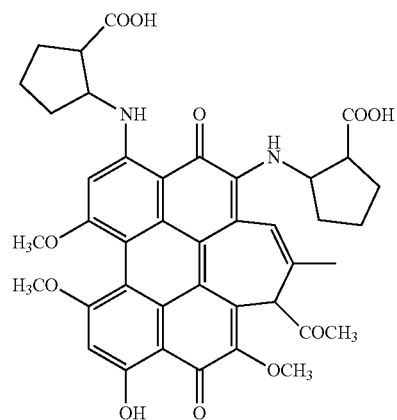

HB-21c

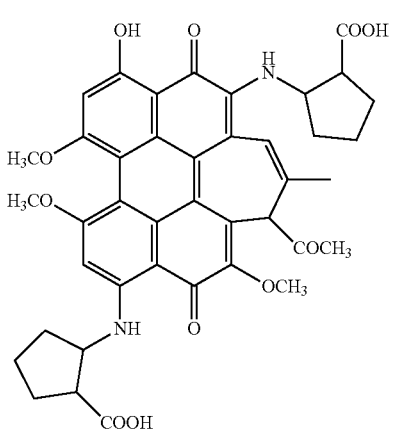

HB-21d

Example 61

Preparation of a 2-aminocyclopentanecarboxylic acid-PEG (of different chain lengths)-substituted hypocrellin B derivative ($R_1=R_2=-C_5H_8-COO-PEGn$, $R_3=-COCH_3$, $R_4=-H$) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-21a-PEGn, HB-21b-PEGn, HB-21c-PEGn, HB-21d-PEGn (n=1, 6, 12) are obtained, respectively. HB-21a-PEG1 (n=1): yield: 8.4%, $R_f$: 0.30; MS (ESI+): 940.6; maximum absorption wavelength: 624 nm; molar extinction coefficient: 31,500 $M^{-1}$ $cm^{-1}$; singlet oxygen yield: 30%. HB-21b-PEG6 (n=6): yield: 9.4%, $R_f$: 0.34; MS (ESI+): 1380.6; maximum absorption wavelength: 624 nm; molar extinction coefficient: 31,500 $M^{-1}cm^{-1}$; singlet oxygen yield: 30%. HB-21c-PEG12 (n=12): yield: 17.2%, $R_f$: 0.38; MS (ESI+): 1908.6; maximum absorption wavelength: 628 nm; molar extinction coefficient: 33,500 $M^{-1}$ $cm^{-1}$; singlet oxygen yield: 38%. HB-21d-PEG6 (n=6): yield: 7.2%, $R_f$: 0.32; MS (ESI+): 1380.6; maximum absorption wavelength: 628 nm; molar extinction coefficient: 31,500 $M^{-1}cm^{-1}$; singlet oxygen yield: 32%. Structural formulas of the above amino-substituted products are as follows:

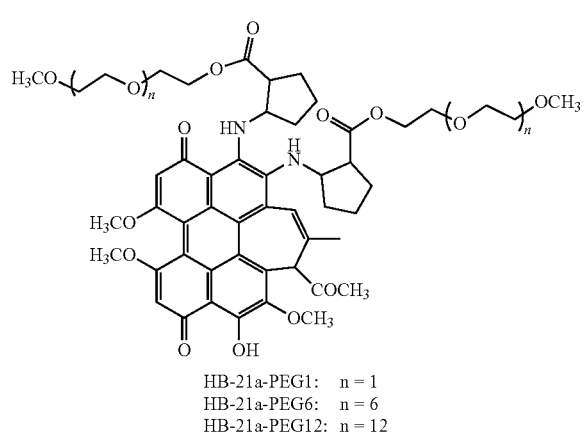

HB-21a-PEG1:   n = 1
HB-21a-PEG6:   n = 6
HB-21a-PEG12:  n = 12

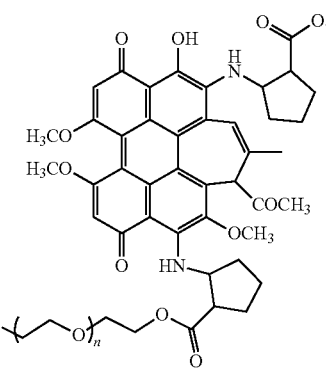

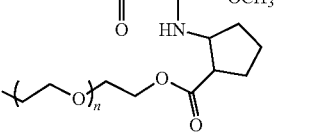

HB-21b-PEG1:   n = 1
HB-21b-PEG6:   n = 6
HB-21b-PEG12:  n = 12

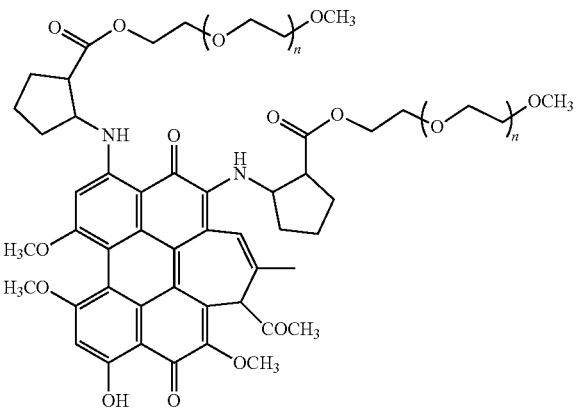

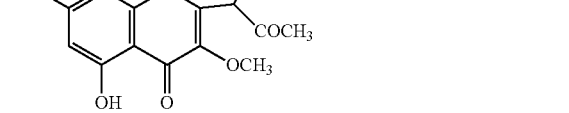

HB-21c-PEG1:   n = 1
HB-21c-PEG6:   n = 6
HB-21c-PEG12:  n = 12

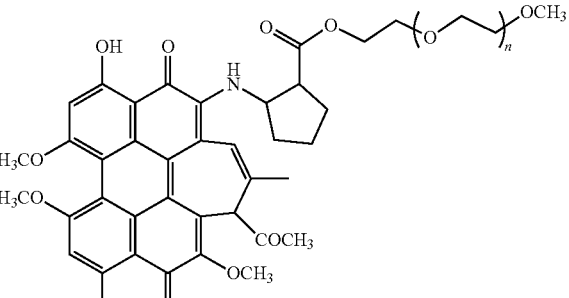

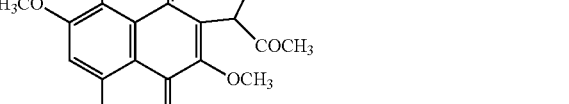

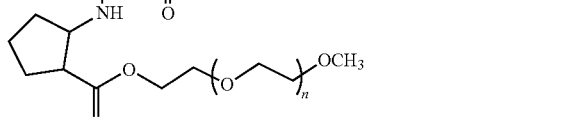

HB-21d-PEG1:   n = 1
HB-21d-PEG6:   n = 6
HB-21d-PEG12:  n = 12

Example 62

Preparation of a 2-aminocyclocarboxylic acid-amino PEG (of different chain lengths)-substituted hypocrellin B derivative ($R_1=R_2=-C_5H_8-COO-PEGn$, $R_3=-COCH_3$, $R_4=-H$) (PEG is polyethylene glycol, n is the number of ethylene glycol units, and n=1, 6, 12): a synthetic route is similar to the preparation of the aminobutyric acid-polyethylene glycol (of different chain lengths)-substituted deacetyl hypocrellin derivative in example 20, and four blue black solid products HB-21a-NH-PEGn, HB-21b-NH-PEGn, HB-21c-NH-PEGn, HB-21d-NH-PEGn (n=1, 6, 12) are obtained, respectively. HB-21a-NH-PEG1 (n=1): yield: 7.0%, $R_f$: 0.31; MS (ESI+): 940.6; maximum absorption wavelength: 622 nm; molar extinction coefficient: 31,000 $M^{-1}$ $cm^{-1}$; singlet oxygen yield: 31%. HB-21b-NH-PEG6 (n=6): yield: 8.4%, $R_f$: 0.35; MS (ESI+): 1380.6; maximum absorption wavelength: 622 nm; molar extinction coefficient: 31,000 $M^{-1}$ $cm^{-1}$; singlet oxygen yield: 32%. HB-21c-NH-PEG12 (n=12): yield: 18.2%, $R_f$: 0.40; MS (ESI+): 1908.6; maximum absorption wavelength: 627 nm; molar extinction coefficient: 33,000 $M^{-1}$ $cm^{-1}$; singlet oxygen yield: 37%. HB-21d-NH-PEG6 (n=6): yield: 7.5%, $R_f$: 0.32; MS (ESI+): 1380.6; maximum absorption wavelength: 628 nm; molar extinction coefficient: 31,000 $M^{-1}cm^{-1}$; singlet oxygen yield: 32%. Structural formulas of the above amino-substituted products are as follows:

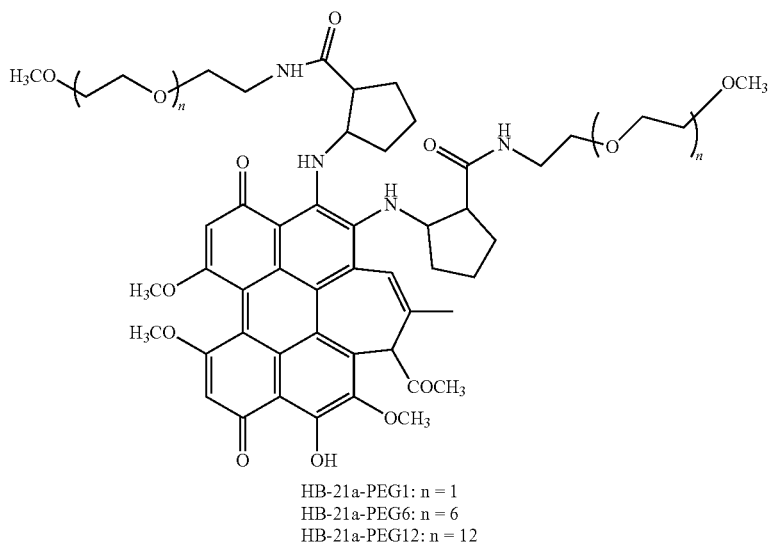

HB-21a-PEG1: n = 1
HB-21a-PEG6: n = 6
HB-21a-PEG12: n = 12

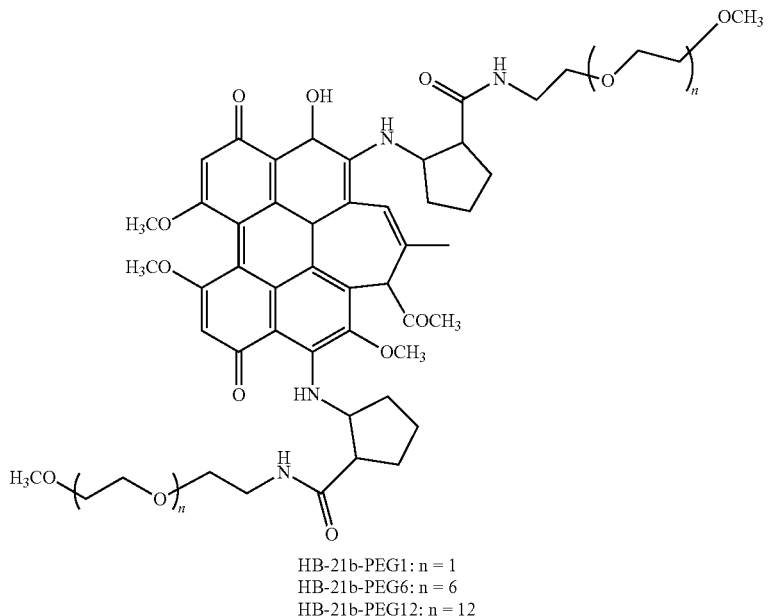

HB-21b-PEG1: n = 1
HB-21b-PEG6: n = 6
HB-21b-PEG12: n = 12

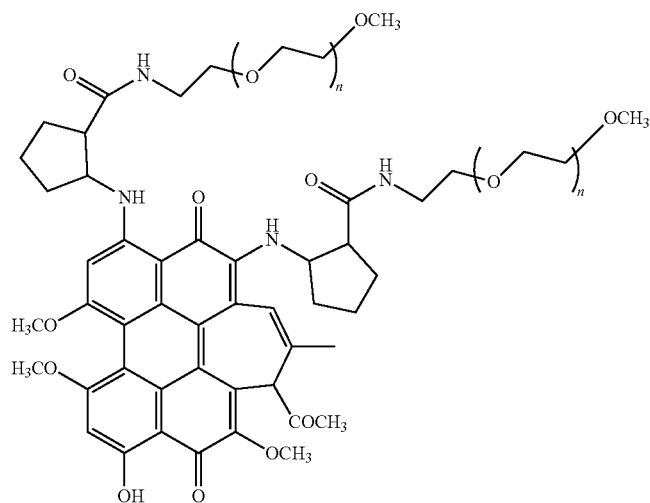

HB-21c-PEG1: n = 1
HB-21c-PEG6: n = 6
HB-21c-PEG12: n = 12

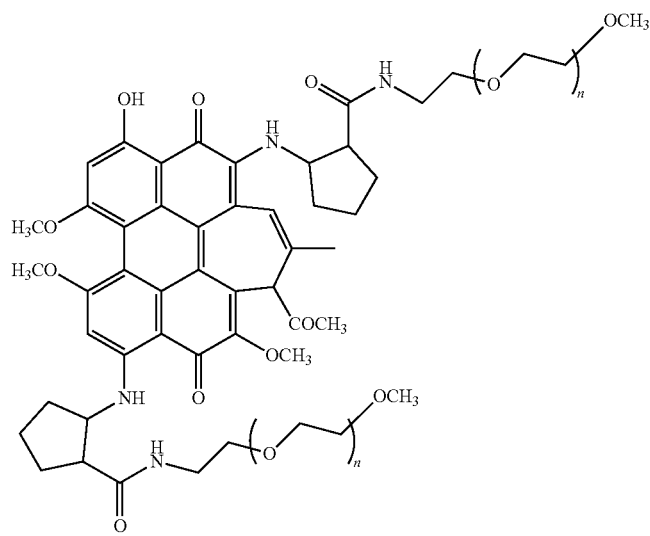

HB-21d-PEG1: n = 1
HB-21d-PEG6: n = 6
HB-21d-PEG12: n = 12

Example 63

Preparation of a di-valine-substituted hypocrellin B derivative ($R_1=R_2=$—CH(CH(CH$_3$)$_2$)—COOH, $R_3=$—COCH$_3$, $R_4=$—H): a substituted amino raw material is valine, a synthetic method is similar to the preparation of the diaminoacetic acid-substituted hypocrellin B derivative in example 17, and four blue black solid products HB-22a-HB-22d are obtained, respectively. HB-22a: yield: 7.2%, $R_f$: 0.38; MS (ESI+): 712.2; maximum absorption wavelength: 621 nm; molar extinction coefficient: 21,000 M$^{-1}$cm$^{-1}$; singlet oxygen yield: 18%. HB-22b: yield: 6.1%, $R_f$: 0.30; MS (ESI+): 712.2; maximum absorption wavelength: 618 nm; molar extinction coefficient: 21,000 M$^{-1}$cm$^{-1}$; singlet oxygen yield: 19%. HB-22c: yield: 5.6%, $R_f$: 0.28; MS (ESI+): 712.2; maximum absorption wavelength: 620 nm; molar extinction coefficient: 21,500 M$^{-1}$cm$^{-1}$; singlet oxygen yield: 22%. HB-22d: yield: 5.9%, $R_f$: 0.26; MS (ESI+): 712.2; maximum absorption wavelength: 625 nm; molar extinction coefficient: 21,500 M$^{-1}$cm$^{-1}$; singlet oxygen yield: 22%. Structural formulas of the above amino-substituted products are as follows:

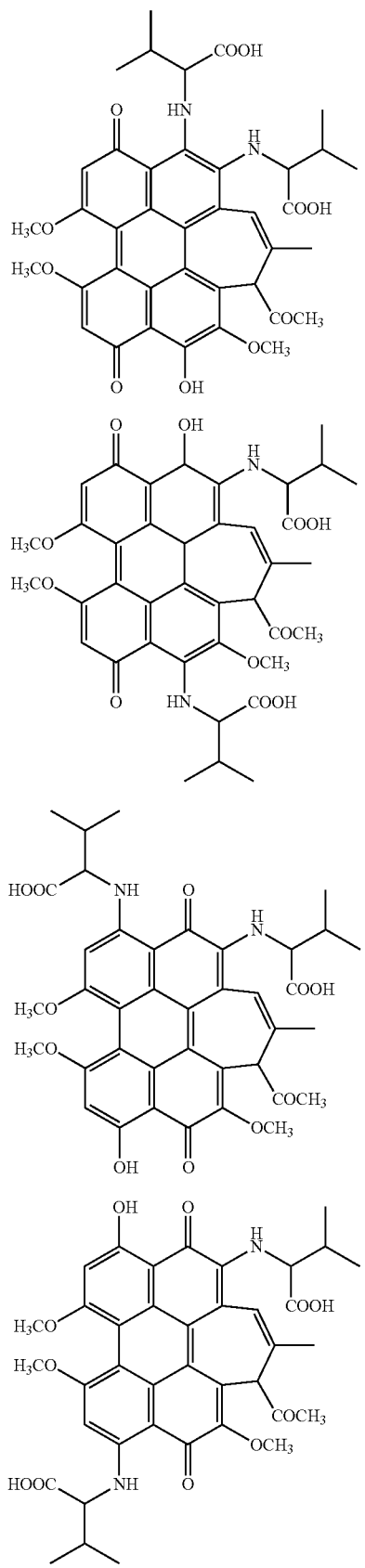

Example 64

Preparation of a di-serine-substituted hypocrellin B derivative ($R_1=R_2=$—CH(CH$_2$OH)—COOH, $R_3=$—COCH$_3$, $R_4=$—H): an amino raw material is serine, a synthetic method is similar to the preparation of the diaminoacetic acid-substituted hypocrellin B derivative in example 17, and four blue black solid products HB-23a-HB-23d are obtained, respectively. HB-23a: yield: 7.4%, $R_f$: 0.37; MS (ESI+): 688.1; maximum absorption wavelength: 625 nm; molar extinction coefficient: 21,500 M$^{-1}$cm$^{-1}$; singlet oxygen yield: 20%. HB-23b: yield: 4.2%, $R_f$: 0.33; MS (ESI+): 688.1; maximum absorption wavelength: 621 nm; molar extinction coefficient: 21,000 M$^{-1}$ cm$^{-1}$; singlet oxygen yield: 18%. HB-23c: yield: 7.9%, $R_f$: 0.35; MS (ESI+): 688.1; maximum absorption wavelength: 622 nm; molar extinction coefficient: 22,000 M$^{-1}$cm$^{-1}$; singlet oxygen yield: 22%. HB-23d: yield: 6.6%, $R_f$: 0.28; MS (ESI+): 688.1; maximum absorption wavelength: 621 nm; molar extinction coefficient: 21,500 M$^{-1}$ cm$^{-1}$; singlet oxygen yield: 18%. Structural formulas of the above amino-substituted products are as follows:

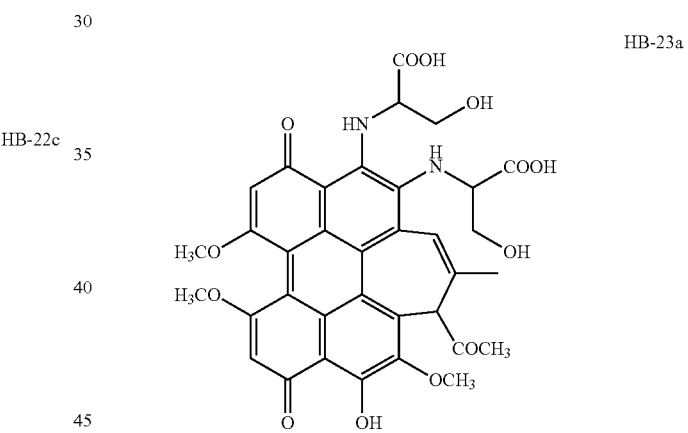

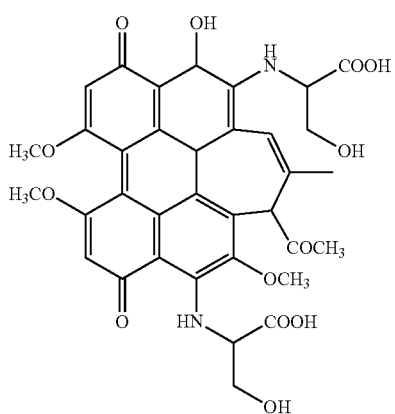

HB-23c

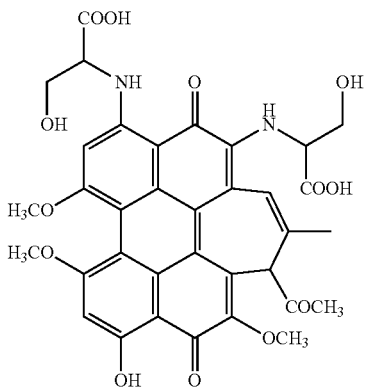

HB-24a

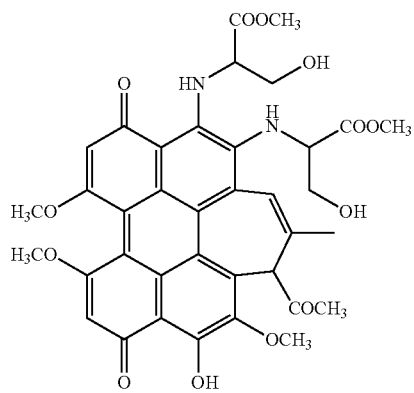

HB-24b

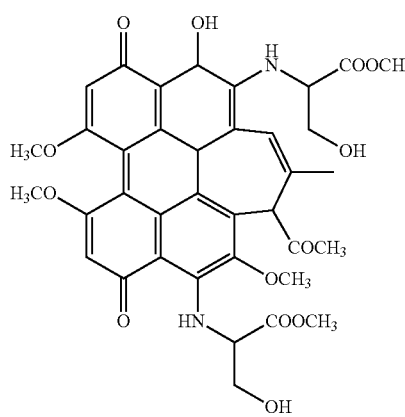

HB-23d

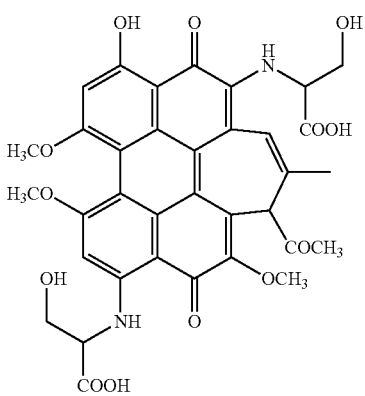

HB-24c

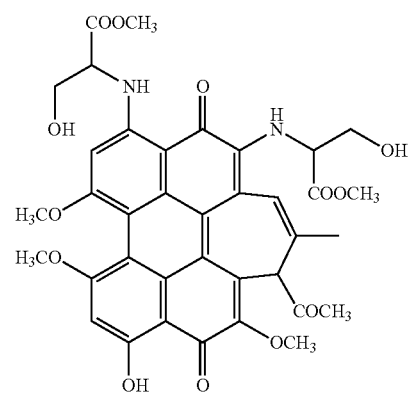

Example 65

Preparation of a serine methylester-substituted hypocrellin B derivative ($R_1=R_2=$—CH(CH$_2$OH)—COOCH$_3$, $R_3=$—COCH$_3$, $R_4=$—H): a substituted amino raw material is serine methylester, a synthetic method is similar to the preparation of the diaminoacetic acid-substituted hypocrellin B derivative in example 17, and four blue black solid products HB-24a-HB-24d are obtained, respectively. HB-24a: yield: 7.4%, $R_f$: 0.37; MS (ESI+): 716.1; maximum absorption wavelength: 625 nm; molar extinction coefficient: 20,500 M$^{-1}$ cm$^{-1}$; singlet oxygen yield: 20%. HB-24b: yield: 4.2%, $R_f$: 0.33; MS (ESI+): 716.1; maximum absorption wavelength: 621 nm; molar extinction coefficient: 21,500 M$^{-1}$ cm$^{-1}$; singlet oxygen yield: 20%. HB-24c: yield: 7.9%, $R_f$: 0.35; MS (ESI+): 716.1; maximum absorption wavelength: 622 nm; molar extinction coefficient: 21,500 M$^{-1}$cm$^{-1}$; singlet oxygen yield: 22%. HB-24d: yield: 6.6%, $R_f$: 0.28; MS (ESI+): 716.1; maximum absorption wavelength: 621 nm; molar extinction coefficient: 20,500 M$^{-1}$cm$^{-1}$; singlet oxygen yield: 20%. Structural formulas of the above amino-substituted products are as follows:

HB-24d

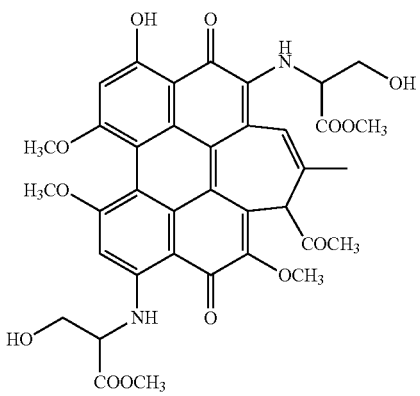

Example 66

Preparation of a cysteine-substituted deacetyl hypocrellin derivative (R$_1$=R$_2$=—CH(CH$_2$SH)—COOH, R$_3$=—COCH$_3$, R$_4$=—H): a substituted amino raw material is cysteine, a synthetic method is similar to the preparation of the diaminoacetic acid-substituted hypocrellin B derivative in example 17, and four blue black solid products HB-25a-HB-25d are obtained, respectively. HB-25a: yield: 6.2%, R$_f$: 0.36; MS (ESI+): 720.0; maximum absorption wavelength: 625 nm; molar extinction coefficient: 21,500 M$^{-1}$cm$^{-1}$; singlet oxygen yield: 18%. HB-25b: yield: 7.8%, R$_f$: 0.34; MS (ESI+): 720.0; maximum absorption wavelength: 629 nm; molar extinction coefficient: 20,500 M$^{-1}$cm$^{-1}$; singlet oxygen yield: 20%. HB-25c: yield: 8.7%, R$_f$: 0.33; MS (ESI+): 720.0; maximum absorption wavelength: 632 nm; molar extinction coefficient: 21,500 M$^{-1}$cm$^{-1}$; singlet oxygen yield: 20%. HB-25d: yield: 4.9%, R$_f$: 0.40; MS (ESI+): 720.0; maximum absorption wavelength: 630 nm; molar extinction coefficient: 20,500 M$^{-1}$cm$^{-1}$; singlet oxygen yield: 18%. Structural formulas of the above amino-substituted products are as follows:

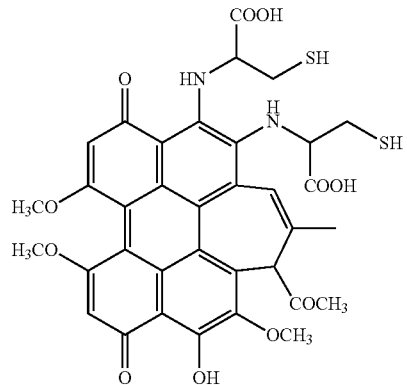
HB-25a

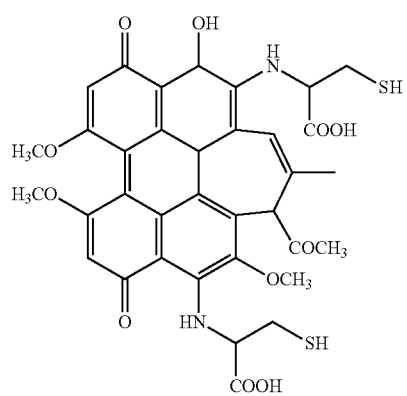
HB-25b

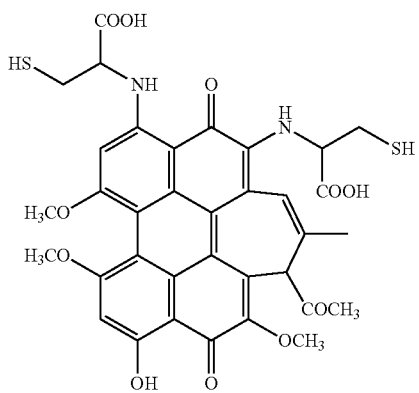
HB-25c

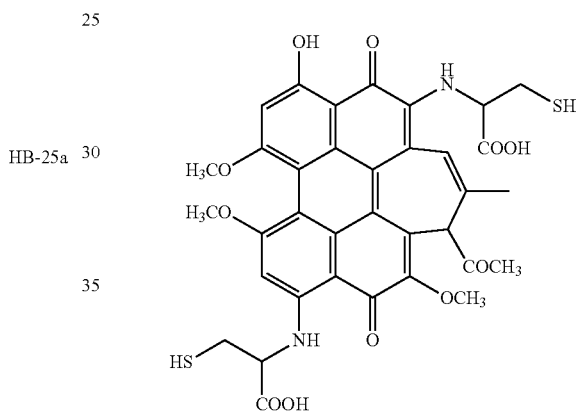
HB-25d

Example 67

Preparation of an asparagine-substituted hypocrellin B derivative (R$_1$=R$_2$=—CH(CH$_2$CONH$_2$)—COOH, R$_3$=—COCH$_3$, R$_4$=—H): a substituted amino raw material is asparagine, a synthetic method is similar to the preparation of the diaminoacetic acid-substituted hypocrellin B derivative in example 17, and four blue black solid products HB-26a-HB-26d are obtained, respectively. HB-26a: yield: 5.1%, R$_f$: 0.32; MS (ESI+): 742.1; maximum absorption wavelength: 614 nm; molar extinction coefficient: 20,500 M$^{-1}$cm$^{-1}$; singlet oxygen yield: 20%. HB-26b: yield: 5.8%, R$_f$: 0.34; MS (ESI+): 742.1; maximum absorption wavelength: 622 nm; molar extinction coefficient: 20,500 M$^{-1}$ cm$^{-1}$; singlet oxygen yield: 18%. HB-26c: yield: 11.1%, R$_f$: 0.37; MS (ESI+): 742.1; maximum absorption wavelength: 614 nm; molar extinction coefficient: 21,500 M$^{-1}$ cm$^{-1}$; singlet oxygen yield: 21%. HB-26d: yield: 3.8%, R$_f$: 0.32; MS (ESI+): 742.1; maximum absorption wavelength: 622 nm; molar extinction coefficient: 20,500 M$^{-1}$ cm$^{-1}$; singlet oxygen yield: 16%. Structural formulas of the above amino-substituted products are as follows:

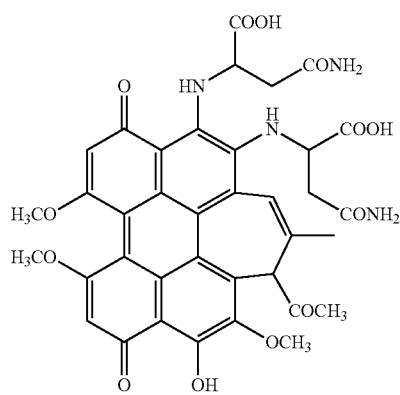

HB-26a

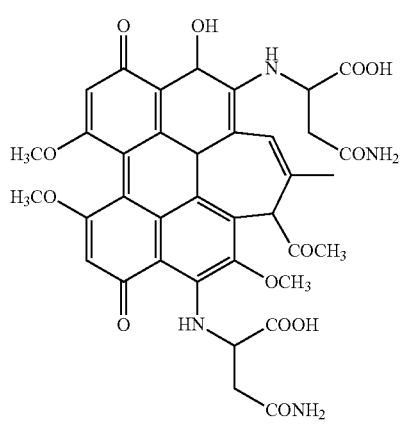

HB-26b

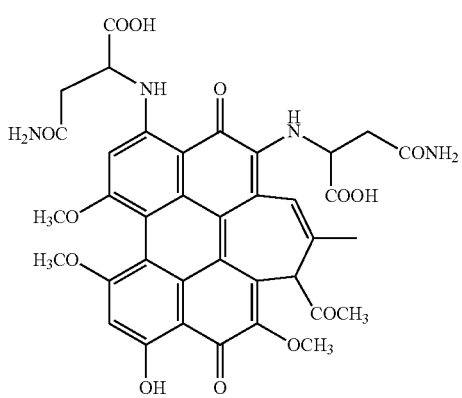

HB-26c

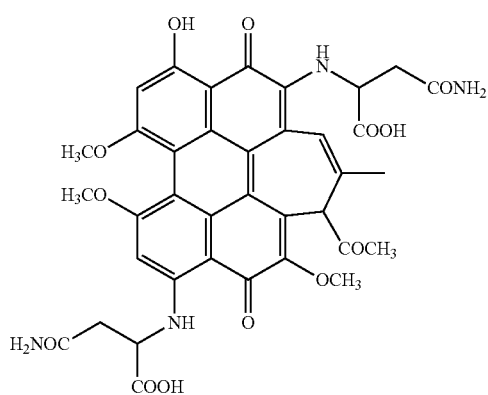

HB-26d

Example 68

Preparation of an aspartic acid-substituted hypocrellin B derivative ($R_1$=$R_2$=—CH(COOH)—CH$_2$COOH, $R_3$=—COCH$_3$, $R_4$=—H): a substituted amino raw material is an aspartic acid, a synthetic method is similar to the preparation of the diaminoacetic acid-substituted hypocrellin B derivative in example 17, and four blue black solid products HB-27a-HB-27d are obtained, respectively. HB-27a: yield: 7.4%, $R_f$: 0.36; MS (ESI+): 744.1; maximum absorption wavelength: 621 nm; molar extinction coefficient: 20,500 $M^{-1}$ cm$^{-1}$; singlet oxygen yield: 18%. HB-27b: yield: 6.6%, $R_f$: 0.32; MS (ESI+): 744.1; maximum absorption wavelength: 620 nm; molar extinction coefficient: 20,000 $M^{-1}$ cm$^{-1}$; singlet oxygen yield: 19%. HB-27c: yield: 7.9%, $R_f$: 0.30; MS (ESI+): 744.1; maximum absorption wavelength: 625 nm; molar extinction coefficient: 21,500 $M^{-1}$cm$^{-1}$; singlet oxygen yield: 21%. HB-27d: yield: 5.2%, $R_f$: 0.28; MS (ESI+): 744.1; maximum absorption wavelength: 620 nm; molar extinction coefficient: 21,500 $M^{-1}$ cm$^{-1}$; singlet oxygen yield: 18%. Structural formulas of the above amino-substituted products are as follows:

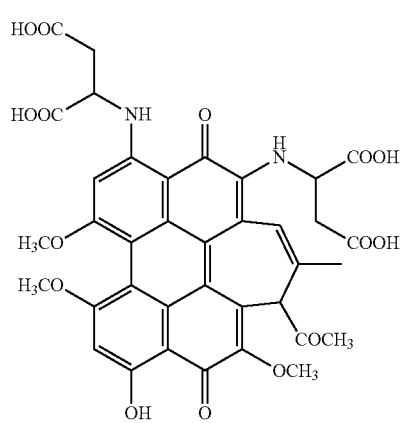

HB-27c

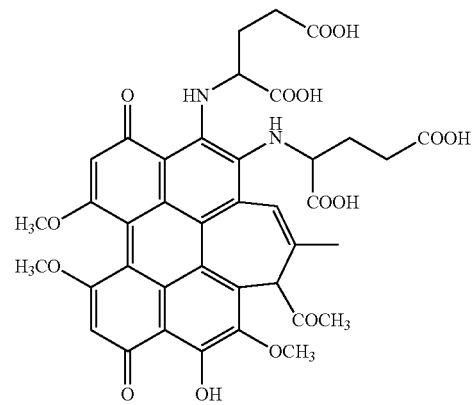

HB-28a

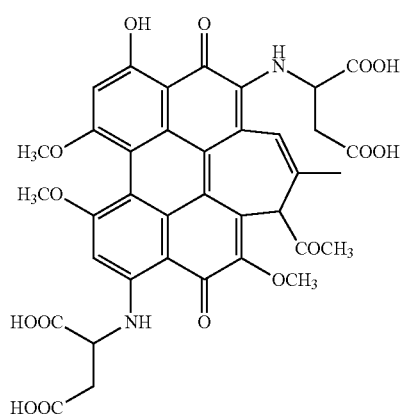

HB-27d

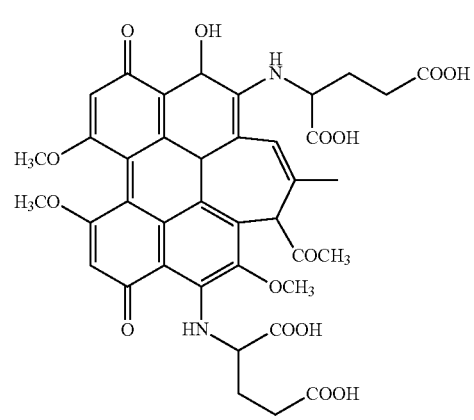

HB-28b

Example 69

Preparation of a di-glutamic acid-substituted hypocrellin B derivative (R$_1$=R$_2$=—CH(COOH)—CH$_2$CH$_2$COOH, R$_3$=—COCH$_3$, R$_4$=—H): a substituted amino raw material is an glutamic acid, a synthetic method is similar to the preparation of the diaminoacetic acid-substituted hypocrellin B derivative in example 14, and four blue black solid products HB-28a-HB-28d are obtained, respectively. HB-28a: yield: 7.4%, R$_f$: 0.36; MS (ESI+): 772.1; maximum absorption wavelength: 621 nm; molar extinction coefficient: 20,500 M$^{-1}$ cm$^{-1}$; singlet oxygen yield: 18%. HB-28b: yield: 6.6%, R$_f$: 0.32; MS (ESI+): 772.1; maximum absorption wavelength: 620 nm; molar extinction coefficient: 21,000 M$^{-1}$cm$^{-1}$; singlet oxygen yield: 19%. HB-28c: yield: 7.9%, R$_f$: 0.30; MS (ESI+): 772.1; maximum absorption wavelength: 625 nm; molar extinction coefficient: 21,500 M$^{-1}$cm$^{-1}$; singlet oxygen yield: 22%. HB-28d: yield: 5.2%, R$_f$: 0.28; MS (ESI+): 772.1; maximum absorption wavelength: 620 nm; molar extinction coefficient: 20,500 M$^{-1}$ cm$^{-1}$; singlet oxygen yield: 18%. Structural formulas of the above amino-substituted products are as follows:

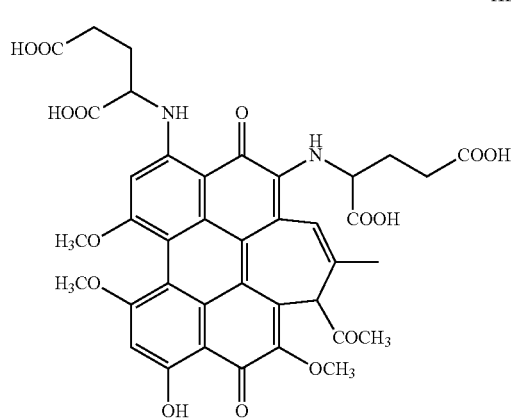

HB-28c

-continued

HB-28d

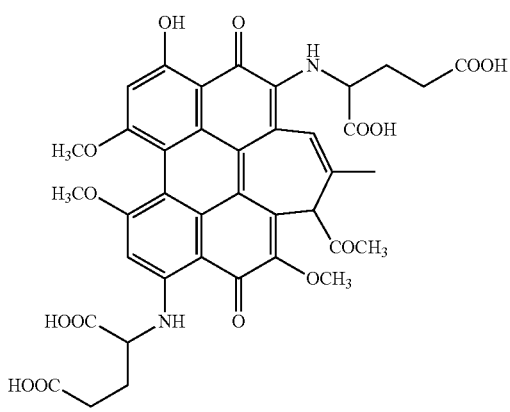

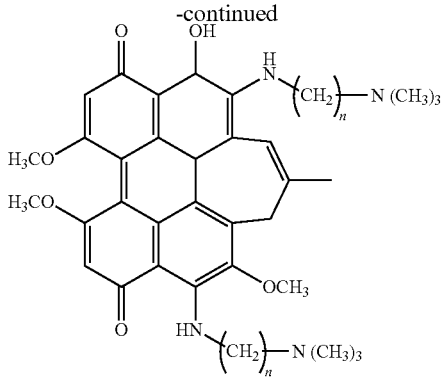

HC-29b-C2-N+: n = 2
HC-29b-C4-N+: n = 4
HC-29b-C6-N+: n = 6

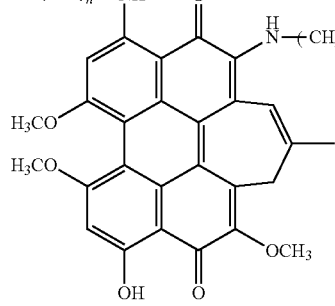

HC-29c-C2-N+: n = 2
HC-29c-C4-N+: n = 4
HC-29c-C6-N+: n = 6

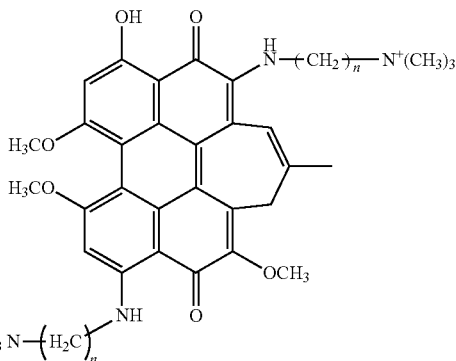

HC-29c-C2-N+: n = 2
HC-29c-C4-N+: n = 4
HC-29c-C6-N+: n = 6

Example 70

Preparation of a diaminosulfonic acid-substituted hypocrellin B derivative ($R_1=R_2=-(CH_2)_n-SO_3H$, $R_3=R_4=-H$): a substituted amino raw material is $NH_2-(CH_2)_m-SO_3H$ (m=2, 3, 4, 6), a synthetic route is similar to the preparation of the aminobutyric acid-polyethylene glycol (of different chain lengths)-substituted deacetyl hypocrellin derivative in example 20, and four blue black solid products HC-29a-Cn-N+, HC-29b-Cn-N+, HC-29c-Cn-N+, HC-29d-Cn-N+ (n=2, 4, 6) are obtained, respectively. HC-29a-C2-N+ (n=2): yield: 11.6%, $R_f$: 0.30; MS (ESI+): 642.3; maximum absorption wavelength: 622 nm; molar extinction coefficient: 31,500 $M^{-1}$ $cm^{-1}$; singlet oxygen yield: 32%. HC-29b-C4-N+ (n=4): yield: 9.8%, $R_f$: 0.38; MS (ESI+): 698.6; maximum absorption wavelength: 622 nm; molar extinction coefficient: 30,500 $M^{-1}cm^{-1}$; singlet oxygen yield: 36%. HC-29c-C6-$N^+$ (n=6): yield: 14.8%, $R_f$: 0.40; MS (ESI+): 754.6; maximum absorption wavelength: 628 nm; molar extinction coefficient: 33,500 $M^{-1}$ $cm^{-1}$; singlet oxygen yield: 39%. HC-29d-C4-$N^+$ (n=4): yield: 13.2%, $R_f$: 0.32; MS (ESI+): 698.6; maximum absorption wavelength: 628 nm; molar extinction coefficient: 32,000 $M^{-1}$ $cm^{-1}$; singlet oxygen yield: 33%. Structural formulas of the above amino-substituted products are as follows:

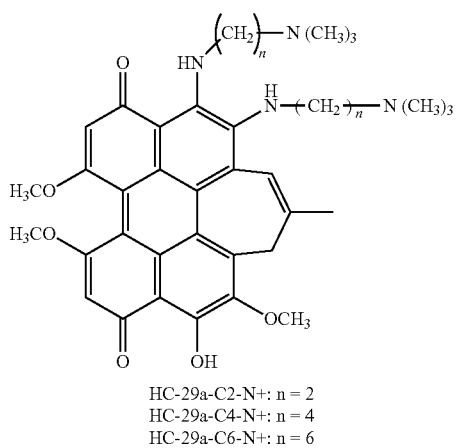

HC-29a-C2-N+: n = 2
HC-29a-C4-N+: n = 4
HC-29a-C6-N+: n = 6

Example 71

Preparation of a 4-tranexamic acid-triphenylphosphine salt (of different chain lengths)-substituted hypocrellin B derivative ($R_1=R_2=-CH_2C_6H_{10}COO-Cn-N(CH_3)_3$, $R_3=R_4=-H$) (n is the number of carbon atoms of the quaternary ammonium salt, and n=2, 4, 6): a synthetic route is similar to the preparation of the aminobutyric acid-polyethylene glycol (of different chain lengths)-substituted deacetyl hypocrellin derivative in example 20, and four blue black solid products HC-30a-Cn-$PPh_3^+$, HC-30b-Cn-$PPh_3^+$, HC-30c-Cn-$PPh_3^+$, HC-30d-Cn-$PPh_3^+$ (n=2, 4, 6) are obtained, respectively. HC-30a-C2-$PPh_3^+$ (n=2): yield: 10.6%, $R_f$: 0.30; MS (ESI+): 1328.5; maximum absorption wavelength: 624 nm; molar extinction coefficient: 31,500 M·cm$^{-1}$; singlet oxygen yield: 32%. HC-30b-C4-PPh$_3{}^+$ (n=4): yield: 9.5%, R$_f$: 0.36; MS (ESI+): 1384.5; maximum absorption wavelength: 624 nm; molar extinction coefficient: 30,500 M$^{-1}$cm$^{-1}$; singlet oxygen yield: 36%. HC-30c-C6-PPh$_3{}^+$ (n=6): yield: 17.5%, R$_f$: 0.42; MS (ESI+): 1440.6; maximum absorption wavelength: 632 nm; molar extinction coefficient: 33,500 M$^{-1}$ cm$^{-1}$; singlet oxygen yield: 40%. HC-30d-C4-PPh$_3{}^+$ (n=4): yield: 11.2%, R$_f$: 0.32; MS (ESI+): 1384.5; maximum absorption wavelength: 630 nm; molar extinction coefficient: 32,500 M$^{-1}$ cm$^{-1}$; singlet oxygen yield: 31%. Structural formulas of the above amino-substituted products are as follows:

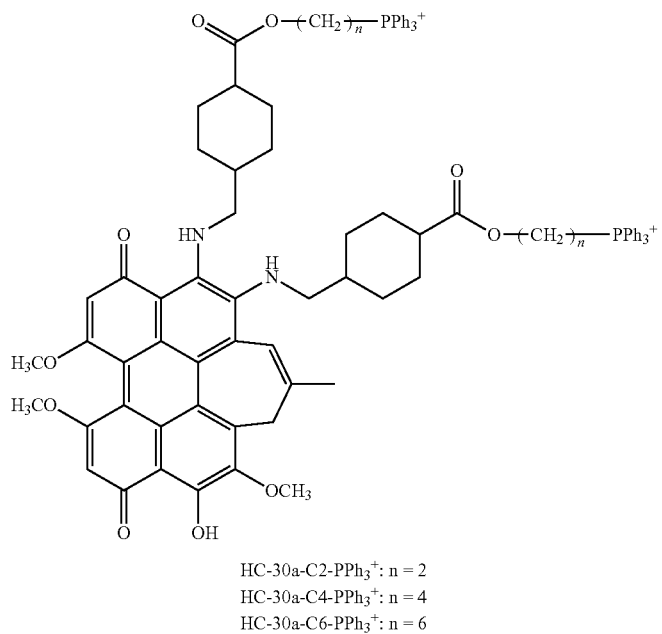

HC-30a-C2-PPh$_3{}^+$: n = 2
HC-30a-C4-PPh$_3{}^+$: n = 4
HC-30a-C6-PPh$_3{}^+$: n = 6

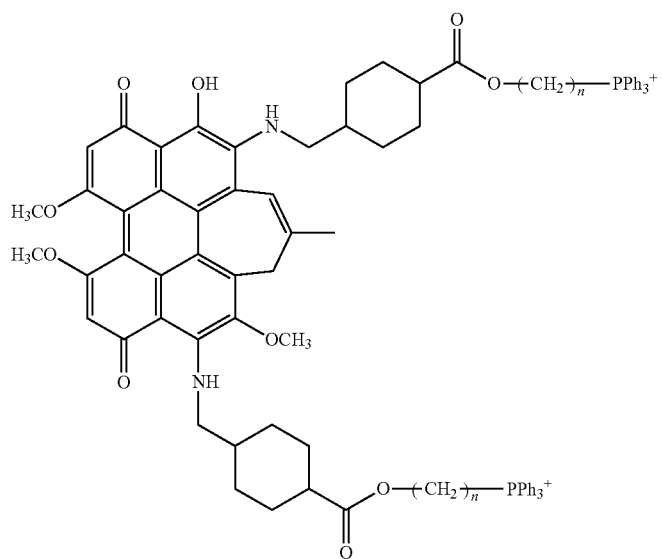

HC-30b-C2-PPh$_3{}^+$: n = 2
HC-30b-C4-PPh$_3{}^+$: n = 4
HC-30b-C6-PPh$_3{}^+$: n = 6

-continued

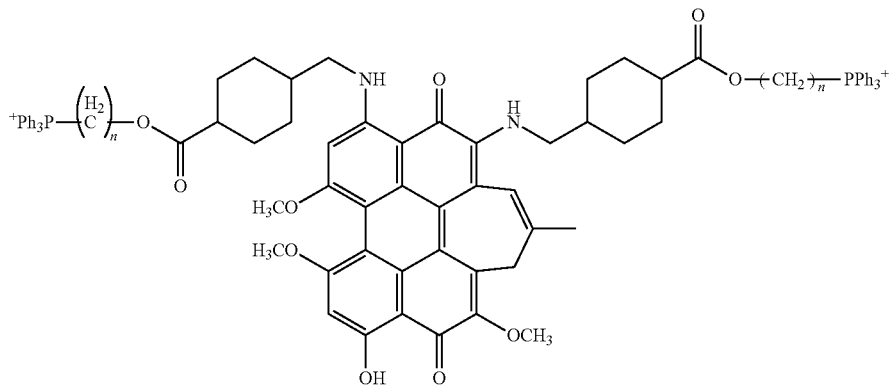

HC-30c-C2-PPh₃⁺: n = 2
HC-30c-C4-PPh₃⁺: n = 4
HC-30c-C6-PPh₃⁺: n = 6

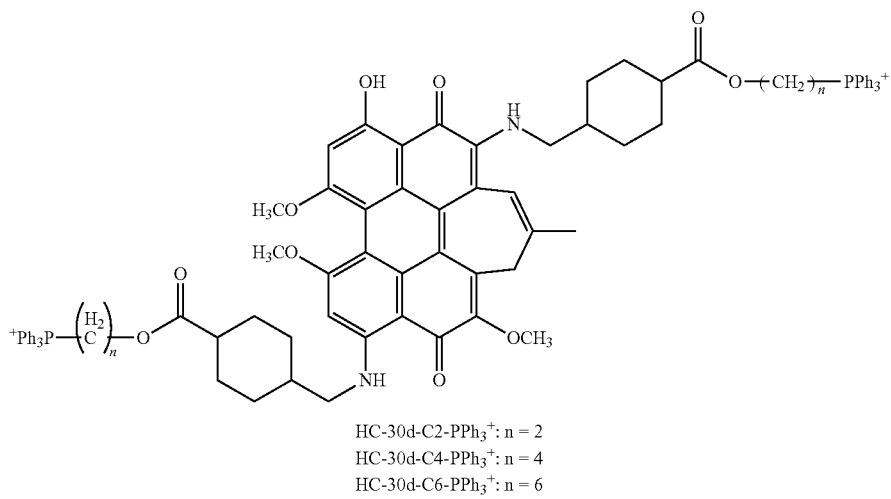

HC-30d-C2-PPh₃⁺: n = 2
HC-30d-C4-PPh₃⁺: n = 4
HC-30d-C6-PPh₃⁺: n = 6

Example 72

Preparation of a 4-tranexamic acid-triphenylphosphine salt (of different chain lengths)-substituted hypocrellin derivative ($R_1=R_2=-CH_2C_6H_{10}CO-NH-Cn-N(CH_3)_3$, $R_3=-COCH_3$, $R_4=-H$) (n is the number of carbon atoms of the quaternary ammonium salt, and n=2, 4, 6): a synthetic route is similar to the preparation of the aminobutyric acid-polyethylene glycol (of different chain lengths)-substituted deacetyl hypocrellin derivative in example 20, and four blue black solid products HB-30a-NH—Cn-PPh₃⁺, HB-30b-NH—Cn-PPh₃+, HB-30c-NH—Cn-PPh₃+, HB-30d-NH—Cn-PPh₃+(n=2, 4, 6) are obtained, respectively. HB-30a-NH—C2-PPh₃⁺ (n=2): yield: 8.6%, $R_f$: 0.32; MS (ESI+): 1371.5; maximum absorption wavelength: 625 nm; molar extinction coefficient: 31,000 $M^{-1}$ $cm^{-1}$; singlet oxygen yield: 34%. HB-30b-NH—C4-PPh₃⁺ (n=4): yield: 9.2%, $R_f$: 0.38; MS (ESI+): 1427.5; maximum absorption wavelength: 625 nm; molar extinction coefficient: 30,000 $M^{-1}$ $cm^{-1}$; singlet oxygen yield: 36%. HB-30c-NH—C6-PPh₃⁺ (n=6): yield: 18.5%, $R_f$: 0.40; MS (ESI+): 1483.6; maximum absorption wavelength: 630 nm; molar extinction coefficient: 33,000 $M^{-1}$ $cm^{-1}$; singlet oxygen yield: 38%. HB-30d-NH—C4-PPh₃⁺ (n=4): yield: 13.2%, $R_f$: 0.30; MS (ESI+): 1427.5; maximum absorption wavelength: 632 nm; molar extinction coefficient: 32,000 $M^{-1}$ $cm^{-1}$; singlet oxygen yield: 34%. Structural formulas of the above amino-substituted products are as follows:

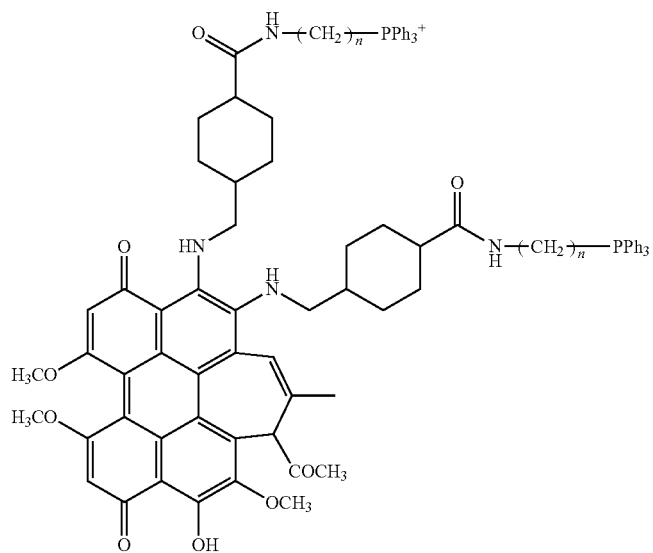
HB-30a-NH-C2-PPh₃⁺: n = 2
HB-30a-NH-C4-PPh₃⁺: n = 4
HB-30a-NH-C6-PPh₃⁺: n = 6
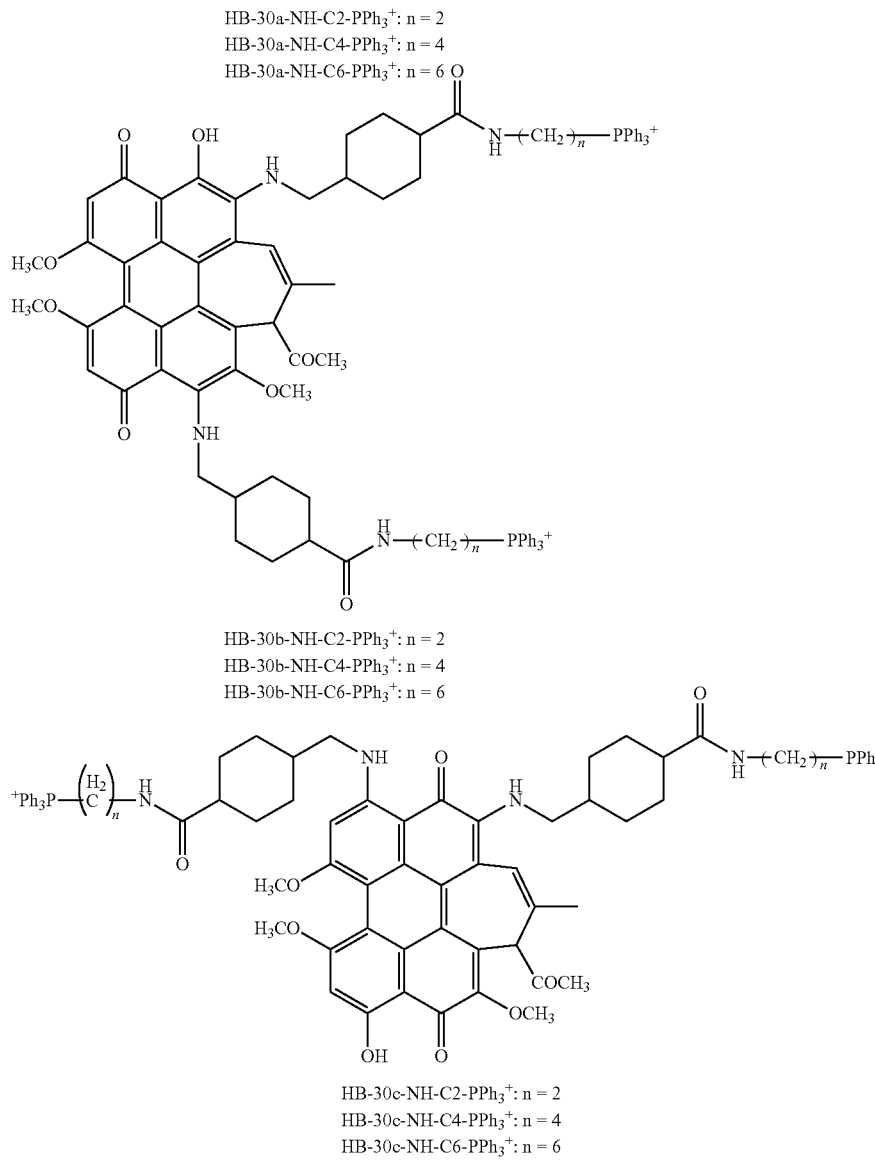
HB-30b-NH-C2-PPh₃⁺: n = 2
HB-30b-NH-C4-PPh₃⁺: n = 4
HB-30b-NH-C6-PPh₃⁺: n = 6
HB-30c-NH-C2-PPh₃⁺: n = 2
HB-30c-NH-C4-PPh₃⁺: n = 4
HB-30c-NH-C6-PPh₃⁺: n = 6

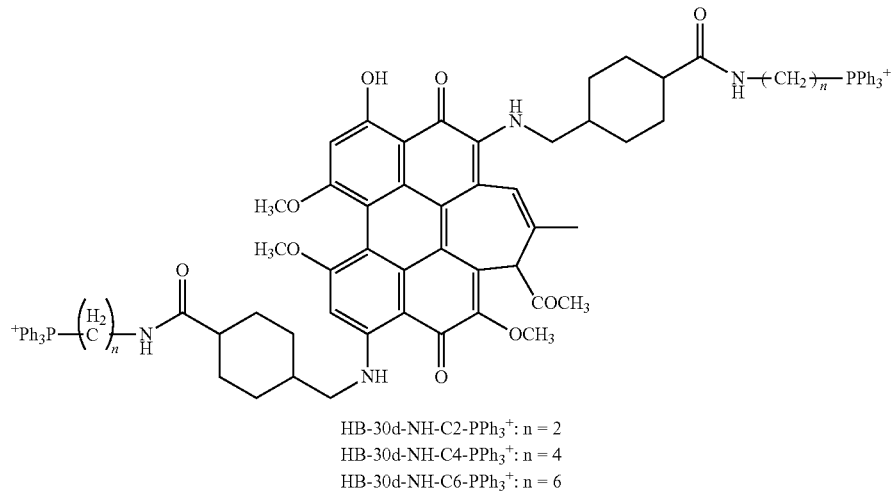

HB-30d-NH-C2-PPh₃⁺: n = 2
HB-30d-NH-C4-PPh₃⁺: n = 4
HB-30d-NH-C6-PPh₃⁺: n = 6

Example 73

Preparation of a 4-aminomethylpiperidine-PEG (of different chain lengths)-substituted hypocrellin derivative ($R_1$=$R_2$=—$CH_2C_5H_9N$—CO-PEGn, $R_3$=—$COCH_3$, $R_4$=—H) (PEG is polyethylene glycol, and n=1, 6, 12): a synthetic route is similar to the preparation of the aminobutyric acid-polyethylene glycol (of different chain lengths)-substituted deacetyl hypocrellin derivative in example 20, and four blue black solid products HB-31a-PEGn, HB-31b-PEGn, HB-31c-PEGn, HB-31d-PEGn (n=1, 6, 12) are obtained, respectively. HB-31a-PEG1 (n=1): yield: 7.6%, $R_f$: 0.30; MS (ESI+): 966.5; maximum absorption wavelength: 622 nm; molar extinction coefficient: 32,000 $M^{-1}cm^{-1}$; singlet oxygen yield: 32%. HB-31b-PEG6 (n=6): yield: 8.2%, $R_f$: 0.35; MS (ESI+): 1406.5; maximum absorption wavelength: 622 nm; molar extinction coefficient: 31,000 $M^{-1}cm^{-1}$; singlet oxygen yield: 38%. HB-31c-PEG6 (n=6): yield: 19.5%, $R_f$: 0.41; MS (ESI+): 1406.6; maximum absorption wavelength: 632 nm; molar extinction coefficient: 33,500 $M^{-1}$ $cm^{-1}$; singlet oxygen yield: 40%. HB-31d-PEG12 (n=12): yield: 13.9%, $R_f$: 0.30; MS (ESI+): 1934.5; maximum absorption wavelength: 632 nm; molar extinction coefficient: 31,500 $M^{-1}$ $cm^{-1}$; singlet oxygen yield: 33%. Structural formulas of the above amino-substituted products are as follows:

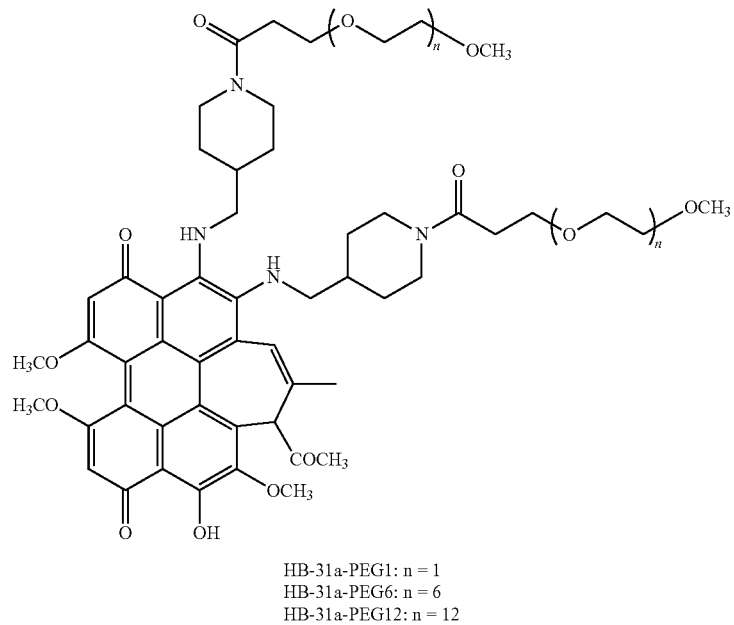

HB-31a-PEG1: n = 1
HB-31a-PEG6: n = 6
HB-31a-PEG12: n = 12

-continued

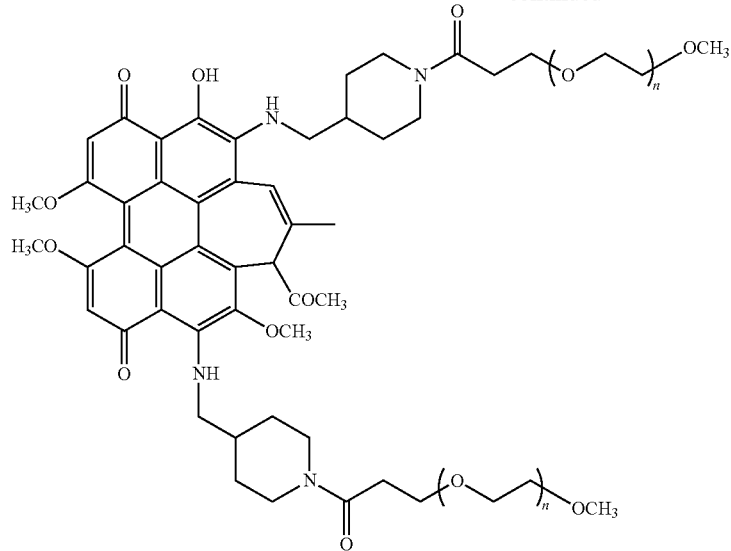

HB-31b-PEG1: n = 1
HB-31b-PEG6: n = 6
HB-31b-PEG12: n = 12

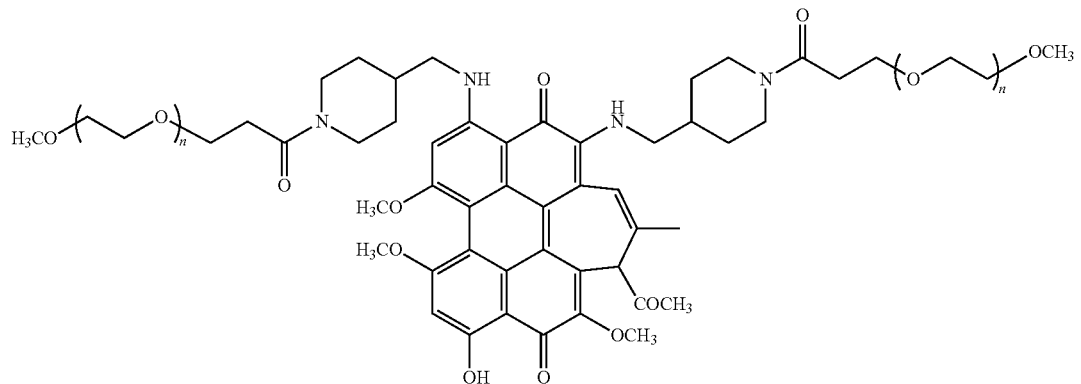

HB-31c-PEG1: n = 1
HB-31c-PEG6: n = 6
HB-31c-PEG12: n = 12

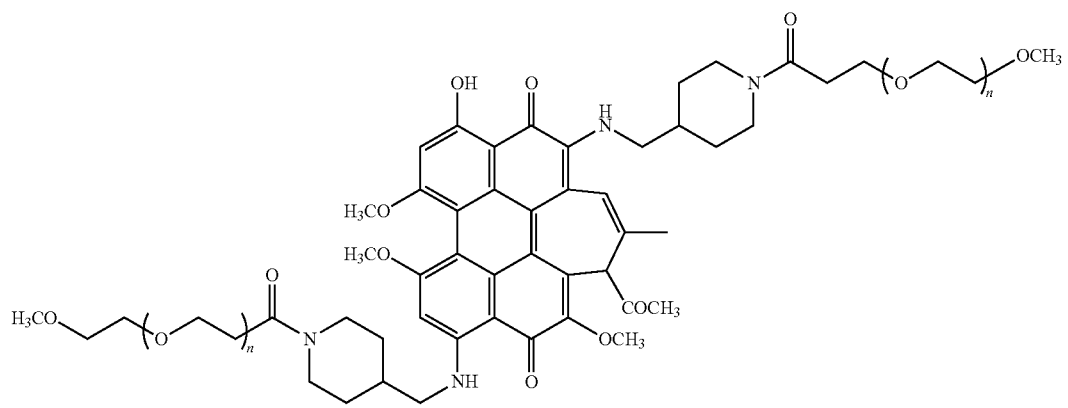

HB-31d-PEG1: n = 1
HB-31d-PEG6: n = 6
HB-31d-PEG12: n = 12

Example 74

Preparation of a 4-aminomethylpiperidine-PEG (of different chain lengths)-substituted bromo-hypocrellin derivative ($R_1=R_2=$—$CH_2C_5H_9N$—CO-PEGn, $R_3=$—$COCH_3$, $R_4=$—Br) (PEG is polyethylene glycol, and n=1, 6, 12): a synthetic route is similar to the preparation of the aminobutyric acid-polyethylene glycol (of different chain lengths)- substituted deacetyl hypocrellin derivative in example 20, and four blue black solid products HB-31a-Br-PEGn, HB-31b-Br-PEGn, HB-31c-Br-PEGn, HB-31d-Br-PEGn (n=1, 6, 12) are obtained, respectively. HB-31a-Br-PEG1 (n=1): yield: 5.6%, $R_f$: 0.35; MS (ESI+): 1045.5; maximum absorption wavelength: 624 nm; molar extinction coefficient: 32,000 $M^{-1}cm^{-1}$; singlet oxygen yield: 33%. HB-31b-Br-PEG6 (n=6): yield: 8.5%, $R_f$: 0.30; MS (ESI+): 1485.5; maximum absorption wavelength: 624 nm; molar extinction coefficient: 31,500 $M^{-1}cm^{-1}$; singlet oxygen yield: 31%. HB-31c-Br-PEG6 (n=6): yield: 16.5%, $R_f$: 0.40; MS (ESI+): 1485.6; maximum absorption wavelength: 631 nm; molar extinction coefficient: 33,000 $M^{-1}$ $cm^{-1}$; singlet oxygen yield: 38%. HB-31d-Br-PEG12 (n=12): yield: 10.9%, $R_f$: 0.32; MS (ESI+): 2013.5; maximum absorption wavelength: 632 nm; molar extinction coefficient: 31,500 $M^{-1}cm^{-1}$; singlet oxygen yield: 33%. Structural formulas of the above amino-substituted products are as follows:

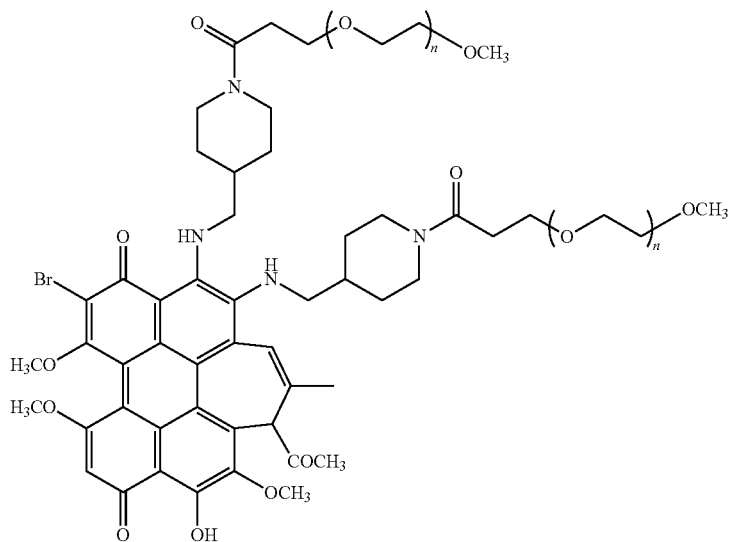

HB-31a-Br-PEG1: n = 1
HB-31a-Br-PEG6: n = 6
HB-31a-Br-PEG12: n = 12

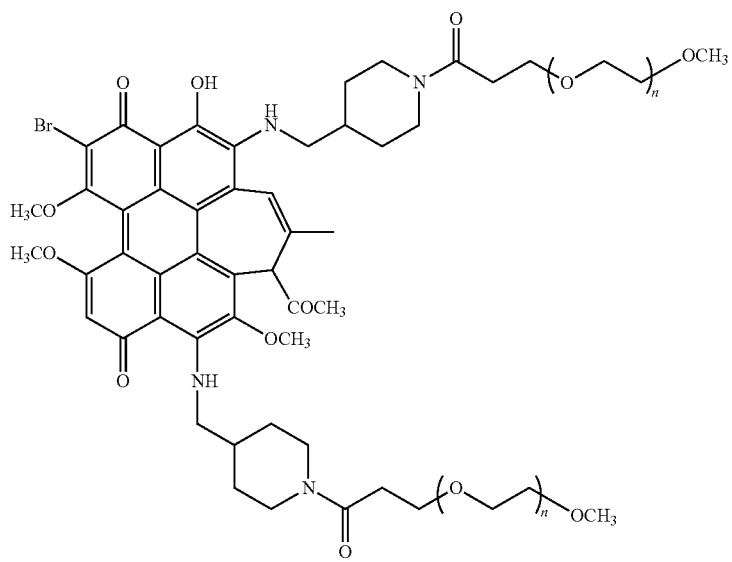

HB-31b-Br-PEG1: n = 1
HB-31b-Br-PEG6: n = 6
HB-31b-Br-PEG12: n = 12

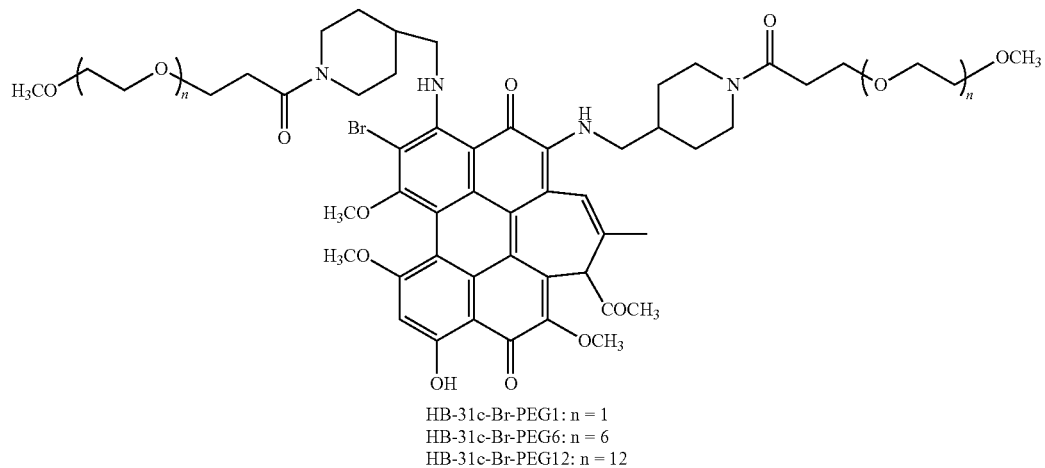

HB-31c-Br-PEG1: n = 1
HB-31c-Br-PEG6: n = 6
HB-31c-Br-PEG12: n = 12

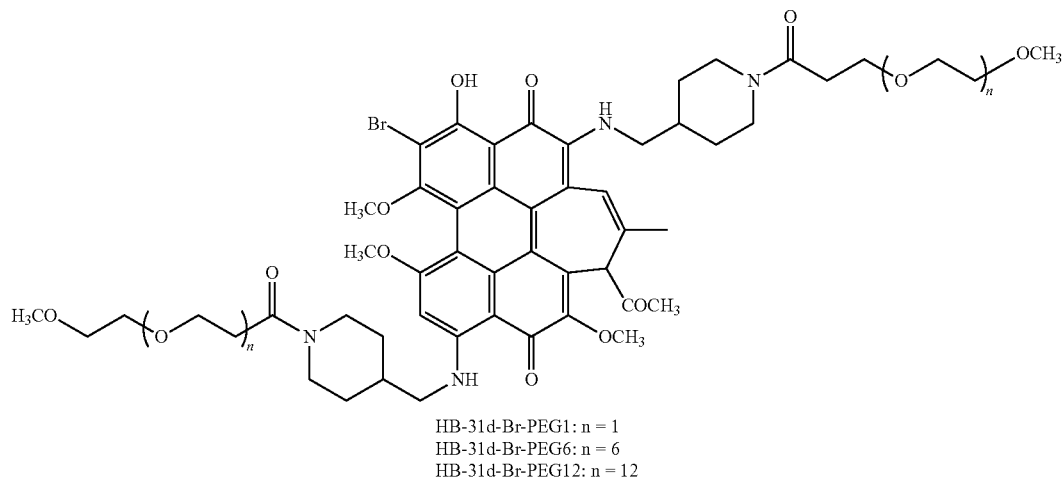

HB-31d-Br-PEG1: n = 1
HB-31d-Br-PEG6: n = 6
HB-31d-Br-PEG12: n = 12

Example 75

Preparation of a 4-aminomethylpiperidine-PEG (of different chain lengths)-substituted hypocrellin derivative ($R_1$=$R_2$=—$CH_2C_5H_9N$-PEGn, $R_3$=—$COCH_3$, $R_4$=—H) (PEG is polyethylene glycol, and n=1, 6, 12): hypocrellin B HB (100 mg, 0.18 mmol) and 4-aminomethylpiperidine (2 mmol) were dissolved in 100 mL of anhydrous acetonitrile, after fully mixed, a mixture was heated to 80° C. under the protection of nitrogen and stirred in a lucifugous condition for a reaction for 20 h, a solvent was distilled off after the reaction, a blue black solid was dissolved in 100 mL of dichloromethane, a solution was washed with distilled water three times, an organic layer was dried and filtered, and an organic phase was spin-dried to obtain a crude product. The obtained crude product was dissolved in 50 mL of anhydrous dichloromethane, $K_2CO_3$ (500 mg) was added, to react with bromo-polyethylene glycol (Br-PEGn-$OCH_3$, 2 g) of different chain lengths, respectively, and a reaction solution was stirred in a lucifugous condition at room temperature for a reaction for 8 h. The reaction solution was added to 100 mL of dichloromethane, a mixed solution was washed once with 100 mL of a dilute hydrochloric acid aqueous solution and then washed with distilled water three times, an organic layer was dried by using anhydrous magnesium sulfate and filtered, and the crude product was separated out by means of thin-layer chromatography, with a developing agent being a mixed solution of ethyl acetate:ethanol=5:1, to obtain blue black solid products HB-32a-PEGn, HB-32b-PEGn, HB-32c-PEGn, HB-32d-PEGn (n=1, 6, 12), respectively. HB-32a-PEG1 (n=1): yield: 7.6%, $R_f$: 0.30; MS (ESI+): 910.5; maximum absorption wavelength: 622 nm; molar extinction coefficient: 32,000 $M^{-1}cm^{-1}$; singlet oxygen yield: 32%. HB-32b-PEG6 (n=6): yield: 8.2%, $R_f$: 0.35; MS (ESI+): 1350.5; maximum absorption wavelength: 622 nm; molar extinction coefficient: 31,000 $M^{-1}$ $cm^{-1}$; singlet oxygen yield: 38%. HB-32c-PEG6 (n=6): yield: 19.5%, $R_f$: 0.41; MS (ESI+): 1350.6; maximum absorption wavelength: 632 nm; molar extinction coefficient: 33,500 $M^{-1}cm^{-1}$; singlet oxygen yield: 40%. HB-32d-PEG12 (n=12): yield: 13.9%, $R_f$: 0.30; MS (ESI+): 1878.5; maximum absorption wavelength: 632 nm; molar extinction coefficient: 31,500 $M^{-1}$ $cm^{-1}$; singlet oxygen yield: 33%. Structural formulas of the above amino-substituted products are as follows:

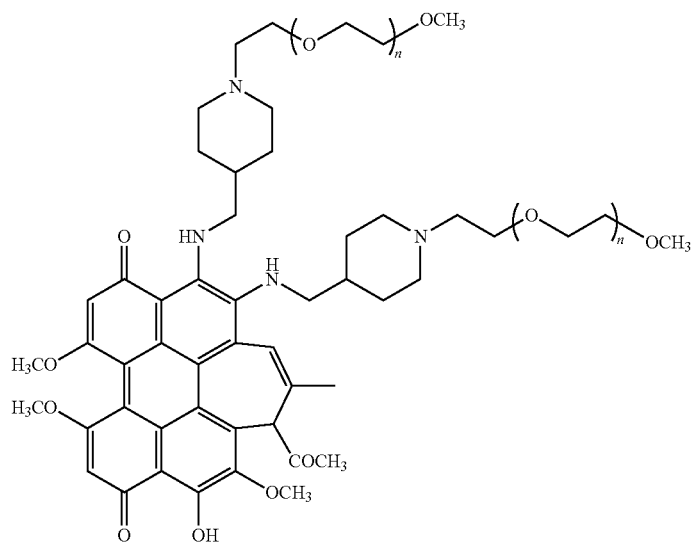
HB-32a-PEG1: n = 1
HB-32a-PEG6: n = 6
HB-32a-PEG12: n = 12
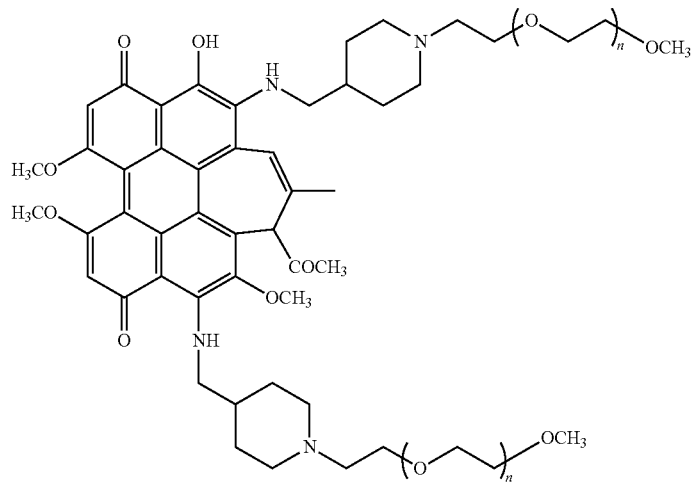
HB-32b-PEG1: n = 1
HB-32b-PEG6: n = 6
HB-32b-PEG12: n = 12
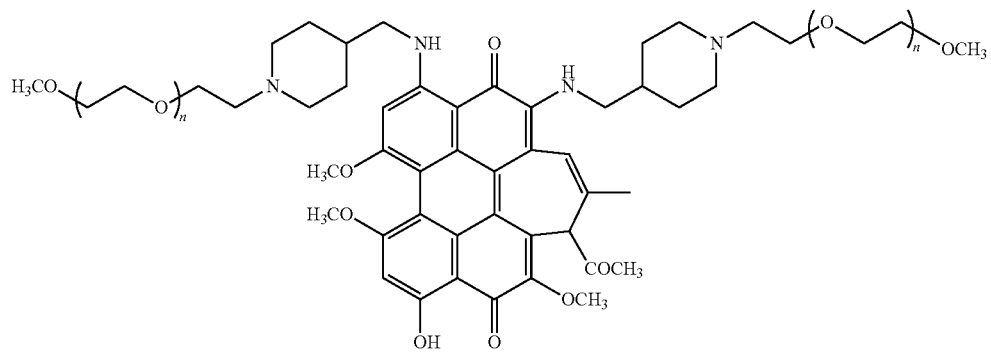
HB-32c-PEG1: n = 1
HB-32c-PEG6: n = 6
HB-32c-PEG12: n = 12

-continued

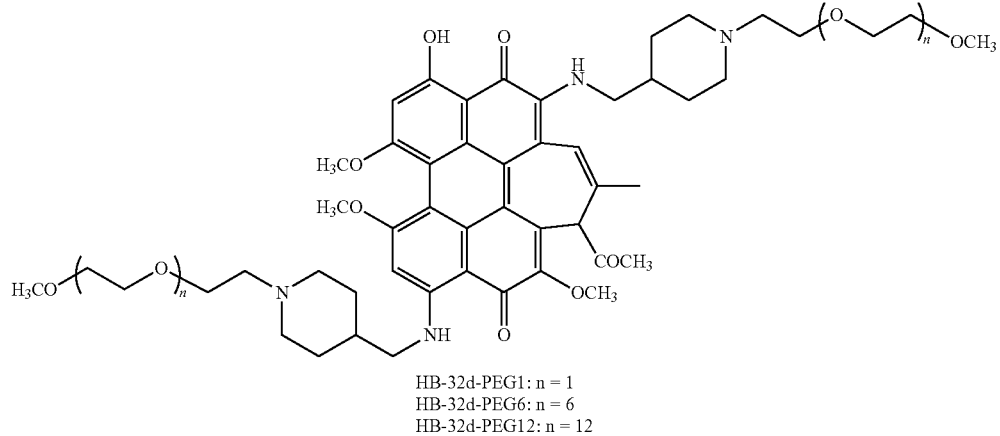

HB-32d-PEG1: n = 1
HB-32d-PEG6: n = 6
HB-32d-PEG12: n = 12

Example 76

Preparation of a di-n-propylamine-substituted hypocrellin B derivative ($R_1=R_2=-CH_2CH_2CH_3$, $R_3=-COCH_3$, $R_4=-H$): a synthetic method is similar to the preparation of the di-2-(2-aminoethoxy)ethanol-substituted hypocrellin B derivative in example 2, and four blue black solid products HB-33a-HB-33d are obtained, respectively. HB-33a: yield: 6.4%, $R_f$: 0.37; MS (ESI+) 596.2; maximum absorption wavelength: 618 nm; molar extinction coefficient: 32,500 $M^{-1}cm^{-1}$; singlet oxygen yield: 30%. HB-33b: yield: 6.5%, $R_f$: 0.39; MS (ESI+): 596.2; maximum absorption wavelength: 615 nm; molar extinction coefficient: 33,000 $M^{-1}cm^{-1}$; singlet oxygen yield: 32%. HB-33c: yield: 5.6%, $R_f$: 0.36; MS (ESI+): 596.2; maximum absorption wavelength: 618 nm; molar extinction coefficient: 34,500 $M^{-1}cm^{-1}$; singlet oxygen yield: 35%. HB-33d: yield: 4.9%, $R_f$: 0.30; MS (ESI+): 596.2; maximum absorption wavelength: 620 nm. molar extinction coefficient: 32,500 $M^{-1}cm^{-1}$; singlet oxygen yield: 32%. Structural formulas of the above amino-substituted products are as follows:

HB-33a

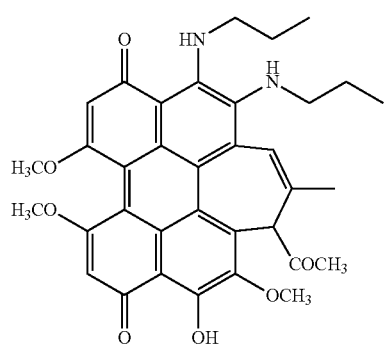

-continued

HB-33b

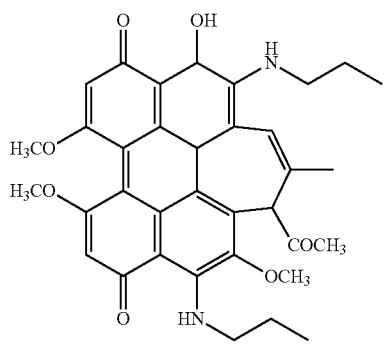

HB-33c

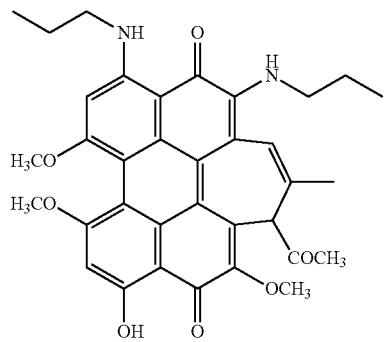

HB-33d

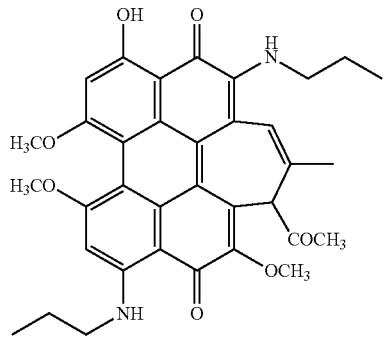

Example 77

Preparation of a diaminohexyl-substituted hypocrellin B derivative ($R_1=R_2=-C_6H_{13}$, $R_3=R_4=-H$): a synthetic method is similar to the preparation of the di-2-(2-amino-ethoxy)ethanol-substituted hypocrellin B derivative in example 2, and four blue black solid products HC-34a-HC-34d are obtained, respectively. HC-34a: yield: 5.4%, $R_f$: 0.35; MS (ESI+): 638.6; maximum absorption wavelength: 625 nm; molar extinction coefficient: 31,500 $M^{-1}cm^{-1}$; singlet oxygen yield: 30%. HC-34b: yield: 6.2%, $R_f$: 0.32; MS (ESI+): 638.6; maximum absorption wavelength: 620 nm; molar extinction coefficient: 31,500 $M^{-1}cm^{-1}$; singlet oxygen yield: 32%. HC-34c: yield: 6.4%, $R_f$: 0.28; MS (ESI+): 638.6; maximum absorption wavelength: 624 nm; molar extinction coefficient: 32,500 $M^{-1}cm^{-1}$; singlet oxygen yield: 38%. HC-34d: yield: 5.5%, $R_f$: 0.16; MS (ESI+): 638.6; maximum absorption wavelength: 628 nm; molar extinction coefficient: 32,000 $M^{-1}cm^{-1}$; singlet oxygen yield: 32%. Structural formulas of the above amino-substituted products are as follows:

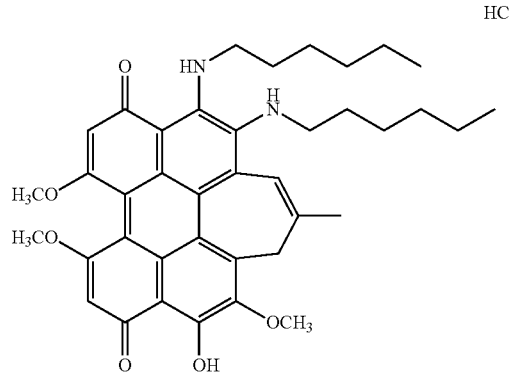

HC-34a

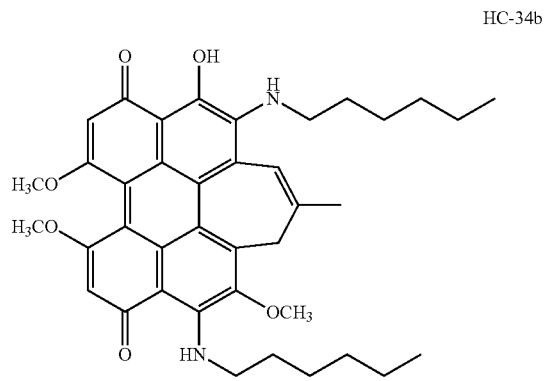

HC-34b

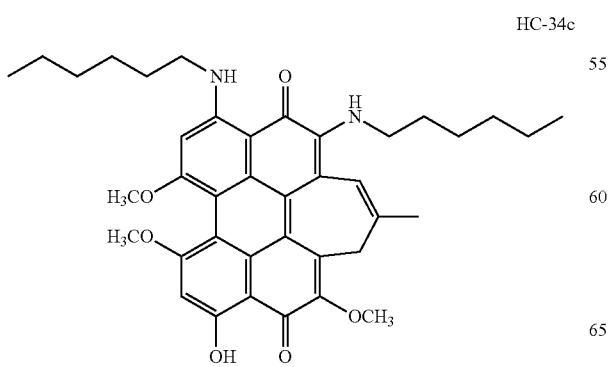

HC-34c

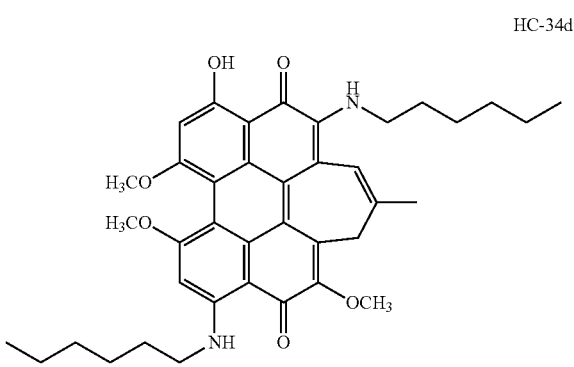

HC-34d

Example 78

Preparation of a hydroxymethyl cyclopropylamine-substituted derivative of dicyclopropylamine-substituted hypocrellin ($R_1$=$R_2$=—$C_3H_4CH_2OH$, $R_3$=—$COCH_3$, $R_4$=—H): a synthetic method is similar to the preparation of the di-2-(2-aminoethoxy)ethanol-substituted hypocrellin B derivative in example 2, and four blue black solid products HB-35a-HB-35d are obtained, respectively. HB-35a: yield: 7.2%, $R_f$: 0.35; MS (ESI+): 652.2; maximum absorption wavelength: 621 nm; molar extinction coefficient: 30,500 $M^{-1}$ $cm^{-1}$; singlet oxygen yield: 32%. HB-35b: yield: 6.7%, $R_f$: 0.34; MS (ESI+): 652.2; maximum absorption wavelength: 620 nm; molar extinction coefficient: 31,500 $M^{-1}cm^{-1}$; singlet oxygen yield: 30%. HB-35c: yield: 6.8%, $R_f$: 0.28; MS (ESI+): 652.2; maximum absorption wavelength: 619 nm; molar extinction coefficient: 32,500 $M^{-1}cm^{-1}$; singlet oxygen yield: 34%. HB-35d: yield: 4.6%, $R_f$: 0.27; MS (ESI+): 652.2; maximum absorption wavelength: 621 nm. molar extinction coefficient: 31,500 $M^{-1}$ $cm^{-1}$; singlet oxygen yield: 30%. Structural formulas of the above amino-substituted products are as follows:

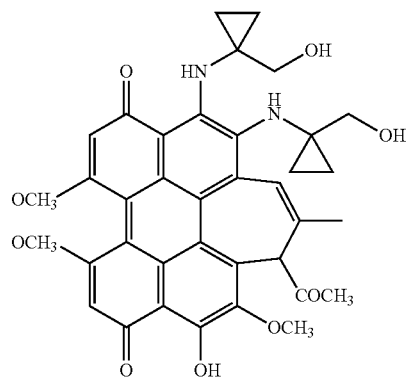

HB-35a

203
-continued

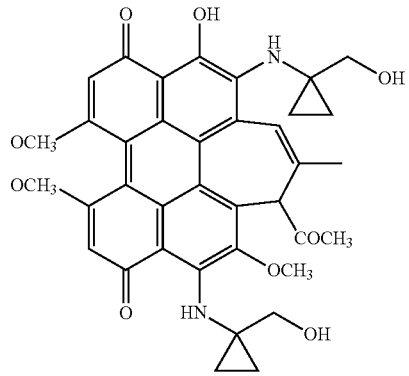
HB-35b

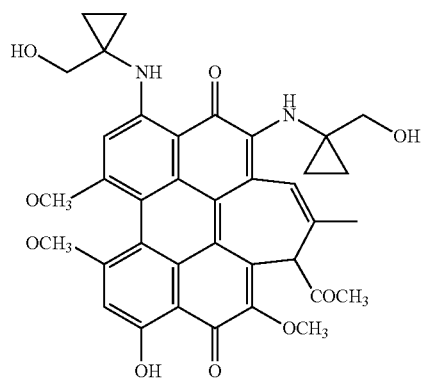
HB-35c

204
-continued

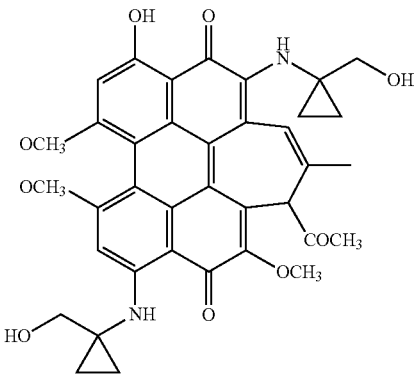
HB-35d

Example 79

Preparation of a hydroxylmethyl cyclopropylamine-polyethylene glycol (of different chain lengths)-substituted hypocrellin derivative ($R_1$=$R_2$=—$C_3H_4CH_2O$—CO-PEGn, $R_3$=—$COCH_3$, $R_4$=—H) (PEG is polyethylene glycol, and n=1, 6, 12): a synthetic route is similar to the preparation of the aminobutyric acid-polyethylene glycol (of different chain lengths)-substituted deacetyl hypocrellin derivative in example 20, and four blue black solid products HB-35a-PEGn-HB-35d-PEGn are obtained, respectively. HB-35a-PEG1 (n=1): yield: 9.2%, $R_f$: 0.35; MS (ESI+): 912.2; maximum absorption wavelength: 624 nm; molar extinction coefficient: 31,500 $M^{-1}cm^{-1}$; singlet oxygen yield: 34%. HB-35b-PEG6 (n=6): yield: 8.7%, $R_f$: 0.34; MS (ESI+): 1352.2; maximum absorption wavelength: 624 nm; molar extinction coefficient: 30,500 $M^{-1}cm^{-1}$; singlet oxygen yield: 32%. HB-35c-PEG6 (n=6): yield: 12.8%, $R_f$: 0.32; MS (ESI+): 1352.2; maximum absorption wavelength: 630 nm; molar extinction coefficient: 33,500 $M^{-1}cm^{-1}$; singlet oxygen yield: 38%. HB-35d-PEG12 (n=12): yield: 5.6%, $R_f$: 0.28; MS (ESI+): 1880.2; maximum absorption wavelength: 625 nm. molar extinction coefficient: 31,500 $M^{-1}cm^{-1}$; singlet oxygen yield: 30%. Structural formulas of the above amino-substituted products are as follows:

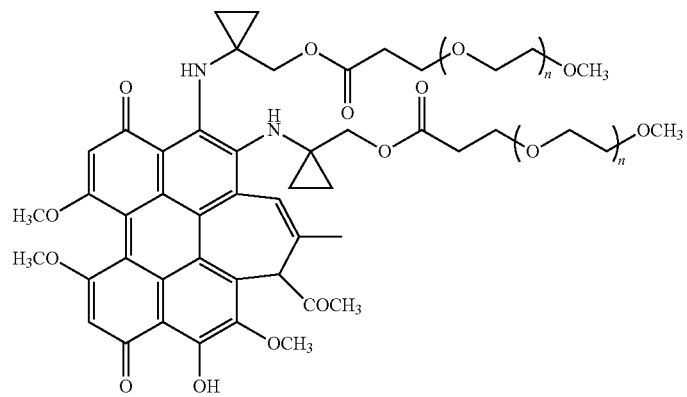

HB-35a-PEG1: n = 1
HB-35a-PEG6: n = 6
HB-35a-PEG12: n = 12

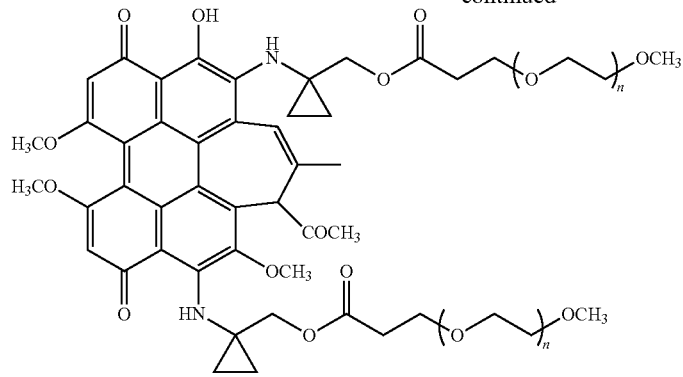

HB-35b-PEG1: n = 1
HB-35b-PEG6: n = 6
HB-35b-PEG12: n = 12

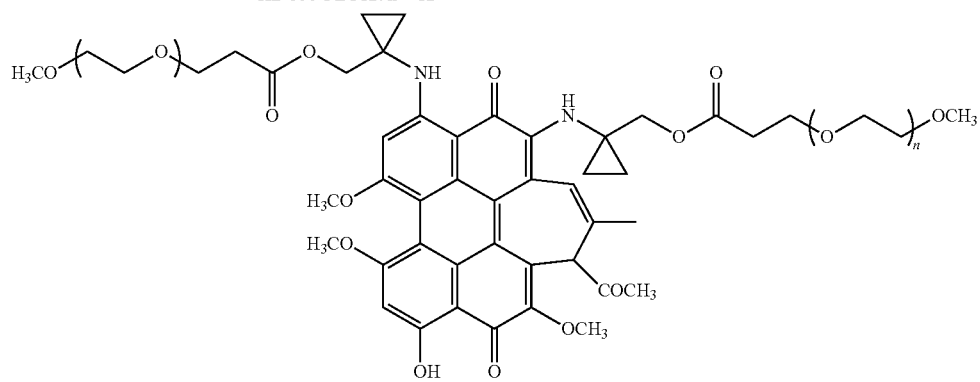

HB-35c-PEG1: n = 1
HB-35c-PEG6: n = 6
HB-35c-PEG12: n = 12

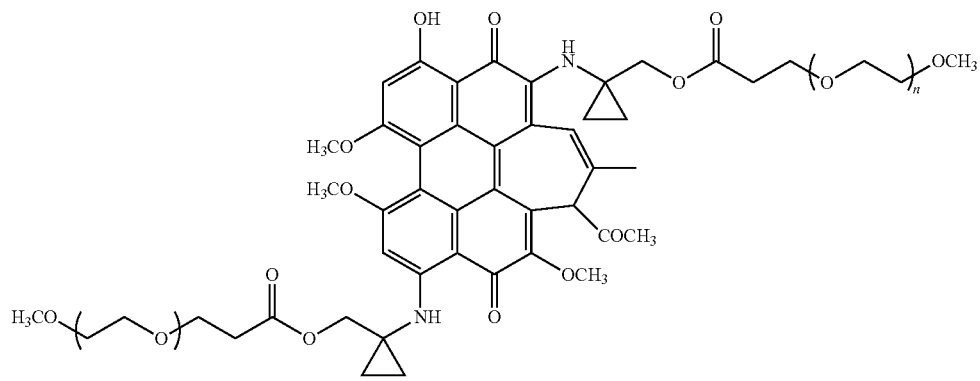

HB-35d-PEG1: n = 1
HB-35d-PEG6: n = 6
HB-35d-PEG12: n = 12

Example 80

Preparation of a hydroxylmethyl cyclopropylamine-polyethylene glycol (of different chain lengths)-substituted hypocrellin derivative ($R_1$=$R_2$=—$C_3H_4CH_2$—COO-PEGn, $R_3$=$R_4$=—H) (PEG is polyethylene glycol, and n=1, 6, 12): a synthetic route is similar to the preparation of the aminobutyric acid-polyethylene glycol (of different chain lengths)-substituted deacetyl hypocrellin derivative in example 20, and four blue black solid products HC-35a-PEGn-HC-35d-PEGn are obtained, respectively. HC-35a-PEG1 (n=1): yield: 7.8%, $R_f$: 0.28; MS (ESI+): 754.2; maximum absorption wavelength: 622 nm; molar extinction coefficient: 31,000 $M^{-1}cm^{-1}$; singlet oxygen yield: 32%. HC-35b-PEG6 (n=6): yield: 8.9%, $R_f$: 0.35; MS (ESI+): 1194.2; maximum absorption wavelength: 622 nm; molar extinction coefficient: 31,500 $M^{-1}$ $cm^{-1}$; singlet oxygen yield: 32%. HC-35c-PEG6 (n=6): yield: 13.8%, $R_f$: 0.35; MS (ESI+): 1194.2; maximum absorption wavelength: 632 nm; molar extinction coefficient: 33,000 $M^{-1}$ $cm^{-1}$; singlet oxygen yield: 39%. HC-35d-PEG12 (n=12): yield: 4.6%, $R_f$: 0.30; MS (ESI+): 1622.2; maximum absorption wavelength:

628 nm. molar extinction coefficient: 32,500 $M^{-1}$ $cm^{-1}$; singlet oxygen yield: 32%. Structural formulas of the above amino-substituted products are as follows:

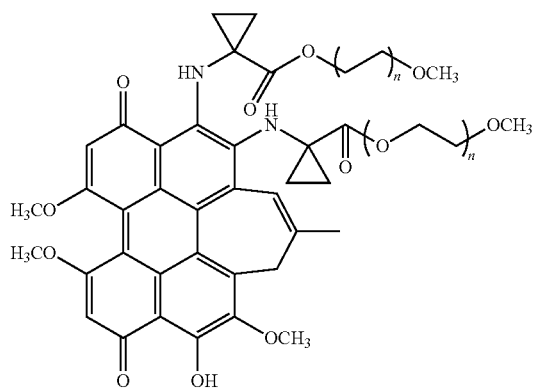

HC-35a-PEG1: n = 1
HC-35a-PEG6: n = 6
HC-35a-PEG12: n = 12

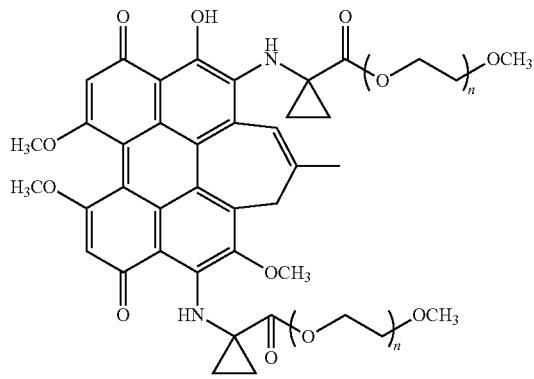

HC-35h-PEG1: n = 1
HC-35h-PEG6: n = 6
HC-35h-PEG12: n = 12

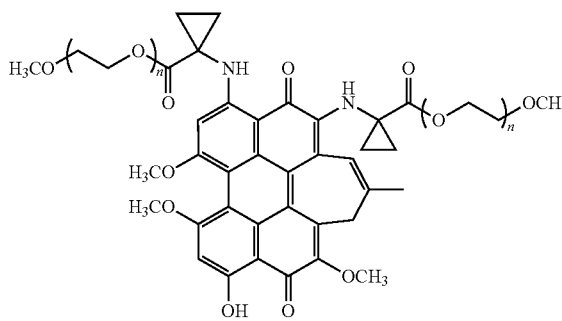

HC-35c-PEG1: n = 1
HC-35c-PEG6: n = 6
HC-35c-PEG12: n = 12

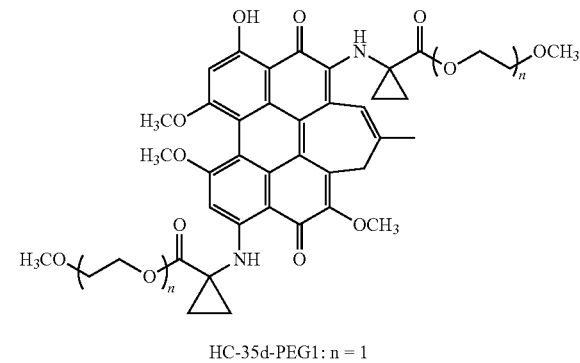

HC-35d-PEG1: n = 1
HC-35d-PEG6: n = 6
HC-35d-PEG12: n = 12

Example 81

Preparation of a diaminoethyl-substituted hypocrellin derivative ($R_1$=$R_2$=—$NHC_2H_5$, $R_3$=—$COCH_3$, $R_4$=—H): a substituted amino group is $NH_2$—$NHC_2H_5$, a synthetic method is similar to the preparation of the di-2-(2-aminoethoxy)ethanol-substituted hypocrellin B derivative in example 2, and four blue black solid products HB-36a-HB-36d are obtained, respectively. HB-36a: yield: 6.2%, $R_f$: 0.38; MS (ESI+): 598.2; maximum absorption wavelength: 621 nm; molar extinction coefficient: 30,500 $M^{-1}cm^{-1}$; singlet oxygen yield: 32%. HB-36b: yield: 5.7%, $R_f$: 0.33; MS (ESI+): 598.2; maximum absorption wavelength: 622 nm; molar extinction coefficient: 31,500 $M^{-1}cm^{-1}$; singlet oxygen yield: 30%. HB-36c: yield: 6.5%, $R_f$: 0.31; MS (ESI+): 598.2; maximum absorption wavelength: 621 nm; molar extinction coefficient: 33,500 $M^{-1}$ $cm^{-1}$; singlet oxygen yield: 35%. HB-36d: yield: 5.6%, $R_f$: 0.27; MS (ESI+): 598.2; maximum absorption wavelength: 621 nm; molar extinction coefficient: 32,000 $M^{-1}cm^{-1}$; singlet oxygen yield: 32%. Structural formulas of the above amino-substituted products are as follows:

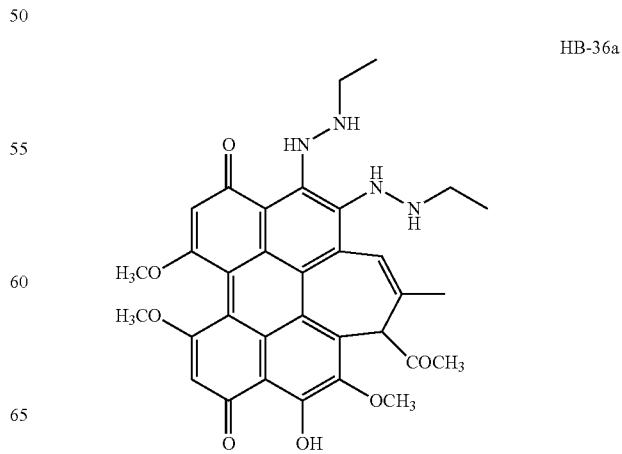

HB-36a

-continued

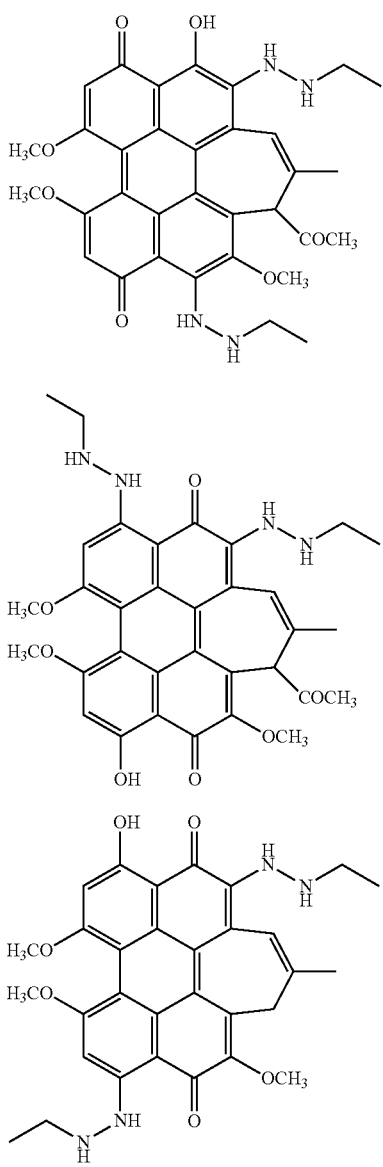

HB-36b

HB-36c

HB-36d

Example 82

Preparation of a dihydroxyamino-substituted hypocrellin derivative ($R_1$=$R_2$=—$NHC_6H_4CH_3$, $R_3$=$R_4$=—H): a substituted amino raw material is $NH_2$—OH, a synthetic method is similar to the preparation of the di-2-(2-aminoethoxy)ethanol-substituted hypocrellin B derivative in example 2, and four blue black solid products HC-37a-HC-37d are obtained, respectively. HC-37a: yield: 8.2%, $R_f$: 0.33; MS (ESI+): 502.5; maximum absorption wavelength: 620 nm; molar extinction coefficient: 30,500 $M^{-1}cm^{-1}$; singlet oxygen yield: 32%. HC-37b: yield: 6.7%, $R_f$: 0.37; MS (ESI+): 502.5; maximum absorption wavelength: 622 nm; molar extinction coefficient: 31,500 $M^{-1}cm^{-1}$; singlet oxygen yield: 31%. HC-37c: yield: 6.0%, $R_f$: 0.31; MS (ESI+): 502.5; maximum absorption wavelength: 624 nm; molar extinction coefficient: 34,000 $M^{-1}cm^{-1}$; singlet oxygen yield: 36%. HC-37d: yield: 6.6%, $R_f$: 0.27; MS (ESI+): 502.5; maximum absorption wavelength: 620 nm; molar extinction coefficient: 32,000 $M^{-1}cm^{-1}$; singlet oxygen yield: 33%. Structural formulas of the above amino-substituted products are as follows:

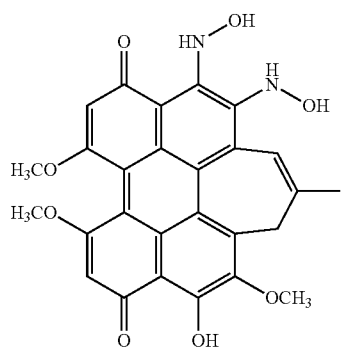

HC-37a

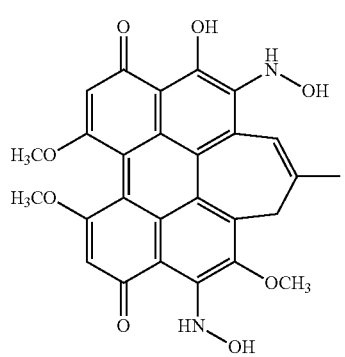

HC-37b

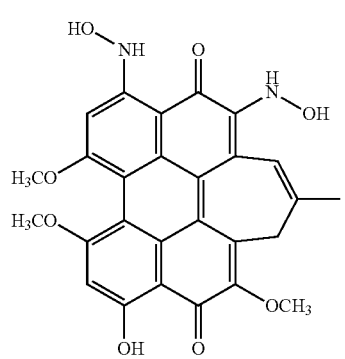

HC-37c

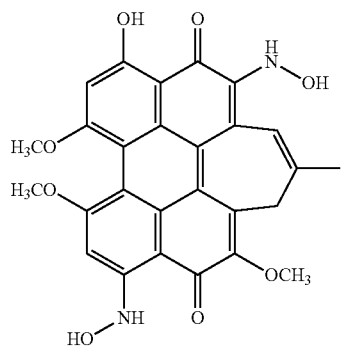

HC-37d

Example 83

Preparation of a benzylaminopyridine-substituted hypocrellin B derivative ($R_1=R_2=$—$CH_2C_5H_4N$, $R_3=$—$COCH_3$, $R_4=$—H): a substituted amino raw material is $NH_2$—$CH_2C_5H_4N$, a synthetic method is similar to the preparation of the di-2-(2-aminoethoxy)ethanol-substituted hypocrellin B derivative in example 2, and four blue black solid products HB-38a-HB-38d are obtained, respectively. HB-38a: yield: 6.4%, $R_f$: 0.36; MS (ESI+): 694.6; maximum absorption wavelength: 624 nm; molar extinction coefficient: 19,000 $M^{-1}$ $cm^{-1}$; singlet oxygen yield: 16%; HB-38b: yield: 7.2%, $R_f$: 0.36; MS (ESI+): 694.6; maximum absorption wavelength: 621 nm; molar extinction coefficient: 18,500 $M^{-1}cm^{-1}$; singlet oxygen yield: 16%; HB-38c: yield: 7.8%, $R_f$: 0.28; MS (ESI+): 694.6; maximum absorption wavelength: 628 nm; molar extinction coefficient: 20,000 $M^{-1}cm^{-1}$; singlet oxygen yield: 18%; HB-38d: yield: 8.6%, $R_f$: 0.25; MS (ESI+): 694.6; maximum absorption wavelength: 624 nm; molar extinction coefficient: 18,500 $M^{-1}$ $cm^{-1}$; singlet oxygen yield: 17%. Structural formulas of the above amino-substituted products are as follows:

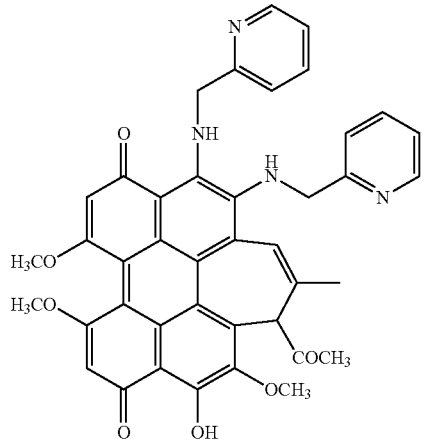
HB-38a

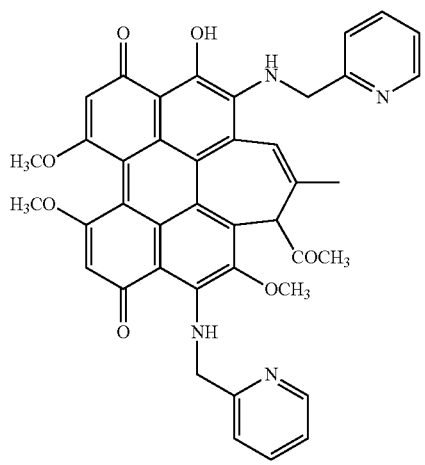
HB-38b

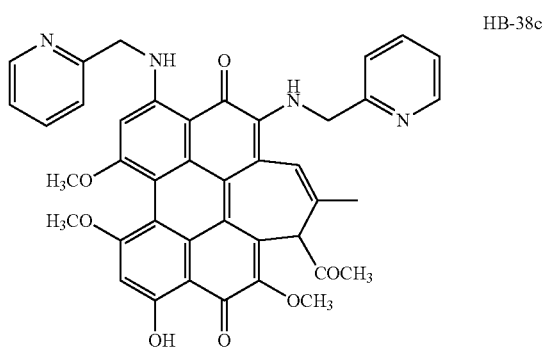
HB-38c

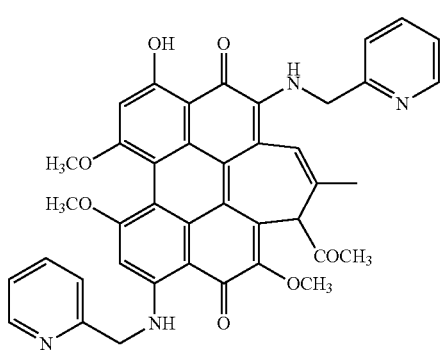
HB-38d

Example 84

Preparation of a di-benzylaminomethylpyridinium-substituted hypocrellin B derivative ($R_1=R_2=$—$CH_2C_5H_4N^+$($CH_3$), $R_3=$—$COCH_3$, $R_4=$—H): a substituted amino raw material is $NH_2$—$CH_2C_5H_4N^+(CH_3)$, a synthetic method is similar to the preparation of the di-2-(2-aminoethoxy)ethanol-substituted hypocrellin B derivative in example 2, and four blue black solid products HB-38a-$N^+$~HB-38d-$N^+$ are obtained, respectively. HB-38a-$N^+$: yield: 4.4%, $R_f$: 0.35; MS (ESI+): 724.8; maximum absorption wavelength: 620 nm; molar extinction coefficient: 22,000 $M^{-1}cm^{-1}$; singlet oxygen yield: 18%; HB-38b-$N^+$: yield: 8.2%, $R_f$: 0.30; MS (ESI+): 724.8; maximum absorption wavelength: 620 nm; molar extinction coefficient: 21,000 $M^{-1}cm^{-1}$; singlet oxygen yield: 20%; HB-38c-$N^+$: yield: 4.4%, $R_f$: 0.20; MS (ESI+): 724.8; maximum absorption wavelength: 622 nm; molar extinction coefficient: 22,500 $M^{-1}cm^{-1}$; singlet oxygen yield: 21%; HB-38d-$N^+$: yield: 5.6%, $R_f$: 0.23; MS (ESI+): 724.8; maximum absorption wavelength: 626 nm; molar extinction coefficient: 21,500 $M^{-1}cm^{-1}$; singlet oxygen yield: 20%. Structural formulas of the above amino-substituted products HB-38a-$N^+$~HB-38d-$N^+$ are as follows:

HB-38a-N+

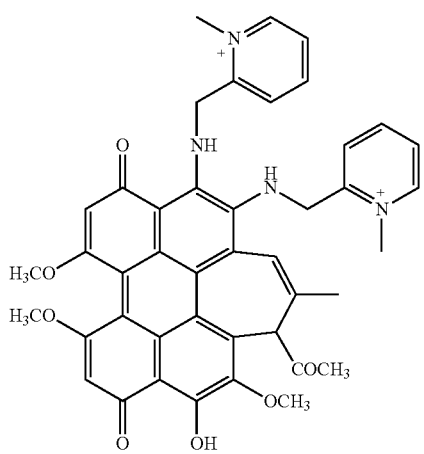

HB-38b-N+

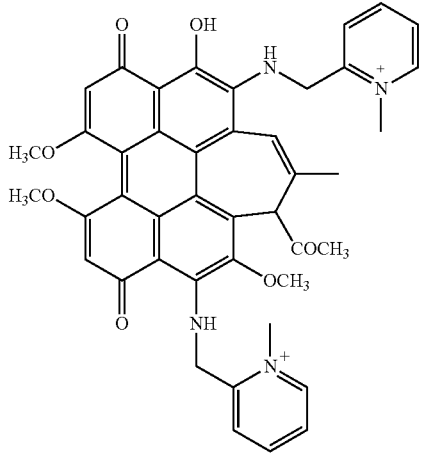

HB-38c-N+

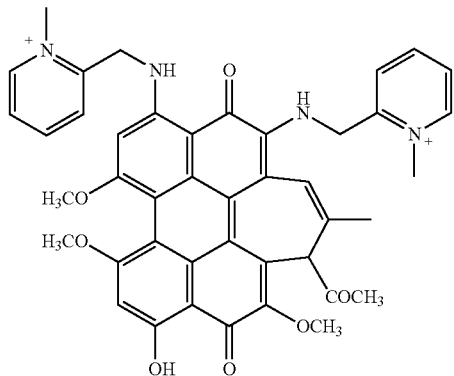

HB-38d-N+

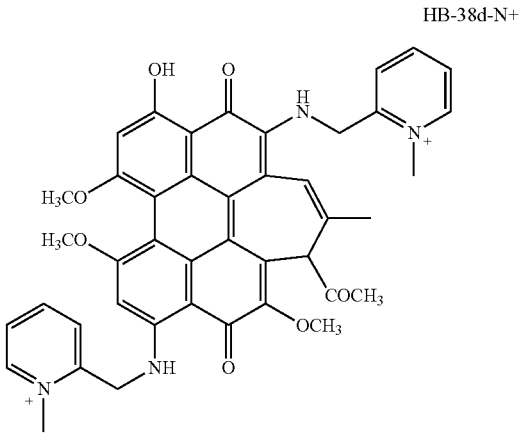

Example 85

Preparation of a diamino quaternary ammonium salt-substituted hypocrellin derivative ($R_1$=$R_2$=—$CH_2C_5H_4N^+(CH_2CH_2CH_2COOH)$, $R_3$=—$COCH_3$, $R_4$=—H): a substituted amino raw material is $NH_2$—$CH_2C_5H_4N^+(CH_2CH_2CH_2COOH)$, a synthetic method is similar to the preparation of the di-2-(2-aminoethoxy)ethanol-substituted hypocrellin B derivative in example 2, and four blue black solid products HB-38a-N—COOH—HB-38d-N—COOH are obtained, respectively. HB-38a-N—COOH: yield: 3.4%, $R_f$: 0.55; MS (ESI+): 868.8; maximum absorption wavelength: 620 nm; molar extinction coefficient: 22,000 $M^{-1}$ $cm^{-1}$; singlet oxygen yield: 20%; HB-38b-N—COOH: yield: 6.2%, $R_f$: 0.50; MS (ESI+): 868.8; maximum absorption wavelength: 620 nm; molar extinction coefficient: 21,500 $M^{-1}cm^{-1}$; singlet oxygen yield: 18%; HB-38c-N—COOH: yield: 10.4%, $R_f$: 0.51; MS (ESI+): 868.8; maximum absorption wavelength: 622 nm; molar extinction coefficient: 21,500 $M^{-1}cm^{-1}$; singlet oxygen yield: 21%; HB-38d-N—COOH: yield: 5.6%, $R_f$: 0.53; MS (ESI+): 868.8; maximum absorption wavelength: 626 nm; molar extinction coefficient: 21,000 $M^{-1}$ $cm^{-1}$; singlet oxygen yield: 20%. Structural formulas of the above amino-substituted products HB-38a-N—COOH—HB-38d-N—COOH are as follows:

HB-38a-N-COOH

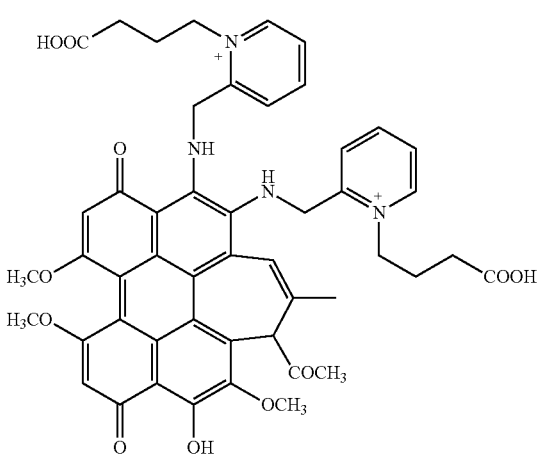

HB-38b-N-COOH

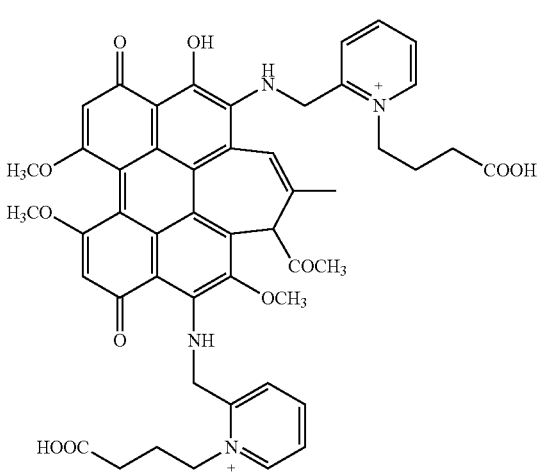

HB-38c-N-COOH

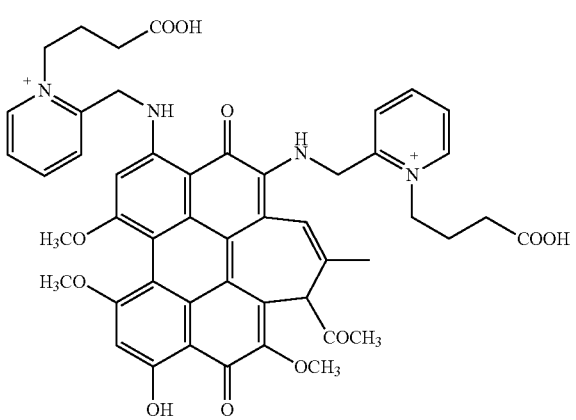

HB-38d-N-COOH

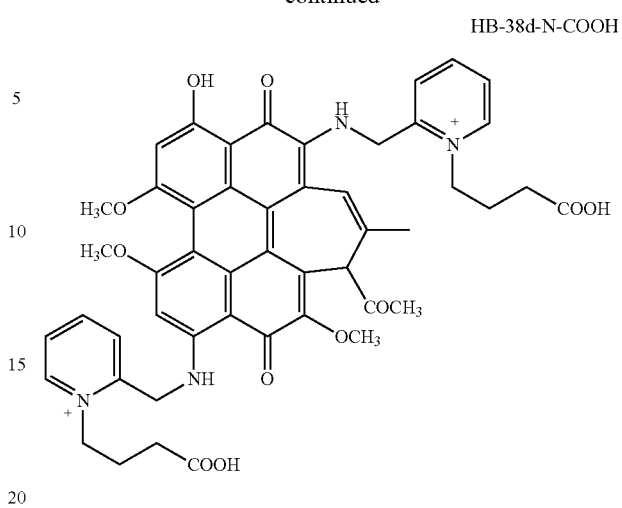

Example 86

Preparation of a dipiperazine-substituted hypocrellin B derivative

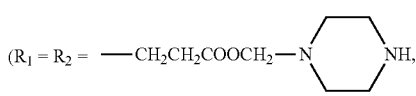

$R_3$=—COCH$_3$, $R_4$=—H): a substituted amino raw material is

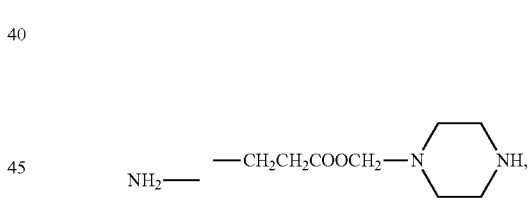

a synthetic route is similar to the preparation of the diaminobutyric acid-substituted polyethylene glycol-modified hypocrellin B derivative in example 17, and four blue black solid products HB-39a-HB-39d are obtained, respectively. HB-39a: yield: 6.4%, $R_f$: 0.35; MS (ESI+): 878.8; maximum absorption wavelength: 622 nm; molar extinction coefficient: 22,500 M$^{-1}$cm$^{-1}$; singlet oxygen yield: 20%. HB-39b: yield: 9.2%, $R_f$: 0.32; MS (ESI+): 878.8; maximum absorption wavelength: 620 nm; molar extinction coefficient: 23,500 M$^{-1}$ cm$^{-1}$; singlet oxygen yield: 21%. HB-39c: yield: 8.4%, $R_f$: 0.26; MS (ESI+): 878.8; maximum absorption wavelength: 628 nm; molar extinction coefficient: 21,000 M$^{-1}$cm$^{-1}$; singlet oxygen yield: 29%. HB-39d: yield: 6.6%, $R_f$: 0.25; MS (ESI+): 878.8; maximum absorption wavelength: 626 nm. molar extinction coefficient: 21,000 M$^{-1}$cm$^{-1}$; singlet oxygen yield: 22%. Structural formulas of the above amino-substituted products are as follows:

217
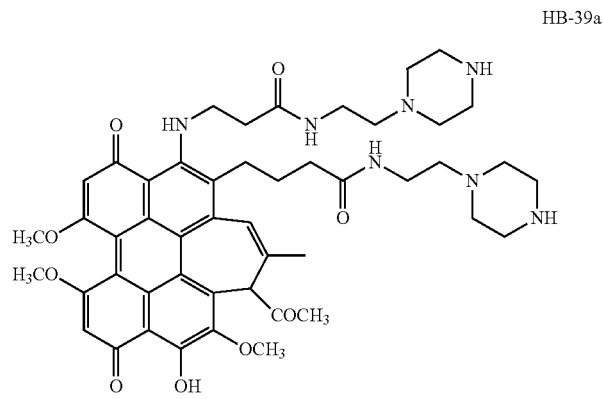
HB-39a
218
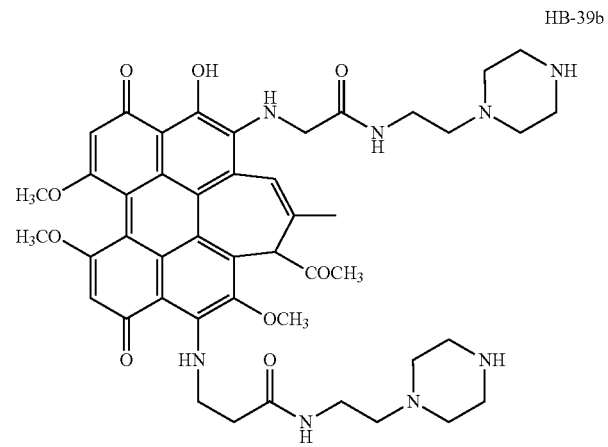
HB-39b
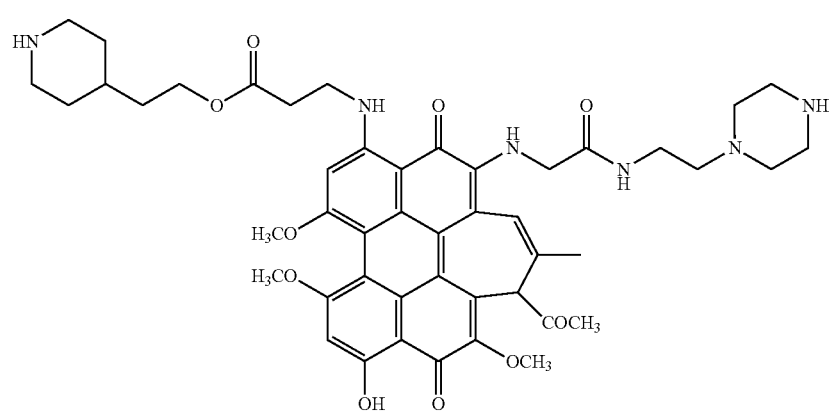
HB-39c
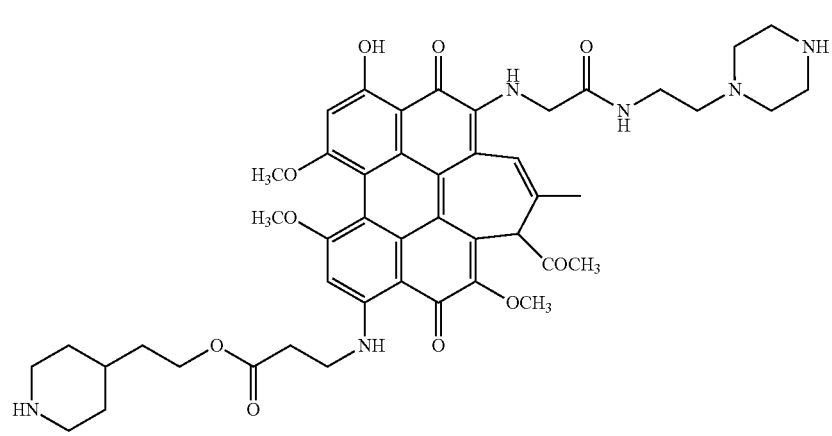
HB-39d

Example 87

Preparation of an aminoethyl diketopiperazine-substituted hypocrellin derivative ($R_1=R_2=$—$CH_2CH_2O$—CO-piperazine, $R_3=$—$COCH_3$, $R_4=$—H): a synthetic method is similar to the preparation of the di-2-(2-aminoethoxy)ethanol-substituted hypocrellin B derivative in example 2, and four blue black solid products HB-40a-HB-40d are obtained, respectively. HB-40a: yield: 4.8%, $R_f$: 0.25; MS (ESI+): 880.2; maximum absorption wavelength: 620 nm; molar extinction coefficient: 31,000 $M^{-1}cm^{-1}$; singlet oxygen yield: 30%. HB-40b: yield: 5.0%, $R_f$: 0.34; MS (ESI+): 880.2; maximum absorption wavelength: 624 nm; molar extinction coefficient: 31,500 $M^{-1}cm^{-1}$; singlet oxygen yield: 34%. HB-40c: yield: 14.5%, $R_f$: 0.42; MS (ESI+): 880.2; maximum absorption wavelength: 632 nm; molar extinction coefficient: 34,000 $M^{-1}$ $cm^{-1}$; singlet oxygen yield: 40%. HB-40d: yield: 6.8%, $R_f$: 0.30; MS (ESI+): 880.2; maximum absorption wavelength: 628 nm. molar extinction coefficient: 31,500 $M^{-1}$ $cm^{-1}$; singlet oxygen yield: 30%. Structural formulas of the above amino-substituted products are as follows:

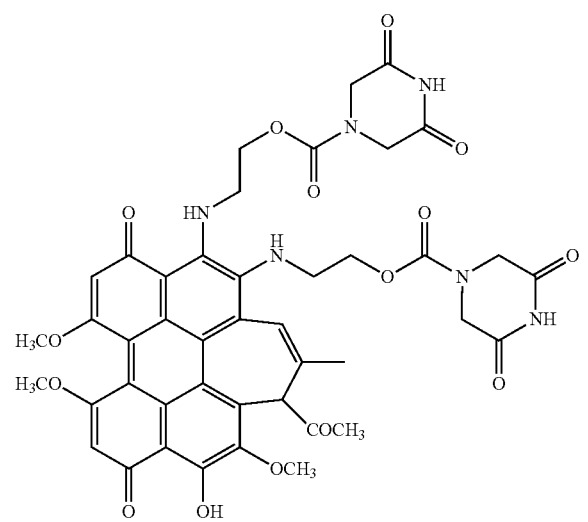

HB-40a

HB-40b

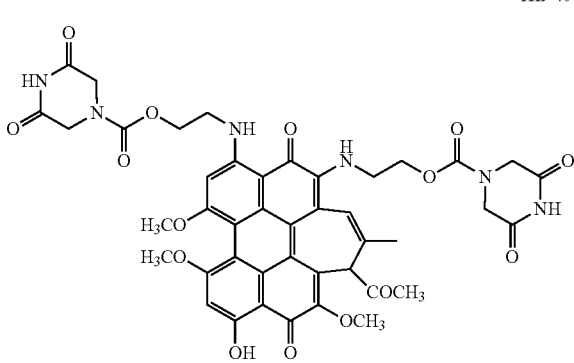

HB-40c

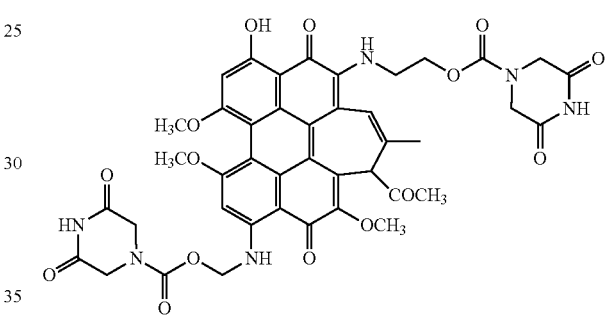

HB-40d

Example 88

Preparation of a diketopiperazine-polyethylene glycol-substituted hypocrellin derivative ($R_1=R_2=$—$CH_2CH_2O$—CO-piperazine-PEGn, $R_3=$—$COCH_3$, $R_4=$—H) (PEG is polyethylene glycol, and n=1, 6, 12): a synthetic route is similar to the preparation of the aminobutyric acid-polyethylene glycol (of different chain lengths)-substituted deacetyl hypocrellin derivative in example 20, and four blue black solid products HB-40a-PEGn-HB-40d-PEGn are obtained, respectively. HB-40a-PEG1 (n=1): yield: 9.8%, $R_f$: 0.25; MS (ESI+): 1084.2; maximum absorption wavelength: 624 nm; molar extinction coefficient: 31,500 $M^{-1}$ $cm^{-1}$; singlet oxygen yield: 32%. HB-40b-PEG6 (n=6): yield: 5.9%, $R_f$: 0.30; MS (ESI+): 1524.2; maximum absorption wavelength: 624 nm; molar extinction coefficient: 31,000 $M^{-1}$ $cm^{-1}$; singlet oxygen yield: 34%. HB-40c-PEG6 (n=6): yield: 12.8%, $R_f$: 0.38; MS (ESI+): 1524.2; maximum absorption wavelength: 630 nm; molar extinction coefficient: 33,500 $M^{-1}cm^{-1}$; singlet oxygen yield: 36%. HB-40d-PEG12 (n=12): yield: 6.1%, $R_f$: 0.30; MS (ESI+): 2052.2; maximum absorption wavelength: 628 nm; molar extinction coefficient: 30,500 $M^{-1}cm^{-1}$; singlet oxygen yield: 30%. Structural formulas of the above amino-substituted products are as follows:

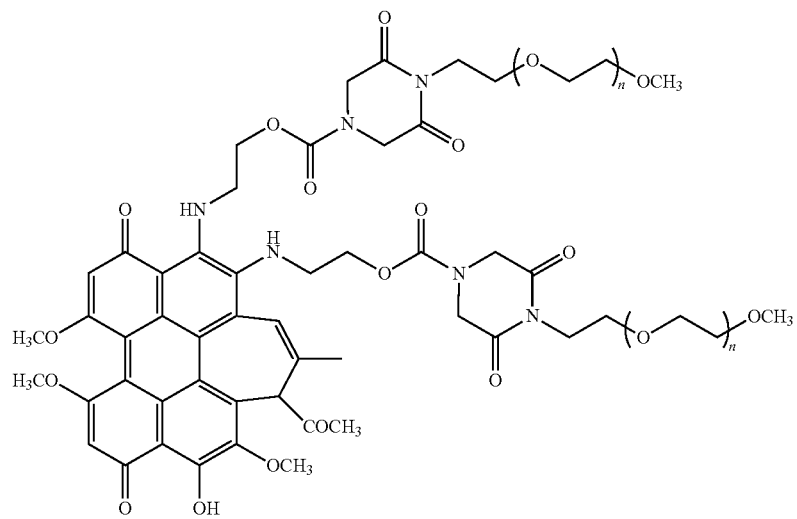
HB-40a-PEG1: m = 1
HB-40a-PEG6: m = 6
HB-40a-PEG12: m = 12
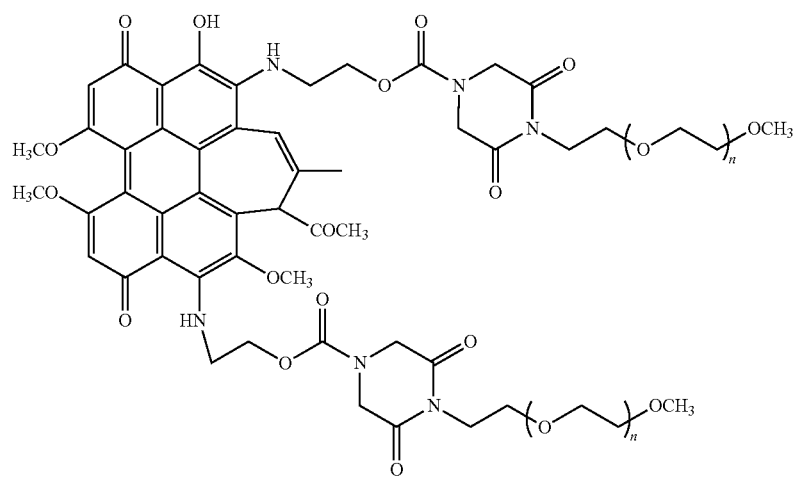
HB-40b-PEG1: m = 1
HB-40b-PEG6: m = 6
HB-40b-PEG12: m = 12
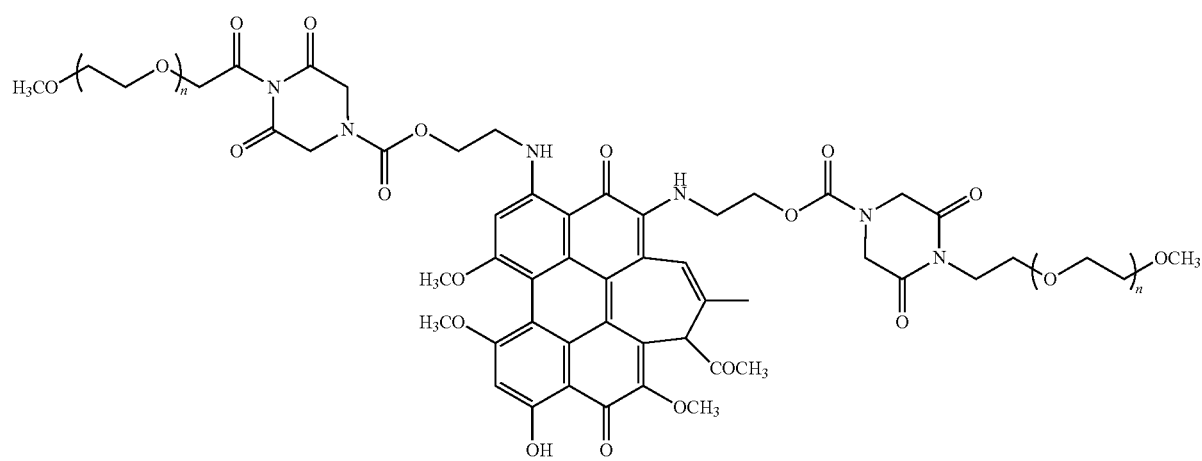
HB-40c-PEG1: m = 1
HB-40c-PEG6: m = 6
HB-40c-PEG12: m = 12

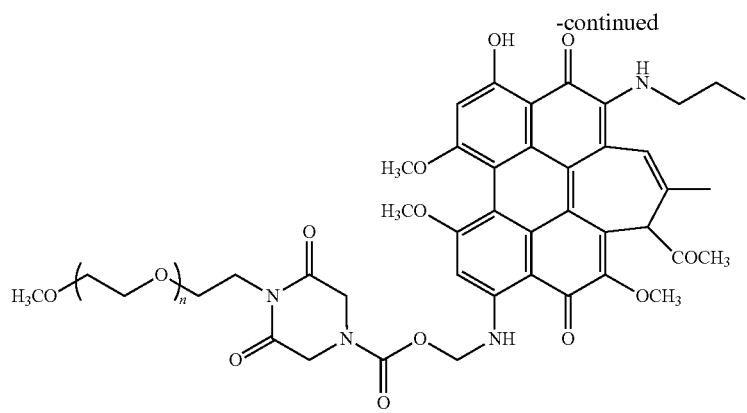

HB-40d-PEG1: m = 1
HB-40d-PEG6: m = 6
HB-40d-PEG12: m = 12

Example 89

Preparation of a DABACO-substituted hypocrellin derivative: a synthetic method is similar to the preparation of the di-2-(2-aminoethoxy)ethanol-substituted hypocrellin B derivative in example 2, and four blue black solid products HB-41a-HB-41d are obtained, respectively. HB-41a: yield: 5.4%, $R_f$: 0.34; MS (ESI+): 820.9; maximum absorption wavelength: 622 nm; molar extinction coefficient: 32,500 $M^{-1}cm^{-1}$; singlet oxygen yield: 31%. HB-41b: yield: 6.8%, $R_f$: 0.38; MS (ESI+): 820.9; maximum absorption wavelength: 624 nm; molar extinction coefficient: 31,500 $M^{-1}cm^{-1}$; singlet oxygen yield: 32%. HB-41c: yield: 4.8%, $R_f$: 0.26; MS (ESI+): 820.9; maximum absorption wavelength: 621 nm; molar extinction coefficient: 33,500 $M^{-1}$ $cm^{-1}$; singlet oxygen yield: 35%. HB-41d: yield: 8.8%, $R_f$: 0.30; MS (ESI+): 820.9; maximum absorption wavelength: 625 nm; molar extinction coefficient: 30,500 $M^{-1}$ $cm^{-1}$; singlet oxygen yield: 28%. Structural formulas of the above amino-substituted products are as follows:

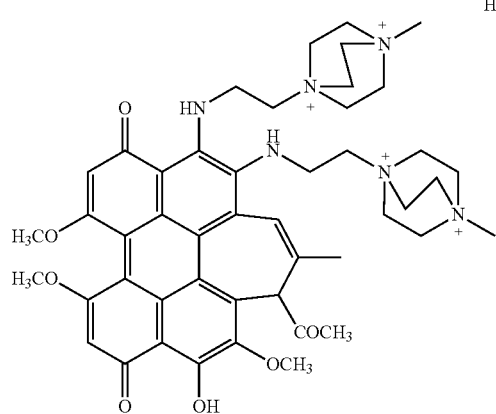
HB-41a

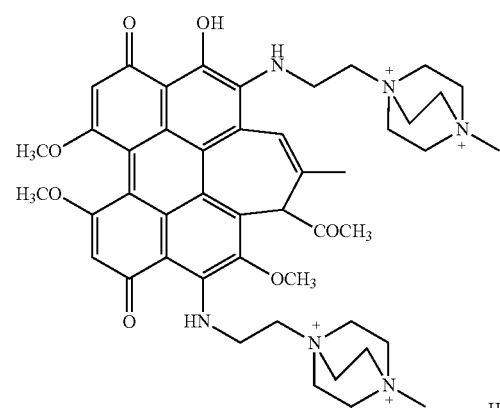
HB-41b

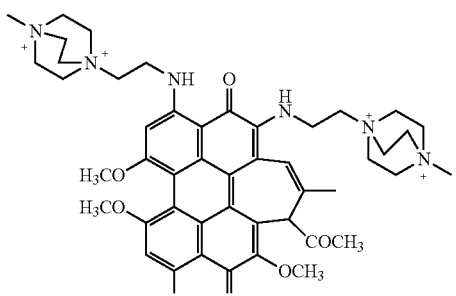
HB-41c

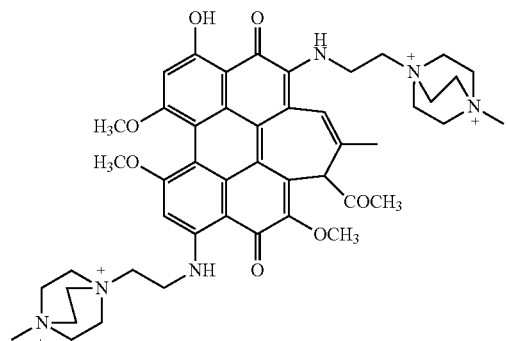
HB-41d

Example 90

Preparation of an aminomorpholine-substituted hypocrellin B derivative

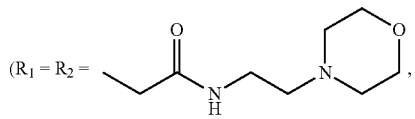

$R_3$=—COCH$_3$, $R_4$=—H): a synthetic route is similar to the preparation of the aminobutyric acid-polyethylene glycol (of different chain lengths)-substituted deacetyl hypocrellin derivative in example 20, and four blue black solid products HB-42a-HB-42d are obtained, respectively. HB-42a: yield: 4.4%, $R_f$: 0.35; MS (ESI+): 881.8; maximum absorption wavelength: 620 nm; molar extinction coefficient: 32,500 $M^{-1}$ $cm^{-1}$; singlet oxygen yield: 33%. HB-42b: yield: 8.2%, $R_f$: 0.30; MS (ESI+): 881.8; maximum absorption wavelength: 620 nm; molar extinction coefficient: 33,000 $M^{-1}$ $cm^{-1}$; singlet oxygen yield: 28%. HB-42c: yield: 4.4%, $R_f$: 0.20; MS (ESI+): 881.8; maximum absorption wavelength: 622 nm; molar extinction coefficient: 32,500 $M^{-1}cm^{-1}$; singlet oxygen yield: 36%. HB-42d: yield: 5.6%, $R_f$: 0.23; MS (ESI+): 881.8; maximum absorption wavelength: 626 nm; molar extinction coefficient: 32,500 $M^{-1}$ $cm^{-1}$; singlet oxygen yield: 30%. Structural formulas of the above amino-substituted products are as follows:

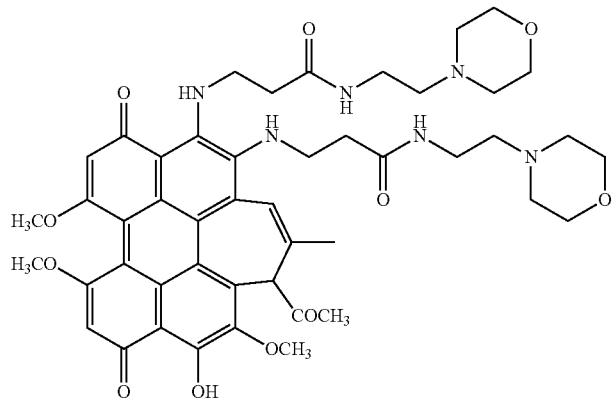

HB-42a

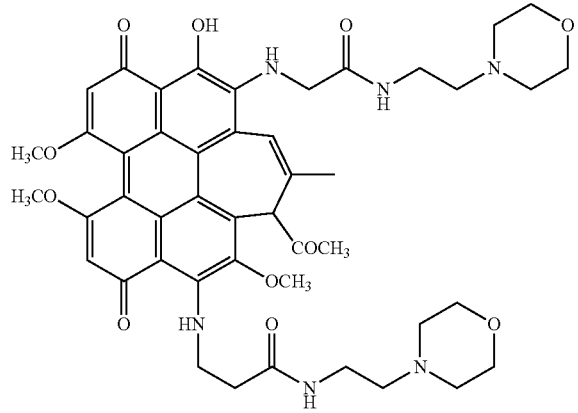

HB-42b

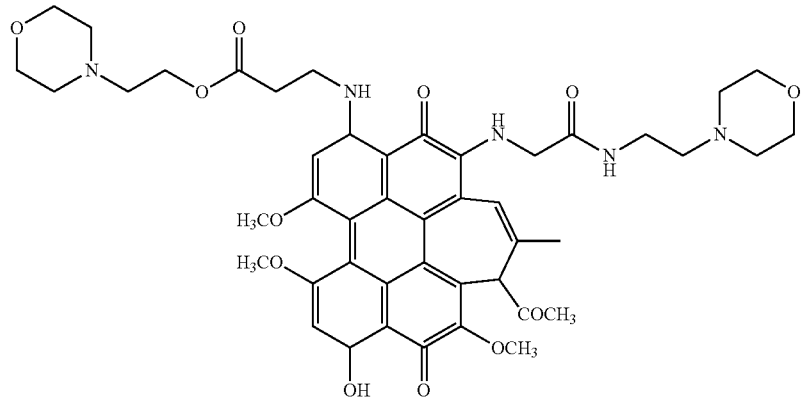

HB-42c

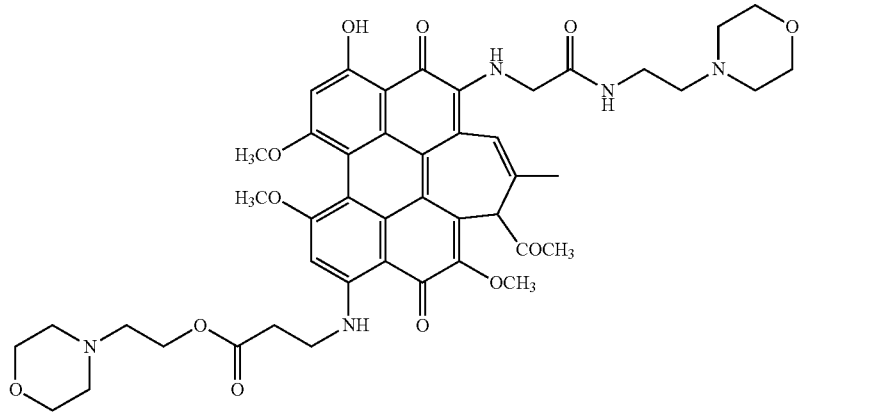

HB-42d

Example 91

Preparation of an aminoacetic acid/aminobutyric acid-substituted hypocrellin B derivative ($R_1$=—$CH_2COOH$, $R_2$=—$CH_2(CH_2)_2COOH$, $R_3$=—$COCH_3$, $R_4$=—H): hypocrellin B HB (100 mg, 0.18 mmol), aminoacetic acid (10 mmol), and NaOH (2 g) were dissolved in 100 mL of a mixed solution of DMF and water (at a volume ratio of 1:1), and after fully mixed, a mixed solution was heated to 120° C. under the protection of nitrogen and stirred in a lucifugous condition for a reaction for 10 h. After the reaction, dilute hydrochloric acid was added to adjust the pH to weak acidity, and filtration was performed to collect a precipitate. An obtained crude product was added to aminobutyric acid (10 mmol), and NaOH (2 g) and dissolved in 100 mL of a mixed solution of DMF and water (at a volume ratio of 1:1), and after fully mixed, a mixed solution was heated to 100° C. under the protection of nitrogen and stirred in a lucifugous condition for a reaction for 8 h. After the reaction, dilute hydrochloric acid was added to adjust the pH to weak acidity, and filtration was performed to collect a precipitate. An obtained blue black solid was dissolved in 200 mL of dichloromethane, a solution was washed once with 100 mL of a dilute hydrochloric acid aqueous solution and then washed twice with distilled water, an organic layer was dried by using anhydrous magnesium sulfate and filtered, and an organic phase was spin-dried to obtain a crude product. The obtained crude product was separated out by means of thin-layer chromatography, with a developing agent being a mixed solution of ethyl acetate, diethylamine, and ethanol (at a volume ratio of 20:1:2), to obtain four blue black solid products HB-43a-HB-43d, respectively. HB-43a: yield: 7.1%, $R_f$: 0.34; MS (ESI+): 656.2; maximum absorption wavelength: 613 nm; molar extinction coefficient: 26,500 $M^{-1}cm^{-1}$; singlet oxygen yield: 28%; HB-43b: yield: 7.0%, $R_f$: 0.39; MS (ESI+): 656.2; maximum absorption wavelength: 618 nm; molar extinction coefficient: 26,000 $M^{-1}$ $cm^{-1}$; singlet oxygen yield: 25%. HB-43c: yield: 6.3%, $R_f$: 0.32; MS (ESI+): 656.2; maximum absorption wavelength: 626 nm; molar extinction coefficient: 26,500 $M^{-1}cm^{-1}$; singlet oxygen yield: 30%. HB-43d: yield: 4.7%, $R_f$: 0.30; MS (ESI+): 656.2; maximum absorption wavelength: 623 nm; molar extinction coefficient: 26,500 $M^{-1}$ $cm^{-1}$; singlet oxygen yield: 24%. Structural formulas of the above amino-substituted products are as follows:

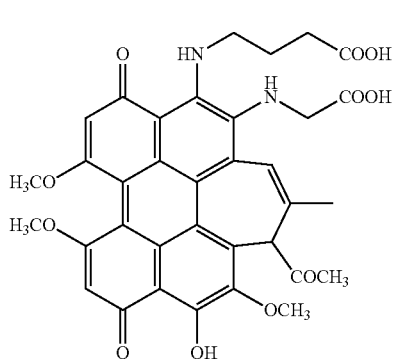

HB-43a

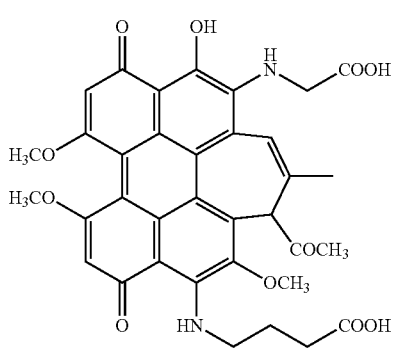

HB-43b

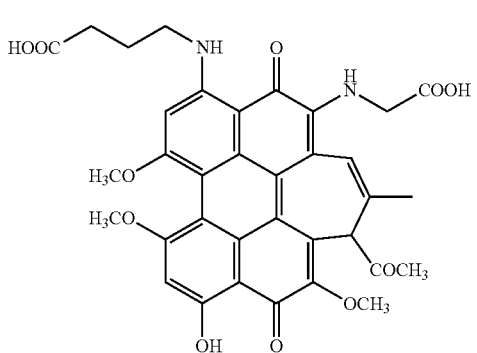

HB-43c

-continued

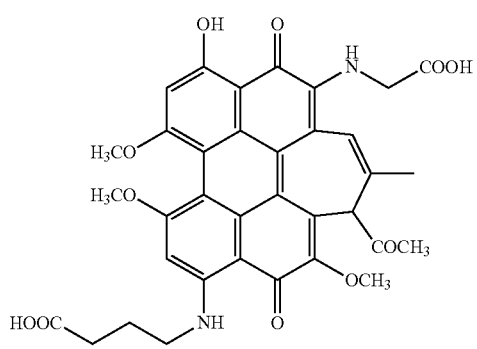

HB-43d

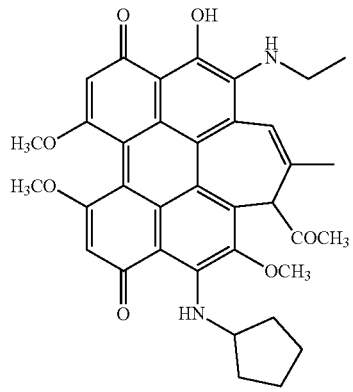

HB-44b

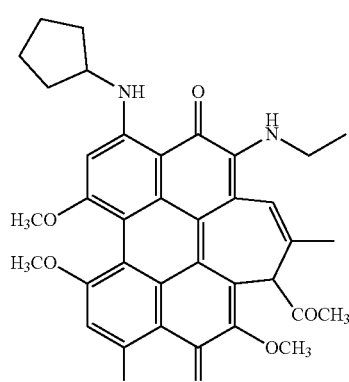

HB-44c

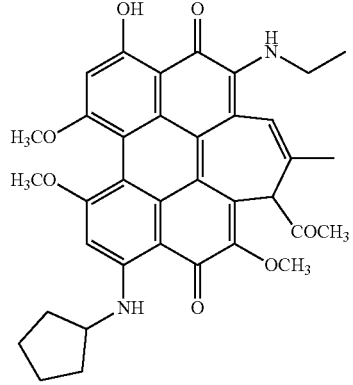

HB-44d

Example 92

Preparation of an ethamine/cyclopentylamine-substituted hypocrellin B derivative ($R_1$=—$C_2H_5$, $R_2$=—$C_5H_9$, $R_3$=—$COCH_3$, $R_4$=—H): substituted amino raw materials are $NH_2$—$C_2H_5$ and $NH_2$—$C_5H_9$, and a synthetic method is similar to the preparation of the aminoacetic acid/aminobutyric acid-modified hypocrellin B in example 83. A developing agent for thin-layer chromatography separation is a mixed solution of ethyl acetate:ethanol=25:1, and four blue black solid products HB-44a-HB-44d are obtained, respectively. HB-44a: yield: 8.0%, $R_f$: 0.38; MS (ESI+): 608.2; maximum absorption wavelength: 628 nm; molar extinction coefficient: 21,500 $M^{-1}cm^{-1}$; singlet oxygen yield: 20%; HB-44b: yield: 6.0%, $R_f$: 0.36; MS (ESI+): 608.2; maximum absorption wavelength: 621 nm; molar extinction coefficient: 21,000 $M^{-1} cm^{-1}$; singlet oxygen yield: 18%; HB-44c: yield: 5.9%, $R_f$: 0.33; MS (ESI+): 608.2; maximum absorption wavelength: 624 nm; molar extinction coefficient: 21,000 $M^{-1}cm^{-1}$; singlet oxygen yield: 20%; HB-44d: yield: 5.1%, $R_f$: 0.29; MS (ESI+): 608.2; maximum absorption wavelength: 622 nm; molar extinction coefficient: 21,500 $M^{-1}cm^{-1}$; singlet oxygen yield: 21%. Structural formulas of the above amino-substituted products are as follows:

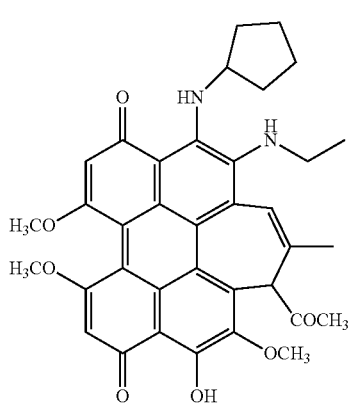

HB-44a

Example 93

Preparation of an ethamine/cyclopentylamine-substituted hypocrellin derivative ($R_1$=—$C_2H_5$, $R_2$=—$C_5H_9$, $R_3$=—$COCH_3$, $R_4$=—$SCH_2CH_2OH$): substituted amino raw materials are $NH_2$—$C_2H_5$ and $NH_2$—$C_5H_9$, and a synthetic method is similar to the preparation of the aminoacetic acid/aminobutyric acid-modified hypocrellin B in example 83. A developing agent for thin-layer chromatography separation is a mixed solution of ethyl acetate:ethanol=25:1, and four blue black solid products HB-S-44a-HB-S-44d are obtained, respectively. HB-S-44a: yield: 8.7%, $R_f$: 0.32; MS (ESI+): 684.2; maximum absorption wavelength: 628 nm; molar extinction coefficient: 21,500 $M^{-1}cm^{-1}$; singlet oxygen yield: 20%; HB-S-44b: yield: 6.5%, $R_f$: 0.35; MS (ESI+): 684.2; maximum absorption wavelength: 622 nm; molar extinction coefficient: 21,000 $M^{-1}cm^{-1}$; singlet oxygen yield: 18%; HB-S-44c: yield: 10.9%, $R_f$: 0.39; MS (ESI+): 684.2; maximum absorption wavelength: 628 nm; molar extinction coefficient: 21,000 $M^{-1}cm^{-1}$; singlet oxygen yield: 20%; HB-S-44d: yield: 4.1%, $R_f$: 0.29; MS (ESI+): 684.2; maximum absorption wavelength: 622 nm; molar extinction coefficient: 21,500 $M^{-1}cm^{-1}$; singlet oxygen yield: 21%. Structural formulas of the above amino-substituted products are as follows:

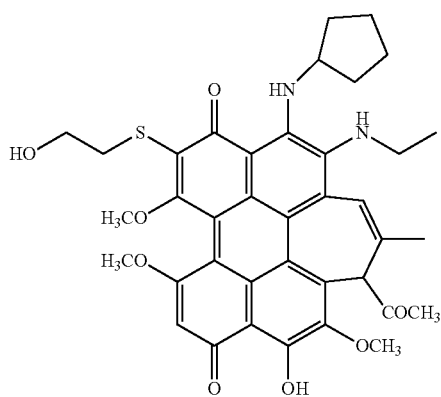

HB-S-44a

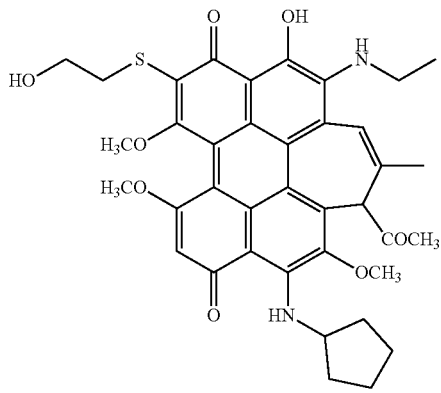

HB-S-44b

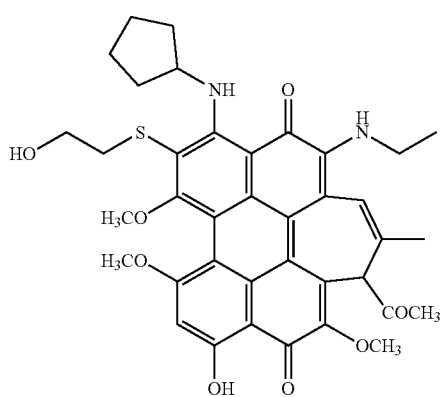

HB-S-44c

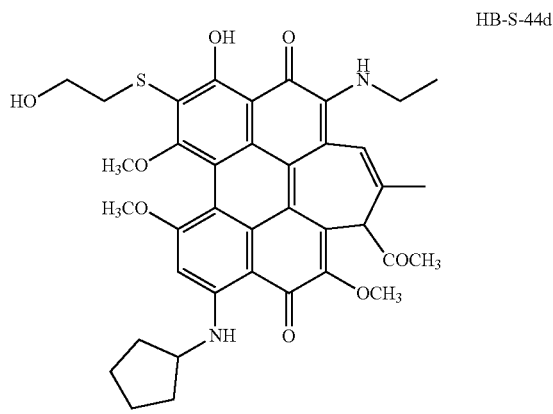

HB-S-44d

Example 94

Preparation of an ethanesulfonic acid/propanesulfonic acid-substituted deacetyl hypocrellin derivative ($R_1$=—$CH_2SO_3H$, $R_2$=—$CH_2(CH_2)_2SO_3H$, $R_3$=$R_4$=—H): substituted amino raw materials are $NH_2$—$CH_2SO_3H$ and $NH_2$—$CH_2(CH_2)_2SO_3H$, and a synthetic method is similar to the preparation of the aminoacetic acid/aminobutyric acid-modified hypocrellin B in example 83. A developing agent for thin-layer chromatography separation is a mixed solution of ethyl acetate:ethanol=8:1, and four blue black solid products HC-45a-HC-45d are obtained, respectively. HC-45a: yield: 7.0%, $R_f$: 0.30; MS (ESI+): 686.9; maximum absorption wavelength: 613 nm; molar extinction coefficient: 21,000 $M^{-1}$ $cm^{-1}$; singlet oxygen yield: 18%; HC-45b: yield: 7.7%, $R_f$: 0.36; MS (ESI+): 686.9; maximum absorption wavelength: 618 nm; molar extinction coefficient: 21,500 $M^{-1}cm^{-1}$; singlet oxygen yield: 20%; HC-45c: yield: 5.3%, $R_f$: 0.32; MS (ESI+): 686.9; maximum absorption wavelength: 627 nm; molar extinction coefficient: 22,000 $M^{-1}cm^{-1}$; singlet oxygen yield: 21%; HC-45d: yield: 4.8%, $R_f$: 0.39; MS (ESI+): 686.9; maximum absorption wavelength: 624 nm; molar extinction coefficient: 21,000 $M^{-1}$ $cm^{-1}$; singlet oxygen yield: 21%. Structural formulas of the above amino-substituted products are as follows:

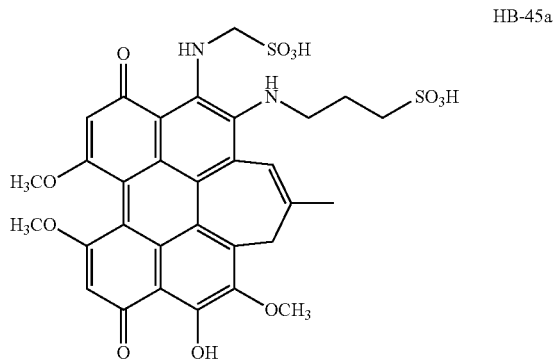

HB-45a

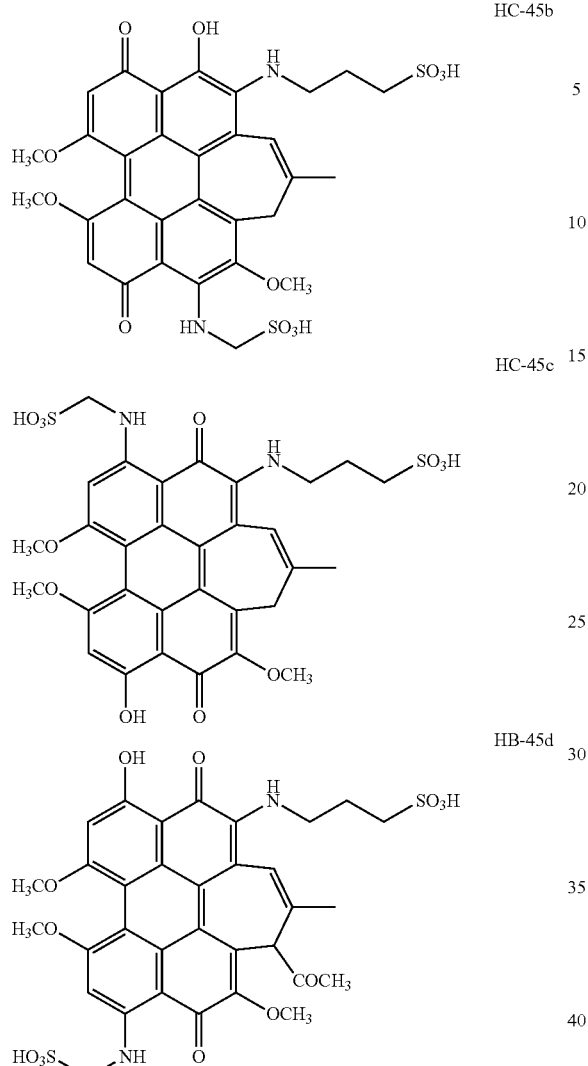

HC-45b

HC-45c

HB-45d

Example 95

Preparation of an ethylhydrazine/aspartic acid-substituted hypocrellin B derivative ($R_1$=—$NHC_2H_5$, $R_2$=—CH(COOH)—$CH_2COOH$, $R_3$=$R_4$=—H): substituted amino raw materials are $NH_2$—$NHC_2H_5$ and $NH_2$—CH(COOH)—$CH_2COOH$, a synthetic method is similar to the preparation of the aminoacetic acid/aminobutyric acid-modified hypocrellin B in example 83, and four blue black solid products HC-46a-HC-46d are obtained, respectively. HC-46a: yield: 5.0%, $R_f$: 0.39; MS (ESI+): 671.2; maximum absorption wavelength: 629 nm; molar extinction coefficient: 22,000 $M^{-1}cm^{-1}$; singlet oxygen yield: 21%; HC-46b: yield: 6.5%, $R_f$: 0.35; MS (ESI+): 671.2; maximum absorption wavelength: 620 nm; molar extinction coefficient: 21,000 $M^{-1}cm^{-1}$; singlet oxygen yield: 18%; HC-46c: yield: 6.9%, $R_f$: 0.33; MS (ESI+): 671.2; maximum absorption wavelength: 625 nm; molar extinction coefficient: 20,000 $M^{-1}$ $cm^{-1}$; singlet oxygen yield: 21%; HC-46d: yield: 4.1%, $R_f$: 0.27; MS (ESI+): 671.2; maximum absorption wavelength: 623 nm; molar extinction coefficient: 22,000 $M^{-1}cm^{-1}$; singlet oxygen yield: 23%. Structural formulas of the above amino-substituted products are as follows:

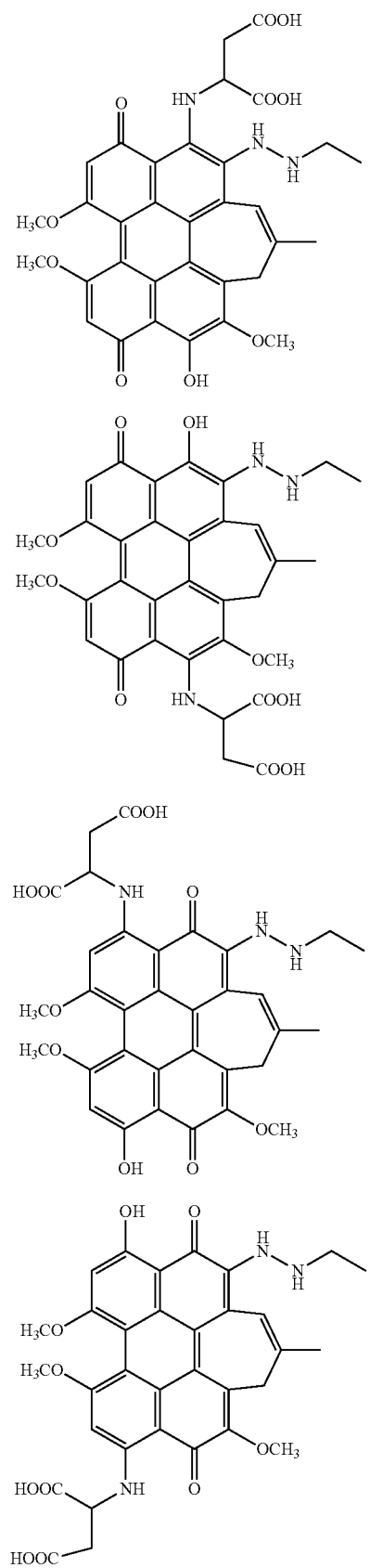

HB-45a

HC-45b

HC-45c

HB-45d

Example 96

Preparation of an aminobutyric acid/amino polyethylene glycol-substituted hypocrellin derivative ($R_1$=—CH$_2$CH$_2$—PEGn-OCH$_3$, $R_2$=—CH$_2$(CH$_2$)$_2$COOH, $R_3$=—COCH$_3$, $R_4$=—H) (PEG is polyethylene glycol, n is the number of ethylene glycol units, and n=1, 6, 12): substituted amino raw materials are aminobutyric acid and NH$_2$—CH$_2$CH$_2$—PEGn-OCH$_3$, a synthetic method is similar to the preparation of the aminoacetic acid/aminobutyric acid-modified hypocrellin B in example 83, and four blue black solid products HB-47a-PEGn, HB-47b-PEGn, HB-47c-PEGn, HB-47d-PEGn (n=1, 6, 12) are obtained, respectively. HB-47a-PEG1 (n=1): yield: 7.4%, $R_f$: 0.25; MS (ESI+): 700.5; maximum absorption wavelength: 622 nm; molar extinction coefficient: 30,500 M$^{-1}$ cm$^{-1}$; singlet oxygen yield: 30%. HB-47b-PEG6 (n=6): yield: 8.4%, $R_f$: 0.30; MS (ESI+): 1140.5; maximum absorption wavelength: 624 nm; molar extinction coefficient: 30,500 M$^{-1}$ cm$^{-1}$; singlet oxygen yield: 30%. HB-47c-PEG12 (n=12): yield: 18.2%, $R_f$: 0.35; MS (ESI+): 1678.5; maximum absorption wavelength: 630 nm; molar extinction coefficient: 33,000 M$^{-1}$cm$^{-1}$; singlet oxygen yield: 38%. HB-47d-PEG6 (n=6): yield: 7.9%, $R_f$: 0.32; MS (ESI+): 1140.5; maximum absorption wavelength: 628 nm; molar extinction coefficient: 32,500 M$^{-1}$ cm$^{-1}$; singlet oxygen yield: 32%. Structural formulas of the above amino-substituted products are as follows:

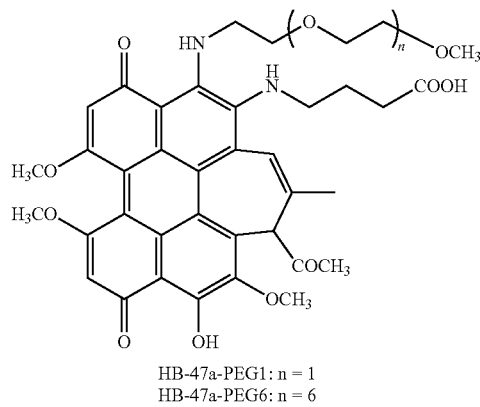

HB-47a-PEG1: n = 1
HB-47a-PEG6: n = 6
HB-47a-PEG12: n = 12

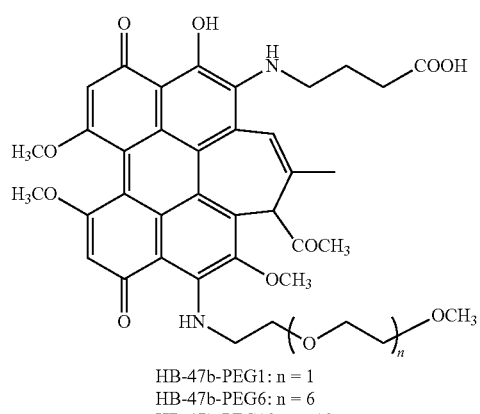

HB-47b-PEG1: n = 1
HB-47b-PEG6: n = 6
HB-47b-PEG12: n = 12

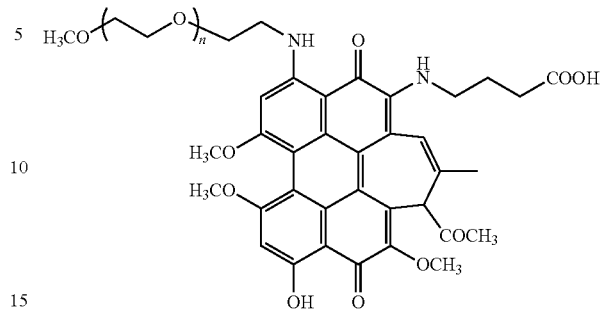

HB-47c-PEG1: n = 1
HB-47c-PEG6: n = 6
HB-47c-PEG12: n = 12

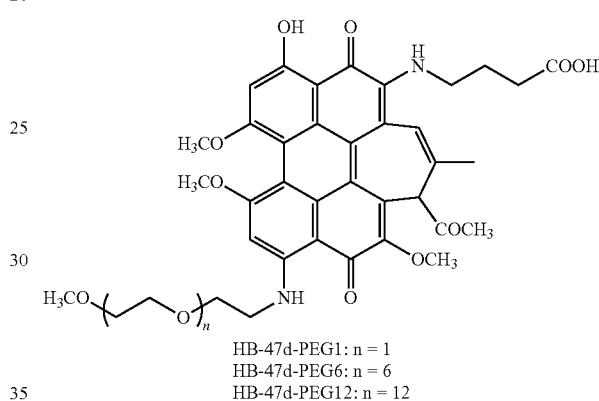

HB-47d-PEG1: n = 1
HB-47d-PEG6: n = 6
HB-47d-PEG12: n = 12

Example 97

Preparation of an aminobutyric acid/(2-aminoethoxy)ethanol-polyethylene glycol-substituted hypocrellin derivative ($R_1$=—CH$_2$(CH$_2$)$_2$COOH, $R_1$=—CH$_2$CH$_2$—O—CH$_2$CH$_2$—O—CO-PEGn-OCH$_3$, $R_3$=—COCH$_3$, $R_4$=—H) (PEG is polyethylene glycol, n is the number of ethylene glycol units, and n=1, 6, 12): substituted amino raw materials are aminobutyric acid and NH$_2$—CH$_2$CH$_2$—O—CH$_2$CH$_2$—O—CO-PEGn-OCH$_3$, a synthetic method is similar to the preparation of the aminoacetic acid/aminobutyric acid-modified hypocrellin B in example 83, and four blue black solid products HB-48a-PEGn, HB-48b-PEGn, HB-48c-PEGn, HB-48d-PEGn (n=1, 6, 12) are obtained, respectively. HB-48a-PEG1 (n=1): yield: 8.4%, $R_f$: 0.28; MS (ESI+): 816.5; maximum absorption wavelength: 628 nm; molar extinction coefficient: 31,500 M$^{-1}$cm$^{-1}$; singlet oxygen yield: 32%. HB-48b-PEG6 (n=6): yield: 9.4%, $R_f$: 0.34; MS (ESI+): 1256.5; maximum absorption wavelength: 628 nm; molar extinction coefficient: 31,500 M$^{-1}$cm$^{-1}$; singlet oxygen yield: 32%. HB-48c-PEG12 (n=12): yield: 20.2%, $R_f$: 0.45; MS (ESI+): 1784.5; maximum absorption wavelength: 636 nm; molar extinction coefficient: 34,000 M$^{-1}$cm$^{-1}$; singlet oxygen yield: 40%. HB-48d-PEG6 (n=6): yield: 8.5%, $R_f$: 0.35; MS (ESI+): 1256.5; maximum absorption wavelength: 632 nm; molar extinction coefficient: 32,000 M$^{-1}$ cm$^{-1}$; singlet oxygen yield: 32%. Structural formulas of the above amino-substituted products are as follows:

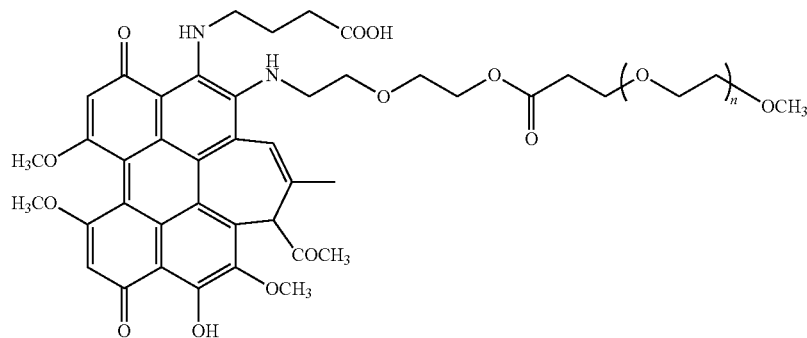
HB-48a-PEG1: n = 1
HB-48a-PEG6: n = 6
HB-48a-PEG12: n = 12
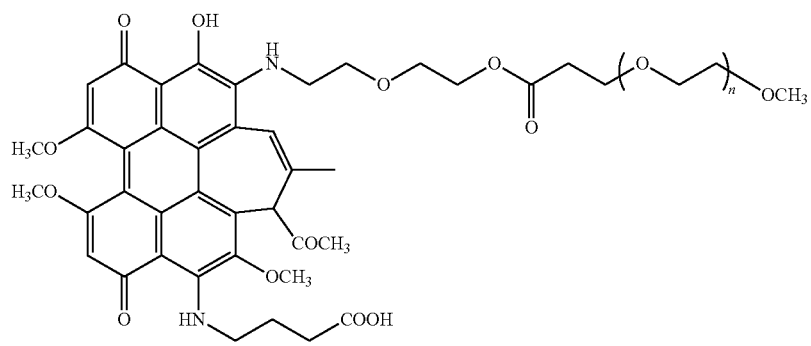
HB-48b-PEG1: n = 1
HB-48b-PEG6: n = 6
HB-48b-PEG12: n = 12
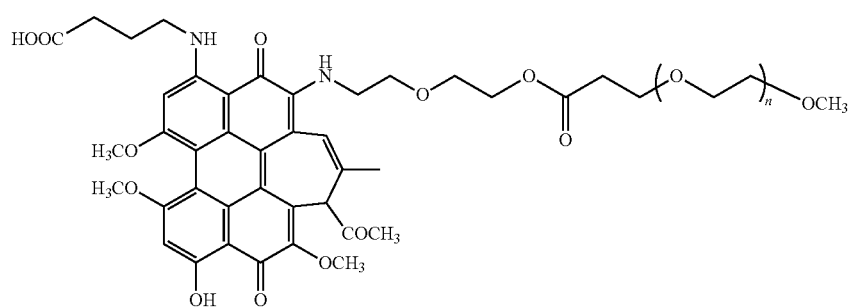
HB-48c-PEG1: n = 1
HB-48c-PEG6: n = 6
HB-48c-PEG12: n = 12
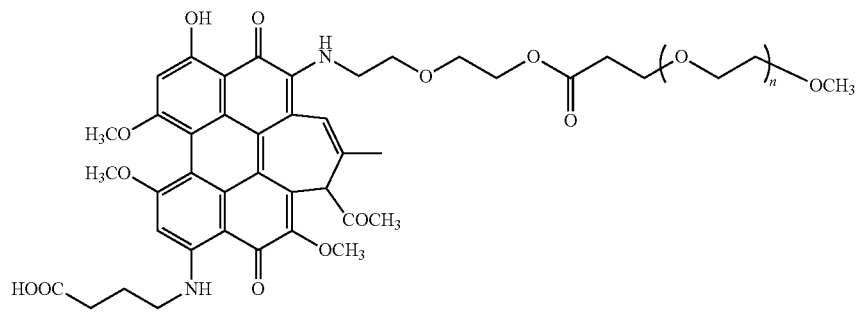
HB-48d-PEG1: n = 1
HB-48d-PEG6: n = 6
HB-48d-PEG12: n = 12

Example 98

Preparation of an aminobutyric acid/4-tranexamic acid-polyethylene glycol-substituted hypocrellin derivative ($R_1$=—$CH_2(CH_2)_2COOH$, $R_2$=—$CH_2C_6H_{10}COO$-PEGn, $R_3$=$R_4$=—H) (PEG is polyethylene glycol, n is the number of ethylene glycol units, and n=1, 6, 12): a synthetic method is similar to the preparation of the aminoacetic acid/aminobutyric acid-modified hypocrellin B in example 83, and four blue black solid products HC-49a-PEGn, HC-49b-PEGn, HC-49c-PEGn, HC-49d-PEGn (n=1, 6, 12) are obtained, respectively. HC-49a-PEG1 (n=1): yield: 8.8%, $R_f$: 0.30; MS (ESI+): 765.5; maximum absorption wavelength: 630 nm; molar extinction coefficient: 31,000 $M^{-1}cm^{-1}$; singlet oxygen yield: 32%. HC-49b-PEG6 (n=6): yield: 9.8%, $R_f$: 0.32; MS (ESI+): 1205.5; maximum absorption wavelength: 630 nm; molar extinction coefficient: 31,000 $M^{-1}cm^{-1}$; singlet oxygen yield: 34%. HC-49c-PEG12 (n=12): yield: 17.2%, $R_f$: 0.40; MS (ESI+): 1733.5; maximum absorption wavelength: 638 nm; molar extinction coefficient: 33,000 $M^{-1}cm^{-1}$; singlet oxygen yield: 38%. HC-49d-PEG6 (n=6): yield: 8.9%, $R_f$: 0.32; MS (ESI+): 1205.5; maximum absorption wavelength: 632 nm; molar extinction coefficient: 31,500 $M^{-1}$ $cm^{-1}$; singlet oxygen yield: 34%. Structural formulas of the above amino-substituted products are as follows:

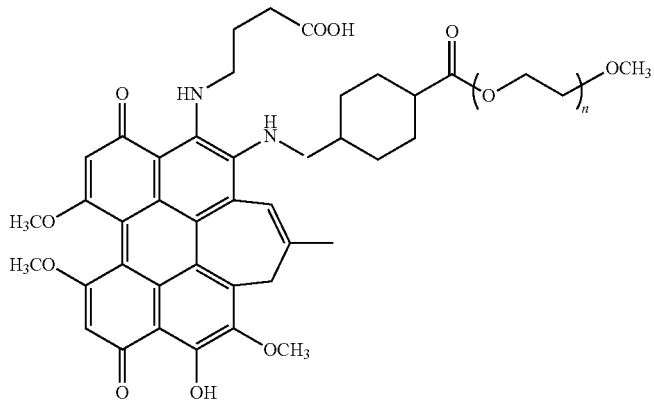

HB-49a-PEG1: n = 1
HB-49a-PEG6: n = 6
HB-49a-PEG12: n = 12

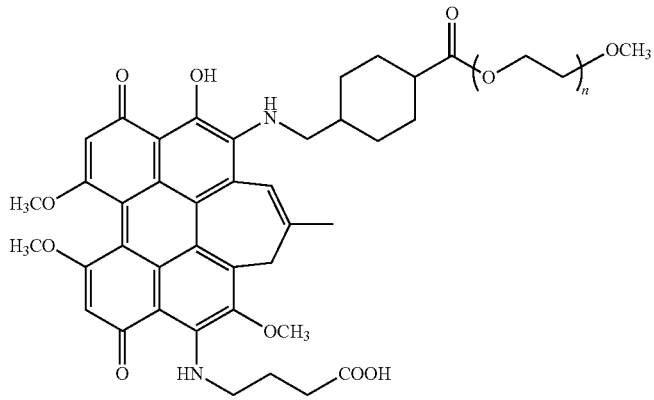

HB-49b-PEG1: n = 1
HB-49b-PEG6: n = 6
HB-49b-PEG12: n = 12

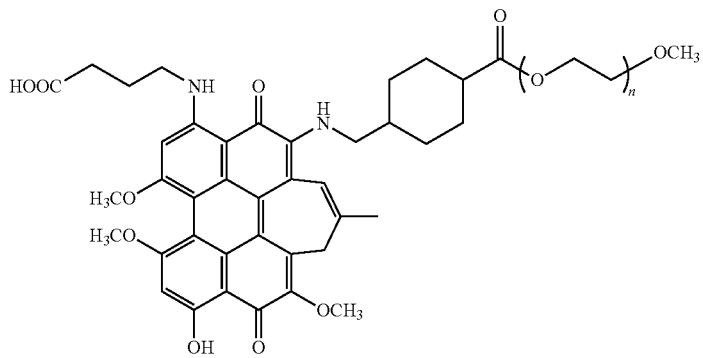

HB-49c-PEG1: n = 1
HB-49c-PEG6: n = 6
HB-49c-PEG12: n = 12

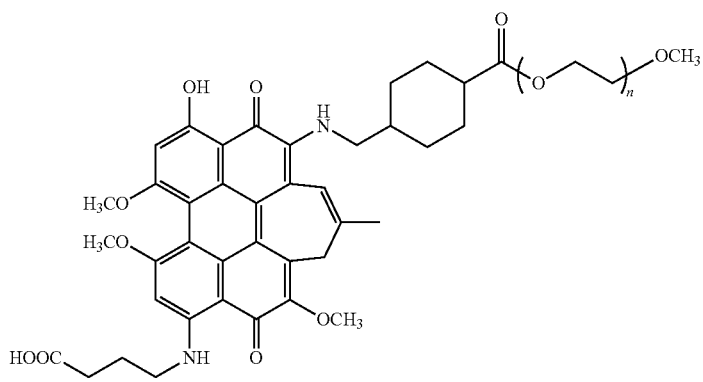

HB-49d-PEG1: n = 1
HB-49d-PEG6: n = 6
HB-49d-PEG12: n = 12

Example 99

Preparation of an aminoacetic acid/4-aminomethylcyclohexanoic acid-polyethylene glycol-substituted hypocrellin B derivative ($R_1$=—$CH_2COOH$, $R_2$=—$CH_2C_6H_{10}COO$-PEGn, $R_3$=$R_4$=—H) (PEG is polyethylene glycol, n is the number of ethylene glycol units, and n=1, 6, 12): a synthetic method is similar to the preparation of the aminoacetic acid/aminobutyric acid-modified hypocrellin B in example 83, and four blue black solid products HC-49a-PEGn, HC-49b-PEGn, HC-49c-PEGn, HC-49d-PEGn (n=1, 6, 12) are obtained, respectively. HC-49a-PEG1 (n=1): yield: 8.8%, $R_f$: 0.30; MS (ESI+): 765.5; maximum absorption wavelength: 630 nm; molar extinction coefficient: 31,000 $M^{-1}$ $cm^{-1}$; singlet oxygen yield: 32%. HC-49b-PEG6 (n=6): yield: 9.8%, $R_f$: 0.32; MS (ESI+): 1205.5; maximum absorption wavelength: 630 nm; molar extinction coefficient: 31,000 $M^{-1}cm^{-1}$; singlet oxygen yield: 34%. HC-49c-PEG12 (n=12): yield: 17.2%, $R_f$: 0.40; MS (ESI+): 1733.5; maximum absorption wavelength: 638 nm; molar extinction coefficient: 33,000 $M^{-1}$ $cm^{-1}$; singlet oxygen yield: 38%. HC-49d-PEG6 (n=6): yield: 8.9%, $R_f$: 0.32; MS (ESI+): 1205.5; maximum absorption wavelength: 632 nm; molar extinction coefficient: 31,500 $M^{-1}$ $cm^{-1}$; singlet oxygen yield: 34%. Structural formulas of the above amino-substituted products are as follows:

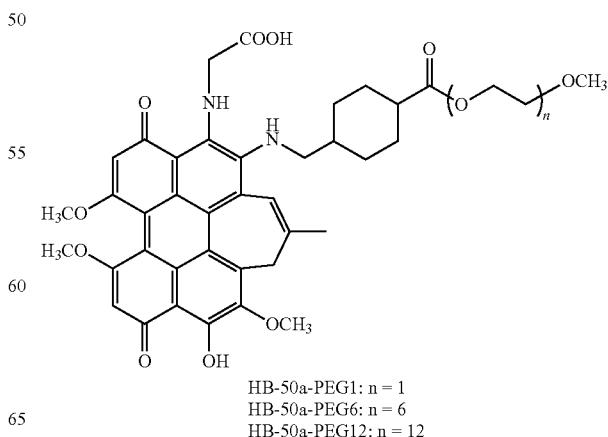

HB-50a-PEG1: n = 1
HB-50a-PEG6: n = 6
HB-50a-PEG12: n = 12

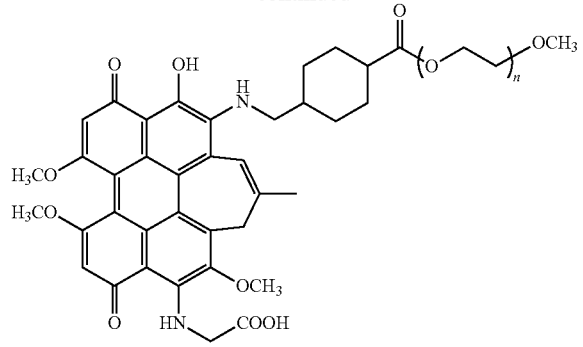

HB-50b-PEG1: n = 1
HB-50b-PEG6: n = 6
HB-50b-PEG12: n = 12

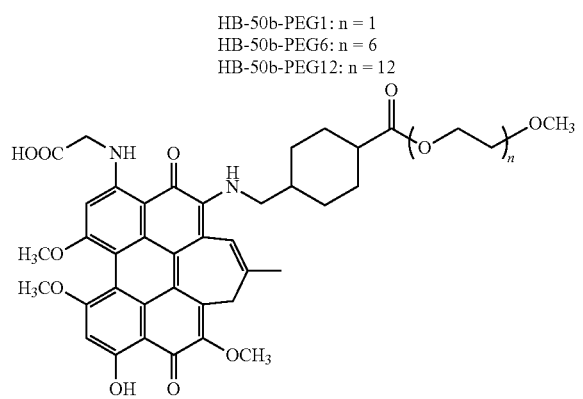

HB-50c-PEG1: n = 1
HB-50c-PEG6: n = 6
HB-50c-PEG12: n = 12

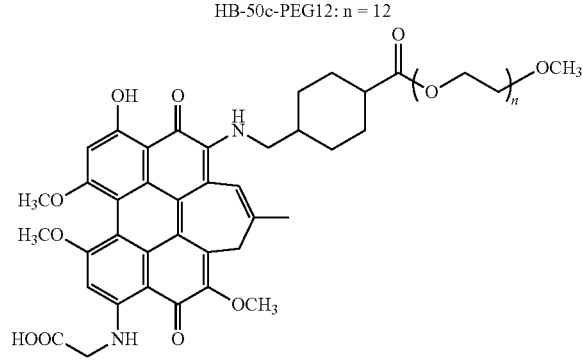

HB-50d-PEG1: n = 1
HB-50d-PEG6: n = 6
HB-50d-PEG12: n = 12

Example 100

Dark cytotoxicity experiment: cultured Hela cells were digested with 0.25% trypsin and pipetted to prepare a single-cell suspension, the number of cells was adjusted to about $2\times10^4$ per milliliter, and 200 uL of the suspension was seeded in a well of a 96-well culture plate, which is placed in a 37° C. incubator containing 5% $CO_2$ for cultivation. After the cells adhere to the wall, a supernatant culture solution was discarded, and photosensitizers of different concentrations, that is, the hematoporphyrin derivative HpD, the hypocrellin B HB, or the compound HB-1c-PEG6 synthesized in example 3, were added in a strictly lucifugous condition in accordance with experimental designs, and the culture plate was placed in the 37° C. incubator containing 5% $CO_2$ for further cultivation and incubation for 1 hour. A cellular survival rate was measured by means of the MTT method. 20 uL of MTT was added to each well, wherein the MTT is MTT prepared with PBS and having a concentration of 5 mg/ml. The culture plate was placed in the 37° C. incubator containing 5% $CO_2$ for further cultivation for 4 hours, after which the cultivation was terminated. A supernatant in the well was extracted and discarded carefully. Then, 150 uL of dimethyl sulfoxide was added to each well, and the culture plate was shaken by using a micro shaker for 10 minutes to fully dissolve a purple crystal substance. A wavelength of 570 nm was selected to measure an optical density value (i.e., OD value) of each well on a microplate reader, and the cellular survival rate was calculated in accordance with the following formula: cellular survival rate=OD value of an experimental group/OD value of a blank group×100%. FIG. 12(a) shows a diagram of dark toxicities. As shown in FIG. 12(a), the cytotoxicity (dark toxicity) research test indicates that HB-1c-PEG6 synthesized in example 3 has a smaller cytotoxicity, which is similar to that of the hypocrellin B HB and commercial photosensitive drug hematoporphyrin HpD. After the Hela cells are incubated by using the photosensitizer HB-1c-PEG6 with the concentration of 10 μmol/L for a half hour, death of many Hela cells is not observed, indicating that such the photosensitizer is basically non-cytotoxic.

Example 101

Photo-cytotoxicity experiment on cell: cultured Hela cells were digested and pipetted with 0.25% trypsin and to prepare a single-cell suspension, the number of cells was adjusted to about $2\times10^4$ per milliliter, and 200 uL of the suspension was seeded in a well of a 96-well culture plate, which is placed in a 37° C. incubator containing 5% $CO_2$ for cultivation. After the cells adhere to the wall, a supernatant culture solution was discarded, and photosensitizers of different concentrations, that is, the hematoporphyrin derivative HpD, the hypocrellin B HB, or HB-1c-PEG6 synthesized in example 3, were added in a strictly lucifugous condition in accordance with experimental designs, and the culture plate was placed in the 37° C. incubator containing 5% $CO_2$ for further cultivation and incubation for 1 hour. Then, a semiconductor laser with a wavelength of 635 nm was used for irradiation, a power density was adjusted to 20 mW/cm$^2$, light beams were evenly and vertically applied onto the 96-well culture plate, and an irradiation time was 1000 S. In addition, each 96-well culture plate is provided with a blank group, and 6 holes were provided for in each condition. After irradiation, the culture plate was placed in the 37° C. incubator containing 5% $CO_2$ for further cultivation and incubation for 24 hours, and then a cellular survival rate was measured. The cellular survival rate was measured by means of the MTT method. 20 uL of MTT was added to each well, wherein the MTT is MTT prepared with PBS and having a concentration of 5 mg/ml. The culture plate was placed in the 37° C. incubator containing 5% $CO_2$ for further cultivation for 4 hours, after which the cultivation was terminated. A supernatant in the well was extracted and discarded carefully. Then, 150 uL of dimethyl sulfoxide (DMSO) was added to each well, and the culture plate was shaken by using a micro shaker for 10 minutes to fully dissolve a purple crystal substance. A wavelength of 570 nm was selected to measure an optical density value (i.e., OD value) of each well on a microplate reader, and the cellular survival rate was calculated in accordance with the following formula: cellular survival rate=OD value of an experimental group/OD value of a blank group×100%. FIG. 12(b)

shows a diagram of phototoxicities. The cell phototoxicity experiment as shown in FIG. 12(b) indicates that HB-1c-PEG6 presents very strong lethality to the Hela cells under irradiation of red light. HB-1c-PEG6 with a concentration range of 160 nM can kill more than 90% of the Hela cells, while in the same condition, the hypocrellin B or commercial photosensitizer hematoporphyrin derivative can kill only about 20% of the Hela cells, indicating that a photodynamic effect of such the hypocrellin derivative having a peri-position substituted by an amino group is significantly better than that of the hypocrellin B HB and commercial photosensitizer hematoporphyrin HpD.

Example 102

Dark cytotoxicity experiment on cell: the experimental method and procedure are the same as those in example 100, except that HB-1c-PEG6 synthesized in example 3 is replaced by the polyethylene glycol-di-2-(2-aminoethoxy) ethanol-substituted deacetyl hypocrellin derivative HC-1c-PEG6 synthesized in example 6. A result is as shown in FIG. 13(a), and the dark cytotoxicity experiment for the diamino-substituted hypocrellin derivative HC-1c-PEG6 synthesized in example 6 has a similar result with example 100.

Example 103

Photo-cytotoxicity experiment on cell: the experimental method and procedure are the same as those in example 101, except that HB-1c-PEG6 synthesized in example 3 is replaced by the diaminobutyric acid-substituted deacetyl hypocrellin derivative HC-8c synthesized in example 22. A result is as shown in FIG. 14(b), and the photo-cytotoxicity experiment for HC-8c synthesized in example 22 has a similar result with example 101.

Example 104

Photo-cytotoxicity experiment on cell: the experimental method and procedure are the same as those in example 101, except that HB-1c-PEG6 synthesized in example 3 is replaced by the polyethylene glycol-diaminobutyric acid-modified deacetyl hypocrellin derivative HC-8c-PEG6 synthesized in example 23. A result is as shown in FIGS. 15(a) and 15(b), and the photo-cytotoxicity experiment for HC-8c-PEG6 synthesized in example 23 has a similar result with example 101.

Obviously, the above embodiments of the present invention are merely examples for clearly explaining the present invention, and are not intended to limit the implementations of the present invention. For those of ordinary skill in the art, based on the above description, they can also make other changes or modifications in different forms. All of the implementations cannot be exhausted herein, and any obvious changes or modifications derived from the technical solutions of the present invention still fall within the protection scope of the present invention.

In addition, it should be noted that the hypocrellin derivatives involved in this patent that require the protection all have two enol tautomers, and the chemical structures of the two isomers certainly fall within the protection scope. For simplicity, only one of the enol tautomers is listed in all of the examples of this patent, and the other enol tautomer and the corresponding general structural formula thereof are described in detail in the specification, the structure thereof certainly falls within the protection scope.

The invention claimed is:

1. A hypocrellin derivative substituted both in a peri-position and in a 2-position by an amino, wherein a general structural formula of the derivative is as represented by formulas I-a to I-d:

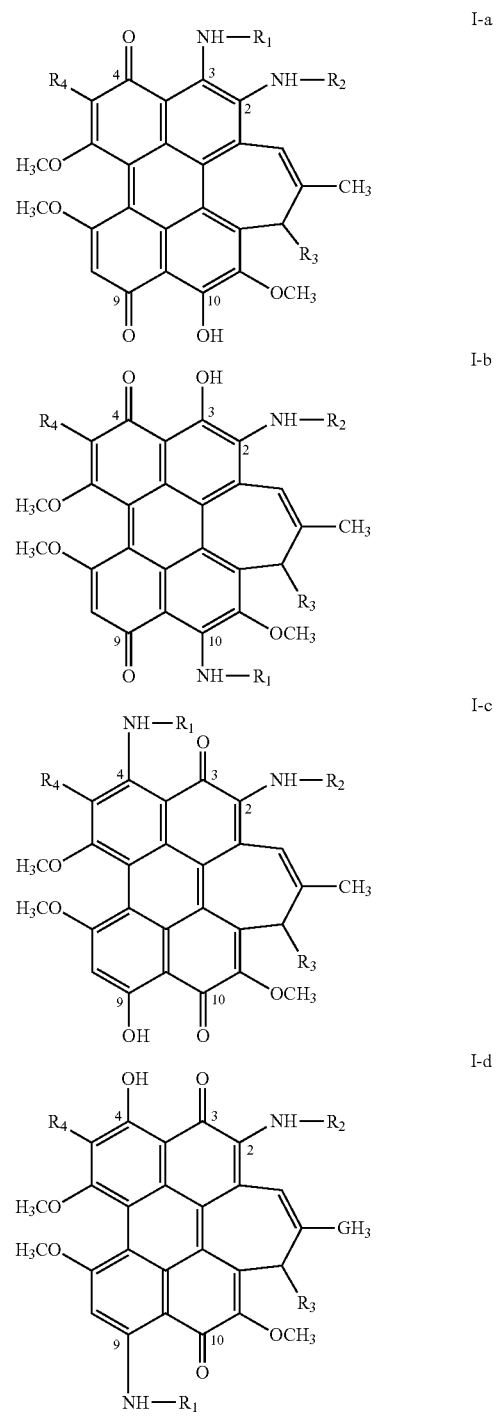

wherein the peri-position of hypocrellin is a 3-, 4-, 9-, or 10-position marked in formulas I-a to I-d;

a substituent $R_3$ is —COOH$_3$ or —H; a substituent $R_4$ is —H, —F, —Cl, —Br, —I, or —S—$R_5$, wherein $R_5$ is a C2-12 alkyl group, a C2-12 alkyl group having a hydroxyl group as a terminal group, or a C2-12 alkyl group having a carboxyl group as a terminal group;

general structural formulas of substituents $R_1$ and $R_2$ are respectively as represented by formula II:

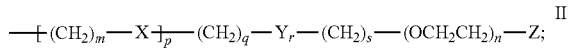

in formula II, $0 \leq m \leq 8$, $0 \leq n \leq 50$, $0 \leq p \leq 8$, $0 \leq q \leq 8$, $0 \leq r \leq 1$, and $0 \leq s \leq 8$; m, n, p, q, r, and s are respectively zero or a positive integer;

linking groups X and Y in formula II are respectively —NH—, —O—, —S—, a carboxylate group, an amide group, a sulfonate group, a sulfonamide group, a carbonyl group, a phosphate group, a C3-12 unsaturated hydrocarbyl group, a C3-12 cyclic hydrocarbyl group, a C6-12 aryl group, or a C3-12 heterocyclic group;

the C3-12 unsaturated hydrocarbyl group is substituted or unsubstituted or heteroatom-containing alkene or alkyne; the C3-12 cyclic hydrocarbyl group is substituted or unsubstituted or heteroatom-containing cycloalkane, cycloalkene, or cycloalkyne, and the heteroatom is an oxygen, nitrogen, or sulfur atom; the C6-12 aryl group is a substituted or unsubstituted aryl group, wherein the substituted aryl group is a mono- or poly-substituted aryl group, and a substituted position is an ortho-position, a meta-position, or a para-position in the aryl group; the C3-12 heterocyclic group is a substituted or unsubstituted heterocyclic group, the substituted heterocyclic group is mono- or poly-substituted, and a substituted position is an ortho-position, a meta-position, or a para-position in a heterocycle; the heterocyclic group is furan, pyrrole, thiophene, pyrazole, imidazole, oxazole, thiazole, pyridine, piperidine, pyrimidine, pyrazine, piperazine, indole, quinoline, isoquinoline, purine, pyrimidine, or acridine;

a substituent in the above cycloalkyl, cycloalkenyl, aryl, or heterocyclic group is respectively a C1-8 alkyl group, a C2-8 alkenyl group, a C2-8 alkynyl group, a C3-8 cycloalkyl group, an aryl group, a C6-12 aralkyl group, or an alkyl group having a terminal group containing a hydroxyl group, a carboxylic acid group, a sulfonic acid group, or a carboxylate group;

a terminal group Z in formula II is selected from hydrogen, a C1-8 alkyl group, a C1-8 alkoxy group, a C3-8 cycloalkyl group, a phenyl group, a pyridyl group, a hydroxyl group, an amino group, a mercapto group, a carboxylic acid group, a carboxylate group, a sulfonic acid group, a sulfonate, a phosphoric acid group, a phosphate, an amino acid, triphenylphosphine, a quaternary ammonium salt, and a pyridine salt;

when the terminal group Z in formula II is a quaternary ammonium salt, three substituents of the quaternary ammonium salt are respectively: a C1-8 alkyl group, a C2-8 alkenyl group, a C2-8 alkynyl group, a C3-8 cycloalkyl group, a C3-8 cycloalkenyl group, an aryl group, a C6-12 aralkyl group, or an alkyl group having a terminal group containing a hydroxyl group, a carboxylic acid group, a sulfonic acid group, or a carboxylate group; and when the terminal group Z in formula II is a pyridine salt, a substituent on a pyridine ring of the pyridine salt is in an ortho-position, a meta-position, or a para-position, and the pyridine salt is obtained by quaternizing pyridine and halogenated hydrocarbons having 1 to 8 carbon atoms of different chain lengths.

2. The derivative according to claim 1, wherein the linking groups X and Y in formula II are respectively: —NH—, —O—, —S—, —COO—, —OC(=O)—, —CONH—, —NHC(=O)—, —SO$_3$—, —SO$_2$NH—, —C(=O)—, —PO$_3$—, —CH=CH—, —C(CH$_3$)=CH—, —C(CH$_3$)=C(CH$_3$)—, —C(COOH)=CH—, —C(CH$_2$COOH)=CH—, —C≡C—, a cyclopropyl group, a methylcyclopropyl group, a hydroxylcyclopropyl group, a hydroxylmethylcyclopropyl group, a carboxylcyclopropyl group, a cyclobutyl group, a methylcyclobutyl group, a hydroxylcyclobutyl group, a carboxylcyclobutyl group, a cyclopentyl group, a methylcyclopentyl group, a hydroxylcyclopentyl group, a carboxylcyclopentyl group, an aminocyclopentyl group, a cyclohexyl group, a methylcyclohexyl group, an ethylcyclohexyl group, a propylcyclohexyl group, a hydroxylcyclohexyl group, an aminocyclohexyl group, a carboxylcyclohexyl group, a carboxylmethylcyclohexyl group, a dicarboxylcyclohexyl group, a cycloheptyl group, a carboxylcycloheptyl group, a hydroxylcycloheptyl group, a methylcycloheptyl group, —C$_6$H$_4$—, —C$_6$H$_3$(CH$_3$)—, —C$_6$H$_3$(C$_2$H$_5$)—, —C$_6$H$_2$(CH$_3$)$_2$—, —C$_6$H$_3$(OH)—, —C$_6$H$_3$(OCH$_3$)—, —C$_6$H$_3$(OC$_2$H$_5$)—, —C$_6$H$_3$(CH$_2$OH)—, —C$_6$H$_3$(NH$_2$)—, —C$_6$H$_3$(CH$_2$NH$_2$)—, —C$_6$H$_3$(F)—, —C$_6$H$_3$(Cl)—, —C$_6$H$_3$(Br)—, —C$_6$H$_3$(I)—, —C$_6$H$_3$(COOH)—, —C$_6$H$_2$(COOH)$_2$—, —C$_6$H$_3$(SO$_3$H)—, —C$_6$H$_3$(CH$_2$COOH)—, —C$_5$H$_3$N—, —C$_5$H$_2$N(CH$_3$)—, —C$_5$H$_2$N(OH)—, —C$_5$H$_2$N(NH$_2$)—, —C$_5$H$_2$N(CH$_2$NH$_2$)—, —C$_5$H$_2$N(COOH)—, —C$_5$H$_9$N—,

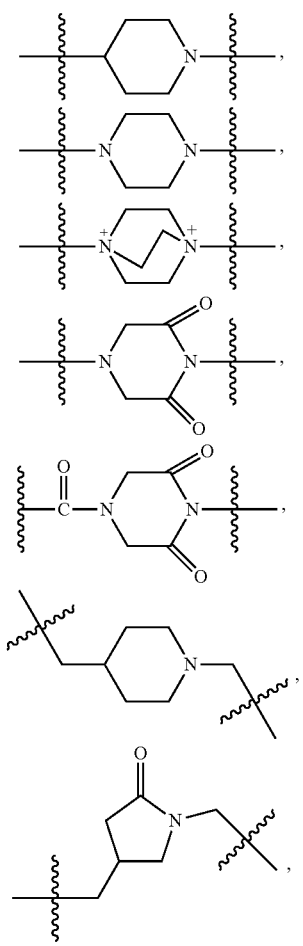

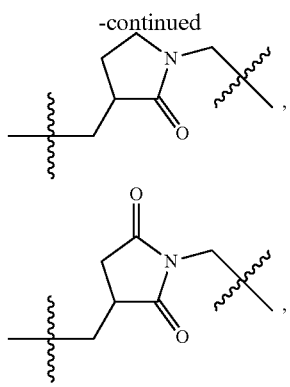

a furan group, a pyrrolyl group, a thienyl group, a pyrazolyl group, an imidazolyl group, an oxazolyl group, a thiazolyl group, a pyridyl group, a piperidinyl group, a pyrimidinyl group, an indolyl group, a quinolinyl group, an isoquinolinyl group, a purinyl group, a pyrimidinyl group, an acridinyl group, a morpholinyl group, or a heterocyclic group containing a substituent.

3. The derivative according to claim 1, wherein the terminal group Z in formula II is: —H, —$CH_3$, —$C_2H_5$, —$C_3H_7$, —$C_4H_9$, —$C_5H_{11}$, —$C_6H_{13}$, —$C_{12}H_{25}$, —$OCH_3$, —$OC_2H_5$, —$OC_3H_7$, —$OC_4H_9$, —$OC_5H_{11}$, —$OC_6H_{13}$, —$OC_{12}H_{25}$, —$C_3H_5$, —$C_4H_7$, —$C_5H_9$, —$C_6H_{11}$, —$C_7H_{13}$, —$C_6H_5$, —OH, —$NH_2$, —SH, —COOH, —$COOCH_3$, —$COOC_2H_5$, —$SO_3H$, —$SO_3CH_3$, —$SO_3C_2H_5$, a glycine group, an alanine group, a valine group, a leucine group, an isoleucine group, a phenylalanine group, a proline group, a tryptophan group, a tyrosine group, a serine group, a cysteine group, a methionine group, an aspartate group, a glutamate group, a threonine group, a lysine group, an arginine group, a histidine group, a cystine group, a glutathione group, —$PPh_3^+$, —$C_5H_4N^+$, —$C_5H_4N^+(CH_3)$, —$C_5H_4N^+(C_2H_5)$, —$C_5H_4N^+(C_{12}H_{25})$, —$N^+(CH_3)_3$, —$N^+(C_2H_5)_3$, —$N^+(C_3H_7)_3$, —$N^+(C_4H_9)_3$, —$N^+(C_6H_{13})_3$, —$N^+(CH_3)_2(C_2H_5)$, —$N^+(CH_3)_2(C_3H_7)$, —$N^+(CH_3)_2(C_4H_9)$, —$N^+(CH_3)_2(C_6H_{13})$, —$N^+(CH_3)_2(C_{12}H_{25})$, —$N^+(C_2H_5)_2(C_3H_7)$, —$N^+(C_2H_5)_2(C_6H_{13})$, —$N^+(C_2H_5)_2(C_{12}H_{25})$, or a quaternary ammonium salt having a terminal group containing a hydroxyl group, a carboxylic acid group, a sulfonic acid group, or a carboxylate.

4. The derivative according to claim 1, wherein $R_1$ and $R_2$ are respectively: —H, —$CH_3$, —$C_2H_5$, —$C_3H_7$, —$C_4H_9$, —$C_5H_{11}$, —$C_6H_{13}$, —$C_{12}H_{25}$, —$C_6H_5$, —$CH_2C_6H_5$, —$CH_2CH_2C_6H_5$, —$CH_2(CH_2)_5C_6H_5$, —$C_6H_4(COOH)$, —$CH_2C_6H_4(COOH)$, —$CH_2C_6H_4(OH)$, —$C_6H_4(CH_2COOH)$, —$CH_2C_6H_4(CH_2COOH)$, a cyclopropyl group, a methylcyclopropyl group, a hydroxylcyclopropyl group, a hydroxylmethylcyclopropyl group, a carboxylcyclopropyl group, a cyclobutyl group, a methylcyclobutyl group, a hydroxylcyclobutyl group, a carboxylcyclobutyl group, —$CH_2C_4H_6(COOH)$, a cyclopentyl group, a methylcyclopentyl group, a hydroxylcyclopentyl group, an aminocyclopentyl group, a carboxylcyclopentyl group, a cyclohexyl group, a methylcyclohexyl group, an ethylcyclohexyl group, a propylcyclohexyl group, a hydroxylcyclohexyl group, an aminocyclohexyl group, a carboxylcyclohexyl group, a carboxylmethylcyclohexyl group, a dicarboxylcyclohexyl group, —$CH_2C_6H_{10}(COOH)$, —$CH_2C_6H_{10}(OH)$, a cycloheptyl group, a carboxylcycloheptyl group, a hydroxylcycloheptyl group, a methylcycloheptyl group, —$CH_2COOH$, —$CH_2CH_2COOH$, —$CH_2(CH_2)_2COOH$, —$CH_2(CH_2)_3COOH$, —$CH_2(CH_2)_4COOH$, —$CH_2(CH_2)_5COOH$, —$CH_2(CH_2)_6COOH$, —$CH_2(CH_2)_{10}COOH$, —$CH_2COOCH_3$, —$CH_2CH_2COOC_6H_{13}$, —$CH_2(CH_2)_2COOCH_3$, —$CH_2(CH_2)_2COOC_2H_5$, —$CH_2(CH_2)_2COOC_6H_{13}$, —$CH_2(CH_2)_4COOCH_3$, —$CH_2(CH_2)_6COOC_6H_{13}$, —$CH_2COONa^+$, —$CH_2(CH_2)_2COONa^+$, —$CH_2(CH_2)_4COONa^+$, —$CH_2SO_3H$, —$CH_2CH_2SO_3H$, —$CH_2(CH_2)_2SO_3H$, —$CH_2(CH_2)_3SO_3H$, —$CH_2(CH_2)_4SO_3H$, —$CH_2(CH_2)_5SO_3H$, —$CH_2(CH_2)_{11}SO_3H$, —$CH_2SO_3CH_3$, —$CH_2SO_3C_6H_{13}$, —$CH_2CH_2SO_3CH_3$, —$CH_2(CH_2)_2SO_3CH_3$, —$CH_2(CH_2)_2SO_3C_6H_{13}$, —$CH_2(CH_2)_4SO_3C_4H_9$, —$CH_2(CH_2)_{11}SO_3C_6H_{13}$, —$CH_2SO_3Na$, —$CH_2CH_2SO_3K$, —OH, —$OCH_3$, —$OC_2H_5$, —$OC_6H_{13}$, —$NH_2$, —$NHC_2H_5$, —$NHC_6H_{13}$, —$NHC_{12}H_{25}$, —$NHC_6H_5$, —$NHC_5H_4N$, —$C_5H_4N$, —$CH_2C_5H_4N$, —$(CH_2)_2C_5H_4N$, —$(CH_2)_6C_5H_4N$, —$C_5H_3N(CH_3)$, —$C_5H_3N(OH)$, —$C_5H_3N(NH_2)$, —$C_5H_3N(COOH)$, —$C_5H_3N(CH_2COOH)$, —$CH_2C_5H_3N(CH_2COOH)$, —$CH_2CH_2$—$(OCH_2CH_2)_n$—OH, —$CH_2CH_2$—$(OCH_2CH_2)_n$—$OCH_3$, —$CH_2CH_2$—$(OCH_2CH_2)_n$—$OC_6H_{13}$, —$CH_2CH_2$—$(OCH_2CH_2)_n$—$OC_{12}H_{25}$, —$CH_2CH_2$—$(OCH_2CH_2)_n$—O—$COCH_3$, —$CH_2CH_2$—$(OCH_2CH_2)_n$—O—$COC_6H_{13}$, —$CH_2CH_2$—O—CO—$CH_2CH_2$—$(OCH_2CH_2)_n$—OH, —$CH_2CH_2$—O—CO—$CH_2CH_2$—$(OCH_2CH_2)_n$—$OCH_3$, —$CH_2CH_2$—$OCH_2CH_2$—O—CO—$CH_2CH_2$—$(OCH_2CH_2)_n$—OH, —$CH_2CH_2$—$OCH_2CH_2$—O—CO—$CH_2CH_2$—$(OCH_2CH_2)_n$—$OCH_3$, —$CH_2CH_2$—$OCH_2CH_2$—O—CO—$CH_2CH_2$—$(OCH_2CH_2)_n$—OH, —$CH_2CH_2$—$OCH_2CH_2$—$OCH_2CH_2$—O—CO—$CH_2CH_2$—$(OCH_2CH_2)_n$—$OCH_3$, —$CH_2CH_2$—O—CO—$CH_2CH_2$—$PPh_3^+$, —$CH_2CH_2$—O—CO—$(CH_2)_3$—$PPh_3^+$, —$CH_2CH_2$—O—CO—$(CH_2)_5$—$PPh_3^+$, —$CH_2CH_2$—$OCH_2CH_2$—O—CO—$CH_2CH_2$—$PPh_3^+$, —$CH_2CH_2$—$OCH_2CH_2$—O—CO—$(CH_2)_3$—$PPh_3^+$, —$CH_2CH_2$—$OCH_2CH_2$—O—CO—$(CH_2)_5$—$PPh_3^+$; —$(CH_2)_3$—OH, —$(CH_2)_3$—$OCH_3$, —$(CH_2)_3$—$OC_2H_5$, —$(CH_2)_3$—$OCOCH_3$, —$(CH_2)_3$—$OCOC_2H_5$, —$(CH_2)_3$—O—$COCH_2$—$(OCH_2CH_2)_n$—$OCH_3$, —$(CH_2)_4$—OH, —$(CH_2)_4$—$OCH_3$, —$(CH_2)_4$—$OCOCH_3$, —$(CH_2)_4$—$OCOC_2H_5$, —$(CH_2)_4$—O—$OCOCH_2CH_2$—$(OCH_2CH_2)_n$—$OCH_3$, —$(CH_2)_6$—OH, —$(CH_2)_6$—$OCH_3$, —$(CH_2)_6$—$OCOCH_3$, —$(CH_2)_6$—O—$COCH_2CH_2$—$(OCH_2CH_2)_n$—$OCH_3$; —$CH_2CH_2$—NH—$CH_2CH_2$—$(OCH_2CH_2)_n$—OH, —$CH_2CH_2$—NH—$CH_2CH_2$—$(OCH_2CH_2)_n$—$OCH_3$, —$CH_2CH_2$—$(NHCH_2CH_2)_n$—$NH_2$, —$CH_2CH_2$—$(NHCH_2CH_2)_n$—$N(CH_3)_2$, —$CH_2CH_2$—$NHCH_2CH_2$—NH—$COCH_2CH_2$—$(OCH_2CH_2)_n$—$OCH_3$, —$CH_2CH_2$—S—$CH_2CH_2$—$(OCH_2CH_2)_n$—OH, —$CH(CH_3)$—COOH, —$CH(CH(CH_3)_2)$—COOH, —$CHCH_2(CH(CH_3)_2)$—COOH, —$CH(CH_2CH_2SCH_3)$—COOH, —$CHCH(CH_3)(C_2H_5)$—COOH, —$CH(CH_2OH)$—COOH, —$CHCH(OH)(CH_3)$—COOH, —$CH(CH_2SH)$—COOH, —$CH(CH_2CONH_2)$—COOH, —$CH(CH_2CH_2CONH_2)$—COOH, —$CH(CH_2C_6H_5)$—COOH, —$CH(CH_2C_6H_5OH)$—COOH, —$CH(CH_2CH_2CH_2CH_2NH_3+)$—COOH, —$CH(COOH)$—$CH_2COOH$, —$CH(COOH)$—$CH_2CH_2COOH$,

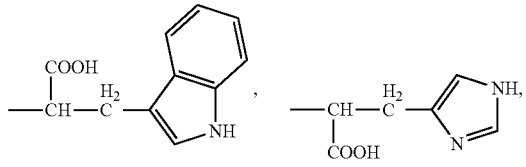

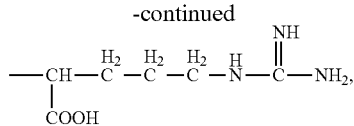

—CH(CH$_3$)—COOCH$_3$, —CH(CH(CH$_3$)$_2$)—COOCH$_3$, —CHCH$_2$(CH(CH$_3$)$_2$)—COOCH$_3$, —CH(CH$_2$CH$_2$SCH$_3$)—COOCH$_3$, —CH(CH$_3$)—COONa$^+$, —CH(CH(CH$_3$)$_2$)—COONa$^+$, —CHCH$_2$(CH(CH$_3$)$_2$)—COOK$^+$, —CH(CH$_2$CH$_2$SCH$_3$)—COOK$^+$; —CH$_2$CO—(OCH$_2$CH$_2$)$_n$—OH, —CH$_2$CO—(OCH$_2$CH$_2$)$_n$—OCH$_3$, —CH$_2$CH$_2$CO—(OCH$_2$CH$_2$)$_n$—OH, —CH$_2$CH$_2$CO—(OCH$_2$CH$_2$)$_n$—OCH$_3$, —CH$_2$(CH$_2$)$_2$CO—(OCH$_2$CH$_2$)$_n$—OH, —CH$_2$(CH$_2$)$_2$CO—(OCH$_2$CH$_2$)$_n$—OCH$_3$, —CH$_2$(CH$_2$)$_4$CO—(OCH$_2$CH$_2$)$_n$—OH, —CH$_2$(CH$_2$)$_4$CO—(OCH$_2$CH$_2$)$_n$—OCH$_3$, —CH$_2$—CO—NH—CH$_2$CH$_2$—(OCH$_2$CH$_2$)$_n$—OH, —CH$_2$—CO—NH—CH$_2$CH$_2$—(OCH$_2$CH$_2$)$_n$—OCH$_3$, —(CH$_2$)$_2$—CO—NH—CH$_2$CH$_2$—(OCH$_2$CH$_2$)$_n$—OH, —(CH$_2$)$_2$—CO—NH—CH$_2$CH$_2$—(OCH$_2$CH$_2$)$_n$—OCH$_3$, —(CH$_2$)$_3$—CO—NH—CH$_2$CH$_2$—(OCH$_2$CH$_2$)$_n$—OH, —(CH$_2$)$_3$—CO—NH—CH$_2$CH$_2$—(OCH$_2$CH$_2$)$_n$—OCH$_3$, —(CH$_2$)$_4$—CO—NH—CH$_2$CH$_2$—(OCH$_2$CH$_2$)$_n$—OH, —(CH$_2$)$_4$—CO—NH—CH$_2$CH$_2$—(OCH$_2$CH$_2$)$_n$—OCH$_3$, —(CH$_2$)$_5$—CO—NH—CH$_2$CH$_2$—(OCH$_2$CH$_2$)$_n$—OH, —(CH$_2$)$_5$—CO—NH—CH$_2$CH$_2$—(OCH$_2$CH$_2$)$_n$—OCH$_3$, —CH$_2$—SO$_2$—(OCH$_2$CH$_2$)$_n$—OH, —CH$_2$—SO$_2$—(OCH$_2$CH$_2$)$_n$—OCH$_3$, —(CH$_2$)$_2$—SO$_2$—(OCH$_2$CH$_2$)$_n$—OH, —(CH$_2$)$_2$—SO$_2$—(OCH$_2$CH$_2$)$_n$—OCH$_3$, —(CH$_2$)$_3$—SO$_2$—(OCH$_2$CH$_2$)$_n$—OH, —(CH$_2$)$_3$—SO$_2$—(OCH$_2$CH$_2$)$_n$—OCH$_3$, —(CH$_2$)$_4$—SO$_2$—(OCH$_2$CH$_2$)$_n$—OH, —(CH$_2$)$_4$—SO$_2$—(OCH$_2$CH$_2$)$_n$—OCH$_3$, —(CH$_2$)$_5$—SO$_2$—(OCH$_2$CH$_2$)$_n$—OH, —(CH$_2$)$_5$—SO$_2$—(OCH$_2$CH$_2$)$_n$—OCH$_3$, —(CH$_2$)$_6$—SO$_2$—(OCH$_2$CH$_2$)$_n$—OH, —(CH$_2$)$_6$—SO$_2$—(OCH$_2$CH$_2$)$_n$—OCH$_3$, —CH$_2$—SO$_2$—NHCH$_2$CH$_2$—(OCH$_2$CH$_2$)$_n$—OH, —CH$_2$—SO$_2$—NHCH$_2$CH$_2$—(OCH$_2$CH$_2$)$_n$—OCH$_3$, —(CH$_2$)$_2$—SO$_2$—NHCH$_2$CH$_2$—(OCH$_2$CH$_2$)$_n$—OH, —(CH$_2$)$_2$—SO$_2$—NHCH$_2$CH$_2$—(OCH$_2$CH$_2$)$_n$—OCH$_3$, —(CH$_2$)$_3$—SO$_2$—NHCH$_2$CH$_2$—(OCH$_2$CH$_2$)$_n$—OCH$_3$, —(CH$_2$)$_4$—SO$_2$—NHCH$_2$CH$_2$—(OCH$_2$CH$_2$)$_n$—OCH$_3$, —(CH$_2$)$_5$—SO$_2$—NHCH$_2$CH$_2$—(OCH$_2$CH$_2$)$_n$—OCH$_3$, —(CH$_2$)$_6$—SO$_2$—NHCH$_2$CH$_2$—(OCH$_2$CH$_2$)$_n$—OCH$_3$, —CH$_2$CH$_2$—N$^+$(CH$_3$)$_3$, —(CH$_2$)$_3$—N$^+$(CH$_3$)$_3$, —(CH$_2$)$_4$—N$^+$(CH$_3$)$_3$, —(CH$_2$)$_5$—N$^+$(CH$_3$)$_3$, —(CH$_2$)$_6$—N$^+$(CH$_3$)$_3$, —(CH$_2$)$_{12}$—N$^+$(CH$_3$)$_3$, —CH$_2$CH$_2$—N$^+$(C$_2$H$_5$)$_3$, —(CH$_2$)$_4$—N$^+$(C$_2$H$_5$)$_3$, —(CH$_2$)$_6$—N$^+$(C$_2$H$_5$)$_3$, —(CH$_2$)$_{12}$—N$^+$(C$_2$H$_5$)$_3$, —CH$_2$CH$_2$—N$^+$(C$_3$H$_7$)$_3$, —(CH$_2$)$_4$—N$^+$(C$_3$H$_7$)$_3$, —(CH$_2$)$_6$—N$^+$(C$_3$H$_7$)$_3$, —CH$_2$CH$_2$—N$^+$(C$_4$H$_9$)$_3$, —(CH$_2$)$_6$—N$^+$(C$_4$H$_9$)$_3$, —CH$_2$CH$_2$—N$^+$(CH$_3$)$_2$(C$_2$H$_5$), —CH$_2$CH$_2$—N$^+$(CH$_3$)$_2$(C$_4$H$_9$), —CH$_2$CH$_2$—N$^+$(CH$_3$)$_2$(C$_6$H$_{13}$), —CH$_2$CH$_2$—N$^+$(CH$_3$)$_2$(C$_{12}$H$_{25}$), —(CH$_2$)$_3$—N$^+$(CH$_3$)$_2$(C$_4$H$_9$), —(CH$_2$)$_3$—N$^+$(CH$_3$)$_2$(C$_6$H$_{13}$), —(CH$_2$)$_3$—N$^+$(CH$_3$)$_2$(C$_{12}$H$_{25}$), —(CH$_2$)$_4$—N$^+$(CH$_3$)$_2$(C$_6$H$_{13}$), —(CH$_2$)$_4$—N$^+$(CH$_3$)$_2$(C$_{12}$H$_{25}$), —(CH$_2$)$_5$—N$^+$(CH$_3$)$_2$(C$_2$H$_5$), —(CH$_2$)$_5$—N$^+$(CH$_3$)$_2$(C$_6$H$_{13}$), —(CH$_2$)$_5$—N$^+$(CH$_3$)$_2$(C$_{12}$H$_{25}$), —(CH$_2$)$_6$—N$^+$(CH$_3$)$_2$(C$_2$H$_5$), —(CH$_2$)$_6$—N$^+$(CH$_3$)$_2$(C$_6$H$_{13}$), —(CH$_2$)$_6$—N$^+$(CH$_3$)$_2$(C$_{12}$H$_{25}$); —CH$_2$CO—OCH$_2$CH$_2$—N$^+$(CH$_3$)$_3$, —CH$_2$CH$_2$CO—OCH$_2$CH$_2$—N$^+$(CH$_3$)$_3$, —CH$_2$(CH$_2$)$_2$CO—OCH$_2$CH$_2$—N$^+$(CH$_3$)$_3$, —CH$_2$(CH$_2$)$_6$CO—OCH$_2$CH$_2$—N$^+$(CH$_3$)$_3$, —CH$_2$CO—O—(CH$_3$)$_3$—N$^+$(CH$_3$)$_3$, —CH$_2$(CH$_2$)$_2$CO—O—(CH$_3$)$_3$—N$^+$(CH$_3$)$_3$, —CH$_2$COOCH$_2$CH$_2$—N$^+$(CH$_3$)$_2$(C$_6$H$_{13}$); —CH$_2$CONH—CH$_2$CH$_2$—N$^+$(CH$_3$)$_3$, —CH$_2$CH$_2$CONH—CH$_2$CH$_2$—N$^+$(CH$_3$)$_3$, —CH$_2$(CH$_2$)$_4$CONH—CH$_2$CH$_2$—N$^+$(CH$_3$)$_3$, —CH$_2$CONH—(CH$_2$)$_3$—N$^+$(CH$_3$)$_3$, —CH$_2$CH$_2$CONH—(CH$_2$)$_3$—N$^+$(CH$_3$)$_3$, —CH$_2$(CH$_2$)$_4$CONH—(CH$_2$)$_3$—N$^+$(CH$_3$)$_3$, —CH$_2$CONH—(CH$_2$)$_4$—N$^+$(CH$_3$)$_3$, —CH$_2$CH$_2$CONH—(CH$_2$)$_4$—N$^+$(CH$_3$)$_3$, —CH$_2$(CH$_2$)$_4$CONH—(CH$_2$)$_4$—N$^+$(CH$_3$)$_3$, —CH$_2$CONH—(CH$_2$)$_5$—N$^+$(CH$_3$)$_3$, —CH$_2$CH$_2$CONH—(CH$_2$)$_5$—N$^+$(CH$_3$)$_3$, —CH$_2$(CH$_2$)$_4$CONH—(CH$_2$)$_5$—N$^+$(CH$_3$)$_3$, —CH$_2$CONH—(CH$_2$)$_6$—N$^+$(CH$_3$)$_3$, —CH$_2$CH$_2$CONH—(CH$_2$)$_6$—N$^+$(CH$_3$)$_3$, —CH$_2$(CH$_2$)$_4$CONH—(CH$_2$)$_6$—N$^+$(CH$_3$)$_3$, —CH$_2$CONH—CH$_2$CH$_2$—N$^+$(CH$_3$)$_2$(C$_6$H$_{13}$), —CH$_2$CONH—CH$_2$CH$_2$—N$^+$(CH$_3$)$_2$(C$_{12}$H$_{25}$); —C$_5$H$_4$N$^+$(CH$_3$), —CH$_2$C$_5$H$_4$N$^+$(CH$_3$), —CH$_2$C$_5$H$_4$N$^+$(C$_6$H$_{13}$), —CH$_2$C$_5$H$_4$N$^+$(CH$_2$COOH), —CH$_2$CH$_2$C$_5$H$_4$N$^+$(CH$_3$), —CH$_2$CH$_2$C$_5$H$_4$N$^+$(C$_6$H$_{13}$), —CH$_2$CH$_2$C$_5$H$_4$N$^+$(CH$_2$COOH),

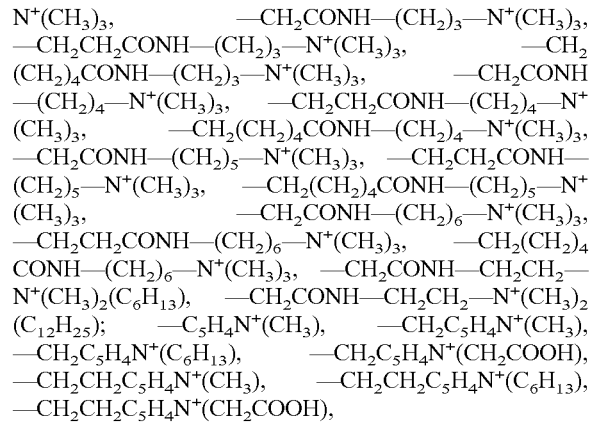

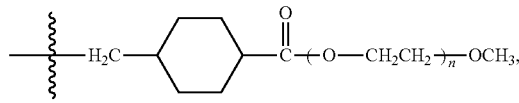

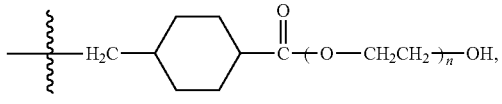

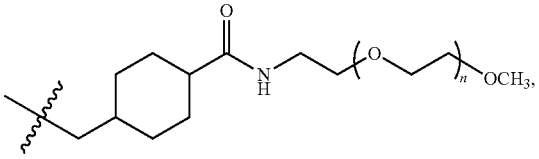

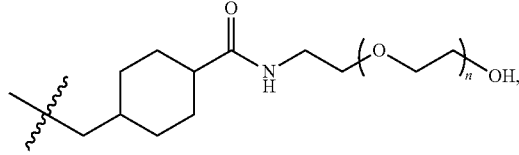

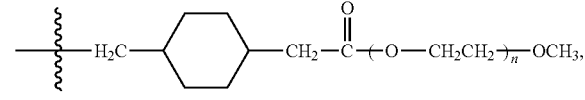

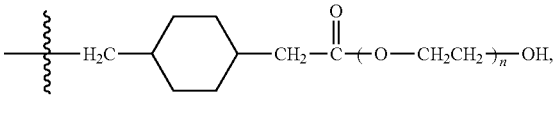

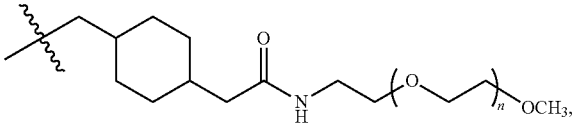

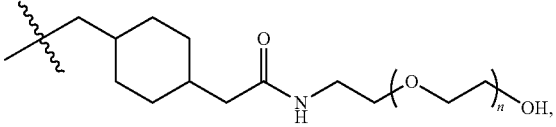

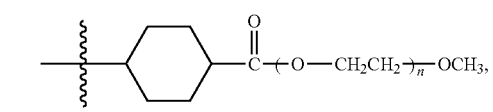

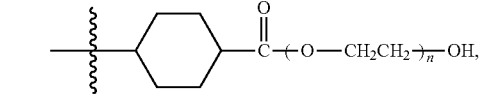

253
-continued
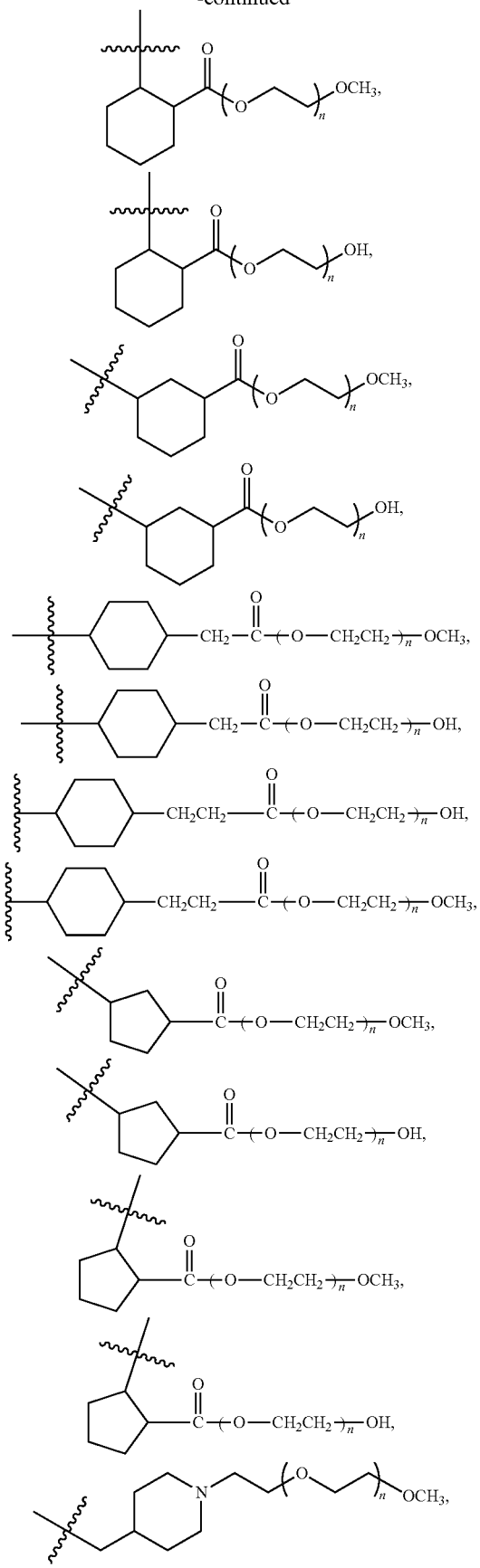
254
-continued
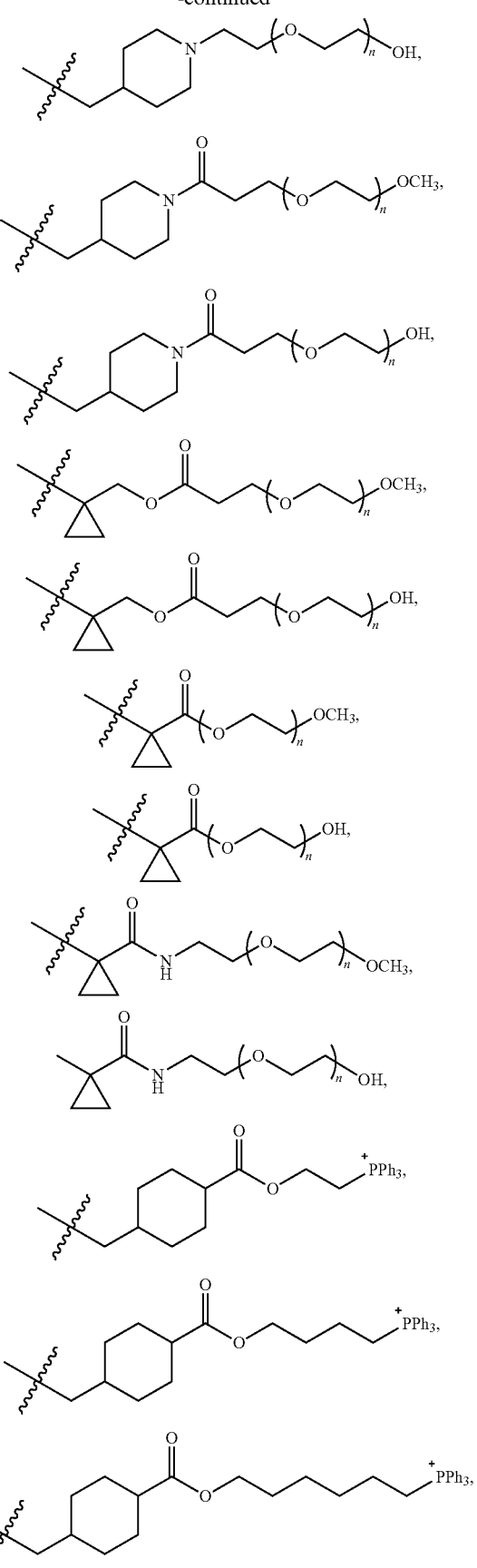

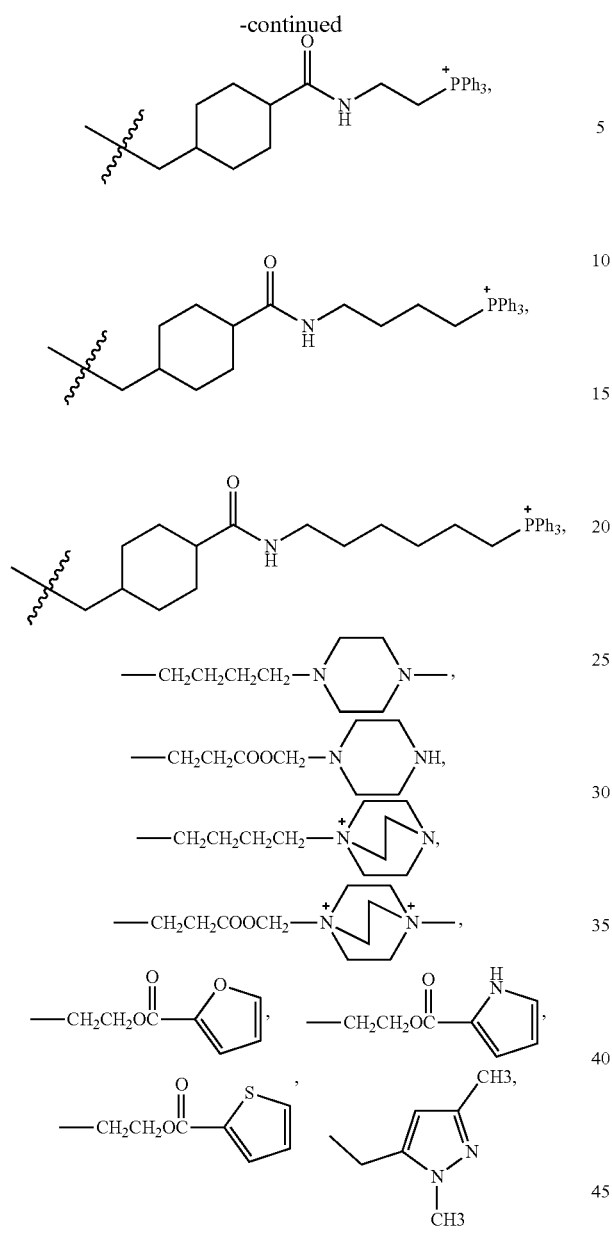

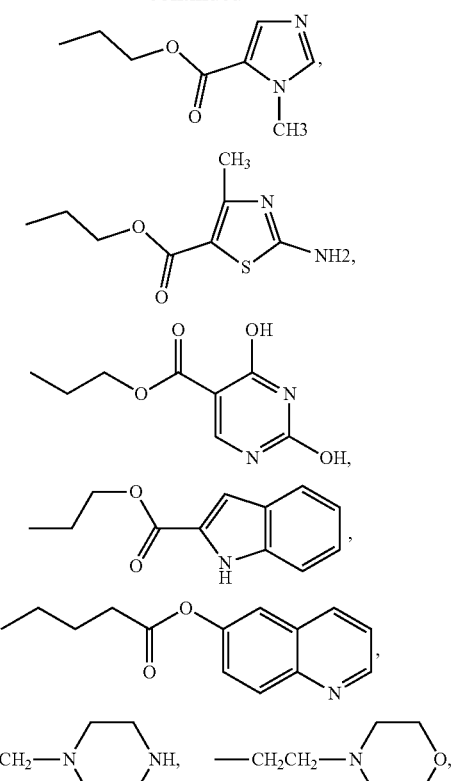

or a heterocyclic group containing a substituent; and wherein n is a positive integer between 0 and 50.

5. The derivative according to claim 1, wherein the derivative has an enol tautomer; and wherein formula I-a and formula I-a' represent enol tautomers regarding positions 9 and 10 in the structural formula; formula I-b and formula I-b' represent enol tautomers regarding positions 3 and 4 in the structural formula; formula I-c and formula I-c' represent enol tautomers regarding positions 9 and 10 in the structural formula; and formula I-d and formula I-d' represent enol tautomers regarding positions 3 and 4 in the structural formula:

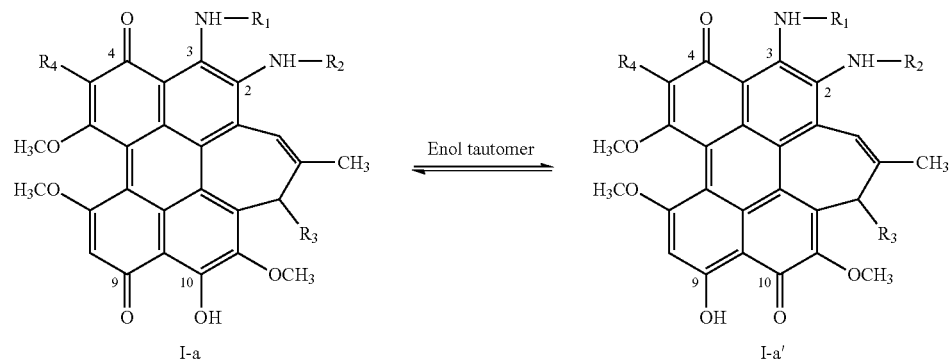

-continued
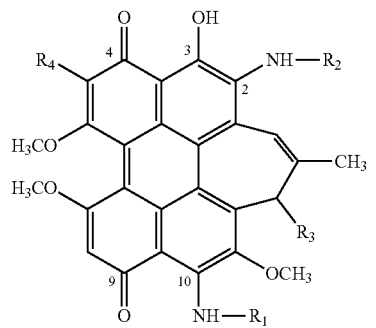
I-b
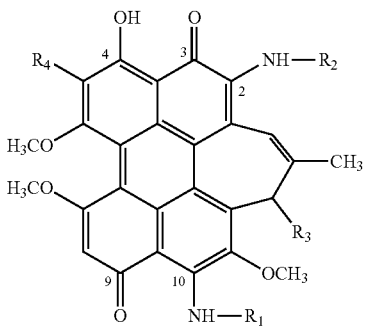
I-b'
Enol tautomer
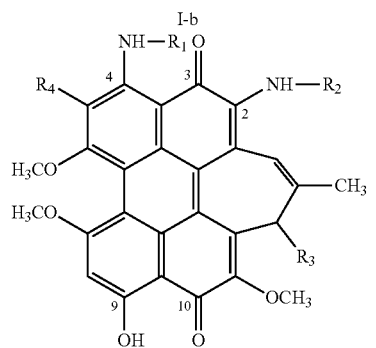
I-c
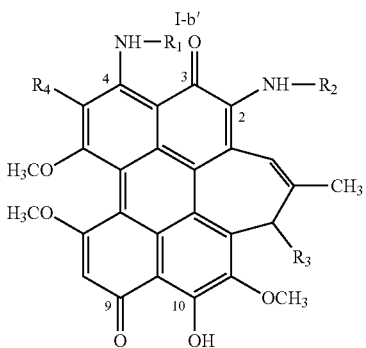
I-c'
Enol tautomer
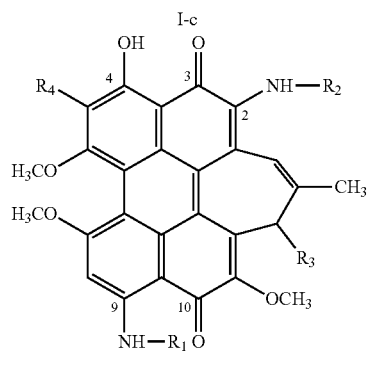
I-d
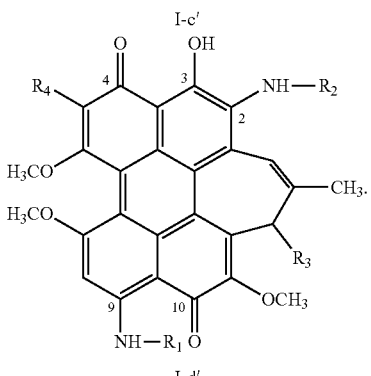
I-d'
Enol tautomer
6. A photosensitizer drug for use in photodynamic therapy, the photosensitizer drug comprising the derivative according to claim 1.
* * * * *